(12) United States Patent
Frudakis et al.

(10) Patent No.: US 6,344,550 B1
(45) Date of Patent: Feb. 5, 2002

(54) COMPOSITIONS AND METHODS FOR THE TREATMENT AND DIAGNOSIS OF BREAST CANCER

(75) Inventors: Tony N. Frudakis, Seattle; John M. Smith, Everett; Steven G. Reed, Bellevue, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/062,451

(22) Filed: Apr. 17, 1998

Related U.S. Application Data

(63) Continuation-in-part of application No. 08/991,789, filed on Dec. 11, 1997, which is a continuation-in-part of application No. 08/838,762, filed as application No. PCT/US97/00485 on Jan. 10, 1997, now abandoned, and a continuation-in-part of application No. 08/700,014, filed on Aug. 20, 1996, now abandoned, which is a continuation-in-part of application No. 08/585,392, filed on Jan. 1, 1996, now abandoned.

(51) Int. Cl.[7] .......................... C07H 21/04; C12N 1/20; C12N 1/14; C12N 1/16; C12N 15/00
(52) U.S. Cl. .............. 536/23.5; 435/252.3; 435/254.11; 435/320.1; 435/325
(58) Field of Search ........................ 536/23.5; 435/6, 435/320.1, 69.1, 325, 252.3, 254.11

(56) References Cited

U.S. PATENT DOCUMENTS

| | | | |
|---|---|---|---|
| 5,231,012 A | 7/1993 | Mosmann et al. | 435/69.52 |
| 5,428,145 A | 6/1995 | Okamoto et al. | 536/23.72 |
| 5,516,650 A | 5/1996 | Foster et al. | 435/68.1 |
| 5,523,225 A | 6/1996 | Kraus | 435/240.1 |
| 5,585,270 A | 12/1996 | Grotendorst et al. | 435/252.3 |
| 5,811,535 A * | 9/1998 | Amadou et al. | 536/23.5 |
| 5,872,237 A * | 2/1999 | Feder et al. | 536/23.5 |

FOREIGN PATENT DOCUMENTS

| | | |
|---|---|---|
| GB | 2 273 099 A | 6/1994 |
| WO | WO 91/02062 | 2/1991 |
| WO | WO 95/10777 | 4/1995 |
| WO | WO 95/19369 | 7/1995 |
| WO | WO 95/32311 | 11/1995 |
| WO | WO 96/38463 | 12/1996 |
| WO | WO 97/06256 | 2/1997 |
| WO | WO 97/25426 | 7/1997 |
| WO | WO 97/25431 | 7/1997 |
| WO | WO 98/45328 | 10/1998 |

OTHER PUBLICATIONS

Anderson et al., "Sequence and organization of the human mitochondrial genome," *Nature* 290:457–465, 1981.
Bauer et al., "Identification of differentially expressed mRNA species by an improved display technique (DDRT-PCR)," *Nucleic Acids Research* 21(18):4272–4280, 1993.
Bratthauer et al., "Expression of LINE–1 Retrotransposons in Human Breast Cancer," *Cancer* 73:2333–2336, 1994.
Byrne et al., "A Screening Method to Identify Genes Commonly Overexpressed in Carcinomas and the Identification of a Novel Complementary DNA Sequence," *Cancer Research* 55:2869–2903, 1995.
Chen and Sager, "Differential Expression of Human Tissue Factor in Normal Mammary Epithelial Cells and in Carcinomas," *Molecular Medicine* 1(2):153–160, 1995.
Cordonnier et al., "Isolation of Novel Human Endogenous Retrovirus–Like Elements with Foamy Virus–Related pol Sequence," *Journal of Virology* 69(9):5890–5897, 1995.
Databank Genebank Accession No. Z34289, 1995.
Ezzell, "Cancer "Vaccines": An Idea Whose Time Has Come?," *The Journal of NIH Research* 7:46–49, 1995.
Gura, "Systems for Identifying New Drugs Are Often Faulty," *Science* 278:1041–1042, 1997.
Haltmeier et al., "Identification of S71–Related Human Endogenous Retroviral Sequences with Full–Length pol Genes," *Virology* 209:550–560, 1995.
Keydar et al., "Properties of retrovirus–like particles produced by a human breast carcinoma cell line: Immunological relationship with mouse mammary tumor virus proteins," *Proc. Natl. Acad. Sci. USA* 81:4188–92, 1984.
Leib–Mösch and Seifarth, "Evolution and Biological Significance of Human Retroelements," *Virus Genes* 11(2/3):133–145, 1996.
Leib–Mösch et al., "Endogenous Retroviral Elements in Human DNA," *Cancer Research* 50:5636s–5642s, 1994.
Leib–Mösch et al., "Genomic Distribution and Transcription of Solitary HERV–K LTRs," *Genomics* 18:261–269, 1993.
Liang et al., "Differential Display of Eukaryotic Messenger RNA by Means of the Polymerase Chain Reaction," *Science* 257:967–971, 1992.
Wang et al., "Detection of Mammary Tumor Virus ENV Gene–like Sequences in Human Breast Cancer," *Cancer Research* 55:5173–5179, 1995.
Watson and Fleming, "Isolation of Differentially Expressed Sequence Tags from Human Breast Cancer," *Cancer Research* 54(17):4598–4602, 1994.
Werner et al., "S71 Is a Phylogenetically Distinct Human Endogenous Retroviral Element with Structural and Sequence Homology to Simian Sarcoma Virus (SSV)," *Virology* 174:225–238, 1990.

(List continued on next page.)

*Primary Examiner*—Anthony C. Caputa
*Assistant Examiner*—Karen A. Canella
(74) *Attorney, Agent, or Firm*—Seed Intellectual Property Law Group PLLC

(57) ABSTRACT

Compositions and methods for the detection and therapy of breast cancer are disclosed. The compounds provided include nucleotide sequences that are preferentially expressed in breast tumor tissue, as well as polypeptides encoded by such nucleotide sequences. Vaccines and pharmaceutical compositions comprising such compounds are also provided and may be used, for example, for the prevention and treatment of breast cancer. The polypeptides may also be used for the production of antibodies, which are useful for diagnosing and monitoring the progression of breast cancer in a patient.

9 Claims, 16 Drawing Sheets

OTHER PUBLICATIONS

Bernard et al., "Cloning and Sequencing of Pro–α1(XI) Collagen cDNA Demonstrates That Type XI Belongs to the Fibrillar Class of Collagens and Reveals That the Expression of the Gene Is Not Restricted to Cartilagenous Tissue," *J. Biol. Chem.* 263(32):17159–17166, 1988.

Yoshioka et al., "Pro–α1(XI) Collagen. Structure Of The Amino–Terminal Propeptide And Expression Of The Gene In Tumor Cell Lines," *J. Biol. Chem.* 265(11):6423–6426, 1990.

Hillier et al., Genbank Accession No. R55637, 1995.
Hillier et al., Genbank Accession No. R60426, 1995.
Hillier et al., Genbank Accession No. R19532, 1995.
Hillier et al., Genbank Accession No. T83348, 1995.
Hillier et al., Genbank Accession No. R35308, 1995.
Hillier et al., Genbank Accession No. H80165, 1995.
Adams et al., Genbank Accession No. Q60347, 1993.
Frank et al., Genbank Accession No. Q70049, 1994.
Adams et al., Genbank Accession No. Q61250, 1993.
Chai et al., Genbank Accession No. U03644, 1994.
Matsubara et al., Genbank Accession No. T24124, 1995.

Critical Synergy: The Biotechnology Industry and Intellectual Property Protection, Presentations of the Intellectual Property Committee of the Biotechnology Industry Organization at the Oct. 17, 1994, Hearing of the U.S. Patent and Trademark Office, San Diego, California, published by the Biotechnology Industry Organization, Washington, D.C., pp. 75, 100–107.

Charnock–Jones et al., "Extension of incomplete cDNAs (ESTs) by biotin/streptavidin–mediated walking using polymerase chain reaction," *J. Biotechno.* 35:205–215, Jun. 1994.

Venter et al., "Genome sequence analysis: Scientific objectives and practical strategies," *Trends Biotechnol.* 10(1–2):8–11, Jan./Feb. 1992.

* cited by examiner

NUCLEOTIDE SEQUENCE OF THE REPRESENTATIVE BREAST-TUMOR SPECIFIC cDNA B18Ag1

```
TTA GAG ACC CAA TTG GGA CCT AAT TGG GAC CCA AAT TTC TCA AGT GGA    48
Leu Glu Thr Gln Leu Gly Pro Asn Trp Asp Pro Asn Phe Ser Ser Gly
 1           5                  10                  15

GGG AGA ACT TTT GAC GAT TTC CAC CGG TAT CTC CTC GTG GGT ATT CAG    96
Gly Arg Thr Phe Asp Asp Phe His Arg Tyr Leu Leu Val Gly Ile Gln
             20                  25                  30

GGA GCT GCC CAG AAA CCT ATA AAC TTG TCT AAG GCG ATT GAA GTC GTC   144
Gly Ala Ala Gln Lys Pro Ile Asn Leu Ser Lys Ala Ile Glu Val Val
         35                  40                  45

CAG GGG CAT GAT GAG TCA CCA GGA GTG TTT TTA GAG CAC CTC CAG GAG   192
Gln Gly His Asp Glu Ser Pro Gly Val Phe Leu Glu His Leu Gln Glu
     50                  55                  60

GCT TAT CGG ATT TAC ACC CCT TTT GAC CTG GCA GCC CCC GAA AAT AGC   240
Ala Tyr Arg Ile Tyr Thr Pro Phe Asp Leu Ala Ala Pro Glu Asn Ser
 65                  70                  75                  80

CAT GCT CTT AAT TTG GCA TTT GTG GCT CAG GCA GCC CCA GAT AGT AAA   288
His Ala Leu Asn Leu Ala Phe Val Ala Gln Ala Ala Pro Asp Ser Lys
             85                  90                  95

AGG AAA CTC CAA AAA CTA GAG GGA TTT TGC TGG AAT GAA TAC CAG TCA   336
Arg Lys Leu Gln Lys Leu Glu Gly Phe Cys Trp Asn Glu Tyr Gln Ser
        100                 105                 110

GCT TTT AGA GAT AGC CTA AAA GGT TTT                               363
Ala Phe Arg Asp Ser Leu Lys Gly Phe
        115                 120
```

*Fig. 6*

NUCLEOTIDE SEQUENCE OF THE REPRESENTATIVE BREAST-TUMOR SPECIFIC cDNA B17Ag1

```
GC TGGGCACAGT GGCTCATACC TGTAATCCTG ACCGTTTCAG AGGCTCAGGT     60

CG CTTGAGCCCA AGATTTCAAG ACTAGTCTGG GTAACATAGT GAGACCCTAT    120

AA AAATAAAAAA ATGAGCCTGG TGTAGTGGCA CACACCAGCT GAGGAGGGAG    180

CT AGGAGA                                                    196
```

*Fig. 7*

NUCLEOTIDE SEQUENCE OF THE REPRESENTATIVE
BREAST-TUMOR SPECIFIC cDNA B17Ag2

```
GC TTGGGGGCTC TGACTAGAAA TTCAAGGAAC CTGGGATTCA AGTCCAACTG    60

AC TTACACTGTG GNCTCCAATA AACTGCTTCT TTCCTATTCC CTCTCTATTA   120

AA GGAAAACGAT GTCTGTGTAT AGCCAAGTCA GNTATCCTAA AAGGAGATAC   180

AT TAAATATCAG AATGTAAAAC CTGGGAACCA GGTTCCCAGC CTGGGATTAA   240

CA AGAAGACTGA ACAGTACTAC TGTGAAAAGC CCGAAGNGGC AATATGTTCA   300

TT GAAGGATGGC TGGGAGAATG AATGCTCTGT CCCCCAGTCC CAAGCTCACT   360

CT CCTTTATAGC CTAGGAGA                                     388
```

*Fig. 8*

NUCLEOTIDE SEQUENCE OF THE REPRESENTATIVE
BREAST-TUMOR SPECIFIC cDNA B13Ag2a

```
GC CTATAATCAT GTTTCTCATT ATTTTCACAT TTTATTAACC AATTTCTGTT    60

AA AATATGAGGG AAATATATGA AACAGGGAGG CAATGTTCAG ATAATTGATC   120

TG ATTTCTACAT CAGATGCTCT TTCCTTTCCT GTTTATTTCC TTTTTATTTC   180

GG TCGAATGTAA TAGCTTTGTT TCAAGAGAGA GTTTTGGCAG TTTCTGTAGC   240

CT GCTCATGTCT CCAGGCATCT ATTTGCACTT TAGGAGGTGT CGTGGGAGAC   300

CT ATTTTTTCCA TATTTGGGCA ACTACTA                           337
```

*Fig. 9*

NUCLEOTIDE SEQUENCE OF THE REPRESENTATIVE BREAST-TUMOR SPECIFIC cDNA B13Ag1b

```
GC CATACAGTGC CTTTCCATTT ATTTAACCCC CACCTGAACG GCATAAACTG    60

GC TGGTGTTTTT TACTGTAAAC AATAAGGAGA CTTTGCTCTT CATTTAAACC   120

AT TTCATATTTT ACGCTCGAGG GTTTTTACCG GTTCCTTTTT ACACTCCTTA   180

TT TAAGTCGTTT GGAACAAGAT ATTTTTTCTT TCCTGGCAGC TTTTAACATT   240

TT TGTGTCTGGG GGACTGCTGG TCACTGTTTC TCACAGTTGC AAATCAAGGC   300

CC AAGAAAAAAA AATTTTTTTG TTTTATTTGA AACTGGACCG GATAAACGGT   360

CG GCTGCTGTAT ATAGTTTTAA ATGGTTTATT GCACCTCCTT AAGTTGCACT   420

GG GGGGNTTTTG NATAGAAAGT NTTTANTCAC ANAGTCACAG GGACTTTTNT   480

NA CTGAGCTAAA AAGGGCTGNT TTCGGGTGG GGGCAGATGA AGGCTCACAG    540

TC TCTTAGAGGG GGGAACTNCT A                                 571
```

*Fig. 10*

NUCLEOTIDE SEQUENCE OF THE REPRESENTATIVE BREAST-TUMOR SPECIFIC cDNA B13Ag1a

```
TA ATAACTTAAA TATATTTTGA TCACCCACTG GGGTGATAAG ACAATAGATA    60

TT TCCAAAAAGC ATAAAACCAA AGTATCATAC CAAACCAAAT TCATACTGCT   120

CC GCACTGAAAC TTCACCTTCT AACTGTCTAC CTAACCAAAT TCTACCCTTC   180

GG TGCGTGCTCA CTACTCTTTT TTTTTTTTT TTTNTTTTGG AGATGGAGTC    240

CA GCCCAGGGGT GGAGTACAAT GGCACAACCT CAGCTCACTG NAACCTCCGC   300

TT CATGAGATTC TCCTGNTTCA GCCTTCCCAG TAGCTGGGAC TACAGGTGTG   360

TG CCTGGNTAAT CTTTTTTNGT TTTNGGGTAG AGATGGGGGT TTTACATGTT   420

TG GTNTCGAACT CCTGACCTCA AGTGATCCAC CCACCTCAGG CTCCCAAAGT   480

TA CAGACATGAG CCACTGNGCC CAGNCCTGGT GCATGCTCAC TTCTCTAGGC   540
```

*Fig. 11*

NUCLEOTIDE SEQUENCE OF THE REPRESENTATIVE
BREAST-TUMOR SPECIFIC cDNA B11Ag1

```
TG CACATGCAGA ATATTCTATC GGTACTTCAG CTATTACTCA TTTTGATGGC    60

AG CCTATCCTCA AGATGAGTAT TTAGAAAGAA TTGATTTAGC GATAGACCAA   120

GC ACTCTGACTA CACGAAATTG TTCAGATGTG ATGGATTTAT GACAGTTGAT   180

GA GATTATTAAG TGATTATTTT AAAGGGAATC CATTAATTCC AGAATATCTT   240

TC AAGATGATAT AGAAATAGAA CAGAAAGAGA CTACAAATGA AGATGTATCA   300

TA TTGAAGAGCC TATAGTAGAA AATGAATTAG CTGCATTTAT TAGCCTTACA   360

TT TTCCTGATGA ATCTTATATT CAGCCATCGA CATAGCATTA CCTGATGGGC   420

GA ATAATAGAAA CTGGGTGCGG GGCTATTGAT GAATTCATCC NCAGTAAATT   480

AC AAAATATAAC TCGATTGCAT TTGGATGATG GAATACTAAA TCTGGCAAAA   540

GG AGCTACTAGT AACCTCTCTT TTTGAGATGC AAAATTTTCT TTAGGGTTT    600

CT ACTTTACGGA TATTGGAGCA TAACGGGA                           638
```

*Fig. 12*

NUCLEOTIDE SEQUENCE OF THE REPRESENTATIVE
BREAST-TUMOR SPECIFIC cDNA B3CA3c

| | | | | | |
|---|---|---|---|---|---|
| ACTGATGGAT | GTCGCCGGAG | GCGAGGGGCC | TTATCTGATG | CTCGGCTGCC | TGTTCGTGAT | 60 |
| GTGCGCGGCG | ATTGGGCTGT | TTATCTCAAA | CACCGCCACG | GCGGTGCTGA | TGGCGCCTAT | 120 |
| TGCCTTAGCG | GCGGCGAAGT | CAATGGGCGT | CTCACCCTAT | CCTTTTGCCA | TGGTGGTGGC | 180 |
| GATGGCGGCT | TCGGCGGCGT | TTATGACCCC | GGTCTCCTCG | CCGGTTAACA | CCCTGGTGCT | 240 |
| TGGCCCTGGC | AAGTACTCAT | TTAGCGATTT | TGTCAAAATA | GGCGTG | | 286 |

*Fig. 13*

NUCLEOTIDE SEQUENCE OF THE REPRESENTATIVE
BREAST-TUMOR SPECIFIC cDNA B9CG1

AG CAGCCCCTTC TTCTCAATTT CATCTGTCAC TACCCTGGTG TAGTATCTCA    60

CA TTTTTATAGC CTCCTCCCTG GTCTGTCTTT TGATTTTCCT GCCTGTAATC   120

AC ATAACTGCAA GTAAACATTT CTAAAGTGTG GTTATGCTCA TGTCACTCCT   180

AA ATAGTTTCCA TTACCGTCTT AATAAAATTC GGATTTGTTC TTTNCTATTN   240

CA CCTATGACCG AA                                            262

*Fig. 14*

NUCLEOTIDE SEQUENCE OF THE REPRESENTATIVE
BREAST-TUMOR SPECIFIC cDNA B9CG3

```
AG CAAAGCCAGT GGTTTGAGCT CTCTACTGTG TAAACTCCTA AACCAAGGCC    60

TA AATGGTGGCA GGATTTTTAT TATAAACATG TACCCATGCA AATTTCCTAT   120

GA TATATTCTTC TACATTTAAA CAATAAAAAT AATCTATTTT TAAAAGCCTA   180

AG TTAGGTAAGA GTGTTTAATG AGAGGGTATA AGGTATAAAT CACCAGTCAA   240

TG CCTATGACCG A                                             261
```

Fig. 15

NUCLEOTIDE SEQUENCE OF THE REPRESENTATIVE
BREAST-TUMOR SPECIFIC cDNA B2CA2

```
CGACGTCGGT AAAATCGGAC ATGAAGCCAC CGCTGGTCTT TTCGTCCGAG CGATAGGCGC    60

CGGCCAGCCA GCGGAACGGT TGCCCGGATG GCGAAGCGAG CCGGAGTTCT TCGGACTGAG   120

TATGAATCTT GTTGTGAAAA TACTCGCCGC CTTCGTTCGA CGACGTCGCG TCGAAATCTT   180

AATCATGGTT GAGCCGGATG CTGCCCCGA AGCCCT                             276
```

Fig. 16

NUCLEOTIDE SEQUENCE OF THE REPRESENTATIVE
BREAST-TUMOR SPECIFIC cDNA B3CA1

| | |
|---|---|
| CCCAGGTCAA CCAGGCTGCA ACACGCAGGT CCTTGGATTG GGCACGAAGC AGCGCTTCGC | 60 |
| TGTTTTCCAG GATTTTCAAC CAGTCGGTCT GGCCGTTCTC ATGGAGCGAG AGCGCCTTGC | 120 |
| CCAGCTCATT TTCCAGCGCC TCGTATTCGC TGGAAAAACG CACATCCTCA CCCGCAAAGA | 180 |
| CATCCTTTGA AATCGGCTGT TCCGCGAGTT CCAGATANTG CGAGGAGAGC TTGCTCGAAT | 240 |
| AGGTCATCCT AACCCTTCAA TGCACACCAT GTGCGCCAAT GAATATCTTA ACAATTCAAC | 300 |
| TAGTTGGCAT AANAACCGAA CGAAAATCCC AATAGTCTGA AGAGCTCTTT TG | 352 |

Fig. 17

NUCLEOTIDE SEQUENCE OF THE REPRESENTATIVE
BREAST-TUMOR SPECIFIC cDNA B3CA2

| | |
|---|---|
| CTGCATGTCC ACGGCCTGGA TTTACGGGTG GTCGGCGTTC ACCCCTGGCA GCTGGCGGCTC | 60 |
| TTCCCGACCA GGCCCAGCAG GATGTGTGGG GCAAGGATAA CGGCGTGCGC ATCGCCTCGA | 120 |
| CCTATATGCC TACTGGCAAG GCCGAGCCCG TGGAAGGCGG ATTCAGGTTC ANCGGTCGCT | 180 |
| GGAGCTTTTC CACCGGCTCC ATGCATTGTG ACTGGCTGTT TCTAGGCGGT CTGTTGCCCA | 240 |
| AGCGTGATGG TACGTCTGGC CTGGAGCATG TGACTTTCTG | 280 |

Fig. 18

NUCLEOTIDE SEQUENCE OF THE REPRESENTATIVE
BREAST-TUMOR SPECIFIC cDNA B3CA3

| | | | | | |
|---|---|---|---|---|---|
| AG | GGAGCAAGGA | GAAGGCATGG | AGAGGCTCAN | GCTGGTCCTG | GCCTACGACT | 60 |
| CT | GTCGCCGGGG | ATGGTGGAGA | ACTGAAGCGG | GACCTCCTCG | AGGTCCTCCG | 120 |
| TC | NCCGTCCAGG | AGGAGGGTCT | TTCCGTGGTC | TNGGAGGAGC | GGGGGGAGAA | 180 |
| TC | ATGGTCNACA | TCCC | | | | 204 |

*Fig. 19*

NUCLEOTIDE SEQUENCE OF THE REPRESENTATIVE
BREAST-TUMOR SPECIFIC cDNA B4CA1

| | | | | | |
|---|---|---|---|---|---|
| TC | AGGAGCGGGT | AGAGTGGCAC | CATTGAGGGG | ATATTCAAAA | ATATTATTTT | 60 |
| TG | ATAGTTGCTG | AGTTTTTCTT | TGACCCATGA | GTTATATTGG | AGTTTATTTT | 120 |
| CC | AATCGCATGG | ACATGTTAGA | CTTATTTTCT | GTTAATGATT | NCTATTTTA | 180 |
| GA | TTTGAGAAAT | TGGTTNTTAT | TATATCAATT | TTTGGTATTT | GTTGAGTTTG | 240 |
| GC | TTAGTATGTG | ACCA | | | | 264 |

*Fig. 20*

COMPOSITIONS AND METHODS FOR THE TREATMENT AND DIAGNOSIS OF BREAST CANCER

CROSS REFERENCE TO RELATED APPLICATIONS

This application is a continuation in part of U.S. patent application Ser. No. 08/991,789, filed Dec. 11, 1997, which is a continuation-in-part of U.S. patent application Ser. No. 08/838,762, filed Apr. 9, 1997, now abandoned which claims priority from International Patent Application No. PCT/US97/00485, filed Jan. 10, 1997, and is a continuation-in-part of U.S. patent application Ser. No. 08/700,014, filed Aug. 20, 1996, now abandoned which is a continuation-in-part of U.S. patent application Ser. No. 08/585,392, filed Jan. 1, 1996 now abandoned.

TECHNICAL FIELD

The present invention relates generally to the detection and therapy of breast cancer. The invention is more specifically related to nucleotide sequences that are preferentially expressed in breast tumor tissue and to polypeptides encoded by such nucleotide sequences. The nucleotide sequences and polypeptides may be used in vaccines and pharmaceutical compositions for the prevention and treatment of breast cancer. The polypeptides may also be used for the production of compounds, such as antibodies, useful for diagnosing and monitoring the progression of breast cancer in a patient.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the subject invention provides compositions and methods for the diagnosis and therapy of breast cancer. In one aspect, isolated DNA molecules are provided, comprising (a) a nucleotide sequence preferentially expressed in breast cancer tissue, relative to normal tissue; (b) a variant of such a sequence that contains one or more nucleotide substitutions, deletions, insertions and/or modifications at no more than 20% (preferably no more than 5%) of the nucleotide positions, such that the antigenic and/or immunogenic properties of the polypeptide encoded by the nucleotide sequence are retained; or (c) a nucleotide sequence encoding an epitope of a polypeptide encoded by at least one of the above sequences. In one embodiment, the isolated DNA molecule comprises a human endogenous retroviral sequence recited in SEQ ID NO:1. In other embodiments, the isolated DNA molecule comprises a nucleotide sequence recited in any one of SEQ ID NO: 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291–297.

In related embodiments, the isolated DNA molecule encodes an epitope of a polypeptide, wherein the polypeptide is encoded by a nucleotide sequence that: (a) hybridizes to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291–297 under stringent conditions; and (b) is at least 80% identical to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291–297; and wherein RNA corresponding to said nucleotide sequence is expressed at a greater level in human breast tumor tissue than in normal breast tissue.

In another embodiment, the present invention provides an isolated DNA molecule encoding an epitope of a polypeptide, the polypeptide being encoded by: (a) a nucleotide sequence transcribed from the sequence of SEQ ID NO: 141; or (b) a variant of said nucleotide sequence that contains one or more nucleotide substitutions, deletions, insertions and/or modifications at no more than 20% of the nucleotide positions, such that the antigenic and/or immunogenic properties of the polypeptide encoded by the nucleotide sequence are retained. Isolated DNA and RNA molecules comprising a nucleotide sequence complementary to a DNA molecule as described above are also provided.

In related aspects, the present invention provides recombinant expression vectors comprising a DNA molecule as described above and host cells transformed or transfected with such expression vectors.

In further aspects, polypeptides, comprising an amino acid sequence encoded by a DNA molecule as described above, and monoclonal antibodies that bind to such polypeptides are provided.

In yet another aspect, methods are provided for determining the presence of breast cancer in a patient. In one embodiment, the method comprises detecting, within a biological sample, a polypeptide as described above. In another embodiment, the method comprises detecting, within a biological sample, an RNA molecule encoding a polypeptide as described above. In yet another embodiment, the method comprises (a) intradermally injecting a patient with a polypeptide as described above; and (b) detecting an immune response on the patient's skin and therefrom detecting the presence of breast cancer in the patient. In further embodiments, the present invention provides methods for determining the presence of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In a related aspect, diagnostic kits useful in the determination of breast cancer are provided. The diagnostic kits generally comprise either one or more monoclonal antibodies as described above, or one or more monoclonal antibodies that bind to a polypeptide encoded by a nucleotide sequence selected from the group consisting of sequences provided in SEQ ID NO: 78–86, 144, 145, 153, 167, 177, 193, 199, 205, 208, 215, 217, 220, 241, 242 and 246, 248, 249, 252, 256, 267, 270, 274, 277, 20 279, 282, 283, 285–287, 289, 290 and a detection reagent.

Within a related aspect, the diagnostic kit comprises a first polymerase chain reaction primer and a second polymerase chain reaction primer, at least one of the primers being specific for an RNA molecule described herein. In one embodiment, at least one of the primers comprises at least about 10 contiguous nucleotides of an RNA molecule as described above, or an RNA molecule encoding a polypeptide encoded by a nucleotide sequence selected from the group consisting of SEQ ID NO: 78–86, 144, 145, 153, 167, 177, 193, 199, 205, 208, 215, 217, 220, 241, 242 246, 248, 249, 252, 256, 267, 270, 274, 277, 279, 282, 283, 285–287, 289 and 290.

Within another related aspect, the diagnostic kit comprises at least one oligonucleotide probe, the probe being specific for a DNA molecule described herein. In one embodiment, the probe comprises at least about 15 contiguous nucleotides of a DNA molecule as described above, or a DNA molecule selected from the group consisting of SEQ ID NO: 78–86, 144, 145, 153, 167, 177, 193, 199, 205, 208, 215, 217, 220, 241, 242 246, 248, 249, 252, 256, 267, 270, 274, 277, 279, 282, 283, 285–287, 289 and 290.

In another related aspect, the present invention provides methods for monitoring the progression of breast cancer in a patient. In one embodiment, the method comprises: (a) detecting an amount, in a biological sample, of a polypeptide as described above at a first point in time; (b) repeating step (a) at a subsequent point in time; and (c) comparing the amounts of polypeptide detected in steps (a) and (b), and therefrom monitoring the progression of breast cancer in the patient. In another embodiment, the method comprises (a) detecting an amount, within a biological sample, of an RNA molecule encoding a polypeptide as described above at a first point in time; (b) repeating step (a) at a subsequent point in time; and (c) comparing the amounts of RNA molecules detected in steps (a) and (b), and therefrom monitoring the progression of breast cancer in the patient. In yet other embodiments, the present invention provides methods for monitoring the progression of breast cancer in a patient as described above wherein the polypeptide is encoded by a nucleotide sequence selected form the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In still other aspects, pharmaceutical compositions, which comprise a polypeptide as described above in combination with a physiologically acceptable carrier, and vaccines, which comprise a polypeptide as described above in combination with an immune response enhancer or adjuvant, are provided. In yet other aspects, the present invention provides pharmaceutical compositions and vaccines comprising a polypeptide encoded by a nucleotide sequence selected from the group consisting of SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and sequences that hybridize thereto under stringent conditions.

In related aspects, the present invention provides methods for inhibiting the development of breast cancer in a patient, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6 shows the nucleotide sequence of the representative breast tumor-specific cDNA B18Ag1 (SEQ ID NO:1).

FIG. 7 shows the nucleotide sequence of the representative breast tumor-specific cDNA B17Ag1 (SEQ ID NO:11).

FIG. 8 shows the nucleotide sequence of the representative breast tumor-specific cDNA B17Ag2 (SEQ ID NO:12).

FIG. 9 shows the nucleotide sequence of the representative breast tumor-specific cDNA B13Ag2a (SEQ ID NO:13).

FIG. 10 shows the nucleotide sequence of the representative breast tumor-specific cDNA B13Ag1b (SEQ ID NO:14).

FIG. 11 shows the nucleotide sequence of the representative breast tumor-specific cDNA B13Ag1a (SEQ ID NO:15).

FIG. 12 shows the nucleotide sequence of the representative breast tumor-specific cDNA B11Ag1 (SEQ ID NO:16).

FIG. 13 shows the nucleotide sequence of the representative breast tumor-specific cDNA B3CA3c (SEQ ID NO:17).

FIG. 14 shows the nucleotide sequence of the representative breast tumor-specific cDNA B9CG1 (SEQ ID NO:18).

FIG. 15 shows the nucleotide sequence of the representative breast tumor-specific cDNA B9CG3 (SEQ ID NO:19).

FIG. 16 shows the nucleotide sequence of the representative breast tumor-specific cDNA B2CA2 (SEQ ID NO:20).

FIG. 17 shows the nucleotide sequence of the representative breast tumor-specific cDNA B3CA1 (SEQ ID NO:21).

FIG. 18 shows the nucleotide sequence of the representative breast tumor-specific cDNA B3CA2 (SEQ ID NO:22).

FIG. 19 shows the nucleotide sequence of the representative breast tumor-specific cDNA B3CA3 (SEQ ID NO:23).

FIG. 20 shows the nucleotide sequence of the representative breast tumor-specific cDNA B4CA1 (SEQ ID NO:24).

DETAILED DESCRIPTION OF THE INVENTION

Figure 1:
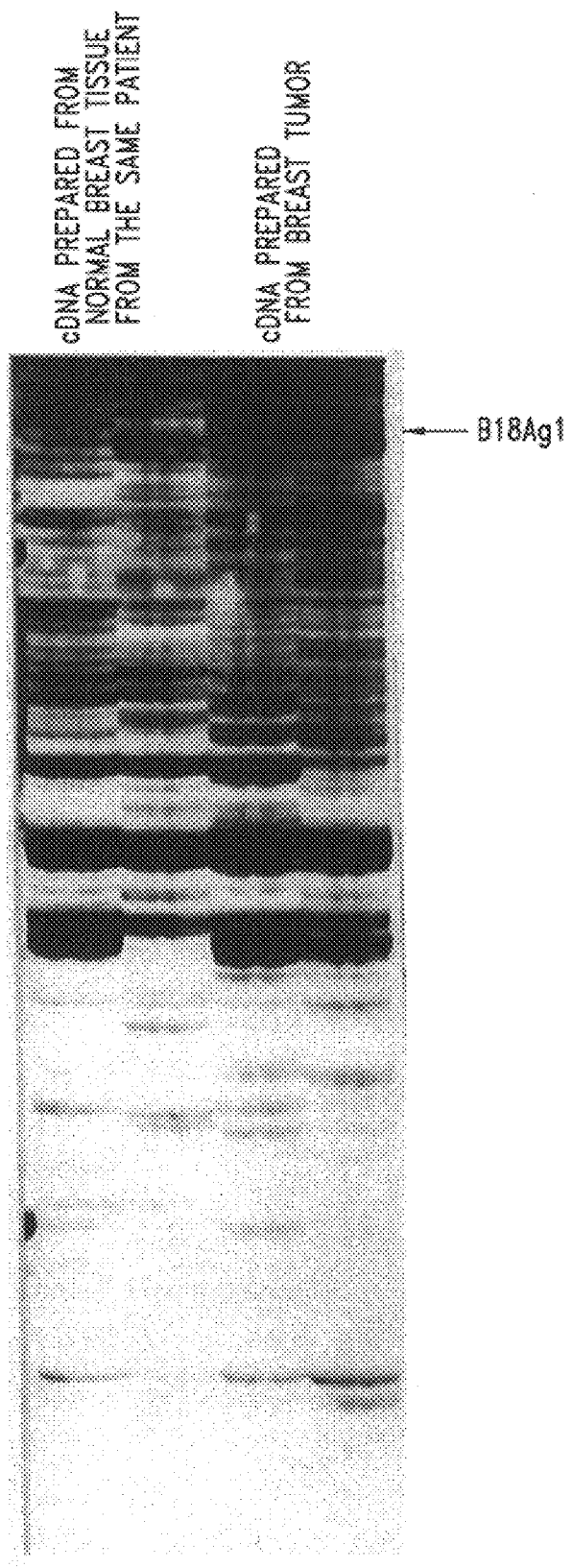
FIG. 1 shows the differential display PCR products, separated by gel electrophoresis, obtained from cDNA prepared from normal breast tissue(lanes 1 and 2) and from cDNA prepared from breast tumor tissue from the same patient (lanes 3 and 4). The arrow indicates the band corresponding to B18Ag1.

As noted above, the present invention is generally directed to compositions and methods for the diagnosis, monitoring and therapy of breast cancer. The compositions described herein include polypeptides, nucleic acid sequences and antibodies. Polypeptides of the present invention generally comprise at least a portion of a protein that is expressed at a greater level in human breast tumor tissue than in normal breast tissue (i.e., the level of RNA encoding the polypeptide is at least 2-fold higher in tumor tissue). Such polypeptides are referred to herein as breast tumor-specific polypeptides, and cDNA molecules encoding such polypeptides are referred to as breast tumor-specific cDNAs. Nucleic acid sequences of the subject invention generally comprise a DNA or RNA sequence that encodes all or a portion of a polypeptide as described above, or that is complementary to such a sequence. Antibodies are generally immune system proteins, or fragments thereof, that are capable of binding to a portion of a polypeptide as described above. Antibodies can be produced by cell culture techniques, including the generation of monoclonal antibodies as described herein, or via transfection of antibody genes into suitable bacterial or mammalian cell hosts, in order to allow for the production of recombinant antibodies.

Polypeptides within the scope of this invention include, but are not limited to, polypeptides (and epitopes thereof) encoded by a human endogenous retroviral sequence, such as the sequence designated B18Ag1 (FIG. 5 and SEQ ID NO:1). Also within the scope of the present invention are polypeptides encoded by other sequences within the retroviral genome containing B18Ag1 (SEQ ID NO: 141). Such sequences include, but are not limited to, the sequences recited in SEQ ID NO:3–SEQ ID NO:10. B18Ag1 has homology to the gag p30 gene of the endogenous human retroviral element S71, as described in Werner et al., Virology 174:225–238 (1990) and also shows homology to about thirty other retroviral gag genes. As discussed in more detail below, the present invention also includes a number of additional breast tumor-specific polypeptides, such as those encoded by the nucleotide sequences recited in SEQ ID NO: 11–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291–297. As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

An "epitope," as used herein is a portion of a polypeptide that is recognized (i.e., specifically bound) by a B-cell and/or T-cell surface antigen receptor. Epitopes may generally be identified using well known techniques, such as those summarized in Paul, Fundamental Immunology, 3rd ed., 243–247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

The compositions and methods of the present invention also encompass variants of the above polypeptides and nucleic acid sequences encoding such polypeptides. A polypeptide "variant," as used herein, is a polypeptide that differs from the native polypeptide in substitutions and/or modifications, such that the antigenic and/or immunogenic properties of the polypeptide are retained. Such variants may generally be identified by modifying one of the above polypeptide sequences and evaluating the reactivity of the modified polypeptide with antisera and/or T-cells as described above. Nucleic acid variants may contain one or more substitutions, deletions, insertions and/or modifications such that the antigenic and/or immunogenic properties of the encoded polypeptide are retained. One preferred variant of the polypeptides described herein is a variant that contains nucleotide substitutions, deletions, insertions and/ or modifications at no more than 20% of the nucleotide positions.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) vat, ile, leu, met, ala, phe; (4) lys, arg, his; and (5) phe, tyr, trp, his.

Variants may also (or alternatively) be modified by, for example, the deletion or addition of amino acids that have minimal influence on the immunogenic or antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, nucleotide sequences encoding all or a portion of the polypeptides described herein may be prepared using any of several techniques. For example, cDNA molecules encoding such polypeptides may be cloned on the basis of the breast tumor-specific expression of the corresponding mRNAs, using differential display PCR. This technique compares the amplified products from RNA template prepared from normal and breast tumor tissue. cDNA may be prepared by reverse transcription of RNA using a $(dT)_{12}AG$ primer. Following amplification of the cDNA using a random primer, a band corresponding to an amplified product specific to the tumor RNA may be cut out from a silver stained gel and subcloned into a suitable vector (e.g., the T-vector, Novagen, Madison, Wis.). Nucleotide sequences encoding all or a portion of the breast tumor-specific polypeptides disclosed herein may be amplified from cDNA prepared as described above using the random primers shown in SEQ ID NO.:87–125.

Alternatively, a gene encoding a polypeptide as described herein (or a portion thereof) may be amplified from human genomic DNA, or from breast tumor cDNA, via polymerase chain reaction. For this approach, B18Ag1 sequence-specific primers may be designed based on the sequence provided in SEQ ID NO:1, and may be purchased or synthesized. One suitable primer pair for amplification from breast tumor cDNA is (5'ATG GCT ATT TTC GGG GGC TGA CA) (SEQ ID NO.:126) and (5'CCG GTA TCT CCT CGT GGG TAT T) (SEQ ID NO.:127). An amplified portion of B18Ag1 may then be used to isolate the full length gene from a human genomic DNA library or from a breast tumor cDNA library, using well known techniques, such as those described in Sambrook et al., *Molecular Cloning: A Laboratory Manual*, Cold Spring Harbor Laboratories, Cold Spring Harbor, N.Y. (1989). Other sequences within the retroviral genome of which B18Ag1 is a part may be similarly prepared by screening human genomic libraries using B18Ag1-specific sequences as probes. Nucleotides translated into protein from the retroviral genome shown in SEQ ID NO: 141 may then be determined by cloning the corresponding cDNAs, predicting the open reading frames and cloning the appropriate cDNAs into a vector containing a viral promoter, such as T7. The resulting constructs can be employed in a translation reaction, using techniques known to those of skill in the art, to identify nucleotide sequences which result in expressed protein. Similarly, primers specific for the remaining breast tumor-specific polypeptides described herein may be designed based on the nucleotide sequences provided in SEQ ID NO:11–SEQ ID NO:86 and SEQ ID NO:142–SEQ ID NO:297.

Recombinant polypeptides encoded by the DNA sequences described above may be readily prepared from the DNA sequences. For example, supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

In general, any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO.

Such techniques may also be used to prepare polypeptides comprising epitopes or variants of the native polypeptides. For example, variants of a native polypeptide may generally be prepared using standard mutagenesis techniques, such as oligonucleotide-directed site-specific mutagenesis, and sections of the DNA sequence may be removed to permit preparation of truncated polypeptides. Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146 (1963). Equipment for automated synthesis of polypeptides is commercially available from suppliers such as Perkin Elmer/Applied BioSystems Division,, Foster City, Calif., and may be operated according to the manufacturer's instructions.

In specific embodiments, polypeptides of the present invention encompass amino acid sequences encoded by a DNA molecule having a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291–297, variants of such polypeptides that are encoded by DNA molecules containing one or more nucleotide substitutions, deletions, insertions and/or modifications at no more than 20% of the nucleotide positions, and epitopes of the above polypeptides. Polypeptides within the scope of the present invention also include polypeptides (and epitopes thereof) encoded by DNA sequences that hybridize to a DNA molecule having a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291–297 under stringent conditions, wherein the DNA sequences are at least 80% identical in overall sequence to a recited sequence and wherein RNA corresponding to the nucleotide sequence is expressed at a greater level in human breast tumor tissue than in normal breast tissue. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. DNA molecules according to the present invention include molecules that encode any of the above polypeptides.

In another aspect of the present invention, antibodies are provided. Such antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519 (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used, for example, in methods for detecting breast cancer in a patient. Such methods involve using an antibody to detect the presence or absence of a breast tumor-specific polypeptide as described herein in a suitable biological sample. As used herein, suitable biological samples include tumor or normal tissue biopsy, mastectomy, blood, lymph node, serum or urine samples, or other tissue, homogenate, or extract thereof obtained from a patient.

There are a variety of assay formats known to those of ordinary skill in the art for using an antibody to detect polypeptide markers in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the polypeptide and remove it from the remainder of the sample. The bound polypeptide may then be detected using a second antibody or reagent that contains a reporter group. Alternatively, a competitive assay may be utilized, in which a polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the concentration of polypeptide in the sample.

The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of antibody ranging from about 10 ng to about 1 $\mu$g, and preferably about 100–200 ng, is sufficient to immobilize an adequate amount of polypeptide.

Covalent attachment of antibody to a solid support may also generally be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

In certain embodiments, the assay for detection of polypeptide in a sample is a two-antibody sandwich assay. This assay may be performed by first contacting an antibody that has been immobilized on a solid support, commonly the well of a microtiter plate, with the biological sample, such that the polypeptide within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then. determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value established from non-tumor tissue. In one preferred embodiment, the cut-off value is the average mean signal obtained when the immobilized antibody is incubated with samples from patients without breast cancer. In general, a sample generating a signal that is three standard deviations above the predetermined cut-off value may be considered positive for breast cancer. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, the polypeptide within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 1 $\mu$g. Such tests can typically be performed with a very small amount of biological sample.

The presence or absence of breast cancer in a patient may also be determined by evaluating the level of mRNA encoding a breast tumor-specific polypeptide as described herein within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction.

For example, polymerase chain reaction may be used to amplify sequences from cDNA prepared from RNA that is isolated from one of the above biological samples. Sequence-specific primers for use in such amplification may be designed based on the sequences provided in any one of SEQ ID NO: 1, 11–86 and 142–297, and may be purchased or synthesized. In the case of B18Ag1, as noted herein, one suitable primer pair is B18Ag1-2 (5'ATG GCT ATT TTC GGG GGC TGA CA) (SEQ ID NO.:126) and B18Ag1-3 (5'CCG GTA TCT CCT CGT GGG TAT T) (SEQ ID NO.:127). The PCR reaction products may then be separated by gel electrophoresis and visualized according to methods well known to those of ordinary skill in the art. Amplification is typically performed on samples obtained from matched pairs of tissue (tumor and non-tumor tissue from the same individual) or from unmatched pairs of tissue (tumor and non-tumor tissue from different individuals). The amplification reaction is preferably performed on several dilutions of cDNA spanning two orders of magnitude. A two-fold or greater increase in expression in several dilutions of the tumor sample as compared to the same dilution of the non-tumor sample is considered positive.

As used herein, the term "primer/probe specific for a DNA/RNA molecule" means an oligonucleotide sequence that has at least about 80% identity, preferably at least about 90% and more preferably at least about 95%, identity to the DNA/RNA molecule in question. Primers and/or probes which may be usefully employed in the inventive diagnostic methods preferably have at least about 10–40 nucleotides. In a preferred embodiment, the polymerase chain reaction primers comprise at least about 10 contiguous nucleotides of a DNA/RNA molecule encoding one of the polypeptides disclosed herein. Preferably, oligonucleotide probes for use in the inventive diagnostic methods comprise at least about 15 contiguous oligonucleotides of a DNA/RNA molecule encoding one of the polypeptides disclosed herein. Techniques for both PCR based assays and in situ hybridization assays are well known in the art.

Conventional RT-PCR protocols using agarose and ethidium bromide staining while important in defining gene specificity do not lend themselves to diagnostic kit development because of the time and effort required in making them quantitative (i.e., construction of saturation and/or titration curves), and their sample throughput. This problem is overcome by the development of procedures such as real time RT-PCR which allows for assays to be performed in single tubes, and in turn can be modified for use in 96 well plate formats. Instrumentation to perform such methodologies are available from Perkin Elmer/Applied Biosystems Division. Alternatively, other high throughput assays using labeled probes (e.g., digoxygenin) in combination with labeled (e.g., enzyme fluorescent, radioactive) antibodies to such probes can also be used in the development of 96 well plate assays.

In yet another method for determining the presence or absence of breast cancer in a patient, one or more of the breast tumor-specific polypeptides described may be used in a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, a response that is greater than about 0.5 cm in diameter, preferably greater than about 5.0 cm in diameter, is a positive response, indicative of breast cancer.

The breast tumor-specific polypeptides described herein are preferably formulated, for use in a skin test, as pharmaceutical compositions containing at least one polypeptide and a physiologically acceptable carrier, such as water, saline, alcohol, or a buffer. Such compositions typically contain one or more of the above polypeptides in an amount ranging from about 1 μg to 100 μg, preferably from about 10 μg to 50 μg in a volume of 0.1 mL. Preferably, the carrier employed in such pharmaceutical compositions is a saline solution with appropriate preservatives, such as phenol and/or Tween 80™.

In other aspects of the present invention, the progression and/or response to treatment of a breast cancer may be monitored by performing any of the above assays over a period of time, and evaluating the change in the level of the response (i.e., the amount of polypeptide or mRNA detected or, in the case of a skin test, the extent of the immune response detected). For example, the assays may be performed every month to every other month for a period of 1 to 2 years. In general, breast cancer is progressing in those patients in whom the level of the response increases over time. In contrast, breast cancer is not progressing when the signal detected either remains constant or decreases with time.

In further aspects of the present invention, the compounds described herein may be used for the immunotherapy of breast cancer. In these aspects, the compounds (which may be polypeptides, antibodies or nucleic acid molecules) are preferably incorporated into pharmaceutical compositions or vaccines. Pharmaceutical compositions comprise one or more such compounds and a physiologically acceptable carrier. Vaccines may comprise one or more polypeptides and an immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, including one or more separate polypeptides.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993), and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The above pharmaceutical compositions and vaccines may be used, for example, for the therapy of breast cancer in a patient. As used herein, a "patient" refers to any warm-blooded animal, preferably a human. A patient may or may not be afflicted with breast cancer. Accordingly, the above pharmaceutical compositions and vaccines may be used to prevent the development of breast cancer or to treat a patient afflicted with breast cancer. To prevent the development of breast cancer, a pharmaceutical composition or vaccine comprising one or more polypeptides as described herein may be administered to a patient. Alternatively, naked DNA or plasmid or viral vector encoding the polypeptide may be administered. For treating a patient with breast cancer, the pharmaceutical composition or vaccine may comprise one or more polypeptides, antibodies or nucleotide sequences complementary to DNA encoding a polypeptide as described herein (e.g., antisense RNA or antisense deoxyribonucleotide oligonucleotides).

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered for a 52-week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 µg to 5 mg. Suitable dose sizes will vary with the size of the patient, but will typically range from about 0.1 mL to about 5 mL.

The following Examples are offered by way of illustration and not by way of limitation.

EXAMPLES

Example 1

Preparation of Breast Tumor-specific cDNAs Using Differential Display RT-PCR

This Example illustrates the preparation of cDNA molecules encoding breast tumor-specific polypeptides using a differential display screen.

A. Preparation of B18Ag1 cDNA and Characterization of mRNA Expression

Tissue samples were prepared from breast tumor and normal tissue of a patient with breast cancer that was confirmed by pathology after removal from the patient. Normal RNA and tumor RNA was extracted from the samples and mRNA was isolated and converted into cDNA using a $(dT)_{12}AG$ (SEQ ID NO.:130) anchored 3' primer. Differential display PCR was then executed using a randomly chosen primer (CTTCAACCTC) (SEQ ID NO.:103). Amplification conditions were standard buffer containing 1.5 mM $MgCl_2$, 20 pmol of primer, 500 pmol dNTP, and 1 unit of Taq DNA polymerase (Perkin-Elmer, Branchburg, N.J.). Forty cycles of amplification were performed using 94° C. denaturation for 30 seconds, 42° C. annealing for 1 minute, and 72° C. extension for 30 seconds. An RNA fingerprint containing 76 amplified products was obtained. Although the RNA fingerprint of breast tumor tissue was over 98% identical to that of the normal breast tissue, a band was repeatedly observed to be specific to the RNA fingerprint pattern of the tumor. This band was cut out of a silver stained gel, subcloned into the T-vector (Novagen, Madison, Wis.) and sequenced.

The sequence of the cDNA, referred to as B18Ag1, is provided in SEQ ID NO:1. A database search of GENBANK and EMBL revealed that the B18Ag1 fragment initially cloned is 77% identical to the endogenous human retroviral element S71, which is a truncated retroviral element homologous to the Simian Sarcoma Virus (SSV). S71 contains an incomplete gag gene, a portion of the pol gene and an LTR-like structure at the 3' terminus (see Werner et al., *Virology* 174:225–238 (1990)). B18Ag1 is also 64% identical to SSV in the region corresponding to the P30 (gag) locus. B18Ag1 contains three separate and incomplete reading frames covering a region which shares considerable homology to a wide variety of gag proteins of retroviruses which infect mammals. In addition, the homology to S71 is not just within the gag gene, but spans several kb of sequence including an LTR.

Figure 2:
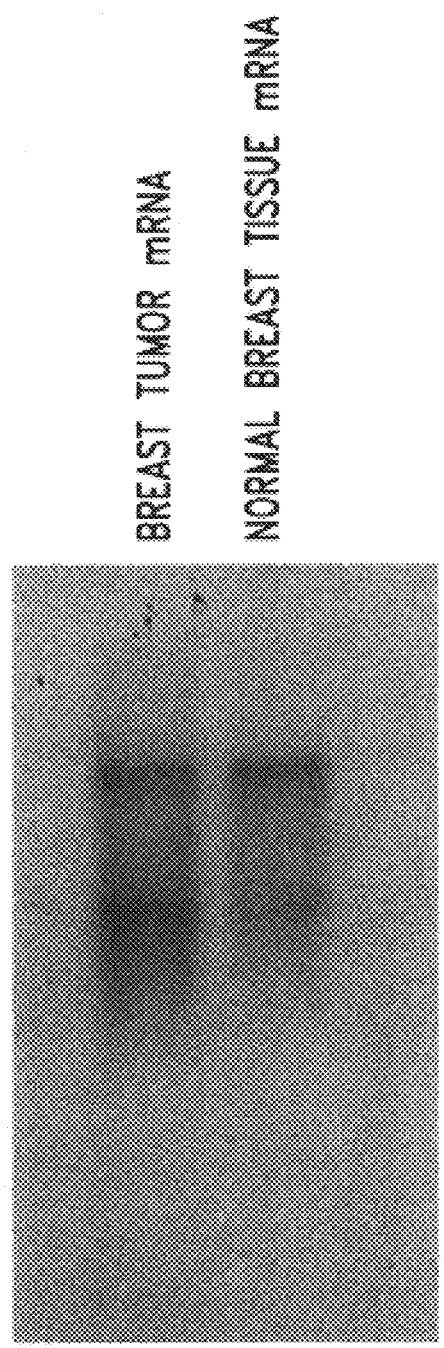
FIG. 2 is a northern blot comparing the level of B18Ag1 mRNA in breast tumor tissue (lane 1) with the level in normal breast tissue.

B18Ag1-specific PCR primers were synthesized using computer analysis guidelines. RT-PCR amplification (94° C., 30 seconds; 60° C.→42° C., 30 seconds; 72° C., 30 seconds for 40 cycles) confirmed that B18Ag1 represents an actual mRNA sequence present at relatively high levels in the patient's breast tumor tissue. The primers used in amplification were B18Ag1-1 (CTG CCT GAG CCA CAA ATG) (SEQ ID NO.:128) and B18Ag1-4 (CCG GAG GAG GAA GCT AGA GGA ATA) (SEQ ID NO.:129) at a 3.5 mM magnesium concentration and a pH of 8.5, and B18Ag1-2 (ATG GCT ATT TTC GGG GCC TGA CA) (SEQ ID NO.:126) and B18Ag1-3 (CCG GTA TCT CCT CGT GGG TAT T) (SEQ ID NO.:127) at 2 mM magnesium at pH 9.5. The same experiments showed exceedingly low to nonexistent levels of expression in this patient's normal breast tissue (see FIG. 1). RT-PCR experiments were then used to show that B18Ag1 mRNA is present in nine other breast tumor samples (from Brazilian and American patients) but absent in, or at exceedingly low levels in, the normal breast tissue corresponding to each cancer patient. RT-PCR analysis has also shown that the B18Ag1 transcript is not present in various normal tissues (including lymph node, myocardium and liver) and present at relatively low levels in PBMC and lung tissue. The presence of B18Ag1 mRNA in breast tumor samples, and its absence from normal breast tissue, has been confirmed by Northern blot analysis, as shown in FIG. 2.

Figure 3:
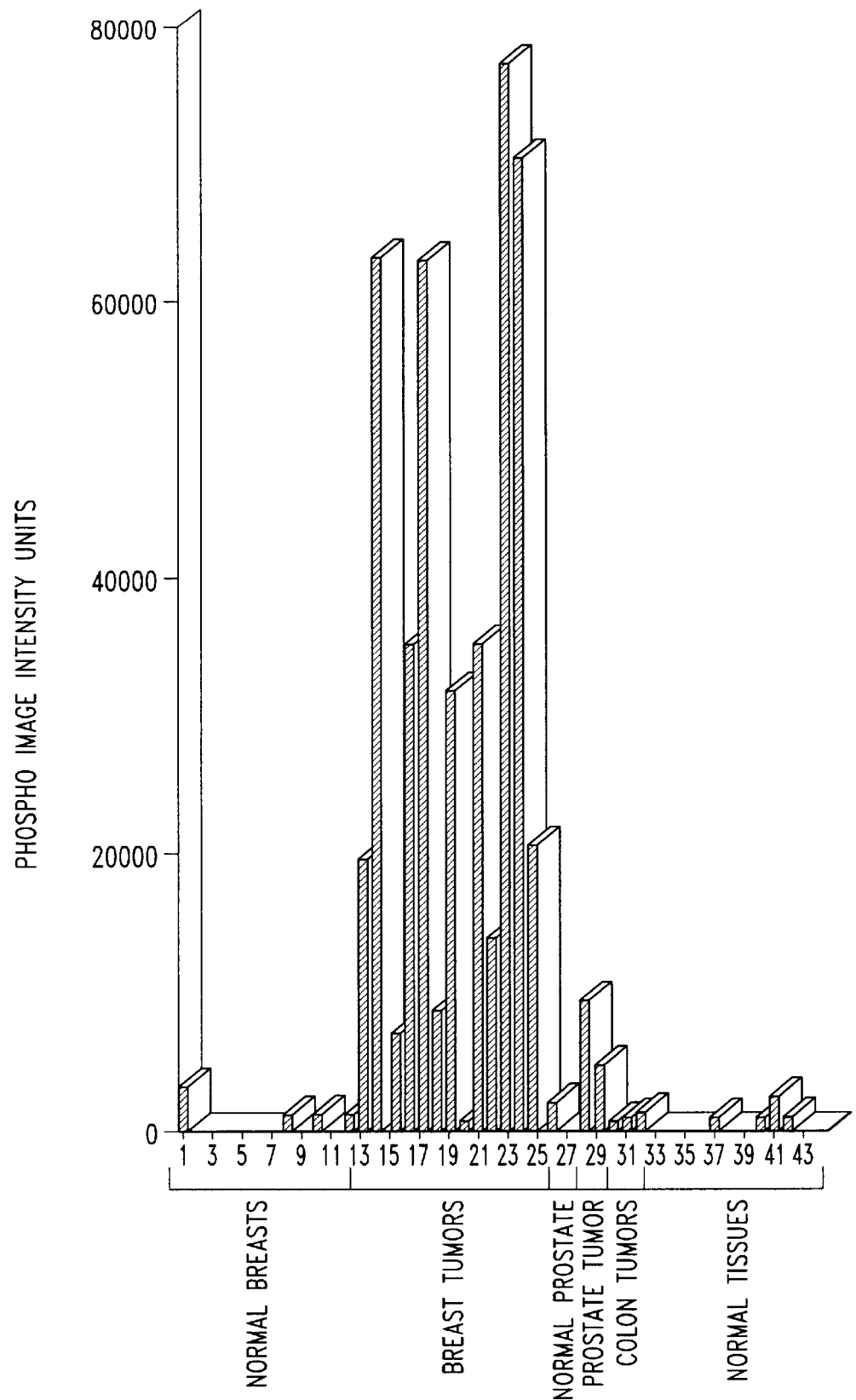
FIG. 3 shows the level of B18Ag1 mRNA in breast tumor tissue compared to that in various normal and non-breast tumor tissues as determined by RNase protection assays.

The differential expression of B18Ag1 in breast tumor tissue was also confirmed by RNase protection assays. FIG. 3 shows the level of B18Ag1 mRNA in various tissue types as determined in four different RNase protection assays. Lanes 1–12 represent various normal breast tissue samples, lanes 13–25 represent various breast tumor samples; lanes 26–27 represent normal prostate samples; lanes 28–29 represent prostate tumor samples; lanes 30–32 represent colon tumor samples; lane 33 represents normal aorta; lane 34 represents normal small intestine; lane 35 represents normal skin, lane 36 represents normal lymph node; lane 37 represents normal ovary; lane 38 represents normal liver; lane 39 represents normal skeletal muscle; lane 40 represents a first normal stomach sample, lane 41 represents a second normal stomach sample; lane 42 represents a normal lung; lane 43 represents normal kidney; and lane 44 represents normal pancreas. Interexperimental comparison was facilitated by including a positive control RNA of known β-actin message abundance in each assay and normalizing the results of the different assays with respect to this positive control.

Figure 4:
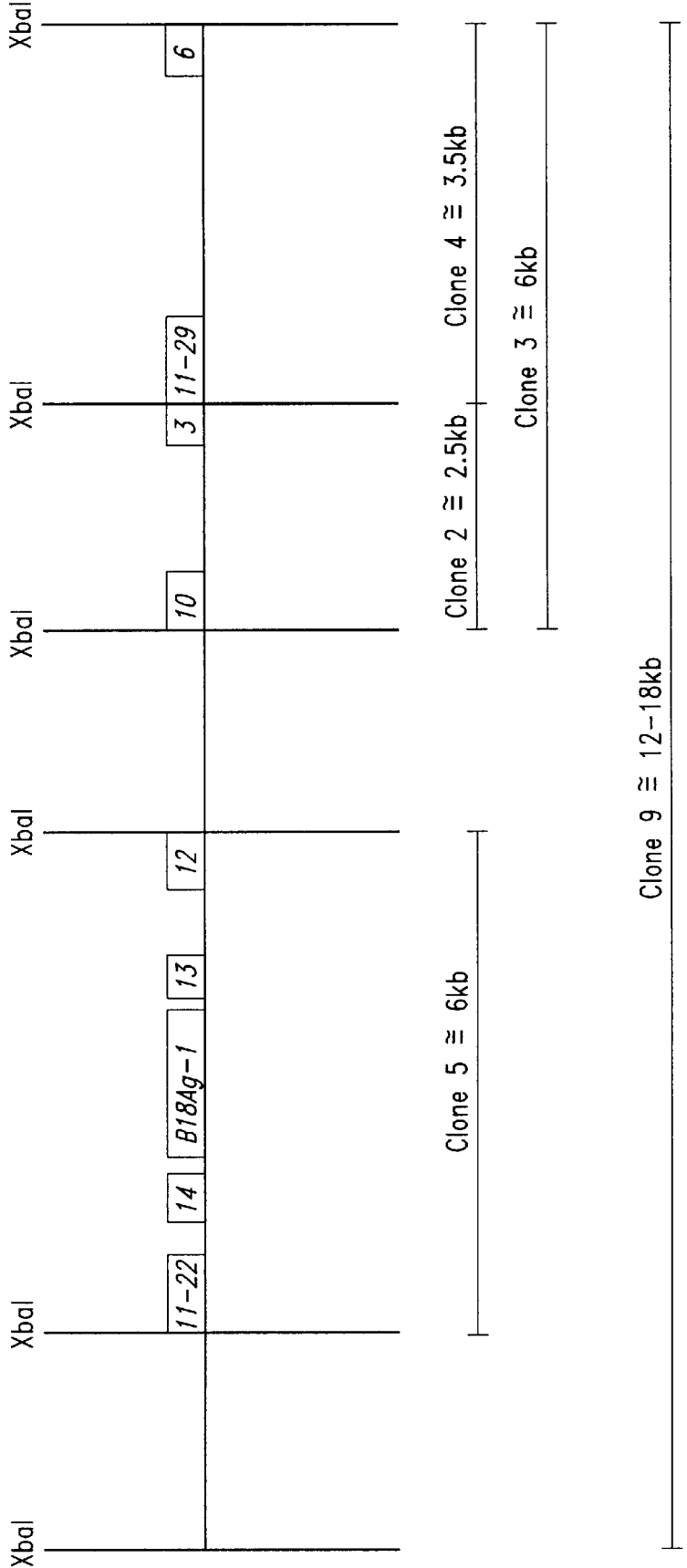
FIG. 4 is a genomic clone map showing the location of additional retroviral sequences obtained from ends of XbaI restriction digests (provided in SEQ ID NO:3–SEQ ID NO:10) relative to B18Ag1.

RT-PCR and Southern Blot analysis has shown the B18Ag1 locus to be present in human genomic DNA as a single copy endogenous retroviral element. A genomic clone of approximately 12–18 kb was isolated using the initial B18Ag1 sequence as a probe. Four additional subclones were also isolated by XbaI digestion. Additional retroviral sequences obtained from the ends of the XbaI digests of these clones (located as shown in FIG. 4) are shown as SEQ ID NO:3–SEQ ID NO:10, where SEQ ID NO:3 shows the location of the sequence labeled 10 in FIG. 4, SEQ ID NO:4 shows the location of the sequence labeled 11–29, SEQ ID NO:5 shows the location of the sequence labeled 3, SEQ ID NO:6 shows the location of the sequence labeled 6, SEQ ID NO:7 shows the location of the sequence labeled 12, SEQ ID NO:8 shows the location of the sequence labeled 13, SEQ ID NO:9 shows the location of the sequence labeled 14 and SEQ ID NO:10 shows the location of the sequence labeled 11–22.

Figures 5A, 5B:
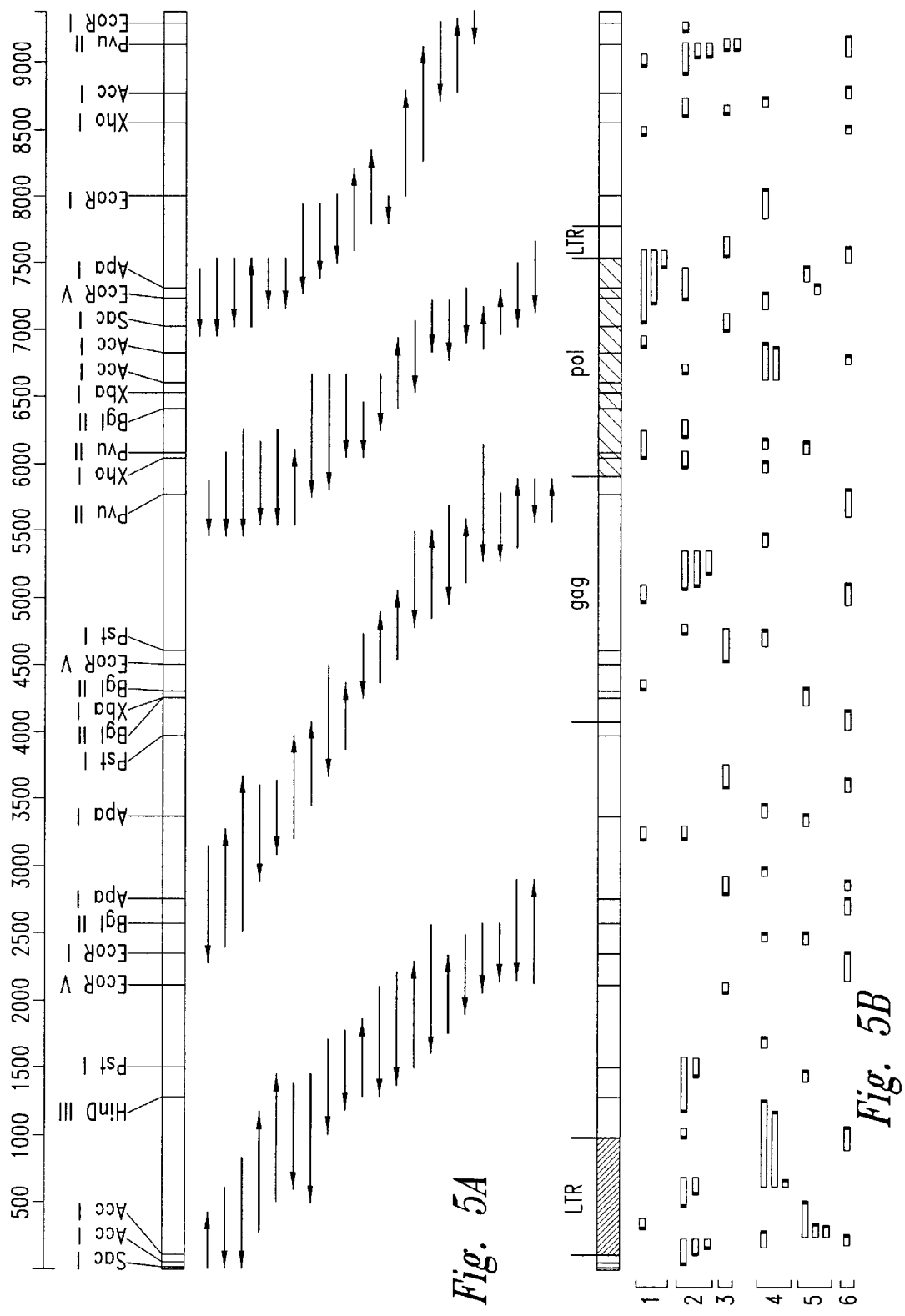
FIGS. 5A and 5B show the sequencing strategy, genomic organization and predicted open reading frame for the retroviral element containing B18Ag1.

Subsequent studies demonstrated that the 12–18 kb genomic clone contains a retroviral element of about 7.75 kb, as shown in FIGS. 5A and 5B. The sequence of this retroviral element is shown in SEQ ID NO: 141. The numbered line at the top of FIG. 5A represents the sense strand sequence of the retroviral genomic clone. The box below this line shows the position of selected restriction sites. The arrows depict the different overlapping clones used to sequence the retroviral element. The direction of the arrow shows whether the single-pass subclone sequence corresponded to the sense or anti-sense strand. FIG. 5B is a schematic diagram of the retroviral element containing B18Ag1 depicting the organization of viral genes within the element. The open boxes correspond to predicted reading frames, starting with a methionine, found throughout the element. Each of the six likely reading frames is shown, as indicated to the left of the boxes, with frames 1–3 corresponding to those found on the sense strand.

Using the cDNA of SEQ ID NO:1 as a probe, a longer cDNA was obtained (SEQ ID NO:227) which contains minor nucleotide differences (less than 1%) compared to the genomic sequence shown in SEQ ID NO:141.

B. Preparation of cDNA Molecules Encoding Other Breast Tumor-Specific Polypeptides Normal RNA and tumor RNA was prepared and mRNA was isolated and converted into cDNA using a $(dT)_{12}AG$ anchored 3' primer, as described above. Differential display PCR was then executed using the randomly chosen primers SEQ ID NO.:87–125. Amplification conditions were as noted above, and bands observed to be specific to the RNA fingerprint pattern of the tumor were cut out of a silver stained gel, subcloned into either the T-vector (Novagen, Madison, Wis.) or the pCRII vector (Invitrogen, San Diego, Calif.) and sequenced. The sequences are provided in SEQ ID NO:11–SEQ ID NO:86. Of the 79 sequences isolated, 67 were found to be novel (SEQ ID NO.:11–26 and 28–77) (see also FIGS. 6–20).

An extended DNA sequence (SEQ ID NO: 290) for the antigen B15Ag1 (originally identified partial sequence provided in SEQ ID NO: 27) was obtained in further studies. Comparison of the sequence of SEQ ID NO: 290 with those in the gene bank as described above, revealed homology to the known human β-A activin gene.

Subsequent studies identified an additional 146 sequences (SEQ ID NOS:142–289), of which 115 appeared to be novel (SEQ ID NOS:142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291). To the best of the inventors' knowledge none of the previously identified sequences have heretofore been shown to be expressed at a greater level in human breast tumor tissue than in normal breast tissue.

In further studies, six different splice forms of the antigen B11Ag1 were isolated, with each of the various splice forms containing slightly different versions of the B11Ag1 coding frame. Splice junction sequences define individual exons which, in various patterns and arrangements, make up the various splice forms. Primers were designed to examine the expression pattern of each of the exons using RT-PCR as described below. Each exon was found to show the same expression pattern as the original B11Ag1 clone, with expression being breast tumor, prostate and testis-specific. The determined cDNA sequences for the isolated protein coding exons are provided in SEQ ID NO: 292–297, respectively.

Example 2

Preparation of B18AG1 DNA from Human Genomic DNA

This Example illustrates the preparation of B18Ag1 DNA by amplification from human genomic DNA.

B18Ag1 DNA may be prepared from 250 ng human genomic DNA using 20 pmol of B18Ag1 specific primers, 500 pmol dNTPS and 1 unit of Taq DNA polymerase (Perkin Elmer, Branchburg, N.J.) using the following amplification parameters: 94° C. for 30 seconds denaturing, 30 seconds 60° C. to 42° C. touchdown annealing in 2° C. increments every two cycles and 72° C. extension for 30 seconds. The last increment (a 42° C. annealing temperature) should cycle 25 times. Primers were selected using computer analysis. Primers synthesized were B18Ag1-1, B18Ag1-2, B18Ag1-3, and B18Ag1-4. Primer pairs that may be used are 1+3, 1+4, 2+3, and 2+4.

Following gel electrophoresis, the band corresponding to B18Ag1 DNA may be excised and cloned into a suitable vector.

Example 3

Preparation of B18AG1 from Breast Tumor cDNA

This Example illustrates the preparation of B18Ag1 DNA by amplification from human breast tumor cDNA.

First strand cDNA is synthesized from RNA prepared from human breast tumor tissue in a reaction mixture containing 500 ng poly A+ RNA, 200 pmol of the primer $(T)_{12}AG$ (i.e., TTT TTT TTT TTT AG) (SEQ ID NO: 130), 1× first strand reverse transcriptase buffer, 6.7 mM DTT, 500 mmol dNTPs, and 1 unit AMV or MMLV reverse transcriptase (from any supplier, such as Gibco-BRL (Grand Island, N.Y.)) in a final volume of 30 μl. After first strand synthesis, the cDNA is diluted approximately 25 fold and 1 μl is used for amplification as described in Example 2. While some primer pairs can result in a heterogeneous population of transcripts, the primers B18Ag1-2 (5'ATG GCT ATT TTC GGG GGC TGA CA) (SEQ ID NO: 126) and B18Ag1-3 (5'CCG GTA TCT CCT CGT GGG TAT T) (SEQ ID NO: 127) yield a single 151 bp amplification product.

Example 4

Identification of B-cell and T-cell Epitopes of B18AG1

This Example illustrates the identification of B18Ag1 epitopes.

The B18Ag1 sequence can be screened using a variety of computer algorithms. To determine B-cell epitopes, the sequence can be screened for hydrophobicity and hydrophilicity values using the method of Hopp, Prog. Clin. Biol. Res. 172B:367–77 (1985) or, alternatively, Cease et al., J. Exp. Med. 164:1779–84 (1986) or Spouge et al., J. Immunol. 138:204–12 (1987). Additional Class II MHC (antibody or B-cell) epitopes can be predicted using programs such as AMPHI (e.g., Margalit et al., J. Immunol. 138:2213 (1987) or the methods of Rothbard and Taylor (e.g., EMBO J. 7:93 (1988).

Once peptides (15–20 amino acids long) are identified using these techniques, individual peptides can be synthesized using automated peptide synthesis equipment (available from manufacturers such as Perkin Elmer/Applied Biosystems Division, Foster City, Calif.) and techniques such as Merrifield synthesis. Following synthesis, the peptides can used to screen sera harvested from either normal or breast cancer patients to determine whether patients with breast cancer possess antibodies reactive with the peptides. Presence of such antibodies in breast cancer patient would confirm the immunogenicity of the specific B-cell epitope in question. The peptides can also be tested for their ability to generate a serologic or humoral immune in animals (mice, rats, rabbits, chimps etc.) following immunization in vivo. Generation of a peptide-specific antiserum following such immunization further confirms the immunogenicity of the specific B-cell epitope in question.

To identify T-cell epitopes, the B18Ag1 sequence can be screened using different computer algorithms which are useful in identifying 8–10 amino acid motifs within the B18Ag1 sequence which are capable of binding to HLA Class I MHC molecules. (see, e.g., Rammensee et al., Immunogenetics 41:178–228 (1995). Following synthesis such peptides can be tested for their ability to bind to class I MHC using standard binding assays (e.g., Sette et al., J. Immunol. 153:5586–92 (1994) and more importantly can be tested for their ability to generate antigen reactive cytotoxic T-cells following in vitro stimulation of patient or normal peripheral mononuclear cells using, for example, the methods of Bakker et al., Cancer Res. 55:5330–34 (1995); Visseren et al., J. Immunol. 154:3991–98 (1995); Kawakami et al., J. Immunol. 154:3961–68 (1995); and Kast et al., J. Immunol. 152:3904–12 (1994). Successful in vitro generation of T-cells capable of killing autologous (bearing the same Class I MHC molecules) tumor cells following in vitro peptide stimulation further confirms the immunogenicity of the B18Ag1 antigen. Furthermore, such peptides may be used to generate murine peptide and B18Ag1 reactive cytotoxic T-cells following in vivo immunization in mice rendered transgenic for expression of a particular human MHC Class I haplotype (Vitiello et al., J. Exp. Med. 173:1007–15 (1991).

A representative list of predicted B18Ag1 B-cell and T-cell epitopes, broken down according to predicted HLA Class I MHC binding antigen, is shown below:

Predicted Th Motifs (B-cell epitopes) (SEQ ID NOS.: 131–133)
SSGGRTFDDFHRYLLVGI
QGAAQKPINLSKXIEVVQGHDE
SPGVFLEHLQEAYRIYTPFDLSA Predicted HLA A2.1 Motifs (T-cell epitopes) (SEQ ID NOS.: 134–140)
YLLVGIQGA
GAAQKPINL
NLSKXIEVV
EVVQGHDES
HLQEAYRIY

NLAFVAQAA
FVAQAAPDS

Example 5

Characterization of Breast Tumor Genes Discovered by Differential Display PCR The specificity and sensitivity of the breast tumor genes discovered by differential display PCR were determined using RT-PCR. This procedure enabled the rapid evaluation of breast tumor gene mRNA expression semiquantitatively without using large amounts of RNA. Using gene specific primers, mRNA expression levels in a variety of tissues were examined, including 8 breast tumors, 5 normal breasts, 2 prostate tumors, 2 colon tumors, 1 lung tumor, and 14 other normal adult human tissues, including normal prostate, colon, kidney, liver, lung, ovary, pancreas, skeletal muscle, skin, stomach and testes.

To ensure the semiquantitative nature of the RT-PCR, β-actin was used as internal control for each of the tissues examined. Serial dilutions of the first strand cDNAs were prepared and RT-PCR assays performed using β-actin specific primers. A dilution was then selected that enabled the linear range amplification of β-actin template, and which was sensitive enough to reflect the difference in the initial copy number. Using this condition, the β-actin levels were determined for each reverse transcription reaction from each tissue. DNA contamination was minimized by DNase treatment and by assuring a negative result when using first strand cDNA that was prepared without adding reverse transcriptase.

Figure 21A:
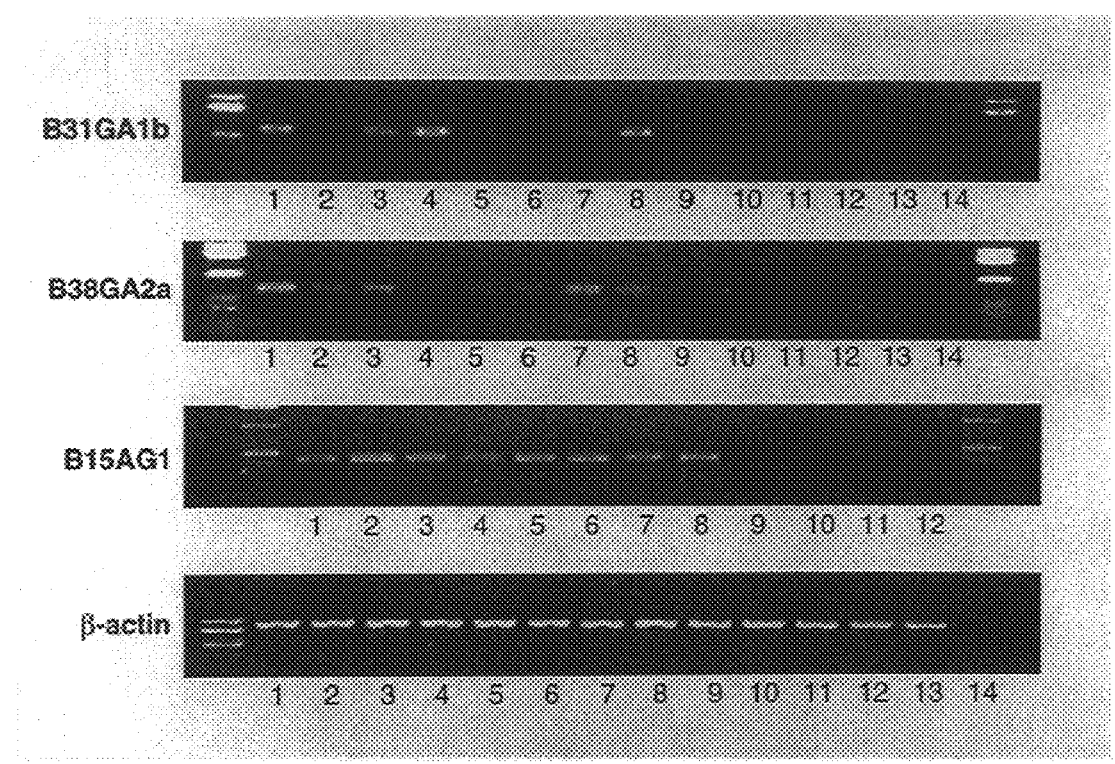
FIG. 21A depicts RT-PCR analysis of breast tumor genes in breast tumor tissues (lanes 1–8) and normal breast tissues (lanes 9–13) and $H_2O$ (lane 14).
Figure 21B:
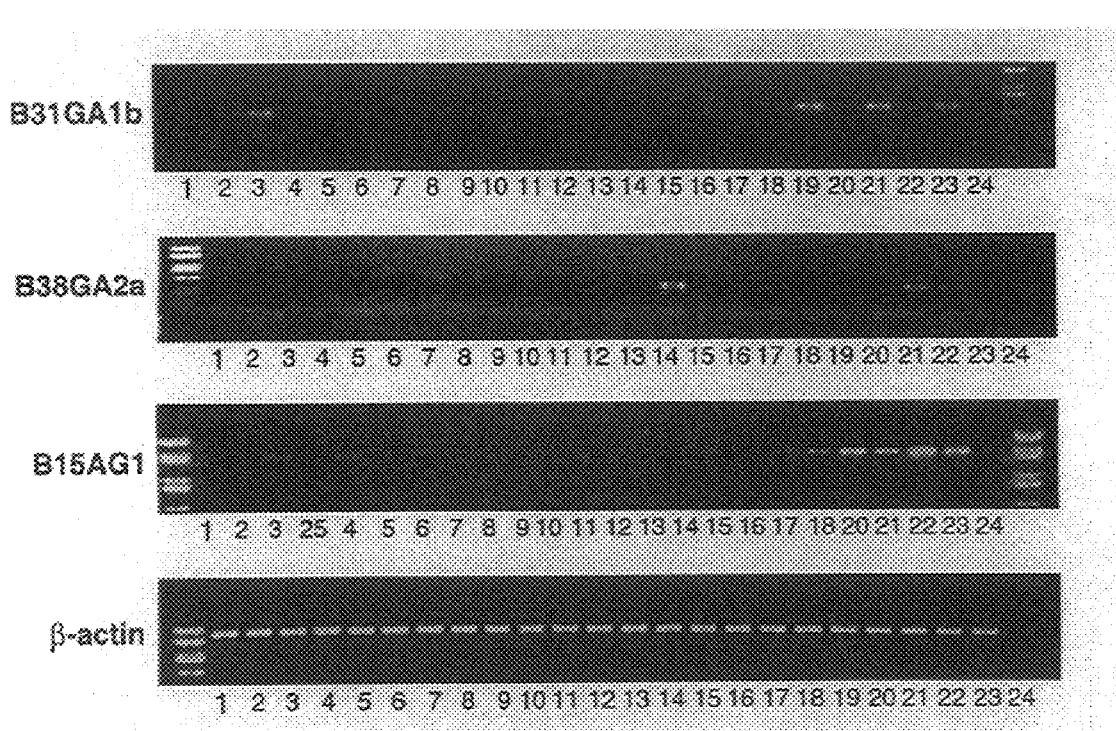
FIG. 21B depicts RT-PCR analysis of breast tumor genes in prostate tumors (lane 1, 2), colon tumors (lane 3), lung tumor (lane 4), normal prostate (lane 5), normal colon (lane 6), normal kidney (lane 7), normal liver (lane 8), normal lung (lane 9), normal ovary (lanes 10, 18), normal pancreases (lanes 11, 12), normal skeletal muscle (lane 13), normal skin (lane 14), normal stomach (lane 15), normal testes (lane 16), normal small intestine (lane 17), HBL-100 (lane 19), MCF-12A (lane 20), breast tumors (lanes 21–23), $H_2O$ (lane 24), and colon tumor (lane 25).

Using gene specific primers, the mRNA expression levels were determined in a variety of tissues. To date, 38 genes have been successfully examined by RT-PCR, five of which exhibit good specificity and sensitivity for breast tumors (B15AG-1, B31GA1b, B38GA2a, B11A1a and B18AG1a). FIGS. 21A and 21B depict the results for three of these genes: B15AG-1 (SEQ ID NO:27), B31GA1b (SEQ ID NO:148) and B38GA2a (SEQ ID NO. 157). Table I summarizes the expression level of all the genes tested in normal breast tissue and breast tumors, and also in other tissues.

TABLE I

Percentage of Breast Cancer Antigens that are Expressed in Various Tissues

| | | |
|---|---|---|
| Breast Tissues | Over-expressed in Breast Tumors | 84% |
| | Equally Expressed in Normals and Tumor | 16% |
| Other Tissues | Over-expressed in Breast Tumors but not in any Normal Tissues | 9% |
| | Over-expressed in Breast Tumors but Expressed in Some Normal Tissues | 30% |
| | Over-expressed in Breast Tumors but Equally Expressed in All Other Tissues | 61% |

From the foregoing, it will be appreciated that, although specific embodiments of the invention have been described herein for the purpose of illustration, various modifications may be made without deviating from the spirit and scope of the invention.

What is claimed is:

1. An isolated DNA molecule comprising SEQ ID NO: 292.
2. An isolated DNA molecule comprising SEQ ID NO: 293.
3. An isolated DNA molecule comprising SEQ ID NO: 294.
4. An isolated DNA molecule comprising SEQ ID NO: 295.
5. An isolated DNA molecule comprising SEQ ID NO: 296.
6. An isolated DNA molecule comprising SEQ ID NO: 297.
7. A recombinant expression vector comprising a DNA molecule according to any one of claims 1–6.
8. A host cell transformed or transfected with an expression vector according to claim 7.
9. A host cell of claim 8 wherein the host cell is selected from the group consisting of *E. coli*, yeast and mammalian cell lines.

* * * * *

SEQUENCE LISTING (1) GENERAL INFORMATION:

(iii) NUMBER OF SEQUENCES: 297

(2) INFORMATION FOR SEQ ID NO:1:

(i) SEQUENCE CHARACTERISTICS:
      (A) LENGTH: 363 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..363

(xi) SEQUENCE DESCRIPTION: SEQ ID NO:1:

```
TTA GAG ACC CAA TTG GGA CCT AAT TGG GAC CCA AAT TTC TCA AGT GGA      48
Leu Glu Thr Gln Leu Gly Pro Asn Trp Asp Pro Asn Phe Ser Ser Gly
 1               5                  10                  15

GGG AGA ACT TTT GAC GAT TTC CAC CGG TAT CTC CTC GTG GGT ATT CAG      96
Gly Arg Thr Phe Asp Asp Phe His Arg Tyr Leu Leu Val Gly Ile Gln
                20                  25                  30

GGA GCT GCC CAG AAA CCT ATA AAC TTG TCT AAG GCG ATT GAA GTC GTC     144
Gly Ala Ala Gln Lys Pro Ile Asn Leu Ser Lys Ala Ile Glu Val Val
            35                  40                  45

CAG GGG CAT GAT GAG TCA CCA GGA GTG TTT TTA GAG CAC CTC CAG GAG     192
Gln Gly His Asp Glu Ser Pro Gly Val Phe Leu Glu His Leu Gln Glu
        50                  55                  60
```

```
GCT TAT CGG ATT TAC ACC CCT TTT GAC CTG GCA GCC CCC GAA AAT AGC         240
Ala Tyr Arg Ile Tyr Thr Pro Phe Asp Leu Ala Ala Pro Glu Asn Ser
 65                  70                  75                  80

CAT GCT CTT AAT TTG GCA TTT GTG GCT CAG GCA GCC CCA GAT AGT AAA         288
His Ala Leu Asn Leu Ala Phe Val Ala Gln Ala Ala Pro Asp Ser Lys
                 85                  90                  95

AGG AAA CTC CAA AAA CTA GAG GGA TTT TGC TGG AAT GAA TAC CAG TCA         336
Arg Lys Leu Gln Lys Leu Glu Gly Phe Cys Trp Asn Glu Tyr Gln Ser
            100                 105                 110

GCT TTT AGA GAT AGC CTA AAA GGT TTT                                     363
Ala Phe Arg Asp Ser Leu Lys Gly Phe
        115                 120
```

(2) INFORMATION FOR SEQ ID NO:2:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Glu Thr Gln Leu Gly Pro Asn Trp Asp Pro Asn Phe Ser Ser Gly
 1               5                  10                  15

Gly Arg Thr Phe Asp Asp Phe His Arg Tyr Leu Leu Val Gly Ile Gln
                20                  25                  30

Gly Ala Ala Gln Lys Pro Ile Asn Leu Ser Lys Ala Ile Glu Val Val
            35                  40                  45

Gln Gly His Asp Glu Ser Pro Gly Val Phe Leu Glu His Leu Gln Glu
     50                  55                  60

Ala Tyr Arg Ile Tyr Thr Pro Phe Asp Leu Ala Ala Pro Glu Asn Ser
 65                  70                  75                  80

His Ala Leu Asn Leu Ala Phe Val Ala Gln Ala Ala Pro Asp Ser Lys
                 85                  90                  95

Arg Lys Leu Gln Lys Leu Glu Gly Phe Cys Trp Asn Glu Tyr Gln Ser
            100                 105                 110

Ala Phe Arg Asp Ser Leu Lys Gly Phe
        115                 120
```

(2) INFORMATION FOR SEQ ID NO:3:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (xi) SEQUENCE DESCRIPTION: SEQ ID NO:3:

```
TCTTAGAATC TTCATACCCC GAACTCTTGG GAAAACTTTA ATCAGTCACC TACAGTCTAC        60

CACCCATTTA GGAGGAGCAA AGCTACCTCA GCTCCTCCGG AGCCGTTTTA AGATCCCCCA       120

TCTTCAAAGC CTAACAGATC AAGCAGCTCT CCGGTGCACA ACCTGCGCCC AGGTAAATGC       180

CAAAAAGGT CCTAAACCCA GCCCAGGCCA CCGTCTCCAA GAAAACTCAC CAGGAGAAAA        240

GTGGAAATT GACTTTACAG AAGTAAAACC ACACCGGGCT GGGTACAAAT ACCTTCTAGT        300

ACTGGTAGAC ACCTTCTCTG GATGGACTGA AGCATTTGCT ACCAAAAACG AAACTGTCAA       360

TATGGTAGTT AAGTTTTTAC TCAATGAAAT CATCCCTCGA CGTGGGCTGC CTGTTGCCAT       420

AGGGTCTGAT AATGGAACGG CCTTCGCCTT GTCTATAGTT TAATCAGTCA GTAAGGCGTT       480
```

```
AAACATTCAA TGGAAGCTCC ATTGTGCCTA TCGACCCAGA GCTCTGGGCA AGTAGAACGC       540

ATGAACTGCA CCCTAAAAAA ACACTCTTAC AAAATTAATC TTAAAAACCG GTGTTAATTG       600

TGTTAGTCTC CTTCCCTTAG CCCTACTTAG AGTTAAGGTG CACCCCTTAC TGGGCTGGGT       660

TCTTTACCTT TTGAAATCAT NTTTNGGAAG GGGCTGCCTA TCTTTNCTTA ACTAAAAAAN       720

GCCCATTTGG CAAAAATTTC NCAACTAATT TNTACGTNCC TACGTCTCCC CAACAGGTAN       780

AAAAATCTNC TGCCCTTTTC AAGGAACCAT CCCATCCATT CCTNAACAAA AGGCCTGCCN       840

TTCTTCCCCC AGTTAACTNT TTTTTNTTAA AATTCCCAAA AAANGAACCN CCTGCTGGAA       900

AAACNCCCCC CTCCAANCCC CGGCCNAAGN GGAAGGTTCC CTTGAATCCC NCCCCCNCNA       960

ANGGCCCGGA ACCNTTAAAN TNGTTCCNGG GGGTNNGGCC TAAAAGNCCN ATTTGGTAAA      1020

CCTANAAATT TTTTCTTTTN TAAAAACCAC NNTTTNNTTT TTCTTAAACA AAACCCTNTT      1080

TNTAGNANCN TATTTCCCNC C                                               1101

(2) INFORMATION FOR SEQ ID NO:4:

(i) SEQUENCE CHARACTERISTICS:
        (A) LENGTH: 1087 base pairs
        (B) TYPE: nucleic acid
        (C) STRANDEDNESS: single
        (D) TOPOLOGY: linear (xi) SEQUENCE DESCRIPTION: SEQ ID NO:4:

TCTAGAGCTG CGCCTGGATC CCGCCACAGT GAGGAGACCT GAAGACCAGA GAAAACACAG        60

CAAGTAGGCC CTTTAAACTA CTCACCTGTG TTGTCTTCTA ATTTATTCTG TTTTATTTTG       120

TTTCCATCAT TTTAAGGGGT TAAAATCATC TTGTTCAGAC CTCAGCATAT AAAATGACCC       180

ATCTGTAGAC CTCAGGCTCC AACCATACCC CAAGAGTTGT CTGGTTTTGT TTAAATTACT       240

GCCAGGTTTC AGCTGCAGAT ATCCCTGGAA GGAATATTCC AGATTCCCTG AGTAGTTTCC       300

AGGTTAAAAT CCTATAGGCT TCTTCTGTTT TGAGGAAGAG TTCCTGTCAG AGAAAAACAT       360

GATTTTGGAT TTTTAACTTT AATGCTTGTG AAACGCTATA AAAAAAATTT TCTACCCCTA       420

GCTTTAAAGT ACTGTTAGTG AGAAATTAAA ATTCCTTCAG GAGGATTAAA CTGCCATTTC       480

AGTTACCCTA ATTCCAAATG TTTTGGTGGT TAGAATCTTC TTTAATGTTC TTGAAGAAGT       540

GTTTTATATT TTCCCATCNA GATAAATTCT CTCNCNCCTT NNTTTTNTNT CTNNTTTTTT       600

AAAACGGANT CTTGCTCCGT TGTCCANGCT GGGAATTTTN TTTTGGCCAA TCTCCGCTNC       660

CTTGCAANAA TNCTGCNTCC CAAAATTACC NCCTTTTTCC CACCTCCACC CCNGGAATT       720

ACCTGGAATT ANAGGCCCCC NCCCCCCCCC CGGCTAATTT GTTTTTGTTT TTAGTAAAAA       780

ACGGGTTTCC TGTTTTAGTT AGGATGGCCC ANNTCTGACC CCNTNATCNT CCCCCTCNGC       840

CCTCNAATNT TNGGNNTANG GCTTACCCCC CCCNGNNGTT TTTCCTCCAT TNAAATTTTC       900

TNTGGANTCT TGAATNNCGG GTTTTCCCTT TTAAACCNAT TTTTTTTTTN NNNCCCCCAN       960

TTTTNCCTCC CCCNTNTNTA ANGGGGGTTT CCCAANCCGG GTCCNCCCCC ANGTCCCCAA      1020

TTTTTCTCCC CCCCCCTCTT TTTTCTTTNC CCCAAAANTC CTATCTTTTC CTNNAAATAT      1080

CNANTNT                                                               1087

(2) INFORMATION FOR SEQ ID NO:5:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear
```

(xi) SEQUENCE DESCRIPTION: SEQ ID NO:5:

```
TCTAGACCAA GAAATGGGAG GATTTTAGAG TGACTGATGA TTTCTCTATC ATCTGCAGTT      60

AGTAAACATT CTCCACAGTT TATGCAAAAA GTAACAAAAC CACTGCAGAT GACAAACACT     120

AGGTAACACA CATACTATCT CCCAAATACC TACCCACAAG CTCAACAATT TTAAACTGTT     180

AGGATCACTG GCTCTAATCA CCATGACATG AGGTCACCAC CAAACCATCA AGCGCTAAAC     240

AGACAGAATG TTTCCACTCC TGATCCACTG TGTGGGAAGA AGCACCGAAC TTACCCACTG     300

GGGGGCCTGC NTCANAANAA AAGCCCATGC CCCCGGGTNT NCCTTTNAAC CGGAACGAAT     360

NAACCCACCA TCCCCACANC TCCTCTGTTC NTGGGCCCTG CATCTTGTGG CCTCNTNTNC     420

TTTNGGGGAN ACNTGGGGAA GGTACCCCAT TTCNTTGACC CCNCNANAAA ACCCCNGTGG     480

CCCTTTGCCC TGATTCNCNT GGGCCTTTTC TCTTTTCCCT TTTGGGTTGT TTAAATTCCC     540

AATGTCCCCN GAACCCTCTC CNTNCTGCCC AAAACCTACC TAAATTNCTC NCTANGNNTT     600

TTCTTGGTGT TNCTTTTCAA AGGTNACCTT NCCTGTTCAN NCCCACNAA AATTTNTTCC      660

NTATNNTGGN CCCNNAAAAA NNNATCNNCC CNAATTGCCC GAATTGGTTN GGTTTTTCCT     720

NCTGGGGGAA ACCCTTTAAA TTTCCCCCTT GGCCGGCCCC CCTTTTTTCC CCCCTTTNGA     780

AGGCAGGNGG TTCTTCCCGA ACTTCCAATT NCAACAGCCN TGCCCATTGN TGAAACCCTT     840

TTCCTAAAAT TAAAAAATAN CCGGTTNNGG NNGGCCTCTT TCCCCTCCNG GNGGGNNGNG     900

AAANTCCTTA CCCCNAAAAA GGTTGCTTAG CCCCCNGTCC CCACTCCCCC NGGAAAAATN     960

AACCTTTTCN AAAAAAGGAA TATAANTTTN CCACTCCTTN GTTCTCTTCC               1010
```

(2) INFORMATION FOR SEQ ID NO:6:

(i) SEQUENCE CHARACTERISTICS:
        (A) LENGTH: 950 base pairs
        (B) TYPE: nucleic acid
        (C) STRANDEDNESS: single
        (D) TOPOLOGY: linear (xi) SEQUENCE DESCRIPTION: SEQ ID NO:6:

```
TCTAGAGCTC GCGGCCGCGA GCTCTAATAC GACTCACTAT AGGGCGTCGA CTCGATCTCA      60

GCTCACTGCA ATCTCTGCCC CCGGGGTCAT GCGATTCTCC TGCCTCAGCC TTCCAAGTAG     120

CTGGGATTAC AGGCGTGCAA CACCACACCC GGCTAATTTT GTATTTTTAA TAGAGATGGG     180

GTTTTCCCTT GTTGGCCANN ATGGTCTCNA ACCCCTGACC TCNNGTGATC CCCCCNCCCN     240

NGANCTCNNA CTGCTGGGGA TNNCCGNNNN NNNCCTCCCN NCNCNNNNNN NCNCNNTCCN     300

TNNTCCTTNC TCNNNNNNNN CNNTCNNTCC NNCTTCTCNC CNNNTNTTNT CNNCNNCCNN     360

CNNNCCNCNT NCCCNCNNNT TCNCNTNCNN TNTCCNNCNN NNTCNNCNNN CNNNNCNTNN     420

CCNNTACNTC NTNNNCNNNT CCNTCTNTNN CCTCNNCNNT CNCTNCNCNT TNTCTCCTCN     480

NTNNNNNNCT CCNNNNNTCT CNTCNCNNCN TNCCTCNNTN NCCNCNCCCC NCCTCNCNNC     540

CTNNTTTNNN CNNCNNNTCC NTNCCNTTCN NNTCCNNTNN CNNCNTCNCN NNCNTTNTTC     600

CCNCCNNTTC CTTNCNCNTN NNNTNTCNNN CNCNTCNNTC NTTTNCTCCT NNNTCCCNNC     660

TCNNTTCNCC CNNNTCCNCC CCCCNCCTNT CTCTCNCCCN NNTNNNTNTN NNNCNTCCNC     720

TNTCNCNTTC NTCNNTNCNT TNCTNTCNNC NNCNNTNCNC TNCCNTNTNT CTNNNTCNCN     780

TCNCNTNTCN CCNTCNCNTTN CTNTCTCCTN TNTCCTTCCC CTCNCCTNCT CNTTCNCCNC     840

CCNNTNTNTN TNNCNCCNNT NCTNNNCNNC CNTCNTTTCN TCTCTNCTNN NNNTNNCCTC     900

NNCCCNTNCC CTNNTNCNCT NCTNNTACCN TNCTNCTCCN TCTTCCTTCC                950
```

(2) INFORMATION FOR SEQ ID NO:7:

(i) SEQUENCE CHARACTERISTICS:
        (A) LENGTH: 1086 base pairs
        (B) TYPE: nucleic acid
        (C) STRANDEDNESS: single
        (D) TOPOLOGY: linear (xi) SEQUENCE DESCRIPTION: SEQ ID NO:7:

```
TCTAGAGCTC GCGGCCGCGA GCTCAATTAA CCCTCACTAA AGGGAGTCGA CTCGATCAGA      60
CTGTTACTGT GTCTATGTAG AAAGAAGTAG ACATAAGAGA TTCCATTTTG TTCTGTACTA     120
AGAAAAATTC TTCTGCCTTG AGATGCTGTT AATCTGTAAC CCTAGCCCCA ACCCTGTGCT     180
CACAGAGACA TGTGCTGTGT TGACTCAAGG TTCAATGGAT TTAGGGCTAT GCTTTGTTAA     240
AAAAGTGCTT GAAGATAATA TGCTTGTTAA AAGTCATCAC CATTCTCTAA TCTCAAGTAC     300
CCAGGGACAC AATACACTGC GGAAGGCCGC AGGGACCTCT GTCTAGGAAA GCCAGGTATT     360
GTCCAAGATT TCTCCCCATG TGATAGCCTG AGATATGGCC TCATGGGAAG GGTAAGACCT     420
GACTGTCCCC CAGCCCGACA TCCCCCAGCC CGACATCCCC CAGCCCGACA CCCGAAAAGG     480
GTCTGTGCTG AGGAAGATTA NTAAAAGAGG AAGGCTCTTT GCATTGAAGT AAGAAGAAGG     540
CTCTGTCTCC TGCTCGTCCC TGGGCAATAA AATGTCTTGG TGTTAAACCC GAATGTATGT     600
TCTACTTACT GAGAATAGGA GAAAACATCC TTAGGGCTGG AGGTGAGACA CCCTGGCGGC     660
ATACTGCTCT TTAATGCACG AGATGTTTGT NTAATTGCCA TCCAGGGCCA NCCCCTTTCC     720
TTAACTTTTT ATGANACAAA AACTTTGTTC NCTTTTCCTG CGAACCTCTC CCCCTATTAN     780
CCTATTGGCC TGCCCATCCC CTCCCCAAAN GGTGAAAANA TGTTCNTAAA TNCGAGGGAA     840
TCCAAAACNT TTTCCCGTTG GTCCCCTTTC CAACCCCGTC CCTGGGCCNN TTTCCTCCCC     900
AACNTGTCCC GGNTCCTTCN TTCCCNCCCC CTTCCCNGAN AAAAACCCC GTNTGANGGN      960
GCCCCCTCAA ATTATAACCT TTCCNAAACA AANNGGTTCN AAGGTGGTTT GNTTCCGGTG    1020
CGGCTGGCCT TGAGGTCCCC CCTNCACCCC AATTTGGAAN CCNGTTTTTT TTATTGCCCN    1080
NTCCCC                                                              1086
```

(2) INFORMATION FOR SEQ ID NO:8:

(i) SEQUENCE CHARACTERISTICS:
        (A) LENGTH: 1177 base pairs
        (B) TYPE: nucleic acid
        (C) STRANDEDNESS: single
        (D) TOPOLOGY: linear (xi) SEQUENCE DESCRIPTION: SEQ ID NO:8:

```
NCCNTTTAGA TGTTGACAAN NTAAACAAGC NGCTCAGGCA GCTGAAAAAA GCCACTGATA      60
AAGCATCCTG GAGTATCAGA GTTTACTGTT AGATCAGCCT CATTTGACTT CCCCTCCCAC     120
ATGGTGTTTA AATCCAGCTA CACTACTTCC TGACTCAAAC TCCACTATTC CTGTTCATGA     180
CTGTCAGGAA CTGTTGGAAA CTACTGAAAC TGGCCGACCT GATCTTCAAA ATGTGCCCCT     240
AGGAAAGGTG GATGCCACCG TGTTCACAGA CAGTACCNCC TTCCTCGAGA AGGGACTACG     300
AGGGGCCGGT GCANCTGTTA CCAAGGAGAC TNATGTGTTG TGGGCTCAGG CTTTACCANC     360
AAACACCTCA NCNCNNAAGG CTGAATTGAT CGCCCTCACT CAGGCTCTCG GATGGGGTAA     420
GGGATATTAA CGTTAACACT GACAGCAGGT ACGCCTTTGC TACTGTGCAT GTACGTGGAG     480
CCATCTACCA GGAGCGTGGG CTACTCACTC GGCAGGTGGC TGTNATCCAC TGTAAANGGA     540
```

```
CATCAAAAGG AAAACNNGGC TGTTGCCCGT GGTAACCANA AANCTGATCN NCAGCTCNAA    600

GATGCTGTGT TGACTTTCAC TCNCNCCTCT TAAACTTGCT GCCCACANTC TCCTTTCCCA    660

ACCAGATCTG CCTGACAATC CCCATACTCA AAAAAAAAAN AANACTGGCC CCGAACCCNA    720

ACCAATAAAA ACGGGGANGG TNGGTNGANC NNCCTGACCC AAAAATAATG GATCCCCCGG    780

GCTGCAGGAA TTCAATTCAN CCTTATCNAT ACCCCCAACN NGGNGGGGGG GGCCNGTNCC    840

CATTNCCCCT NTATTNATTC TTTNNCCCCC CCCCCGGCNT CCTTTTTNAA CTCGTGAAAG    900

GGAAAACCTG NCTTACCAAN TTATCNCCTG GACCNTCCCC TTCCNCGGTN GNTTANAAAA    960

AAAAGCCCNC ANTCCCNTCC NAAATTTGCA CNGAAAGGNA AGGAATTTAA CCTTTATTTT   1020

TTNNTCCTTT ANTTTGTNNN CCCCCTTTTA CCCAGGCGAA CNGCCATCNT TTAANAAAAA   1080

AAANAGAANG TTTATTTTTC CTTNGAACCA TCCCAATANA AANCACCCGC NGGGGAACGG   1140

GGNGGNAGGC CNCTCACCCC CTTTNTGTNG GNGGGNC                            1177
```

(2) INFORMATION FOR SEQ ID NO:9:

(i) SEQUENCE CHARACTERISTICS:
        (A) LENGTH: 1146 base pairs
        (B) TYPE: nucleic acid
        (C) STRANDEDNESS: single
        (D) TOPOLOGY: linear (xi) SEQUENCE DESCRIPTION: SEQ ID NO:9:

```
NCCNNTTNNT GATGTTGTCT TTTTGGCCTC TCTTTGGATA CTTTCCCTCT CTTCAGAGGT     60

GAAAAGGGTC AAAAGGAGCT GTTGACAGTC ATCCCAGGTG GGCCAATGTG TCCAGAGTAC    120

AGACTCCATC AGTGAGGTCA AAGCCTGGGG CTTTTCAGAG AAGGGAGGAT TATGGGTTTT    180

CCAATTATAC AAGTCAGAAG TAGAAAGAAG GGACATAAAC CAGGAAGGGG GTGGAGCACT    240

CATCACCCAG AGGGACTTGT GCCTCTCTCA GTGGTAGTAG AGGGGCTACT TCCTCCCACC    300

ACGGTTGCAA CCAAGAGGCA ATGGGTGATG AGCCTACAGG GGACATANCC GAGGAGACAT    360

GGGATGACCC TAAGGGAGTA GGCTGGTTTT AAGGCGGTGG GACTGGGTGA GGGAAACTCT    420

CCTCTTCTTC AGAGAGAAGC AGTACAGGGC GAGCTGAACC GGCTGAAGGT CGAGGCGAAA    480

ACACGGTCTG GCTCAGGAAG ACCTTGGAAG TAAAATTATG AATGGTGCAT GAATGGAGCC    540

ATGGAAGGGG TGCTCCTGAC CAAACTCAGC CATTGATCAA TGTTAGGGAA ACTGATCAGG    600

GAAGCCGGGA ATTTCATTAA CAACCCGCCA CACAGCTTGA ACATTGTGAG GTTCAGTGAC    660

CCTTCAAGGG GCCACTCCAC TCCAACTTTG GCCATTCTAC TTTGCNAAAT TTCCAAAACT    720

TCCTTTTTTA AGGCCGAATC CNTANTCCCT NAAAAACNAA AAAAAATCTG CNCCTATTCT    780

GGAAAAGGCC CANCCCTTAC CAGGCTGGAA GAAATTTTNC CTTTTTTTTT TTTTTGAAGG    840

CNTTTNTTAA ATTGAACCTN AATTCNCCCC CCCAAAAAAA AACCCNCCNG GGGGCGGAT    900

TTCCAAAAAC NAATTCCCTT ACCAAAAAAC AAAAACCCNC CCTTNTTCCC TTCCNCCCTN    960

TTCTTTTAAT TAGGGAGAGA TNAAGCCCCC CAATTTCCNG GNCTNGATNN GTTTCCCCCC   1020

CCCCCATTTT CCNAAACTTT TTCCCANCNA GGAANCCNCC CTTTTTTTNG GTCNGATTNA   1080

NCAACCTTCC AAACCATTTT TCCNNAAAAA NTTTGNTNGG NGGGAAAAAN ACCTNNTTTT   1140

ATAGAN                                                              1146
```

(2) INFORMATION FOR SEQ ID NO:10:

(i) SEQUENCE CHARACTERISTICS:
        (A) LENGTH: 545 base pairs
        (B) TYPE: nucleic acid (C) STRANDEDNESS: single
        (D) TOPOLOGY: linear (xi) SEQUENCE DESCRIPTION: SEQ ID NO:10:

```
CTTCATTGGG TACGGGCCCC CTCGAGGTCG ACGGTATCGA TAAGCTTGAT ATCGAATTCC    60

TGCAGCCCGG GGGATCCACT AGTTCTAGAG TCAGGAAGAA CCACCAACCT TCCTGATTTT   120

TATTGGCTCT GAGTTCTGAG GCCAGTTTTC TTCTTCTGTT GAGTATGCGG GATTGTCAGG   180

CAGATCTGGC TGTGGAAAGG AGACTGTGGG CAGCAAGTTT AGAGGCGTGA CTGAAAGTCA   240

CACTGCATCT TGAGCTGCTG AATCAGCTTT CTGGTTACCA CGGGCAACAG CCGTGTTTTC   300

CTTTTGATGT CCTTTACAGT GGATTACAGC CACCTGCTGA GGTGAGTAGC CCACGCTCCT   360

GGTAGATGGC TCCACGTACA TGCACAGTAG CAAAGGCGTA CCTGCTGTCA GTGTTAACGT   420

TAATATCCTT ACCCCATCGG AGAGCCTGAG TGAGGGCGAT CAATTCAGCC CTTTTGTGCT   480

GAGGTGTTTG CTGGTTAAGC CCTGAACCCA CAACACATCT GTCTCCATGG TAACAGCTGC   540

ACCGG                                                              545
```

(2) INFORMATION FOR SEQ ID NO:11:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO:11:

```
TCTCCTAGGC TGGGCACAGT GGCTCATACC TGTAATCCTG ACCGTTTCAG AGGCTCAGGT    60

GGGGGGATCG CTTGAGCCCA AGATTTCAAG ACTAGTCTGG GTAACATAGT GAGACCCTAT   120

CTCTACGAAA AATAAAAAA ATGAGCCTGG TGTAGTGGCA CACACCAGCT GAGGAGGGAG   180

AATCGAGCCT AGGAGA                                                  196
```

(2) INFORMATION FOR SEQ ID NO:12:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (xi) SEQUENCE DESCRIPTION: SEQ ID NO:12:

```
TCTCCTAGGC TTGGGGGCTC TGACTAGAAA TTCAAGGAAC CTGGGATTCA AGTCCAACTG    60

TGACACCAAC TTACACTGTG GNCTCCAATA AACTGCTTCT TTCCTATTCC CTCTCTATTA   120

AATAAAATAA GGAAAACGAT GTCTGTGTAT AGCCAAGTCA GNTATCCTAA AAGGAGATAC   180

TAAGTGACAT TAAATATCAG AATGTAAAAC CTGGGAACCA GGTTCCCAGC CTGGGATTAA   240

ACTGACAGCA AGAAGACTGA ACAGTACTAC TGTGAAAAGC CCGAAGNGGC AATATGTTCA   300

CTCTACCGTT GAAGGATGGC TGGGAGAATG AATGCTCTGT CCCCCAGTCC CAAGCTCACT   360

TACTATACCT CCTTTATAGC CTAGGAGA                                     388
```

(2) INFORMATION FOR SEQ ID NO:13:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (xi) SEQUENCE DESCRIPTION: SEQ ID NO:13:

```
TAGTAGTTGC CTATAATCAT GTTTCTCATT ATTTTCACAT TTTATTAACC AATTTCTGTT    60

TACCCTGAAA AATATGAGGG AAATATATGA AACAGGGAGG CAATGTTCAG ATAATTGATC   120

ACAAGATATG ATTTCTACAT CAGATGCTCT TTCCTTTCCT GTTTATTTCC TTTTTATTTC   180

GGTTGTGGGG TCGAATGTAA TAGCTTTGTT TCAAGAGAGA GTTTTGGCAG TTTCTGTAGC   240

TTCTGACACT GCTCATGTCT CCAGGCATCT ATTTGCACTT TAGGAGGTGT CGTGGGAGAC   300

TGAGAGGTCT ATTTTTTCCA TATTTGGGCA ACTACTA                            337
```

(2) INFORMATION FOR SEQ ID NO:14:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (xi) SEQUENCE DESCRIPTION: SEQ ID NO:14:

```
TAGTAGTTGC CATACAGTGC CTTTCCATTT ATTTAACCCC CACCTGAACG GCATAAACTG    60

AGTGTTCAGC TGGTGTTTTT TACTGTAAAC AATAAGGAGA CTTTGCTCTT CATTTAAACC   120

AAAATCATAT TTCATATTTT ACGCTCGAGG GTTTTTACCG GTTCCTTTTT ACACTCCTTA   180

AAACAGTTTT TAAGTCGTTT GGAACAAGAT ATTTTTTCTT TCCTGGCAGC TTTTAACATT   240

ATAGCAAATT TGTGTCTGGG GGACTGCTGG TCACTGTTTC TCACAGTTGC AAATCAAGGC   300

ATTTGCAACC AAGAAAAAAA AATTTTTTTG TTTTATTTGA AACTGGACCG GATAAACGGT   360

GTTTGGAGCG GCTGCTGTAT ATAGTTTTAA ATGGTTTATT GCACCTCCTT AAGTTGCACT   420

TATGTGGGGG GGGGNTTTTG NATAGAAAGT NTTTANTCAC ANAGTCACAG GGACTTTTNT   480

CTTTTGGNNA CTGAGCTAAA AAGGGCTGNT TTTCGGGTGG GGGCAGATGA AGGCTCACAG   540

GAGGCCTTTC TCTTAGAGGG GGGAACTNCT A                                  571
```

(2) INFORMATION FOR SEQ ID NO:15:

(i) SEQUENCE CHARACTERISTICS:
        (A) LENGTH: 548 base pairs
        (B) TYPE: nucleic acid
        (C) STRANDEDNESS: single
        (D) TOPOLOGY: linear (xi) SEQUENCE DESCRIPTION: SEQ ID NO:15:

```
TATATATTTA ATAACTTAAA TATATTTTGA TCACCCACTG GGGTGATAAG ACAATAGATA    60

TAAAAGTATT TCCAAAAAGC ATAAAACCAA AGTATCATAC CAAACCAAAT TCATACTGCT   120

TCCCCCACCC GCACTGAAAC TTCACCTTCT AACTGTCTAC CTAACCAAAT TCTACCCTTC   180

AAGTCTTTGG TGCGTGCTCA CTACTCTTTT TTTTTTTTTT TTTNTTTTGG AGATGGAGTC   240

TGGCTGTGCA GCCCAGGGGT GGAGTACAAT GGCACAACCT CAGCTCACTG NAACCTCCGC   300

CTCCCAGGTT CATGAGATTC TCCTGNTTCA GCCTTCCCAG TAGCTGGGAC TACAGGTGTG   360

CATCACCATG CCTGGNTAAT CTTTTTTNGT TTTNGGGTAG AGATGGGGGT TTTACATGTT   420

GGCCAGGNTG GTNTCGAACT CCTGACCTCA AGTGATCCAC CCACCTCAGG CTCCCAAAGT   480

GCTAGGATTA CAGACATGAG CCACTGNGCC CAGNCCTGGT GCATGCTCAC TTCTCTAGGC   540

AACTACTA                                                            548
```

(2) INFORMATION FOR SEQ ID NO:16:

(i) SEQUENCE CHARACTERISTICS:

(A) LENGTH: 638 base pairs
(B) TYPE: nucleic acid
(C) STRANDEDNESS: single
(D) TOPOLOGY: linear (xi) SEQUENCE DESCRIPTION: SEQ ID NO:16:

| | | | | | |
|---|---|---|---|---|---|
| TTCCGTTATG | CACATGCAGA | ATATTCTATC | GGTACTTCAG | CTATTACTCA | TTTTGATGGC | 60 |
| GCAATCCGAG | CCTATCCTCA | AGATGAGTAT | TTAGAAAGAA | TTGATTTAGC | GATAGACCAA | 120 |
| GCTGGTAAGC | ACTCTGACTA | CACGAAATTG | TTCAGATGTG | ATGGATTTAT | GACAGTTGAT | 180 |
| CTTTGGAAGA | GATTATTAAG | TGATTATTTT | AAAGGGAATC | CATTAATTCC | AGAATATCTT | 240 |
| GGTTTAGCTC | AAGATGATAT | AGAAATAGAA | CAGAAAGAGA | CTACAAATGA | AGATGTATCA | 300 |
| CCAACTGATA | TTGAAGAGCC | TATAGTAGAA | AATGAATTAG | CTGCATTTAT | TAGCCTTACA | 360 |
| CATAGCGATT | TTCCTGATGA | ATCTTATATT | CAGCCATCGA | CATAGCATTA | CCTGATGGGC | 420 |
| AACCTTACGA | ATAATAGAAA | CTGGGTGCGG | GGCTATTGAT | GAATTCATCC | NCAGTAAATT | 480 |
| TGGATATNAC | AAAATATAAC | TCGATTGCAT | TTGGATGATG | GAATACTAAA | TCTGGCAAAA | 540 |
| GTAACTTTGG | AGCTACTAGT | AACCTCTCTT | TTTGAGATGC | AAAATTTTCT | TTTAGGGTTT | 600 |
| CTTATTCTCT | ACTTTACGGA | TATTGGAGCA | TAACGGGA | | | 638 |

(2) INFORMATION FOR SEQ ID NO:17:

(i) SEQUENCE CHARACTERISTICS:
(A) LENGTH: 286 base pairs
(B) TYPE: nucleic acid
(C) STRANDEDNESS: single
(D) TOPOLOGY: linear (xi) SEQUENCE DESCRIPTION: SEQ ID NO:17:

| | | | | | |
|---|---|---|---|---|---|
| ACTGATGGAT | GTCGCCGGAG | GCGAGGGGCC | TTATCTGATG | CTCGGCTGCC | TGTTCGTGAT | 60 |
| GTGCGCGGCG | ATTGGGCTGT | TTATCTCAAA | CACCGCCACG | GCGGTGCTGA | TGGCGCCTAT | 120 |
| TGCCTTAGCG | GCGGCGAAGT | CAATGGGCGT | CTCACCCTAT | CCTTTTGCCA | TGGTGGTGGC | 180 |
| GATGGCGGCT | TCGGCGGCGT | TTATGACCCC | GGTCTCCTCG | CCGGTTAACA | CCCTGGTGCT | 240 |
| TGGCCCTGGC | AAGTACTCAT | TTAGCGATTT | TGTCAAAATA | GGCGTG | | 286 |

(2) INFORMATION FOR SEQ ID NO:18:

(i) SEQUENCE CHARACTERISTICS:
(A) LENGTH: 262 base pairs
(B) TYPE: nucleic acid
(C) STRANDEDNESS: single
(D) TOPOLOGY: linear (xi) SEQUENCE DESCRIPTION: SEQ ID NO:18:

| | | | | | |
|---|---|---|---|---|---|
| TCGGTCATAG | CAGCCCCTTC | TTCTCAATTT | CATCTGTCAC | TACCCTGGTG | TAGTATCTCA | 60 |
| TAGCCTTACA | TTTTTATAGC | CTCCTCCCTG | GTCTGTCTTT | TGATTTTCCT | GCCTGTAATC | 120 |
| CATATCACAC | ATAACTGCAA | GTAAACATTT | CTAAAGTGTG | GTTATGCTCA | TGTCACTCCT | 180 |
| GTGNCAAGAA | ATAGTTTCCA | TTACCGTCTT | AATAAAATTC | GGATTTGTTC | TTTNCTATTN | 240 |
| TCACTCTTCA | CCTATGACCG | AA | | | | 262 |

(2) INFORMATION FOR SEQ ID NO:19:

(i) SEQUENCE CHARACTERISTICS:
(A) LENGTH: 261 base pairs
(B) TYPE: nucleic acid
(C) STRANDEDNESS: single
(D) TOPOLOGY: linear (xi) SEQUENCE DESCRIPTION: SEQ ID NO:19:

```
TCGGTCATAG CAAAGCCAGT GGTTTGAGCT CTCTACTGTG TAAACTCCTA AACCAAGGCC    60
ATTTATGATA AATGGTGGCA GGATTTTTAT TATAAACATG TACCCATGCA AATTTCCTAT   120
AACTCTGAGA TATATTCTTC TACATTTAAA CAATAAAAAT AATCTATTTT TAAAAGCCTA   180
ATTTGCGTAG TTAGGTAAGA GTGTTTAATG AGAGGGTATA AGGTATAAAT CACCAGTCAA   240
CGTTTCTCTG CCTATGACCG A                                             261
```

(2) INFORMATION FOR SEQ ID NO:20:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:20:

```
TACAACGAGG CGACGTCGGT AAAATCGGAC ATGAAGCCAC CGCTGGTCTT TTCGTCCGAG    60
CGATAGGCGC CGGCCAGCCA GCGGAACGGT TGCCCGGATG GCGAAGCGAG CCGGAGTTCT   120
TCGGACTGAG TATGAATCTT GTTGTGAAAA TACTCGCCGC CTTCGTTCGA CGACGTCGCG   180
TCGAAATCTT CGANCTCCTT ACGATCGAAG TCTTCGTGGG CGACGATCGC GGTCAGTTCC   240
GCCCCACCGA AATCATGGTT GAGCCGGATG CTGNCCCCGA AGNCCTCGTT TGTN          294
```

(2) INFORMATION FOR SEQ ID NO:21:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (xi) SEQUENCE DESCRIPTION: SEQ ID NO:21:

```
TTGGTAAAGG GCATGGACGC AGACGCCTGA CGTTTGGCTG AAAATCTTTC ATTGATTCGT    60
ATCAATGAAT AGGAAAATTC CCAAAGAGGG AATGTCCTGT TGCTCGCCAG TTTTTNTGTT   120
GTTCTCATGG ANAAGGCAAN GAGCTCTTCA GACTATTGGN ATTNTCGTTC GGTCTTCTGC   180
CAACTAGTCG NCTTGCNANG ATCTTCAT                                      208
```

(2) INFORMATION FOR SEQ ID NO:22:

(i) SEQUENCE CHARACTERISTICS:
        (A) LENGTH: 287 base pairs
        (B) TYPE: nucleic acid
        (C) STRANDEDNESS: single
        (D) TOPOLOGY: linear (xi) SEQUENCE DESCRIPTION: SEQ ID NO:22:

```
NCCNTTGAGC TGAGTGATTG AGATNTGTAA TGGTTGTAAG GGTGATTCAG GCGGATTAGG    60
GTGGCGGGTC ACCCGGCAGT GGGTCTCCCG ACAGGCCAGC AGGATTTGGG GCAGGTACGG   120
NGTGCGCATC GCTCGACTAT ATGCTATGGC AGGCGAGCCG TGGAAGGNGG ATCAGGTCAC   180
GGCGCTGGAG CTTTCCACGG TCCATGNATT GNGATGGCTG TTCTAGGCGG CTGTTGCCAA   240
GCGTGATGGT ACGCTGGCTG GAGCATTGAT TTCTGGTGCC AAGGTGG                 287
```

(2) INFORMATION FOR SEQ ID NO:23:

(i) SEQUENCE CHARACTERISTICS:
        (A) LENGTH: 204 base pairs (B) TYPE: nucleic acid
        (C) STRANDEDNESS: single
        (D) TOPOLOGY: linear (xi) SEQUENCE DESCRIPTION: SEQ ID NO:23:

TTGGGTAAAG GGAGCAAGGA GAAGGCATGG AGAGGCTCAN GCTGGTCCTG GCCTACGACT        60

GGGCCAAGCT GTCGCCGGGG ATGGTGGAGA ACTGAAGCGG GACCTCCTCG AGGTCCTCCG       120

NCGTTACTTC NCCGTCCAGG AGGAGGGTCT TTCCGTGGTC TNGGAGGAGC GGGGGGAGAA       180

GATNCTCCTC ATGGTCNACA TCCC                                              204

(2) INFORMATION FOR SEQ ID NO:24:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (xi) SEQUENCE DESCRIPTION: SEQ ID NO:24:

TGGATTGGTC AGGAGCGGGT AGAGTGGCAC CATTGAGGGG ATATTCAAAA ATATTATTTT        60

GTCCTAAATG ATAGTTGCTG AGTTTTTCTT TGACCCATGA GTTATATTGG AGTTTATTTT       120

TTAACTTTCC AATCGCATGG ACATGTTAGA CTTATTTTCT GTTAATGATT NCTATTTTA        180

TTAAATTGGA TTTGAGAAAT TGGTTNTTAT TATATCAATT TTTGGTATTT GTTGAGTTTG       240

ACATTATAGC TTAGTATGTG ACCA                                              264

(2) INFORMATION FOR SEQ ID NO:25:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (xi) SEQUENCE DESCRIPTION: SEQ ID NO:25:

TTACAACGAG GGGAAACTCC GTCTCTACAA AAATTAAAAA ATTAGCCAGG TGTGGTGGTG        60

TGCACCCGCA ATCCCAGCTA CTTGGGAGGT TGAGACACAA GANTCACCTA NATGTGGGAG       120

GTCAAGGTTG CATGAGTCAT GATTGTGCCA CTGCACTCCA GCCTGGGTGA CAGACCGAGA       180

CCCTGCCTCA ANAGANAAAG AATAGGAAGT TCAGAAATCN TGGNTGTGGN GCCCAGCAAT       240

CTGCATCTAT NCAACCCCTG CAGGCAANGC TGATGCAGCC TANGTTCAAG AGCTGCTGTT       300

TCTGGAGGCA GCAGTTNGGG CTTCCATCCA GTATCACGGC CACACTCGCA CNAGCCATCT       360

GTCCTCCGTN TGTNAC                                                       376

(2) INFORMATION FOR SEQ ID NO:26:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO:26:

TTACAACGAG GGGAAACTCC GTCTCTACAA AAATTAAAAA ATTAGCCAGG TGTGGTGGTG        60

TGCACCTGTA ATCCCAGCTA CTTGGGCGGC TGAGACACAA GAACCACCTA AATGTGGGAG       120

GGTCAAGGTT GCATGAGTCA TGATCGCGCC ACTGCACTCC AGCCTGGGTG ACAGACTGAG       180

ACCCTGCCTC AAAAGAAAAA GAATAGGAAG TTCAGAAACC CTGGGTGTGG NGCCCAGCAA       240

```
TCTGCATTTA AACAATCCCT GCAGGCAATG CTGATGCAGC CTAAGTTCAA GAGCTGCTGT      300

TCTGGAGGCA GNAGTAAGGG CTTCCATCCA GCATCACGGN CAACACTGCA AAAGCACCTG      360

TCCTCGTTGG TA                                                          372

(2) INFORMATION FOR SEQ ID NO:27:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (xi) SEQUENCE DESCRIPTION: SEQ ID NO:27:

TTCTGTCCAC ATCTACAAGT TTTATTTATT TTGTGGGTTT TCAGGGTGAC TAAGTTTTTC       60

CCTACATTGA AAAGAGAAGT TGCTAAAAGG TGCACAGGAA ATCATTTTTT TAAGTGAATA      120

TGATAATATG GGTCCGTGCT TAATACAACT GAGACATATT TGTTCTCTGT TTTTTTAGAG      180

TCACCTCTTA AAGTCCAATC CCACAATGGT GAAAAAAAA TAGAAAGTAT TTGTTCTACC       240

TTTAAGGAGA CTGCAGGGAT TCTCCTTGAA AACGGAGTAT GGAATCAATC TTAAATAAAT      300

ATGAAATTGG TTGGTCTTCT GGGATAAGAA ATTCCCAACT CAGTGTGCTG AAATTCACCT      360

GACTTTTTTT GGGAAAAAAT AGTCGAAAAT GTCAATTTGG TCCATAAAAT ACATGTTACT      420

ATTAAAAGAT ATTTAAAGAC AAATTCTTTC AGAGCTCTAA GATTGGTGTG GACAGAA        477

(2) INFORMATION FOR SEQ ID NO:28:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (xi) SEQUENCE DESCRIPTION: SEQ ID NO:28:

TCTNCAACCT CTTGANTGTC AAAAACCTTN TAGGCTATCT CTAAAAGCTG ACTGGTATTC       60

ATTCCAGCAA AATCCCTCTA GTTTTTGGAG TTTCCTTTTA CTATCTGGGG CTGCCTGAGC      120

CACAAATGCC AAATTAAGAG CATGGCTATT TTCGGGGGCT GACAGGTCAA AAGGGGTGTA      180

AATCCGATAA GCCTCCTGGA GGTGCTCTAA AAACACTCC GGTGACTCAT CATGCCCCTG       240

GACGACTTCA ATCGNCTTAG ACAAGTTTAT AGGTTTCTGG GCAGCTCCCT GAATACCCAC      300

GAGGAGATAC CGGTGGAAAT CGTCAAAAGT CTCCCTCCA CTTGAGAAAT TTGGGTCCCA       360

ATTAGGTCCC AATTGGGTCT CTAATCACTA TTCCTCTAGC TTCCTCCTCC GGNCTATTGG      420

TTGATGTGAG GTTGAAGA                                                    438

(2) INFORMATION FOR SEQ ID NO:29:

(i) SEQUENCE CHARACTERISTICS:
        (A) LENGTH: 620 base pairs
        (B) TYPE: nucleic acid
        (C) STRANDEDNESS: single
        (D) TOPOLOGY: linear (xi) SEQUENCE DESCRIPTION: SEQ ID NO:29:

AAGAGGGTAC CAGCCCCAAG CCTTGACAAC TTCCATAGGG TGTCAAGCCT GTGGGTGCAC       60

AGAAGTCAAA AATTGAGTTT TGGGATCCTC AGCCTAGATT TCAGAGGATA TAAAGAAACA      120

CCTAACACCT AGATATTCAG ACAAAAGTTT ACTACAGGGA TGAAGCTTTC ACGGAAAACC      180

TCTACTAGGA AAGTACAGAA GAGAAATGTG GGTTTGGAGC CCCCAAACAG AATCCCCTCT      240
```

```
AGAACACTGC CTAATGAAAC TGTGAGAAGA TGGCCACTGT CATCCAGACA CCAGAATGAT      300

AGACCCACCA AAAACTTATG CCATATTGCC TATAAAACCT ACAGACACTC AATGCCAGCC      360

CCATGAAAAA AAAACTGAGA AGAAGACTGT NCCCTACAAT GCCACGGAG CAGAACTGCC       420

CCAGGCCATG GAAGCACAGC TCTTATATCA ATGTGACCTG GATGTTGAGA CATGGAATCC      480

NANGAAATCN TTTTAANACT TCCACGGTTN AATGACTGCC CTATTANATT CNGAACTTAN      540

ATCCNGGCCT GTGACCTCTT TGCTTTGGCC ATTCCCCCTT TTTGGAATGG CTNTTTTTTT      600

CCCATGCCTG TNCCCTCTTA                                                  620

(2) INFORMATION FOR SEQ ID NO:30:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO:30:

TTACAACGAG GGGGTCAATG TCATAAATGT CACAATAAAA CAATCTCTTC TTTTTTTTTT       60

TTTTTTTTTT TTTTTTTTTT TTTTTTTTTT TTTTTTTTTT                            100

(2) INFORMATION FOR SEQ ID NO:31:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (xi) SEQUENCE DESCRIPTION: SEQ ID NO:31:

TAGTCTATGC GCCGGACAGA GCAGAATTAA ATTGGAAGTT GCCCTCCGGA CTTTCTACCC       60

ACACTCTTCC TGAAAAGAGA AAGAAAAGAG GCAGGAAAGA GGTTAGGATT TCATTTTCAA      120

GAGTCAGCTA ATTAGGAGAG CAGAGTTTAG ACAGCAGTAG GCACCCCATG ATACAAACCA      180

TGGACAAAGT CCCTGTTTAG TAACTGCCAG ACATGATCCT GCTCAGGTTT TGAAATCTCT      240

CTGCCCATAA AAGATGGAGA GCAGGAGTGC CATCCACATC AACACGTGTC CAAGAAAGAG      300

TCTCAGGGAG ACAAGGGTAT CAAAAAACAA GATTCTTAAT GGGAAGGAAA TCAAACCAAA      360

AAATTAGATT TTTCTCTACA TATATATAAT ATACAGATAT TTAACACATT ATTCCAGAGG      420

TGGCTCCAGT CCTTGGGGCT TGAGAGATGG TGAAAACTTT TGTTCCACAT TAACTTCTGC      480

TCTCAAATTC TGAAGTATAT CAGAATGGGA CAGGCAATGT TTTGCTCCAC ACTGGGGCAC      540

AGACCCAAAT GGTTCTGTGC CCGAAGAAGA GAAGCCCGAA AGACATGAAG GATGCTTAAG      600

GGGGGTTGGG AAAGCCAAAT TGGTANTATC TTTTCCTCCT GCCTGTGTTC CNGAAGTCTC      660

CNCTGAAGGA ATTCTTAAAA CCCTTTGTGA GGAAATGCCC CCTTACCATG ACAANTGGTC      720

CCATTGCTTT TAGGGNGATG GAAACACCAA GGGTTTTGAT CC                         762

(2) INFORMATION FOR SEQ ID NO:32:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (xi) SEQUENCE DESCRIPTION: SEQ ID NO:32:

TAGTCTATGC GTGTATTAAC CTCCCCTCCC TCAGTAACAA CCAAAGAGGC AGGAGCTGTT       60
```

```
ATTACCAACC CCATTTTACA GATGCATCAA TAATGACAGA GAAGTGAAGT GACTTGCGCA      120

CACAACCAGT AAATTGGCAG AGTCAGATTT GAATCCATGG AGTCTGGTCT GCACTTTCAA      180

TCACCGAATA CCCTTTCTAA GAAACGTGTG CTGAATGAGT GCATGGATAA ATCAGTGTCT      240

ACTCAACATC TTTGCCTAGA TATCCCGCAT AGACTA                                276
```

(2) INFORMATION FOR SEQ ID NO:33:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (xi) SEQUENCE DESCRIPTION: SEQ ID NO:33:

```
TAGTAGTTGC CAAATATTTG AAAATTTACC CAGAAGTGAT TGAAAACTTT TTGGAAACAA       60

AAACAAATAA AGCCAAAAGG TAAAATAAAA ATATCTTTGC ACTCTCGTTA TTACCTATCC      120

ATAACTTTTT CACCGTAAGC TCTCCTGCTT GTTAGTGTAG TGTGGTTATA TTAAACTTTT      180

TAGTTATTAT TTTTTATTCA CTTTTCCACT AGAAAGTCAT TATTGATTTA GCACACATGT      240

TGATCTCATT TCATTTTTTC TTTTTATAGG CAAAATTTGA TGCTATGCAA CAAAAATACT      300

CAAGCCCATT ATCTTTTTTC CCCCCGAAAT CTGAAAATTG CAGGGGACAG AGGGAAGTTA      360

TCCCATTAAA AAATTGTAAA TATGTTCAGT TTATGTTTAA AAATGCACAA AACATAAGAA      420

AATTGTGTTT ACTTGAGCTG CTGATTGTAA GCAGTTTTAT CTCAGGGGCA ACTACTA        477
```

(2) INFORMATION FOR SEQ ID NO:34:

(i) SEQUENCE CHARACTERISTICS:
        (A) LENGTH: 631 base pairs
        (B) TYPE: nucleic acid
        (C) STRANDEDNESS: single
        (D) TOPOLOGY: linear (xi) SEQUENCE DESCRIPTION: SEQ ID NO:34:

```
TAGTAGTTGC CAATTCAGAT GATCAGAAAT GCTGCTTTCC TCAGCATTGT CTTGTTAAAC       60

CGCATGCCAT TTGGAACTTT GGCAGTGAGA AGCCAAAAGG AAGAGGTGAA TGACATATAT      120

ATATATATAT ATTCAATGAA AGTAAAATGT ATATGCTCAT ATACTTTCTA GTTATCAGAA      180

TGAGTTAAGC TTTATGCCAT TGGGCTGCTG CATATTTTAA TCAGAAGATA AAGAAAATC      240

TGGGCATTTT TAGAATGTGA TACATGTTTT TTTAAAACTG TTAAATATTA TTTCGATATT      300

TGTCTAAGAA CCGGAATGTT CTTAAAATTT ACTAAAACAG TATTGTTTGA GGAAGAGAAA      360

ACTGTACTGT TTGCCATTAT TACAGTCGTA CAAGTGCATG TCAAGTCACC CACTCTCTCA      420

GGCATCAGTA TCCACCTCAT AGCTTTACAC ATTTTGACGG GGAATATTGC AGCATCCTCA      480

GGCCTGACAT CTGGGAAAGG CTCAGATCCA CCTACTGCTC CTTGCTCGTT GATTTGTTTT      540

AAAATATTGT GCCTGGTGTC ACTTTTAAGC CACAGCCCTG CCTAAAAGCC AGCAGAGAAC      600

AGAACCCGCA CCATTCTATA GGCAACTACT A                                    631
```

(2) INFORMATION FOR SEQ ID NO:35:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO:35:

```
TAGTAGTTGC CATCCCATAT TACAGAAGGC TCTGTATACA TGACTTATTT GGAAGTGATC        60

TGTTTTCTCT CCAAACCCAT TTATCGTAAT TTCACCAGTC TTGGATCAAT CTTGGTTTCC       120

ACTGATACCA TGAAACCTAC TTGGAGCAGA CATTGCACAG TTTTCTGTGG TAAAAACTAA       180

AGGTTTATTT GCTAAGCTGT CATCTTATGC TTAGTATTTT TTTTTTACAG TGGGGAATTG       240

CTGAGATTAC ATTTTGTTAT TCATTAGATA CTTTGGGATA ACTTGACACT GTCTTCTTTT       300

TTTCGCTTTT AATTGCTATC ATCATGCTTT TGAAACAAGA ACACATTAGT CCTCAAGTAT       360

TACATAAGCT TGCTTGTTAC GCCTGGTGGT TTAAAGGACT ATCTTTGGCC TCAGGTTCAC       420

AAGAATGGGC AAAGTGTTTC CTTATGTTCT GTAGTTCTCA ATAAAAGATT GCCAGGGGCC       480

GGGTACTGTG GCTCGCACTG TAATCCCAGC ACTTTGGGAA GCTGAGGCTG GCGGATCATG       540

TTAGGGCAGG TGTTCGAAAC CAGCCTGGGC AACTACTA                              578

(2) INFORMATION FOR SEQ ID NO:36:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (xi) SEQUENCE DESCRIPTION: SEQ ID NO:36:

TAGTAGTTGC CTGTAATCCC AGCAACTCAG GAGGCTGGGG CAGGAGAATC AGTTGAACCT        60

GGGAGGCAGA AGTTGTAATT AGCAAAGATC GCACCATTGC ACTTCAGCCT GGGCAACAAG       120

AGTGAGATTC CATCTCAAAA ACAAAAAAAA GAAAAGAAA AGAAAAGGAA AAAACGTATA       180

AACCCAGCCA AAACAAAATG ATCATTCTTT TAATAAGCAA GACTAATTTA ATGTGTTTAT       240

TTAATCAAAG CAGTTGAATC TTCTGAGTTA TTGGTGAAAA TACCCATGTA GTTAATTTAG       300

GGTTCTTACT TGGGTGAACG TTTGATGTTC ACAGGTTATA AAATGGTTAA CAAGGAAAAT       360

GATGCATAAA GAATCTTATA AACTACTAAA ATAAATAAA ATATAAATGG ATAGGTGCTA       420

TGGATGGAGT TTTTGTGTAA TTTAAAATCT TGAAGTCATT TTGGATGCTC ATTGGTTGTC       480

TGGTAATTTC CATTAGGAAA AGGTTATGAT ATGGGGAAAC TGTTTCTGGA AATTGCGGAA       540

TGTTTCTCAT CTGTAAAATG CTAGTATCTC AGGGCAACTA CTA                        583

(2) INFORMATION FOR SEQ ID NO:37:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (xi) SEQUENCE DESCRIPTION: SEQ ID NO:37:

GATCTACTAG TCATNTGGAT TCTATCCATG GCAGCTAAGC CTTTCTGAAT GGATTCTACT        60

GCTTTCTTGT TCTTTAATCC AGACCCTTAT ATATGTTTAT GTTCACAGGC AGGGCAATGT       120

TTAGTGAAAA CAATTCTAAA TTTTTTATTT TGCATTTTCA TGCTAATTTC CGTCACACTC       180

CAGCAGGCTT CCTGGGAGAA TAAGGAGAAA TACAGCTAAA GACATTGTCC CTGCTTACTT       240

ACAGCCTAAT GGTATGCAAA ACCACTTCAA TAAAGTAACA GGAAAAGTAC TAACCAGGTA       300

GAATGGACCA AAACTGATAT AGAAAAATCA GAGGAAGAGA GGAACAAATA TTTACTGAGT       360

CCTAGAATGT ACAAGGCTTT TTAATTACAT ATTTTATGTA AGGCCTGCAA AAAACAGGTG       420

AGTAATCAAC ATTTGTCCCA TTTTACATAT AAGGAAACTG AAGCTTAAAT TGAATAATTT       480

AATGCATAGA TTTTATAGTT AGACCATGTT CAGGTCCCTA TGTTATACTT ACTAGCTGTA       540
```

```
TGAATATGAG AAAATAATTT TGTTATTTTC TTGGCATCAG TATTTTCATC TGCAAAATAA        600

AGCTAAAGTT ATTTAGCAAA CAGTCAGCAT AGTGCCTGAT ACATAGTAGG TGCTCCAAAC        660

ATGATTACNC TANTATTNGG TATTANAAAA ATCCAATATA GGCNTGGATA AAACCG            716
```

(2) INFORMATION FOR SEQ ID NO:38:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (xi) SEQUENCE DESCRIPTION: SEQ ID NO:38:

```
TTCTGTCCAC ATATCATCCC ACTTTAATTG TTAATCAGCA AAACTTTCAA TGAAAAATCA         60

TCCATTTTAA CCAGGATCAC ACCAGGAAAC TGAAGGTGTA TTTTTTTTTA CCTTAAAAAA        120

AAAAAAAAAA ACCAAACAAA CCAAAACAGA TTAACAGCAA AGAGTTCTAA AAAATTTACA        180

TTTCTCTTAC AACTGTCATT CAGAGAACAA TAGTTCTTAA GTCTGTTAAA TCTTGGCATT        240

AACAGAGAAA CTTGATGAAN AGTTGTACTT GGAATATTGT GGATTTTTTT TTTTGTCTAA        300

TCTCCCCCTA TTGTTTTGCC AACAGTAATT TAAGTTTGTG TGGAACATCC CCGTAGTTGA        360

AGTGTAAACA ATGTATAGGA AGGAATATAT GATAAGATGA TGCATCACAT ATGCATTACA        420

TGTAGGGACC TTCACAACTT CATGCACTCA GAAAACATGC TTGAAGAGGA GGAGAGGACG        480

GCCCAGGGTC ACCATCCAGG TGCCTTGAGG ACAGAGAATG CAGAAGTGGC ACTGTTGAAA        540

TTTAGAAGAC CATGTGTGAA TGGTTTCAGG CCTGGGATGT TTGCCACCAA GAAGTGCCTC        600

CGAGAAATTT CTTTCCCATT TGGAATACAG GGTGGCTTGA TGGGTACGGT GGGTGACCCA        660

ACGAAGAAAA TGAAATTCTG CCCTTTCC                                          688
```

(2) INFORMATION FOR SEQ ID NO:39:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (xi) SEQUENCE DESCRIPTION: SEQ ID NO:39:

```
TAGTAGTTGC CGCNNACCTA AAANTTGGAA AGCATGATGT CTAGGAAACA TANTAAAATA         60

GGGTATGCCT ATGTGCTACA GAGAGATGTT AGCATTTAAA GTGCATANTT TTATGTATTT        120

TGACAAATGC ATATNCCTCT ATAATCCACA ACTGATTACG AAGCTATTAC AATTAAAAAG        180

TTTGGCCGGG CGTGGTGGGC GGTGGCTGAC GCCTGTAATC CCAGCACTTT GGGAGGCCGA        240

GGCACGCGGA TCACGAGGTC GGGAGTTCAA GACCATCCTG GCTAACACGG TGAAAGTCCA        300

TCTCTACTAA AAATACGAAA AAATTACCCC GGCGTGGTGG CGGGCGCCTG TAGTCCCAGC        360

TACTCCGGAG GCTGAGGCAG GAGAATGGCG TGAACCCAGG ACACGGAGCT TGCAGTGTGC        420

CAACATCACG TCACTGCCCT CCAGCCTGGG GGACAGGAAC AAGANTCCCG TCCTCANAAA        480

AGAAAAATAC TACTNATANT TTCNACTTTA TTTTAANTTA CACAGAACTN CCTCTTGGTA        540

CCCCCTTACC ATTCATCTCA CCCACCTCCT ATAGGGCACN NCTAA                       585
```

(2) INFORMATION FOR SEQ ID NO:40:

(i) SEQUENCE CHARACTERISTICS:
        (A) LENGTH: 475 base pairs
        (B) TYPE: nucleic acid (C) STRANDEDNESS: single
                (D) TOPOLOGY: linear (xi) SEQUENCE DESCRIPTION: SEQ ID NO:40:

```
TCTGTCCACA CCAATCTTAG AAGCTCTGAA AAGAATTTGT CTTTAAATAT CTTTTAATAG      60

TAACATGTAT TTTATGGACC AAATTGACAT TTTCGACTGT TTTTTCCAAA AAAGTCAGGT     120

GAATTTCAGC ACACTGAGTT GGGAATTTCT TATCCCAGAA GACCAACCAA TTTCATATTT     180

ATTTAAGATT GATTCCATAC TCCGTTTTCA AGGAGAATCC CTGCAGTCTC CTTAAAGGTA     240

GAACAAATAC TTCCTATTTT TTTTTCACCA TTGTGGGATT GGACTTTAAG AGGTGACTCT     300

AAAAAAACAG AGAACAAATA TGTCTCAGTT GTATTAAGCA CGGACCCATA TTATCATATT     360

CACTTAAAAA AATGATTTCC TGTGCACCTT TTGGCAACTT CTCTTTTCAA TGTAGGGAAA     420

AACTTAGTCA CCCTGAAAAC CCACAAAATA AATAAAACTT GTAGATGTGG ACAGA          475
```

(2) INFORMATION FOR SEQ ID NO:41:

(i) SEQUENCE CHARACTERISTICS:
                (A) LENGTH: 423 base pairs
                (B) TYPE: nucleic acid
                (C) STRANDEDNESS: single
                (D) TOPOLOGY: linear (xi) SEQUENCE DESCRIPTION: SEQ ID NO:41:

```
TAAGAGGGTA CATCGGGTAA GAACGTAGGC ACATCTAGAG CTTAGAGAAG TCTGGGGTAG      60

GAAAAAAATC TAAGTATTTA TAAGGGTATA GGTAACATTT AAAAGTAGGG CTAGCTGACA     120

TTATTTAGAA AGAACACATA CGGAGAGATA AGGGCAAAGG ACTAAGACCA GAGGAACACT     180

AATATTTAGT GATCACTTCC ATTCTTGGTA AAAATAGTAA CTTTTAAGTT AGCTTCAAGG     240

AAGATTTTTG GCCATGATTA GTTGTCAAAA GTTAGTTCTC TTGGGTTTAT ATTACTAATT     300

TTGTTTTAAG ATCCTTGTTA GTGCTTTAAT AAAGTCATGT TATATCAAAC GCTCTAAAAC     360

ATTGTAGCAT GTTAAATGTC ACAATATACT TACCATTTGT TGTATATGGC TGTACCCTCT     420

CTA                                                                   423
```

(2) INFORMATION FOR SEQ ID NO:42:

(i) SEQUENCE CHARACTERISTICS:
                (A) LENGTH: 527 base pairs
                (B) TYPE: nucleic acid
                (C) STRANDEDNESS: single
                (D) TOPOLOGY: linear (xi) SEQUENCE DESCRIPTION: SEQ ID NO:42:

```
TCTCCTAGGC TAATGTGTGT GTTTCTGTAA AAGTAAAAAG TTAAAAATTT TAAAAATAGA      60

AAAAAGCTTA TAGAATAAGA ATATGAAGAA AGAAAATATT TTTGTACATT TGCACAATGA     120

GTTTATGTTT TAAGCTAAGT GTTATTACAA AAGAGCCAAA AAGGTTTTAA AAATTAAAAC     180

GTTTGTAAAG TTACAGTACC CTTATGTTAA TTTATAATTG AAGAAAGAAA AACTTTTTTT     240

TATAAATGTA GTGTAGCCTA AGCATACAGT ATTTATAAAG TCTGGCAGTG TTCAATAATG     300

TCCTAGGCCT TCACATTCAC TCACTGACTC ACCCAGAGCA ACTTCCAGTC CTGTAAGCTC     360

CATTCGTGGT AAGTGCCCTA TACAGGTGCA CCATTTATTT TACAGTATTT TTACTGTACC     420

TTCTCTATGT TTCCATATGT TTCGATATAC AAATACCACT GGTTACTATN GCCCNACAGG     480

TAATTCCAGT AACACGGCCT GTATACGTCT GGTANCCCTA GNGAAGA                   527
```

(2) INFORMATION FOR SEQ ID NO:43:

(i) SEQUENCE CHARACTERISTICS:
    (A) LENGTH: 331 base pairs
    (B) TYPE: nucleic acid
    (C) STRANDEDNESS: single
    (D) TOPOLOGY: linear (xi) SEQUENCE DESCRIPTION: SEQ ID NO:43:

| | | | | | |
|---|---|---|---|---|---|
| TCTTCAACCT | CGTAGGACAA | CTCTCATATG | CCTGGGCACT | ATTTTTAGGT | TACTACCTTG | 60 |
| GCTGCCCTTC | TTTAAGAAAA | AAAAAAGAAG | AAAAAAGAAC | TTTTCCACAA | GTTTCTCTTC | 120 |
| CTCTAGTTGG | AAAATTAGAG | AAATCATGTT | TTTAATTTTG | TGTTATTTCA | GATCACAAAT | 180 |
| TCAAACACTT | GTAAACATTA | AGCTTCTGTT | CAATCCCCTG | GAAGAGGAT | TCATTCTGAT | 240 |
| ATTTACGGTT | CAAAAGAAGT | TGTAATATTG | TGCTTGGAAC | ACAGAGAACC | AGTTATTAAC | 300 |
| TTCCTACTAC | TATTATATAA | TAAATAATAA | C | | | 331 |

(2) INFORMATION FOR SEQ ID NO:44:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (xi) SEQUENCE DESCRIPTION: SEQ ID NO:44:

GGCTTAGTAG TTGCCAGGCA AAATARCGTT GATTCTCCTC AGGAGCCACC CCCAACACCC     60
CTGTTTGCTT CTAGACCTAT ACCTAGACTA AAGTCCCAGC AGACCCCTAG AGGTGAGGTT    120
CAGAGTGACC CTTGAGGAGA TGTGCTACAC TAGAAAAGAA CTGCTTGAGT TTTCTAATTT    180
ATATAAGCAG AAATCTGGAG AAGAGTCATA GGAATGGATA TTAAGGGTGT GAGATAATGG    240
CGGAAGGAAT ATAGAGTTGG ATCAGGCTGG ACTTATTGAT TTGAACCCAC TAAGTAGAGA    300
TTCTGCTTTT GATGTTGCAG CTCAGGGAGT TAAAAAAGGT TTTAATGGTT CTAATAGTTT    360
ATTTGCTTGG TTAGCTGAAA TATGGATAAA AGATGGCCCA CTGTGAGCAA GCTGGAAATG    420
CCTGATCTCT CTCAGTTTAA TGTAGAGGAA GGGATCCAAA AGTTTAGGGA GANTTGGATG    480
CTGGRAKTGG ATTGGTCACT TTGRGACCTA CCCWTCCCAG CTGGGAGGGT CCAGAAGATA    540
CACCCTTGAC CAACGCTTTG CGAAATGGAT TTGTGATGGC GGCAACTACT AA            592

(2) INFORMATION FOR SEQ ID NO:45:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (xi) SEQUENCE DESCRIPTION: SEQ ID NO:45:

GGCTTAGTAG TTGCCATTGC GAGTGCTTGC TCAACGAGCG TTGAACATGG CGGATTGTCT     60
AGATTCAACG GATTTGAGTT TTACCAGCAA AGCGAACCAA GCGCGGCCCA GAGAATTATG    120
GGTTGGTTGG CTTTGAAAAG ATGGAAATCC TGTAGGCCTA GTCAGAAAAG CCTTCTTGCA    180
GAACAGTTGG TTCTCGGGCG AACGCTCATC AAGATGCCCA TTGGAAAGGC TAGCGTGTAT    240
TTGGGAGAGC CTGATAGCGT GTCTTCTGAT GATGTTTGTG CTTGGACAGT GACAAAAGAT    300
ATGCAAAGCA AGTCCGAACT AGACGTCAAG CTTCGTGAGC AAATTATTGT AGACTCCTAC    360
TTATACTGTG AGGAATGATA GCCAAGGGTG GGACTTTAA GACTAAGGTG GTTTGTACTT    420
GCGCCGATGA TCCCAGGCAG AAAGAMCTGA TCGCTAGTTT TATACGGGCA ACTACTAAGC    480

```
CGAATTCCAG CACACTGGCG GCCGTTACTA ATTGGATCCG ANCTCGGTAC CAGCTTGATG        540

CATASCTTGA GTTWTCTATA NTGTCNC                                            567

(2) INFORMATION FOR SEQ ID NO:46:

(i) SEQUENCE CHARACTERISTICS:
        (A) LENGTH: 908 base pairs
        (B) TYPE: nucleic acid
        (C) STRANDEDNESS: single
        (D) TOPOLOGY: linear (xi) SEQUENCE DESCRIPTION: SEQ ID NO:46:

GAGCGAAAGA CCGAGGGCAG NGNNTANGNG CGANGAAGCG GAGAGGGCCA AAAAGCAACC         60

GCTTTCCCCG GGGGGTGCCG ATTCATTAAG GCAGGTGGAG GACAGGTTTC CCGATGGAAG        120

GCGGCAGGGG CGCAAGCAAT TAATGTGAGT AGGCCATTCA TTAGCACCCG GGCTTAACAT        180

TTAAGCTTCG GGTTGGTATG TGGTGGGAAT TGTGAGCGGA TAACAATTTC ACACAGGAAA        240

CAGCTATGAC CATGATTACG CCAAGCTATT TAGGTGACAT TATAGAATAA CTCAAGTTAT        300

GCATCAAGCT TGGTACCGAG TTCGGATCCA CTAGTAACGG CCGCCAGTGT GTGGAATTCG        360

GCTTAGTAGT TGCCGACCAT GGAGTGCTAC CTAGGCTAGA ATACCTGAGY TCCTCCCTAG        420

CCTCACTCAC ATTAAATTGT ATCTTTTCTA CATTAGATGT CCTCAGCGCC TTATTTCTGC        480

TGGACWATCG ATAAATTAAT CCTGATAGGA TGATAGCAGC AGATTAATTA CTGAGAGTAT        540

GTTAATGTGT CATCCCTCCT ATATAACGTA TTTGCATTTT AATGGAGCAA TTCTGGAGAT        600

AATCCCTGAA GGCAAAGGAA TGAATCTTGA GGGTGAGAAA GCCAGAATCA GTGTCCAGCT        660

GCAGTTGTGG GAGAAGGTGA TATTATGTAT GTCTCAGAAG TGACACCATA TGGGCAACTA        720

CTAAGCCCGA ATTCCAGCAC ACTGGCGGGC GTTACTAATG GATCCGAGCT CGGTACCAAG        780

CTTGATGCAT AGCTTGAGTA TCTATAGTGT CACTAAATAG CCTGGCGTTA TCATGGTCAT        840

AGCTGTTTCC TGTGTGAAAT TGTTATCCGC TCCCAATTCC CCCCACCATA CGAGCCGGAA        900

CATAAAGT                                                                908

(2) INFORMATION FOR SEQ ID NO:47:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (xi) SEQUENCE DESCRIPTION: SEQ ID NO:47:

TGCCAACAAG GAAAGTTTTA AATTTCCCCT TGAGGATTCT TGGTGATCAT CAAATTCAGT         60

GGTTTTTAAG GTTGTTTTCT GTCAAATAAC TCTAACTTTA AGCCAAACAG TATATGGAAG        120

CACAGATAKA ATATTACACA GATAAAAGAG GAGTTGATCA AAAGTARAGA TAGTTGGGGG        180

CTTTAATTTC TGGAACCTAG GTCTCCCCAT CTTCTTCTGT GCTGAGGAAC TTCTTGGAAG        240

CGGGGATTCT AAAGTTCTTT GGAAGACAGT TTGAAAACCA CCATGTTGTT CTCAGTACCT        300

TTATTTTTAA AAAGTAGGTG AACATTTTGA GAGAGAAAAG GGCTTGGTTG AGATGAAGTC        360

CCCCCCCCCC CTTTTTTTTT TTTTAGCTGA AATAGATACC CTATGTTNAA RGAARGGATT        420

ATTATTTACC ATGCCAYTAR SCACATGCTC TTTGATGGGC NYCTCCSTAC CCTCCTTAAG        480

(2) INFORMATION FOR SEQ ID NO:48:

(i) SEQUENCE CHARACTERISTICS:
        (A) LENGTH: 591 base pairs
```

(B) TYPE: nucleic acid
        (C) STRANDEDNESS: single
        (D) TOPOLOGY: linear (xi) SEQUENCE DESCRIPTION: SEQ ID NO:48:

```
AAGAGGGTAC CGAGTGGAAT TCCGCTTCA CTAGTCTGGT GTGGCTAGTC GGTTTCGTGG      60

TGGCCAACAT TACGAACTTC CAACTCAACC GTTCTTGGAC GTTCAAGCGG GAGTACCGGC     120

GAGGATGGTG GCGTGAATTC TGGCCTTTCT TTGCCGTGGG ATCGGTAGCC GCCATCATCG     180

GTATGTTTAT CAAGATCTTC TTTACTAACC CGACCTCTCC GATTTACCTG CCCGAGCCGT     240

GGTTTAACGA GGGGAGGGGG ATCCAGTCAC GCGAGTACTG GTCCCAGATC TTCGCCATCG     300

TCGTGACAAT GCCTATCAAC TTCGTCGTCA ATAAGTTGTG GACCTTCCGA ACGGTGAAGC     360

ACTCCGAAAA CGTCCGGTGG CTGCTGTGCG GTGACTCCCA AAATCTTGAT AACAACAAGG     420

TAACCGAATC GCGCTAAGGA ACCCCGGCAT CTCGGGTACT CTGCATATGC GTACCCCTTA     480

AGCCGAATTC CAGCACACTG GCGGCCGTTA CTAATTGGAT CCGAACTCCG TAACCAAGCC     540

TGATGCGTAA CTTGAGTTAT TCTATAGTGT CCCTAAAATA ACCTGGCGTT A             591
```

(2) INFORMATION FOR SEQ ID NO:49:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO:49:

```
AAGAGGGTAC CTGCCTTGAA ATTTAAATGT CTAAGGAAAR TGGGAGATGA TTAAGAGTTG      60

GTGTGGCYTA GTCACACCAA AATGTATTTA TTACATCCTG CTCCTTTCTA GTTGACAGGA     120

AAGAAAGCTG CTGTGGGGAA AGGAGGGATA AATACTGAAG GGATTTACTA AACAAATGTC     180

CATCACAGAG TTTTCCTTTT TTTTTTTTTG AGACAGAGTC TTGCTCTGTC ACCCAGGCTG     240

GAATGAAGWG GTATGATCTC AGTTGAATGC AACCTCTACC TCCTAGGTTC AAGCGATTCT     300

CATGCCTCAG CCTCCTGAGC AGCTGGGACT ATAGGCGCAT GCTACCATGC CAGGCTAATT     360

TTTATATTTT TATTAGAGAC GGGGTGTTGC CATGTTGGCC AGGCAGGTCT CGAACTCCTG     420

GGCCTCAGAT GATCTGCCCC ACCGTACCCT CTTA                                454
```

(2) INFORMATION FOR SEQ ID NO:50:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (xi) SEQUENCE DESCRIPTION: SEQ ID NO:50:

```
AAGAGGGTAC CAAAAAAAAG AAAAAGGAAA AAAAGAAAAA CAACTTGTAT AAGGCTTTCT      60

GCTGCATACA GCTTTTTTTT TTTAAATAAA TGGTGCCAAC AAATGTTTTT GCATTCACAC     120

CAATTGCTGG TTTTGAAATC GTACTCTTCA AAGGTATTTG TGCAGATCAA TCCAATAGTG     180

ATGCCCCGTA GGTTTTGTGG ACTGCCCACG TTGTCTACCT TCTCATGTAG GAGCCATTGA     240

GAGACTGTTT GGACATGCCT GTGTTCATGT AGCCGTGATG TCCGGGGCC GTGTACATCA      300

TGTTACCGTG GGGTGGGGTC TGCATTGGCT GCTGGGCATA TGGCTGGGTG CCCATCATGC     360

CCATCTGCAT CTGCATAGGG TATTGGGGCG TTTGATCCAT ATAGCCATGA TTGCTGTGGT     420

AGCCACTGTT CATCATTGGC TGGGACATGC TGTTACCCTC TTA                      463
```

(2) INFORMATION FOR SEQ ID NO:51:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (xi) SEQUENCE DESCRIPTION: SEQ ID NO:51:

```
CTTCAACCTC CCAAAGTGCT GGGATTACAG GACTGAGCCA CCACGCTCAG CCTAAGCCTC      60

TTTTTCACTA CCCTCTAAGC GATCTACCAC AGTGATGAGG GGCTAAAGAG CAGTGCAATT     120

TGATTACAAT AATGGAACTT AGATTTATTA ATTAACAATT TTTCCTTAGC ATGTTGGTTC     180

CATAATTATT AAGAGTATGG ACTTACTTAG AAATGAGCTT TCATTTTAAG AATTTCATCT     240

TTGACCTTCT CTATTAGTCT GAGCAGTATG ACACTATACG TATTTTATTT AACTAACCTA     300

CCTTGAGCTA TTACTTTTTA AAAGGCTATA TACATGAATG TGTATTGTCA ACTGTAAAGC     360

CCCACAGTAT TTAATTATAT CATGATGTCT TTGAGGTTG                            399
```

(2) INFORMATION FOR SEQ ID NO:52:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (xi) SEQUENCE DESCRIPTION: SEQ ID NO:52:

```
CTTCAACCTC AATCAACCTT GGTAATTGAT AAAATCATCA CTTAACTTTC TGATATAATG      60

GCAATAATTA TCTGAGAAAA AAAAGTGGTG AAAGATTAAA CTTGCATTTC TCTCAGAATC     120

TTGAAGGATA TTTGAATAAT TCAAAAGCGG AATCAGTAGT ATCAGCCGAA GAAACTCACT     180

TAGCTAGAAC GTTGGACCCA TGGATCTAAG TCCCTGCCCT TCCACTAACC AGCTGATTGG     240

TTTTGTGTAA ACCTCCTACA CGCTTGGGCT TGGTCGCCTC ATTTGTCAAA GTAAAGGCTG     300

AAATAGGAAG ATAATGAACC GTGTCTTTTT GGTCTCTTTT CCATCCATTA CTCTGATTTT     360

ACAAAGAGGC CTGTATTCCC CTGGTGAGGT TG                                   392
```

(2) INFORMATION FOR SEQ ID NO:53:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (xi) SEQUENCE DESCRIPTION: SEQ ID NO:53:

```
TTCGGGTGAT GCCTCCTCAG GCTACAGTGA AGACTGGATT ACAGAAAGGT GCCAGCGAGA      60

TTTCAGATTC CTGTAAACCT CTAAAGAAAA GGAGTCGCGC CTCAACTGAT GTAGAAATGA     120

CTAGTTCAGC ATACNGAGAC ACNTCTGACT CCGATTCTAG AGGACTGAGT GACCTGCAN     179
```

(2) INFORMATION FOR SEQ ID NO:54:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (xi) SEQUENCE DESCRIPTION: SEQ ID NO:54:

-continued

```
TTCGGGTGAT GCCTCCTCAG GCTACATCAT NATAGAAGCA AAGTAGAANA ATCNNGTTTG      60

TGCATTTTCC CACANACAAA ATTCAAATGA NTGGAAGAAA TTGGGANAGT AT             112
```

(2) INFORMATION FOR SEQ ID NO:55:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (xi) SEQUENCE DESCRIPTION: SEQ ID NO:55:

```
TGAGCTTCCG CTTCTGACAA CTCAATAGAT AATCAAAGGA CAACTTTAAC AGGGATTCAC      60

AAAGGAGTAT ATCCAAATGC CAATAAACAT ATAAAAAGGA ATTCAGCTTC ATCATCATCA     120

GAAGWATGCA AATTAAAACC ATAATGAGAA ACCACTATGT CCCACTAGAA TAGATAAAAT     180

CTTAAAAGAC TGGTAAAACC AAGTGTTGGT AAGGCAAGAG GAGCA                    225
```

(2) INFORMATION FOR SEQ ID NO:56:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (xi) SEQUENCE DESCRIPTION: SEQ ID NO:56:

```
GCTCCTCTTG CCTTACCAAC ACATTCTCAA AAACCTGTTA GAGTCCTAAG CATTCTCCTG      60

TTAGTATTGG GATTTTACCC CTGTCCTATA AAGATGTTAT GTACCAAAAA TGAAGTGGAG     120

GGCCATACCC TGAGGGAGGG GAGGGATCTC TAGTGTTGTC AGAAGCGGAA GCTCA         175
```

(2) INFORMATION FOR SEQ ID NO:57:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (xi) SEQUENCE DESCRIPTION: SEQ ID NO:57:

```
AGCCATTTAC CACCCATGGA TGAATGGATT TTGTAATTCT AGCTGTTGTA TTTTGTGAAT      60

TTGTTAATTT TGTTGTTTTT CTGTGAAACA CATACATTGG ATATGGGAGG TAAAGGAGTG     120

TCCCAGTTGC TCCTGGTCAC TCCCTTTATA GCCATTACTG TCTTGTTTCT TGTAACTCAG     180

GTTAGGTTTT GGTCTCTCTT GCTCCACTGC AAAAAAAAAA AAA                      223
```

(2) INFORMATION FOR SEQ ID NO:58:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (xi) SEQUENCE DESCRIPTION: SEQ ID NO:58:

```
GTTCGAAGGT GAACGTGTAG GTAGCGGATC TCACAACTGG GGAACTGTCA AAGACGAATT      60

AACTGACTTG GATCAATCAA ATGTGACTGA GGAAACACCT GAAGGTGAAG AACATCATCC     120

AGTGGCAGAC ACTGAAAATA AGGAGAATGA AGTTGAAGAG GTAAAAGAGG AGGGTCCAAA     180

AGAGATGACT TTGGATGGGT GGTAAATGGC T                                   211
```

(2) INFORMATION FOR SEQ ID NO:59:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (xi) SEQUENCE DESCRIPTION: SEQ ID NO:59:

```
GCTCCTCTTG CCTTACCAAC TTTGCACCCA TCATCAACCA TGTGGCCAGG TTTGCAGCCC      60

AGGCTGCACA TCAGGGGACT GCCTCGCAAT ACTTCATGCT GTTGCTGCTG ACTGATGGTG     120

CTGTGACGGA TGTGGAAGCC ACACGTGAGG CTGTGGTGCG TGCCTCGAAC CTGCCCATGT     180

CAGTGATCAT TATGGGTGGT AAATGGCT                                        208
```

(2) INFORMATION FOR SEQ ID NO:60:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (xi) SEQUENCE DESCRIPTION: SEQ ID NO:60:

```
AGCCATTTAC CACCCATACT AAATTCTAGT TCAAACTCCA ACTTCTTCCA TAAAACATCT      60

AACCACTGAC ACCAGTTGGC AATAGCTTCT TCCTTCTTTA ACCTCTTAGA GTATTTATGG     120

TCAATGCCAC ACATTTCTGC AACTGAATAA AGTTGGTAAG GCAAGAGGAG C              171
```

(2) INFORMATION FOR SEQ ID NO:61:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO:61:

```
CGGGTGATGC CTCCTCAGGC TTTGGTGTGT CCACTCNACT CACTGGCCTC TTCTCCAGCA      60

ACTGGTGAAN ATGTCCTCAN GAAAANCNCC ACACGCNGCT CAGGGTGGGG TGGGAANCAT     120

CANAATCATC NGGC                                                       134
```

(2) INFORMATION FOR SEQ ID NO:62:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (xi) SEQUENCE DESCRIPTION: SEQ ID NO:62:

```
AGAGGGTACA TATGCAACAG TATATAAAGG AAGAAGTGCA CTGAGAGGAA CTTCATCAAG      60

GCCATTTAAT CAATAAGTGA TAGAGTCAAG GCTCAACCCA GGTGTGACGG ATTCCAGGTC     120

CCAAGCTCCT TACTGGTACC CTCTT                                           145
```

(2) INFORMATION FOR SEQ ID NO:63:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:63:

```
TGCACTGAGA GGAATTCAAA GGGTTTATGC CAAAGAACAA ACCAGTCCTC TGCAGCCTAA      60

CTCATTTGTT TTTGGGCTGC GAAGCCATGT AGAGGGCGAT CAGGCAGTAG ATGGTCCCTC     120

CCACAGTCAG CGCCATGGTG GTCCGGTAAA GCATTTGGTC AGGCAGGCCT CGTTTCAGGT     180

AGACGGGCAC ACATCAGCTT TCTGGAAAAA CTTTTGTAGC TCTGGAGCTT TGTTTTTCCC     240

AGCATAATCA TACACTGTGG AATCGGAGGT CAGTTTAGTT GGTAAGGCAA GAGGAGC        297
```

(2) INFORMATION FOR SEQ ID NO:64:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (xi) SEQUENCE DESCRIPTION: SEQ ID NO:64:

```
GCACTGAGAG GAACTTCCAA TACTATGTTG AATAGGAGTG GTGAGAGAGG GCATCCTTGT      60

CTTGTGCCGG TTTTCAAAGG GAATGCTTCC AGCTTTTGCC CATTCAGTAT AATATTAAAG     120

AATGTTTTAC CATTTTCTGT CTTGCCTGTT TTTCTGTGTT TTTGTTGGTC TCTTCATTCT     180

CCATTTTTAG GCCTTTACAT GTTAGGAATA TATTTCTTTT AATGATACTT CACCTTTGGT     240

ATCTTTTGTG AGACTCTACT CATAGTGTGA TAAGCACTGG GTTGGTAAGG CAAGAGGAGC     300
```

(2) INFORMATION FOR SEQ ID NO:65:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (xi) SEQUENCE DESCRIPTION: SEQ ID NO:65:

```
GCTCCTCTTG CCTTACCAAC TCACCCAGTA TGTCAGCAAT TTTATCRGCT TTACCTACGA      60

AACAGCCTGT ATCCAAACAC TTAACACACT CACCTGAAAA GTTCAGGCAA CAATCGCCTT     120

CTCATGGGTC TCTCTGCTCC AGTTCTGAAC CTTTCTCTTT TCCTAGAACA TGCATTTARG     180

TCGATAGAAG TTCCTCTCAG TGC                                             203
```

(2) INFORMATION FOR SEQ ID NO:66:

(i) SEQUENCE CHARACTERISTICS:
        (A) LENGTH: 344 base pairs
        (B) TYPE: nucleic acid
        (C) STRANDEDNESS: single
        (D) TOPOLOGY: linear (xi) SEQUENCE DESCRIPTION: SEQ ID NO:66:

```
TACGGGACC CCTGCATTGA GAAAGCGAGA CTCACTCTGA AGCTGAAATG CTGTTGCCCT       60

TGCAGTGCTG GTAGCAGGAG TTCTGTGCTT TGTGGGCTAA GGCTCCTGGA TGACCCCTGA     120

CATGGAGAAG GCAGAGTTGT GTGCCCCTTC TCATGGCCTC GTCAAGGCAT CATGGACTGC     180

CACACACAAA ATGCCGTTTT TATTAACGAC ATGAAATTGA AGGAGAGAAC ACAATTCACT     240

GATGTGGCTC GTAACCATGG ATATGGTCAC ATACAGAGGT GTGATTATGT AAAGGTTAAT     300

TCCACCCACC TCATGTGGAA ACTAGCCTCA ATGCAGGGGT CCCA                      344
```

(2) INFORMATION FOR SEQ ID NO:67:

(i) SEQUENCE CHARACTERISTICS:
        (A) LENGTH: 157 base pairs (B) TYPE: nucleic acid
        (C) STRANDEDNESS: single
        (D) TOPOLOGY: linear (xi) SEQUENCE DESCRIPTION: SEQ ID NO:67:

GCACTGAGAG GAACTTCGTA GGGAGGTTGA ACTGGCTGCT GAGGAGGGGG AACAACAGGG      60

TAACCAGACT GATAGCCATT GGATGGATAA TATGGTGGTT GAGGAGGGAC ACTACTTATA     120

GCAGAGGGTT GTGTATAGCC TGAGGAGGCA TCACCCG                              157

(2) INFORMATION FOR SEQ ID NO:68:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO:68:

GCACTGAGAG GAACTTCTAG AAAGTGAAAG TCTAGACATA AAATAAAATA AAAATTTAAA      60

ACTCAGGAGA GACAGCCCAG CACGGTGGCT CACGCCTGTA ATCCCAGAAC TTTGGGAGCC     120

TGAGGAGGCA TCACCCG                                                    137

(2) INFORMATION FOR SEQ ID NO:69:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO:69:

CGGGTGATGC CTCCTCAGGC TGTATTTTGA AGACTATCGA CTGGACTTCT TATCAACTGA      60

AGAATCCGTT AAAAATACCA GTTGTATTAT TTCTACCTGT CAAAATCCAT TTCAAATGTT     120

GAAGTTCCTC TCAGTGC                                                    137

(2) INFORMATION FOR SEQ ID NO:70:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (xi) SEQUENCE DESCRIPTION: SEQ ID NO:70:

AGCATGTTGA GCCCAGACAC GCAATCTGAA TGAGTGTGCA CCTCAAGTAA ATGTCTACAC      60

GCTGCCTGGT CTGACATGGC ACACCATCNC GTGGAGGGCA CASCTCTGCT CNGCCTACWA     120

CGAGGGCANT CTCATWGACA GGTTCCACCC ACCAAACTGC AAGAGGCTCA NNAAGTACTR     180

CCAGGGTMYA SGGACMASGG TGGGAYTYCA YCACWCATCT                           220

(2) INFORMATION FOR SEQ ID NO:71:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (xi) SEQUENCE DESCRIPTION: SEQ ID NO:71:

CGTTAGGGTC TCTATCCACT GCTAAACCAT ACACCTGGGT AAACAGGGAC CATTTAACAT      60

TCCCANCTAA ATATGCCAAG TGACTTCACA TGTTTATCTT AAAGATGTCC AAAACGCAAC     120

```
TGATTTTCTC CCCTAAACCT GTGATGGTGG GATGATTAAN CCTGAGTGGT CTACAGCAAG      180

TTAAGTGCAA GGTGCTAAAT GAANGTGACC TGAGATACAG CATCTACAAG GCAGTACCTC      240

TCAACNCAGG GCAACTTTGC TTCTCANAGG GCATTTAGCA GTGTCTGAAG TAATTTCTGT      300

ATTACAACTC ACGGGGCGGG GGGTGAATAT CTANTGGANA GNAGACCCTA ACG             353

(2) INFORMATION FOR SEQ ID NO:72:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (xi) SEQUENCE DESCRIPTION: SEQ ID NO:72:

GCACTGAGAG GAACTTCCAA TACYATKATC AGAGTGAACA RGCARCCYAC AGAACAGGAG       60

AAAATGTTYG CAATCTCTCC ATCTGACAAA AGGCTAATAT CCAGAWTCTA AWAGGAACTT     120

AAACAAATTT ATGAGAAAAG AACARACAAC CTCAWCAAAA AGTGGGTGAA GGAWATGCTS     180

AAARGAAGAC ATYTATTCAG CCAGTAAACA YATGAAAAAA AGGCTCATSA TCACTGAWCA     240

TTAGAGAAAT GCAAATCAAA ACCACAATGA GATACCATCT YAYRCCAGTT AGAAYGGTGA     300

TCATTAAAAR STCAGGAAAC AACAGATGCT GGACAAGGTG TCA                       343

(2) INFORMATION FOR SEQ ID NO:73:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:73:

GCACTGAGAG GAACTTCAGA GAGAGAGAGA GAGTTCCACC CTGTACTTGG GGAGAGAAAC      60

AGAAGGTGAG AAAGTCTTTG GTTCTGAAGC AGCTTCTAAG ATCTTTTCAT TTGCTTCATT     120

TCAAAGTTCC CATGCTGCCA AAGTGCCATC CTTTGGGGTA CTGTTTTCTG AGCTCCAGTG     180

ATAACTCATT TATACAAGGG AGATACCCAG AAAAAAAGTG AGCAAATCTT AAAAAGGTGG     240

CTTGAGTTCA GCCTTAAATA CCATCTTGAA ATGCACAGA GAAAGAANGA TGTTGGGTGG     300

GAGTGGATAG AGACCCTAAC G                                               321

(2) INFORMATION FOR SEQ ID NO:74:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:74:

GCACTGAGAG GAACTTCAGA GAGAGAGAGA GAGTTCCACC CTGTACTTGG GGAGAGAAAC      60

AGAAGGTGAG AAAGTCTTTG GTTCTGAAGC AGCTTCTAAG ATCTTTTCAT TTGCTTCATT     120

TCAAAGTTCC CATGCTGCCA AAGTGCCATC CTTTGGGGTA CTGTTTTCTG AGCTCCAGTG     180

ATAACTCATT TATACAAGGG AGATACCCAG AAAAAAAGTG AGCAAATCTT AAAAAGGTGG     240

CTTGAGTTCA GYCTTAAATA CCATCTTGAA ATGAMACAGA GAAAGAAGGA TGTTGGGTGG     300

GAGTGGATAG AGACCCTAAC G                                               321
```

(2) INFORMATION FOR SEQ ID NO:75:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO:75:

```
GCACTGAGAG GAACTTCCAC ATGCACTGAG AAATGCATGT TCACAAGGAC TGAAGTCTGG      60

AACTCAGTTT CTCAGTTCCA ATCCTGATTC AGGTGTTTAC CAGCTACACA ACCTTAAGCA     120

AGTCAGATAA CCTTAGCTTC CTCATATGCA AAATGAGAAT GAAAAGTACT CATCGCTGAA     180

TTGTTTTGAG GATTAGAAAA ACATCTGGCA TGCAGTAGAA ATTCAATTAG TATTCATTTT     240

CATTCTTCTA AATTAAACAA ATAGGATTTT TAGTGGTGGA ACTTCAGACA CCAGAAATGG     300

GAGTGGATAG AGACCCT                                                   317
```

(2) INFORMATION FOR SEQ ID NO:76:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (xi) SEQUENCE DESCRIPTION: SEQ ID NO:76:

```
CGTTAGGGTC TCTATCCACT CCCACTACTG ATCAAACTCT ATTTATTTAA TTATTTTTAT      60

CATACTTTAA GTTCTGGGAT ACACGTGCAG CATGCGCAGG TTTGTTGCAT AGGTATACAC     120

TTGCCATGGT GGTTTGCTGC ACCCATCAGT CCATCATCTA CATTAGGTAT TTCTCCTAAT     180

GCTATCCCTC CCCTAGCCCC TTACACCCCC AACAGGCTCT AGTGTGTGAA GTTCCTCTCA     240

GTGC                                                                 244
```

(2) INFORMATION FOR SEQ ID NO:77:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (xi) SEQUENCE DESCRIPTION: SEQ ID NO:77:

```
CGTTAGGGTC TCTATCCACT GAAATCTGAA GCACAGGAGG AAGAGAAGCA GTYCTAGTGA      60

GATGGCAAGT TCWTTTACCA CACTCTTTAA CATTTGTTTT AGTTTTAACC TTTATTTATG     120

GATAATAAAG GTTAATATTA ATAATGATTT ATTTTAAGGC ATTCCCRAAT TTGCATAATT     180

CTCCTTTTGG AGATACCCTT TTATCTCCAG TGCAAGTCTG GATCAAAGTG ATASAMAGAA     240

GTTCCTCTCA GTGC                                                      254
```

(2) INFORMATION FOR SEQ ID NO:78:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (xi) SEQUENCE DESCRIPTION: SEQ ID NO:78:

```
TTCGATACAG GCAAACATGA ACTGCAGGAG GGTGGTGACG ATCATGATGT TGCCGATGGT      60

CCGGATGGNC ACGAAGACGC ACTGGANCAC GTGCTTACGT CCTTTTGCTC TGTTGATGGC     120
```

-continued

```
CCTGAGGGGA CGCAGGACCC TTATGACCCT CAGAATCTTC ACAACGGGAG ATGGCACTGG        180

ATTGANTCCC ANTGACACCA GAGACACCCC AACCACCAGN ATATCANTAT ATTGATGTAG        240

TTCCTGTAGA NGGCCCCCTT GTGGAGGAAA GCTCCATNAG TTGGTCATCT TCAACAGGAT        300

CTCAACAGTT TCCGATGGCT GTGATGGGCA TAGTCATANT TAACCNTGTN TCGAA            355
```

(2) INFORMATION FOR SEQ ID NO:79:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (xi) SEQUENCE DESCRIPTION: SEQ ID NO:79:

```
TAAGAGGGTA CCAGCAGAAA GGTTAGTATC ATCAGATAGC ATCTTATACG AGTAATATGC        60

CTGCTATTTG AAGTGTAATT GAGAAGGAAA ATTTTAGCGT GCTCACTGAC CTGCCTGTAG        120

CCCCAGTGAC AGCTAGGATG TGCATTCTCC AGCCATCAAG AGACTGAGTC AAGTTGTTCC        180

TTAAGTCAGA ACAGCAGACT CAGCTCTGAC ATTCTGATTC GAATGACACT GTTCAGGAAT        240

CGGAATCCTG TCGATTAGAC TGGACAGCTT GTGGCAAGTG AATTTGCCTG TAACAAGCCA        300

GATTTTTTAA AATTTATATT GTAAATAATG TGTGTGTGTG TGTGTGTATA TATATATATA        360

TGTACAGTTA TCTAAGTTAA TTTAAAAGTT GTTTGGTACC CTCTTA                      406
```

(2) INFORMATION FOR SEQ ID NO:80:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (xi) SEQUENCE DESCRIPTION: SEQ ID NO:80:

```
TTTTTTTTTT TTTACTCGGC TCAGTCTAAT CCTTTTTGTA GTCACTCATA GGCCAGACTT        60

AGGGCTAGGA TGATGATTAA TAAGAGGGAT GACATAACTA TTAGTGGCAG GTTAGTTGTT        120

TGTAGGGCTC ATGGTAGGGG TAAAAGGAGG GCAATTTCTA GATCAAATAA TAAGAAGGTA        180

ATAGCTACTA AGAAGAATTT TATGGAGAAA GGGACGCGGG CGGGGGATAT AGGGTCGAAG        240

CCGCACTCGT AAGGGGTGGA TTTTTCTATG TAGCCGTTGA GTTGTGGTAG TCAAAATGTA        300

ATAATTATTA GTAGTAAGCC TAGGAGA                                           327
```

(2) INFORMATION FOR SEQ ID NO:81:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO:81:

```
TAGTCTATGC GGTTGATTCG GCAATCCATT ATTTGCTGGA TTTTGTCATG TGTTTTGCCA        60

ATTGCATTCA TAATTTATTA TGCATTTATG CTTGTATCTC CTAAGTCATG GTATATAATC       120

CATGCTTTTT ATGTTTTGTC TGACATAAAC TCTTATCAGA GCCCTTTGCA CACAGGGATT       180

CAATAAATAT TAACACAGTC TACATTTATT TGGTGAATAT TGCATATCTG CTGTACTGAA       240

AGCACATTAA GTAACAAAGG CAAGTGAGAA GAATGAAAAG CACTACTCAC AACAGTTATC       300

ATGATTGCGC ATAGACTA                                                    318
```

(2) INFORMATION FOR SEQ ID NO:82:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (xi) SEQUENCE DESCRIPTION: SEQ ID NO:82:

```
TCTTCAACCT CTACTCCCAC TAATAGCTTT TTGATGACTT CTAGCAAGCC TCGCTAACCT      60

CGCCTTACCC CCCACTATTA ACCTACTGGG AGAACTCTCT GTGCTAGTAA CCACGTTCTC     120

CTGATCAAAT ATCACTCTCC TACTTACAGG ACTCAACATA CTAGTCACAG CCCTATACTC     180

CCTCTACATA TTTACCACAA CACAATGGGG CTCACTCACC CACCACATTA ACAACATAAA     240

ACCCTCATTC ACACGAGAAA ACACCCTCAT GTTCATACAC CTATCCCCCA TTCTCCTCCT     300

ATCCCTCAAC CCCGACATCA TTACCGGGTT TTCCTCTT                             338
```

(2) INFORMATION FOR SEQ ID NO:83:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO:83:

```
AGCCATTTAC CACCCATCCA CAAAAAAAAA AAAAAAAAG AAAAATATCA AGGAATAAAA      60

ATAGACTTTG AACAAAAAGG AACATTTGCT GGCCTGAGGA GGCATCACCC G             111
```

(2) INFORMATION FOR SEQ ID NO:84:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (xi) SEQUENCE DESCRIPTION: SEQ ID NO:84:

```
TCGGGTGATG CCTCCTCAGG CCAAGAAGAT AAAGCTTCAG ACCCCTAACA CATTTCCAAA      60

AAGGAAGAAA GGAGAAAAAA GGGCATCATC CCCGTTCCGA AGGGTCAGGG AGGAGGAAAT     120

TGAGGTGGAT TCACGAGTTG CGGACAACTC CTTTGATGCC AAGCGAGGTG CAGCCGGAGA     180

CTGGGGAGAG CGAGCCAATC AGGTTTTGAA GTTCCTCTCA GTGC                      224
```

(2) INFORMATION FOR SEQ ID NO:85:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (xi) SEQUENCE DESCRIPTION: SEQ ID NO:85:

```
GCACTGAGAG GAACTTCGTT GGAAACGGGT TTTTTTCATG TAAGGCTAGA CAGAAGAATT      60

CTCAGTAACT TCCTTGTGTT GTGTGTATTC AACTCACASA GTTGAACGAT CCTTTACACA     120

GAGCAGACTT GTAACACTCT TWTTGTGGAA TTTGCAAGTG GAGATTTCAG SCGCTTTGAA     180

GTSAAAGGTA GAAAAGGAAA TATCTTCCTA TAAAAACTAG ACAGAATGAT TCTCAGAAAC     240

TCCTTTGTGA TGTGTGCGTT CAACTCACAG AGTTTAACCT TTCWTTTCAT AGAAGCAGTT     300

AGGAAACACT CTGTTTGTAA AGTCTGCAAG TGGATAGAGA CCCTAACG                  348
```

(2) INFORMATION FOR SEQ ID NO:86:

(i) SEQUENCE CHARACTERISTICS:
        (A) LENGTH: 293 base pairs
        (B) TYPE: nucleic acid
        (C) STRANDEDNESS: single
        (D) TOPOLOGY: linear (xi) SEQUENCE DESCRIPTION: SEQ ID NO:86:

```
GCACTGAGAG GAACTTCYTT GTGWTGTKTG YATTCAACTC ACAGAGTTGA ASSWTSMTTT    60

ACABAGWKCA GGCTTKCAAA CACTCTTTTT GTMGAATYTG CAAGWGGAKA TTTSRRCCRC   120

TTTGWGGYCW WYSKTMGAAW MGGRWATATC TTCWYATMRA AMCTAGACAG AAKSATTCTC   180

AKAAWSTYYY YTGTGAWGWS TGCRTTCAAC TCACAGAGKT KAACMWTYCT KYTSATRGAG   240

CAGTTWKGAA ACTCTMTTTC TTTGGATTCT GCAAGTGGAT AGAGACCCTA ACG          293
```

(2) INFORMATION FOR SEQ ID NO:87:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:87:

```
CTCCTAGGCT                                                           10
```

(2) INFORMATION FOR SEQ ID NO:88:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:88:

```
AGTAGTTGCC                                                           10
```

(2) INFORMATION FOR SEQ ID NO:89:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:89:

```
TTCCGTTATG C                                                         11
```

(2) INFORMATION FOR SEQ ID NO:90:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:90:

```
TGGTAAAGGG                                                           10
```

(2) INFORMATION FOR SEQ ID NO:91:

(i) SEQUENCE CHARACTERISTICS:
        (A) LENGTH: 10 base pairs (B) TYPE: nucleic acid
        (C) STRANDEDNESS: single
        (D) TOPOLOGY: linear (xi) SEQUENCE DESCRIPTION: SEQ ID NO:91:

TCGGTCATAG                                                              10

(2) INFORMATION FOR SEQ ID NO:92:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:92:

TACAACGAGG                                                              10

(2) INFORMATION FOR SEQ ID NO:93:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:93:

TGGATTGGTC                                                              10

(2) INFORMATION FOR SEQ ID NO:94:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:94:

CTTTCTACCC                                                              10

(2) INFORMATION FOR SEQ ID NO:95:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:95:

TTTTGGCTCC                                                              10

(2) INFORMATION FOR SEQ ID NO:96:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:96:

GGAACCAATC                                                              10

(2) INFORMATION FOR SEQ ID NO:97:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (xi) SEQUENCE DESCRIPTION: SEQ ID NO:97:

TCGATACAGG                                                              10

(2) INFORMATION FOR SEQ ID NO:98:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:98:

GGTACTAAGG                                                              10

(2) INFORMATION FOR SEQ ID NO:99:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:99:

AGTCTATGCG                                                              10

(2) INFORMATION FOR SEQ ID NO:100:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:100:

CTATCCATGG                                                              10

(2) INFORMATION FOR SEQ ID NO:101:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:101:

TCTGTCCACA                                                              10

(2) INFORMATION FOR SEQ ID NO:102:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:102:

AAGAGGGTAC                                                              10

(2) INFORMATION FOR SEQ ID NO:103:

(i) SEQUENCE CHARACTERISTICS:
        (A) LENGTH: 10 base pairs
        (B) TYPE: nucleic acid
        (C) STRANDEDNESS: single
```

```
            (D) TOPOLOGY: linear (xi) SEQUENCE DESCRIPTION: SEQ ID NO:103:

CTTCAACCTC                                                           10

(2) INFORMATION FOR SEQ ID NO:104:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:104:

GCTCCTCTTG CCTTACCAAC                                                20

(2) INFORMATION FOR SEQ ID NO:105:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:105:

GTAAGTCGAG CAGTGTGATG                                                20

(2) INFORMATION FOR SEQ ID NO:106:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:106:

GTAAGTCGAG CAGTCTGATG                                                20

(2) INFORMATION FOR SEQ ID NO:107:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:107:

GACTTAGTGG AAAGAATGTA                                                20

(2) INFORMATION FOR SEQ ID NO:108:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:108:

GTAATTCCGC CAACCGTAGT                                                20

(2) INFORMATION FOR SEQ ID NO:109:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(xi) SEQUENCE DESCRIPTION: SEQ ID NO:109:

ATGGTTGATC GATAGTGGAA                                               20

(2) INFORMATION FOR SEQ ID NO:110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:110:

ACGGGGACCC CTGCATTGAG                                               20

(2) INFORMATION FOR SEQ ID NO:111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:111:

TATTCTAGAC CATTCGCTAC                                               20

(2) INFORMATION FOR SEQ ID NO:112:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:112:

ACATAACCAC TTTAGCGTTC                                               20

(2) INFORMATION FOR SEQ ID NO:113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:113:

CGGGTGATGC CTCCTCAGGC                                               20

(2) INFORMATION FOR SEQ ID NO:114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:114:

AGCATGTTGA GCCCAGACAC                                               20

(2) INFORMATION FOR SEQ ID NO:115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:115:

GACACCTTGT CCAGCATCTG                                           20

(2) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:116:

TACGCTGCAA CACTGTGGAG                                           20

(2) INFORMATION FOR SEQ ID NO:117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:117:

CGTTAGGGTC TCTATCCACT                                           20

(2) INFORMATION FOR SEQ ID NO:118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:118:

AGACTGACTC ATGTCCCCTA                                           20

(2) INFORMATION FOR SEQ ID NO:119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:119:

TCATCGCTCG GTGACTCAAG                                           20

(2) INFORMATION FOR SEQ ID NO:120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:120:

CAAGATTCCA TAGGCTGACC                                           20

(2) INFORMATION FOR SEQ ID NO:121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:121:

```
ACGTACTGGT CTTGAAGGTC                                              20

(2) INFORMATION FOR SEQ ID NO:122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:122:

GACGCTTGGC CACTTGACAC                                              20

(2) INFORMATION FOR SEQ ID NO:123:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:123:

GTATCGACGT AGTGGTCTCC                                              20

(2) INFORMATION FOR SEQ ID NO:124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:124:

TAGTGACATT ACGACGCTGG                                              20

(2) INFORMATION FOR SEQ ID NO:125:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:125:

CGGGTGATGC CTCCTCAGGC                                              20

(2) INFORMATION FOR SEQ ID NO:126:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:126:

ATGGCTATTT TCGGGGCTG ACA                                           23

(2) INFORMATION FOR SEQ ID NO:127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:127:
```

```
CCGGTATCTC CTCGTGGGTA TT                                                  22

(2) INFORMATION FOR SEQ ID NO:128:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO:128:

CTGCCTGAGC CACAAATG                                                       18

(2) INFORMATION FOR SEQ ID NO:129:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:129:

CCGGAGGAGG AAGCTAGAGG AATA                                                24

(2) INFORMATION FOR SEQ ID NO:130:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (xi) SEQUENCE DESCRIPTION: SEQ ID NO:130:

TTTTTTTTTT TTAG                                                           14

(2) INFORMATION FOR SEQ ID NO:131:

(i) SEQUENCE CHARACTERISTICS:
         (A) LENGTH: 18 amino acids
         (B) TYPE: amino acid
         (C) STRANDEDNESS: single
         (D) TOPOLOGY: linear (xi) SEQUENCE DESCRIPTION: SEQ ID NO:131:

Ser Ser Gly Gly Arg Thr Phe Asp Asp Phe His Arg Tyr Leu Leu Val
1               5                   10                  15

Gly Ile (2) INFORMATION FOR SEQ ID NO:132:

(i) SEQUENCE CHARACTERISTICS:
         (A) LENGTH: 22 amino acids
         (B) TYPE: amino acid
         (C) STRANDEDNESS: single
         (D) TOPOLOGY: linear (xi) SEQUENCE DESCRIPTION: SEQ ID NO:132:

Gln Gly Ala Ala Gln Lys Pro Ile Asn Leu Ser Lys Xaa Ile Glu Val
1               5                   10                  15

Val Gln Gly His Asp Glu
            20

(2) INFORMATION FOR SEQ ID NO:133:

(i) SEQUENCE CHARACTERISTICS:
         (A) LENGTH: 23 amino acids
```

(B) TYPE: amino acid
        (C) STRANDEDNESS: single
        (D) TOPOLOGY: linear (xi) SEQUENCE DESCRIPTION: SEQ ID NO:133:

Ser Pro Gly Val Phe Leu Glu His Leu Gln Glu Ala Tyr Arg Ile Tyr
1               5                  10                  15

Thr Pro Phe Asp Leu Ser Ala
            20

(2) INFORMATION FOR SEQ ID NO:134:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:134:

Tyr Leu Leu Val Gly Ile Gln Gly Ala
1               5

(2) INFORMATION FOR SEQ ID NO:135:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:135:

Gly Ala Ala Gln Lys Pro Ile Asn Leu
1               5

(2) INFORMATION FOR SEQ ID NO:136:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:136:

Asn Leu Ser Lys Xaa Ile Glu Val Val
1               5

(2) INFORMATION FOR SEQ ID NO:137:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:137:

Glu Val Val Gln Gly His Asp Glu Ser
1               5

(2) INFORMATION FOR SEQ ID NO:138:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:138:

His Leu Gln Glu Ala Tyr Arg Ile Tyr
1               5

(2) INFORMATION FOR SEQ ID NO:139:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:139:

Asn Leu Ala Phe Val Ala Gln Ala Ala
1               5

(2) INFORMATION FOR SEQ ID NO:140:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:140:

Phe Val Ala Gln Ala Ala Pro Asp Ser
1               5

(2) INFORMATION FOR SEQ ID NO:141:

(i) SEQUENCE CHARACTERISTICS:
        (A) LENGTH: 9388 base pairs
        (B) TYPE: nucleic acid
        (C) STRANDEDNESS: single
        (D) TOPOLOGY: linear (xi) SEQUENCE DESCRIPTION: SEQ ID NO:141:

| | | | | | |
|---|---|---|---|---|---|
| GCTCGCGGCC | GCGAGCTCAA | TTAACCCTCA | CTAAAGGGAG | TCGACTCGAT | CAGACTGTTA | 60 |
| CTGTGTCTAT | GTAGAAAGAA | GTAGACATAA | GAGATTCCAT | TTTGTTCTGT | ACTAAGAAAA | 120 |
| ATTCTTCTGC | CTTGAGATGC | TGTTAATCTG | TAACCCTAGC | CCCAACCCTG | TGCTCACAGA | 180 |
| GACATGTGCT | GTGTTGACTC | AAGGTTCAAT | GGATTTAGGG | CTATGCTTTG | TTAAAAAAGT | 240 |
| GCTTGAAGAT | AATATGCTTG | TTAAAAGTCA | TCACCATTCT | CTAATCTCAA | GTACCCAGGG | 300 |
| ACACAATACA | CTGCGGAAGG | CCGCAGGGAC | CTCTGTCTAG | GAAAGCCAGG | TATTGTCCAA | 360 |
| GATTTCTCCC | CATGTGATAG | CCTGAGATAT | GGCCTCATGG | GAAGGGTAAG | ACCTGACTGT | 420 |
| CCCCCAGCCC | GACATCCCCC | AGCCCGACAT | CCCCCAGCCC | GACACCCGAA | AAGGGTCTGT | 480 |
| GCTGAGGAGG | ATTAGTAAAA | GAGGAAGGCC | TCTTTGCAGT | TGAGGTAAGA | GGAAGGCATC | 540 |
| TGTCTCCTGC | TCGTCCCTGG | GCAATAGAAT | GTCTTGGTGT | AAAACCCGAT | TGTATGTTCT | 600 |
| ACTTACTGAG | ATAGGAGAAA | ACATCCTTAG | GGCTGGAGGT | GAGACACGCT | GGCGGCAATA | 660 |
| CTGCTCTTTA | ATGCACCGAG | ATGTTTGTAT | AAGTGCACAT | CAAGGCACAG | CACCTTTCCT | 720 |
| TAAACTTATT | TATGCACACAG | AGACCTTTGT | TCACGTTTTC | CTGCTGACCC | TCTCCCCACT | 780 |
| ATTACCCTAT | TGGCCTGCCA | CATCCCCCTC | TCCGAGATGG | TAGAGATAAT | GATCAATAAA | 840 |
| TACTGAGGGA | ACTCAGAGAC | CAGTGTCCCT | GTAGGTCCTC | CGTGTGCTGA | GCGCCGGTCC | 900 |
| CTTGGGCTCA | CTTTTCTTTC | TCTATACTTT | GTCTCTGTGT | CTCTTTCTTT | TCTCAGTCTC | 960 |
| TCGTTCCACC | TGACGAGAAA | TACCCACAGG | TGTGGAGGGG | CAGGCCACCC | CTTCAATAAT | 1020 |
| TTACTAGCCT | GTTCGCTGAC | AACAAGACTG | GTGGTGCAGA | AGGTTGGGTC | TTGGTGTTCA | 1080 |
| CCGGGTGGCA | GGCATGGGCC | AGGTGGGAGG | GTCTCCAGCG | CCTGGTGCAA | ATCTCCAAGA | 1140 |

-continued

```
AAGTGCAGGA AACAGCACCA AGGGTGATTG TAAATTTTGA TTTGGCGCGG CAGGTAGCCA    1200

TTCCAGCGCA AAAATGCGCA GGAAAGCTTT TGCTGTGCTT GTAGGCAGGT AGGCCCCAAG    1260

CACTTCTTAT TGGCTAATGT GGAGGGAACC TGCACATCCA TTGGCTGAAA TCTCCGTCTA    1320

TTTGAGGCTG ACTGAGCGCG TTCCTTTCTT CTGTGTTGCC TGGAAACGGA CTGTCTGCCT    1380

AGTAACATCT GATCACGTTT CCCATTGGCC GCCGTTTCCG GAAGCCCGCC CTCCCATTTC    1440

CGGAAGCCTG GCGCAAGGTT GGTCTGCAGG TGGCCTCCAG GTGCAAAGTG GGAAGTGTGA    1500

GTCCTCAGTC TTGGGCTATT CGGCCACGTG CCTGCCGGAC ATGGGACGCT GGAGGGTCAG    1560

CAGCGTGGAG TCCTGGCCTT TTGCGTCCAC GGGTGGGAAA TTGGCCATTG CCACGGCGGG    1620

AACTGGGACT CAGGCTGCCC CCCGGCCGTT TCTCATCCGT CCACCGGACT CGTGGGCGCT    1680

CGCACTGGCG CTGATGTAGT TTCCTGACCT CTGACCCGTA TTGTCTCCAG ATTAAAGGTA    1740

AAAACGGGGC TTTTTCAGCC CACTCGGGTA AAACGCCTTT TGATTTCTAG GCAGGTGTTT    1800

TGTTGCACGC CTGGGAGGGA GTGACCCGCA GGTTGAGGTT TATTAAAATA CATTCCTGGT    1860

TTATGTTATG TTTATAATAA AGCACCCCAA CCTTTACAAA ATCTCACTTT TTGCCAGTTG    1920

TATTATTTAG TGGACTGTCT CTGATAAGGA CAGCCAGTTA AAATGGAATT TTGTTGTTGC    1980

TAATTAAACC AATTTTTAGT TTTGGTGTTT GTCCTAATAG CAACAACTTC TCAGGCTTTA    2040

TAAAACCATA TTTCTTGGGG GAAATTTCTG TGTAAGGCAC AGCGAGTTAG TTTGGAATTG    2100

TTTTAAAGGA AGTAAGTTCC TGGTTTTGAT ATCTTAGTAG TGTAATGCCC AACCTGGTTT    2160

TTACTAACCC TGTTTTTAGA CTCTCCCTTT CCTTAAATCA CCTAGCCTTG TTTCCACCTG    2220

AATTGACTCT CCCTTAGCTA AGAGCGCCAG ATGGACTCCA TCTTGGCTCT TTCACTGGCA    2280

GCCCCTTCCT CAAGGACTTA ACTTGTGCAA GCTGACTCCC AGCACATCCA AGAATGCAAT    2340

TAACTGTTAA GATACTGTGG CAAGCTATAT CCGCAGTTCC GAGGAATTCA TCCGATTGAT    2400

TATGCCCAAA AGCCCCGCGT CTATCACCTT GTAATAATCT TAAAGCCCCT GCACCTGGAA    2460

CTATTAACTT TCCTGTAACC ATTTATCCTT TTAACTTTTT TGCTTACTTT ATTTCTGTAA    2520

AATTGTTTTA ACTAGACCTC CCCTCCCCTT TCTAAACCAA AGTATAAAAG AAGATCTAGC    2580

CCCTTCTTCA GAGCGGAGAG AATTTTGAGC ATTAGCCATC TCTTGGCGGC CAGCTAAATA    2640

AATGGACTTT TAATTTGTCT CAAAGTGTGG CGTTTTCTCT AACTCGCTCA GGTACGACAT    2700

TTGGAGGCCC CAGCGAGAAA CGTCACCGGG AGAAACGTCA CCGGGCGAGA GCCGGGCCCG    2760

CTGTGTGCTC CCCCGGAAGG ACAGCCAGCT TGTAGGGGGG AGTGCCACCT GAAAAAAAAA    2820

TTTCCAGGTC CCCAAAGGGT GACCGTCTTC CGGAGGACAG CGGATCGACT ACCATGCGGG    2880

TGCCCACCAA AATTCCACCT CTGAGTCCTC AACTGCTGAC CCCGGGGTCA GGTAGGTCAG    2940

ATTTGACTTT GGTTCTGGCA GAGGGAAGCG ACCCTGATGA GGGTGTCCCT CTTTTGACTC    3000

TGCCCATTTC TCTAGGATGC TAGAGGGTAG AGCCCTGGTT TTCTGTTAGA CGCCTCTGTG    3060

TCTCTGTCTG GGAGGGAAGT GGCCCTGACA GGGGCCATCC CTTGAGTCAG TCCACATCCC    3120

AGGATGCTGG GGGACTGAGT CCTGGTTTCT GGCAGACTGG TCTCTCTCTC TCTCTTTTTC    3180

TATCTCTAAT CTTTCCTTGT TCAGGTTTCT TGGAGAATCT CTGGGAAAGA AAAAAGAAAA    3240

ACTGTTATAA ACTCTGTGTG AATGGTGAAT GAATGGGGGA GGACAAGGGC TTGCGCTTGT    3300

CCTCCAGTTT GTAGCTCCAC GGCGAAAGCT ACGGAGTTCA AGTGGGCCCT CACCTGCGGT    3360

TCCGTGGCGA CCTCATAAGG CTTAAGGCAG CATCCGGCAT AGCTCGATCC GAGCCGGGGG    3420

TTTATACCGG CCTGTCAATG CTAAGAGGAG CCCAAGTCCC CTAAGGGGGA GCGGCCAGGC    3480
```

```
-continued

GGGCATCTGA CTGATCCCAT CACGGGACCC CCTCCCCTTG TTTGTCTAAA AAAAAAAAAA   3540

GAAGAAACTG TCATAACTGT TTACATGCCC TAGGGTCAAC TGTTTGTTTT ATGTTTATTG   3600

TTCTGTTCGG TGTCTATTGT CTTGTTTAGT GGTTGTCAAG GTTTTGCATG TCAGGACGTC   3660

GATATTGCCC AAGACGTCTG GGTAAGAACT TCTGCAAGGT CCTTAGTGCT GATTTTTTGT   3720

CACAGGAGGT TAAATTTCTC ATCAATCATT TAGGCTGGCC ACCACAGTCC TGTCTTTTCT   3780

GCCAGAAGCA AGTCAGGTGT TGTTACGGGA ATGAGTGTAA AAAAACATTC GCCTGATTGG   3840

GATTTCTGGC ACCATGATGG TTGTATTTAG ATTGTCATAC CCCACATCCA GGTTGATTGG   3900

ACCTCCTCTA AACTAAACTG GTGGTGGGTT CAAAACAGCC ACCCTGCAGA TTTCCTTGCT   3960

CACCTCTTTG GTCATTCTGT AACTTTTCCT GTGCCCTTAA ATAGCACACT GTGTAGGGAA   4020

ACCTACCCTC GTACTGCTTT ACTTCGTTTA GATTCTTACT CTGTTCCTCT GTGGCTACTC   4080

TCCCATCTTA AAAACGATCC AAGTGGTCCT TTTCCTCCTC CCTGCCCCCT ACCCCACACA   4140

TCTCGTTTTC CAGTGCGACA GCAAGTTCAG CGTCTCCAGG ACTTGGCTCT GCTCTCACTC   4200

CTTGAACCCT TAAAAGAAAA AGCTGGGTTT GAGCTATTTG CCTTTGAGTC ATGGAGACAC   4260

AAAAGGTATT TAGGGTACAG ATCTAGAAGA AGAGAGAGAA CACCTAGATC CAACTGACCC   4320

AGGAGATCTC GGGCTGGCCT CTAGTCCTCC TCCCTCAATC TTAAAGCTAC AGTGATGTGG   4380

CAAGTGGTAT TTAGCTGTTG TGGTTTTTCT GCTCTTTCTG GTCATGTTGA TTCTGTTCTT   4440

TCGATACTCC AGCCCCCCAG GGAGTGAGTT TCTCTGTCTG TGCTGGGTTT GATATCTATG   4500

TTCAAATCTT ATTAAATTGC CTTCAAAAAA AAAAAAAAA GGGAAACACT TCCTCCCAGC    4560

CTTGTAAGGG TTGGAGCCCT CTCCAGTATA TGCTGCAGAA TTTTTCTCTC GGTTTCTCAG   4620

AGGATTATGG AGTCCGCCTT AAAAAAGGCA AGCTCTGGAC ACTCTGCAAA GTAGAATGGC   4680

CAAAGTTTGG AGTTGAGTGG CCCCTTGAAG GGTCACTGAA CCTCACAATT GTTCAAGCTG   4740

TGTGGCGGGT TGTTACTGAA ACTCCCGGCC TCCCTGATCA GTTTCCCTAC ATTGATCAAT   4800

GGCTGAGTTT GGTCAGGAGC ACCCCTTCCA TGGCTCCACT CATGCACCAT TCATAATTTT   4860

ACCTCCAAGG TCCTCCTGAG CCAGACCGTG TTTTCGCCTC GACCCTCAGC CGGTTCAGCT   4920

CGCCCTGTAC TGCCTCTCTC TGAAGAAGAG GAGAGTCTCC CTCACCCAGT CCCACCGCCT   4980

TAAAACCAGC CTACTCCCTT AGGGTCATCC CATGTCTCCT CGGCTATGTC CCCTGTAGGC   5040

TCATCACCCA TTGCCTCTTG GTTGCAACCG TGGTGGGAGG AAGTAGCCCC TCTACTACCA   5100

CTGAGAGAGG CACAAGTCCC TCTGGGTGAT GAGTGCTCCA CCCCCTTCCT GGTTTATGTC   5160

CCTTCTTTCT ACTTCTGACT TGTATAATTG GAAAACCCAT AATCCTCCCT TCTCTGAAAA   5220

GCCCCAGGCT TTGACCTCAC TGATGGAGTC TGTACTCTGG ACACATTGGC CCACCTGGGA   5280

TGACTGTCAA CAGCTCCTTT TGACCCTTTT CACCTCTGAA GAGAGGGAAA GTATCCAAAG   5340

AGAGGCCAAA AAGTACAACC TCACATCAAC CAATAGGCCG GAGGAGGAAG CTAGAGGAAT   5400

AGTGATTAGA GACCCAATTG GGACCTAATT GGGACCCAAA TTTCTCAAGT GGAGGGAGAA   5460

CTTTTGACGA TTTCCACCGG TATCTCCTCG TGGGTATTCA GGGAGCTGCT CAGAAACCTA   5520

TAAACTTGTC TAAGGCGACT GAAGTCGTCC AGGGGCATGA TGAGTCACCA GGAGTGTTTT   5580

TAGAGCACCT CCAGGAGGCT TATCGGATTT ACACCCCTTT TGACCTGGCA GCCCCCGAAA   5640

ATAGCCATGC TCTTAATTTG GCATTTGTGG CTCAGGCAGC CCCAGATAGT AAAAGGAAAC   5700

TCCAAAAACT AGAGGGATTT TGCTGGAATG AATACCAGTC AGCTTTTAGA GATAGCCTAA   5760

AAGGTTTTTG ACAGTCAAGA GGTTGAAAAA CAAAACAAG CAGCTCAGGC AGCTGAAAAA    5820

AGCCACTGAT AAAGCATCCT GGAGTATCAG AGTTTACTGT TAGATCAGCC TCATTTGACT   5880
```

-continued

```
TCCCCTCCCA CATGGTGTTT AAATCCAGCT ACACTACTTC CTGACTCAAA CTCCACTATT    5940

CCTGTTCATG ACTGTCAGGA ACTGTTGGAA ACTACTGAAA CTGGCCGACC TGATCTTCAA    6000

AATGTGCCCC TAGGAAAGGT GGATGCCACC GTGTTCACAG ACAGTAGCAG CTTCCTCGAG    6060

AAGGGACTAC GAAAGGCCGG TGCAGCTGTT ACCATGGAGA CAGATGTGTT GTGGGCTCAG    6120

GCTTTACCAG CAAACACCTC AGCACAAAAG GCTGAATTGA TCGCCCTCAC TCAGGCTCTC    6180

CGATGGGGTA AGGATATTAA CGTTAACACT GACAGCAGGT ACGCCTTTGC TACTGTGCAT    6240

GTACGTGGAG CCATCTACCA GGAGCGTGGG CTACTCACCT CAGCAGGTGG CTGTAATCCA    6300

CTGTAAAGGA CATCAAAAGG AAAACACGGC TGTTGCCCGT GGTAACCAGA AAGCTGATTC    6360

AGCAGCTCAA GATGCAGTGT GACTTTCAGT CACGCCTCTA AACTTGCTGC CCACAGTCTC    6420

CTTTCCACAG CCAGATCTGC CTGACAATCC CGCATACTCA ACAGAAGAAG AAAACTGGCC    6480

TCAGAACTCA GAGCCAATAA AAATCAGGAA GGTTGGTGGA TTCTTCCTGA CTCTAGAATC    6540

TTCATACCCC GAACTCTTGG GAAAACTTTA ATCAGTCACC TACAGTCTAC CACCCATTTA    6600

GGAGGAGCAA AGCTACCTCA GCTCCTCCGG AGCCGTTTTA AGATCCCCCA TCTTCAAAGC    6660

CTAACAGATC AAGCAGCTCT CCGGTGCACA ACCTGCGCCC AGGTAAATGC CAAAAAGGT    6720

CCTAAACCCA GCCCAGGCCA CCGTCTCCAA GAAAACTCAC CAGGAGAAAA GTGGGAAATT    6780

GACTTTACAG AAGTAAAACC ACACCGGGCT GGGTACAAAT ACCTTCTAGT ACTGGTAGAC    6840

ACCTTCTCTG GATGGACTGA AGCATTTGCT ACCAAAAACG AAACTGTCAA TATGGTAGTT    6900

AAGTTTTTAC TCAATGAAAT CATCCCTCGA CGTGGGCTGC CTGTTGCCAT AGGGTCTGAT    6960

AATGGACCGG CCTTCGCCTT GTCTATAGTT TAGTCAGTCA GTAAGGCGTT AAACATTCAA    7020

TGGAAGCTCC ATTGTGCCTA TCGACCCCAG AGCTCTGGGC AAGTAGAACG CATGAACTGC    7080

ACCCTAAAAA ACACTCTTAC AAAATTAATC TTAGAAACCG GTGTAAATTG TGTAAGTCTC    7140

CTTCCTTTAG CCCTACTTAG AGTAAGGTGC ACCCCTTACT GGGCTGGGTT CTTACCTTTT    7200

GAAATCATGT ATGGGAGGGC GCTGCCTATC TTGCCTAAGC TAAGAGATGC CCAATTGGCA    7260

AAAATATCAC AAACTAATTT ATTACAGTAC CTACAGTCTC CCCAACAGGT ACAAGATATC    7320

ATCCTGCCAC TTGTTCGAGG AACCCATCCC AATCCAATTC CTGAACAGAC AGGGCCCTGC    7380

CATTCATTCC CGCCAGGTGA CCTGTTGTTT GTTAAAAAGT TCCAGAGAGA AGGACTCCCT    7440

CCTGCTTGGA AGAGACCTCA CACCGTCATC ACGATGCCAA CGGCTCTGAA GGTGGATGGC    7500

ATTCCTGCGT GGATTCATCA CTCCCGCATC AAAAAGGCCA ACGGAGCCCA ACTAGAAACA    7560

TGGGTCCCCA GGGCTGGGTC AGGCCCCTTA AAACTGCACC TAAGTTGGGT GAAGCCATTA    7620

GATTAATTCT TTTTCTTAAT TTTGTAAAAC AATGCATAGC TTCTGTCAAA CTTATGTATC    7680

TTAAGACTCA ATATAACCCC CTTGTTATAA CTGAGGAATC AATGATTTGA TTCCCCAAAA    7740

ACACAAGTGG GGAATGTAGT GTCCAACCTG GTTTTTACTA ACCCTGTTTT TAGACTCTCC    7800

CTTTCCTTTA ATCACTCAGC CTTGTTTCCA CCTGAATTGA CTCTCCCTTA GCTAAGAGCG    7860

CCAGATGGAC TCCATCTTGG CTCTTTCACT GGCAGCCGCT TCCTCAAGGA CTTAACTTGT    7920

GCAAGCTGAC TCCCAGCACA TCCAAGAATG CAATTAACTG ATAAGATACT GTGGCAAGCT    7980

ATATCCGCAG TTCCCAGGAA TTCGTCCAAT TGATTACACC CAAAAGCCCC GCGTCTATCA    8040

CCTTGTAATA ATCTTAAAGC CCCTGCACCT GGAACTATTA ACGTTCCTGT AACCATTTAT    8100

CCTTTTAACT TTTTTGCCTA CTTTATTTCT GTAAAATTGT TTTAACTAGA CCCCCCCTCT    8160

CCTTTCTAAA CCAAAGTATA AAAGCAAATC TAGCCCCTTC TTCAGGCCGA GAGAATTTCG    8220
```

```
AGCGTTAGCC GTCTCTTGGC CACCAGCTAA ATAAACGGAT TCTTCATGTG TCTCAAAGTG      8280

TGGCGTTTTC TCTAACTCGC TCAGGTACGA CCGTGGTAGT ATTTTCCCCA ACGTCTTATT      8340

TTTAGGGCAC GTATGTAGAG TAACTTTTAT GAAAGAAACC AGTTAAGGAG GTTTTGGGAT      8400

TTCCTTTATC AACTGTAATA CTGGTTTTGA TTATTTATTT ATTTATTTAT TTTTTTTGAG      8460

AAGGAGTTTC ACTCTTGTTG CCCAGGCTGG AGTGCAATGG TGCGATCTTG GCTCACTGCA      8520

ACTTCCGCCT CCCAGGTTCA AGCGATTCTC CTGCCTCAGC CTCGAGAGTA GCTGGGATTA      8580

TAGGCATGCG CCACCACACC CAGCTAATTT TGTATTTTTA GTAAAGATGG GGTTTCTTCA      8640

TGTTGGTCAA GCTGGTCTGG AACTCCCCGC CTCGGGTGAT CTGCCCGCCT CGGCCTCCGA      8700

AAGTGCTGGG ATTACAGGTG TGATCCACCA CACCCAGCCG ATTTATATGT ATATAAATCA      8760

CATTCCTCTA ACCAAAATGT AGTGTTTCCT TCCATCTTGA ATATAGGCTG TAGACCCCGT      8820

GGGTATGGGA CATTGTTAAC AGTGAGACCA CAGCAGTTTT TATGTCATCT GACAGCATCT      8880

CCAAATAGCC TTCATGGTTG TCACTGCTTC CCAAGACAAT TCCAAATAAC ACTTCCCAGT      8940

GATGACTTGC TACTTGCTAT TGTTACTTAA TGTGTTAAGG TGGCTGTTAC AGACACTATT      9000

AGTATGTCAG GAATTACACC AAAATTTAGT GGCTCAAACA ATCATTTTAT TATGTATGTG      9060

GATTCTCATG GTCAGGTCAG GATTTCAGAC AGGGCACAAG GGTAGCCCAC TTGTCTCTGT      9120

CTATGATGTC TGGCCTCAGC ACAGGAGACT CAACAGCTGG GGTCTGGGAC CATTTGGAGG      9180

CTTGTTCCCT CACATCTGAT ACCTGGCTTG GGATGTTGGA AGAGGGGTG AGCTGAGACT       9240

GAGTGCCTAT ATGTAGTGTT TCCATATGGC CTTGACTTCC TTACAGCCTG GCAGCCTCAG      9300

GGTAGTCAGA ATTCTTAGGA GGCACAGGGC TCCAGGGCAG ATGCTGAGGG GTCTTTTATG      9360

AGGTAGCACA GCAAATCCAC CCAGGATC                                        9388

(2) INFORMATION FOR SEQ ID NO:142:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (xi) SEQUENCE DESCRIPTION: SEQ ID NO:142:

TGTAAGTCGA GCAGTGTGAT GGAAGGAATG GTCTTTGGAG AGAGCATATC CATCTCCTCC        60

TCACTGCCTC CTAATGTCAT GAGGTACACT GAGCAGAATT AAACAGGGTA GTCTTAACCA       120

CACTATTTTT AGCTACCTTG TCAAGCTAAT GGTTAAAGAA CACTTTTGGT TTACACTTGT       180

TGGGTCATAG AAGTTGCTTT CCGCCATCAC GCAATAAGTT TGTGTGTAAT CAGAAGGAGT       240

TACCTTATGG TTTCAGTGTC ATTCTTTAGT TAACTTGGGA GCTGTGTAAT TTAGGCTTTG       300

CGTATTATTT CACTTCTGTT CTCCACTTAT GAAGTGATTG TGTGTTCGCG TGTGTGTGCG       360

TGCGCATGTG CTTCCGGCAG TTAACATAAG CAAATACCCA ACATCACACT GCTCGACTT        419

(2) INFORMATION FOR SEQ ID NO:143:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO:143:

TGTAAGTCGA GCAGTGTGAT GTCCACTGCA GTGTGTTGCT GGGAACAGTT AATGAGCAAA        60

TTGTATACAA TGGCTAGTAC ATTGACCGGG ATTTGTTGAA GCTGGTGAGT GTTATGACTT       120
```

AGCCTGTTAG ACTAGTCTAT GCACATGGCT CTGGTCAACT ACCGCTCTCT CATTTCTCCA        180

GATAAATCCC CCATGCTTTA TATTCTCTTC CAAACATACT ATCCTCATCA CCACATAGTT        240

CCTTTGTTAA TGCTTTGTTC TAGACTTTCC CTTTTCTGTT TTCTTATTCA AACCTATATC        300

TCTTTGCATA GATTGTAAAT TCAAATGCCC TCAGGGTGCA GGCAGTTCAT GTAAGGGAGG        360

GAGGCTAGCC AGTGAGATCT GCATCACACT GCTCGACTTA CA                          402

(2) INFORMATION FOR SEQ ID NO:144:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (xi) SEQUENCE DESCRIPTION: SEQ ID NO:144:

TCGGGTGATG CCTCCTCAGG CCAAGAAGAT AAAGCTTCAG ACCCCTAACA CATTTCCAAA         60

AAGGAAGAAA GGAGAAAAAA GGGCATCATC CCCGTTCCGA AGGGTCAGGG AGGAGGAAAT        120

TGAGGTGGAT TCACGAGTTG CGGACAACTC CTTTGATGCC AAGCGAGGTG CAGCCGGAGA        180

CTGGGGAGAG CGAGCCAATC AGGTTTTGAA GTTCCTCTCA GTGC                        224

(2) INFORMATION FOR SEQ ID NO:145:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO:145:

AGCCATTTAC CACCCATCCA CAAAAAAAAA AAAAAAAAAG AAAAATATCA AGGAATAAAA         60

ATAGACTTTG AACAAAAAGG AACATTTGCT GGCCTGAGGA GGCATCACCC G                111

(2) INFORMATION FOR SEQ ID NO:146:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (xi) SEQUENCE DESCRIPTION: SEQ ID NO:146:

TAGCATGTTG AGCCCAGACA CTTGTAGAGA GAGGAGGACA GTTAGAAGAA GAAGAAAAGT         60

TTTTAAATGC TGAAAGTTAC TATAAGAAAG CTTTGGCTTT GGATGAGACT TTTAAAGATG        120

CAGAGGATGC TTTGCAGAAA CTTCATAAAT ATATGCAGGT GATTCCTTAT TTCCTCCTAG        180

AAATTTAGTG ATATTTGAAA TAATGCCCAA ACTTAATTTT CTCCTGAGGA AAACTATTCT        240

ACATTACTTA AGTAAGGCAT TATGAAAAGT TTCTTTTTAG GTATAGTTTT TCCTAATTGG        300

GTTTGACATT GCTTCATAGT GCCTCTGTTT TTGTCCATAA TCGAAAGTAA AGATAGCTGT        360

GAGAAAACTA TTACCTAAAT TTGGTATGTT GTTTTGAGAA ATGTCCTTAT AGGGAGCTCA        420

CCTGGTGGTT TTTAAATTAT TGTTGCTACT ATAATTGAGC TAATTATAAA AACCTTTTTG        480

AGACATATTT TAAATTGTCT TTTCCTGTAA TACTGATGAT GATGTTTTCT CATGCATTTT        540

CTTCTGAATT GGGACCATTG CTGCTGTGTC TGGGCTCACA TGCTA                       585

(2) INFORMATION FOR SEQ ID NO:147:

(i) SEQUENCE CHARACTERISTICS:
    (A) LENGTH: 579 base pairs
    (B) TYPE: nucleic acid
    (C) STRANDEDNESS: single
    (D) TOPOLOGY: linear (xi) SEQUENCE DESCRIPTION: SEQ ID NO:147:

| | | | | | |
|---|---|---|---|---|---|
| TAGCATGTTG | AGCCCAGACA | CTGGGCAGCG | GGGGTGGCCA | CGGCAGCTCC | TGCCGAGCCC | 60 |
| AAGCGTGTTT | GTCTGTGAAG | GACCCTGACG | TCACCTGCCA | GGCTAGGGAG | GGGTCAATGT | 120 |
| GGAGTGAATG | TTCACCGACT | TTCGCAGGAG | TGTGCAGAAG | CCAGGTGCAA | CTTGGTTTGC | 180 |
| TTGTGTTCAT | CACCCCTCAA | GATATGCACA | CTGCTTTCCA | AATAAAGCAT | CAACTGTCAT | 240 |
| CTCCAGATGG | GGAAGACTTT | TTCTCCAACC | AGCAGGCAGG | TCCCCATCCA | CTCAGACACC | 300 |
| AGCACGTCCA | CCTTCTCGGG | CAGCACCACG | TCCTCCACCT | TCTGCTGGTA | CACGGTGATG | 360 |
| ATGTCAGCAA | AGCCGTTCTG | CANGACCAGC | TGCCCCGTGT | GCTGTGCCAT | CTCACTGGCC | 420 |
| TCCACCGCGT | ACACCGCTCT | AGGCCGCGCA | TANTGTGCAC | AGAANAAATG | ATGATCCAGT | 480 |
| CCCACAGCCC | ACGTCCAAGA | NGACTTTATC | CGTCAGGGAT | TCTTTATTCT | GCAGGATGAC | 540 |
| CTGTGGTATT | AATTGTTCGT | GTCTGGGCTC | AACATGCTA  |            |            | 579 |

(2) INFORMATION FOR SEQ ID NO:148:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (xi) SEQUENCE DESCRIPTION: SEQ ID NO:148:

| | | | | | |
|---|---|---|---|---|---|
| TGACACCTTG | TCCAGCATCT | GCAAGCCAGG | AAGAGAGTCC | TCACCAAGAT | CCCCACCCCG | 60 |
| TTGGCACCAG | GATCTTGGAC | TTCCAATCTC | CAGAACTGTG | AGAAATAAGT | ATTTGTCGCT | 120 |
| AAATAAATCT | TTGTGGTTTC | AGATATTTAG | CTATAGCAGA | TCAGGCTGAC | TAAGAGAAAC | 180 |
| CCCATAAGAG | TTACATACTC | ATTAATCTCC | GTCTCTATCC | CCAGGTCTCA | GATGCTGGAC | 240 |
| AAGGTGTCA  |            |            |            |            |            | 249 |

(2) INFORMATION FOR SEQ ID NO:149:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (xi) SEQUENCE DESCRIPTION: SEQ ID NO:149:

| | | | | | |
|---|---|---|---|---|---|
| TGACACCTTG | TCCAGCATCT | GCTATTTTGT | GACTTTTTAA | TAATAGCCAT | TCTGACTGGT | 60 |
| GTGAGATGGT | AACTCATTGT | GGGTTTGGTC | TGCATTTCTC | TAATGATCAG | TGATATTAAG | 120 |
| CTTTTTTTAA | ATATGCTTGT | TGACCACATG | TATATCATCT | TTTGAGAAGT | GTCTGTTCAT | 180 |
| ATCCTTTGCC | CACTTTTTAA | TTTTTTTATC | TTGTAAATTT | GTTTAATTTC | CTTACAGATG | 240 |
| CTGGACAAGG | TGTCA      |            |            |            |            | 255 |

(2) INFORMATION FOR SEQ ID NO:150:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO:150:

TTACGCTGCA ACACTGTGGA GGCCAAGCTG GGATCACTTC TTCATTCTAA CTGGAGAGGA      60

GGGAAGTTCA AGTCCAGCAG AGGGTGGGTG GGTAGACAGT GGCACTCAGA AATGTCAGCT     120

GGACCCCTGT CCCCGCATAG GCAGGACAGC AAGGCTGTGG CTCTCCAGGG CCAGCTGAAG     180

AACAGGACAC TGTCTCCGCT GCCACAAAGC GTCAGAGACT CCCATCTTTG AAGCACGGCC     240

TTCTTGGTCT TCCTGCACTT CCCTGTTCTG TTAGAGACCT GGTTATAGAC AAGGCTTCTC     300

CACAGTGTTG CAGCGTAA                                                   318

(2) INFORMATION FOR SEQ ID NO:151:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (xi) SEQUENCE DESCRIPTION: SEQ ID NO:151:

TNACGCNGCN ACNNTGTAGA GANGGNAAGG CNTTCCCCAC ATTNCCCCTT CATNANAGAA      60

TTATTCNACC AAGNNTGACC NATGCCNTTT ATGACTTACA TGCNNACTNC NTAATCTGTN     120

TCNNGCCTTA AAAGCNNNTC CACTACATGC NTCANCACTG TNTGTGTNAC NTCATNAACT     180

GTCNGNAATA GGGGCNCATA ACTACAGAAA TGCANTTCAT ACTGCTTCCA NTGCCATCNG     240

CGTGTGGCCT TNCCTACTCT TCTTNTATTC CAAGTAGCAT CTCTGGANTG CTTCCCCACT     300

CTCCACATTG TTGCAGCNAT AAT                                             323

(2) INFORMATION FOR SEQ ID NO:152:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (xi) SEQUENCE DESCRIPTION: SEQ ID NO:152:

TCAAGATTCC ATAGGCTGAC CAGTCCAAGG AGAGTTGAAA TCATGAAGGA GAGTCTATCT      60

GGAGAGAGCT GTAGTTTTGA GGGTTGCAAA GACTTAGGAT GGAGTTGGTG GGTGTGGTTA     120

GTCTCTAAGG TTGATTTTGT TCATAAATTT CATGCCCTGA ATGCCTTGCT TGCCTCACCC     180

TGGTCCAAGC CTTAGTGAAC ACCTAAAAGT CTCTGTCTTC TTGCTCTCCA AACTTCTCCT     240

GAGGATTTCC TCAGATTGTC TACATTCAGA TCGAAGCCAG TTGGCAAACA AGATGCAGTC     300

CAGAGGGTCA G                                                          311

(2) INFORMATION FOR SEQ ID NO:153:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (xi) SEQUENCE DESCRIPTION: SEQ ID NO:153:

CAAGATTCCA TAGGCTGACC AGGAGGCTAT TCAAGATCTC TGGCAGTTGA GGAAGTCTCT      60

TTAAGAAAAT AGTTTAAACA ATTTGTTAAA ATTTTTCTGT CTTACTTCAT TTCTGTAGCA     120

GTTGATATCT GGCTGTCCTT TTTATAATGC AGAGTGGGAA CTTTCCCTAC CATGTTTGAT     180

AAATGTTGTC CAGGCTCCAT TGCCAATAAT GTGTTGTCCA AAATGCCTGT TTAGTTTTTA     240

```
AAGACGGAAC TCCACCCTTT GCTTGGTCTT AAGTATGTAT GGAATGTTAT GATAGGACAT      300

AGTAGTAGCG GTGGTCAGCC TATGGAATCT TG                                   332

(2) INFORMATION FOR SEQ ID NO:154:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO:154:

TCAAGATTCC ATAGGCTGAC CTGGACAGAG ATCTCCTGGG TCTGGCCCAG GACAGCAGGC       60

TCAAGCTCAG TGGAGAAGGT TTCCATGACC CTCAGATTCC CCCAAACCTT GGATTGGGTG      120

ACATTGCATC TCCTCAGAGA GGGAGGAGAT GTANGTCTGG GCTTCCACAG GGACCTGGTA      180

TTTTAGGATC AGGGTACCGC TGGCCTGAGG CTTGGATCAT TCANAGCCTG GGGGTGGAAT      240

GGCTGGCAGC CTGTGGCCCC ATTGAAATAG GCTCTGGGGC ACTCCCTCTG TTCCTANTTG      300

AACTTGGGTA AGGAACAGGA ATGTGGTCAN CCTATGGAAT CTTGA                     345

(2) INFORMATION FOR SEQ ID NO:155:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (xi) SEQUENCE DESCRIPTION: SEQ ID NO:155:

GACGCTTGGC CACTTGACAC ATTAAACAGT TTTGCATAAT CACTANCATG TATTTCTAGT       60

TTGCTGTCTG CTGTGATGCC CTGCCCTGAT TCTCTGGCGT TAATGATGGC AAGCATAATC      120

AAACGCTGTT CTGTTAATTC CAAGTTATAA CTGGCATTGA TTAAAGCATT ATCTTTCACA      180

ACTAAACTGT TCTTCATANA ACAGCCCATA TTATTATCAA ATTAAGAGAC AATGTATTCC      240

AATATCCTTT ANGGCCAATA TATTTNATGT CCCTTAATTA AGAGCTACTG TCCGT          295

(2) INFORMATION FOR SEQ ID NO:156:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (xi) SEQUENCE DESCRIPTION: SEQ ID NO:156:

GACGCTTGGC CACTTGACAC TGCAGTGGGA AAACCAGCAT GAGCCGCTGC CCCCAAGGAA       60

CCTCGAAGCC CAGGCAGAGG ACCAGCCATC CCAGCCTGCA GGTAAAGTGT GTCACCTGTC      120

AGGTGGGCTT GGGGTGAGTG GGTGGGGGAA GTGTGTGTGC AAAGGGGGTG TNAATGTNTA      180

TGCGTGTGAG CATGAGTGAT GGCTAGTGTG ACTGCATGTC AGGGAGTGTG AACAAGCGTG      240

CGGGGGTGTG TGTGCAAGTG CGTATGCATA TGAGAATATG TGTCTGTGGA TGAGTGCATT      300

TGAAAGTCTG TGTGTGTGCG TGTGGTCATG ANGGTAANTT ANTGACTGCG CAGGATGTGT      360

GAGTGTGCAT GGAACACTCA NTGTGTGTGT CAAGTGGCCN ANCGTC                    406

(2) INFORMATION FOR SEQ ID NO:157:

(i) SEQUENCE CHARACTERISTICS:
        (A) LENGTH: 208 base pairs
        (B) TYPE: nucleic acid
```

(C) STRANDEDNESS: single
        (D) TOPOLOGY: linear (xi) SEQUENCE DESCRIPTION: SEQ ID NO:157:

TGACGCTTGG CCACTTGACA CACTAAAGGG TGTTACTCAT CACTTTCTTC TCTCCTCGGT    60

GGCATGTGAG TGCATCTATT CACTTGGCAC TCATTTGTTT GGCAGTGACT GTAANCCANA   120

TCTGATGCAT ACACCAGCTT GTAAATTGAA TAAATGTCTC TAATACTATG TGCTCACAAT   180

ANGGTANGGG TGAGGAGAAG GGGAGAGA                                      208

(2) INFORMATION FOR SEQ ID NO:158:

(i) SEQUENCE CHARACTERISTICS:
        (A) LENGTH: 547 base pairs
        (B) TYPE: nucleic acid
        (C) STRANDEDNESS: single
        (D) TOPOLOGY: linear (xi) SEQUENCE DESCRIPTION: SEQ ID NO:158:

CTTCAACCTC CTTCAACCTC CTTCAACCTC CTGGATTCAA ACAATCATCC CACCTCAGAC    60

TCCTTAGTAG CTGAGACTAC AGACTCACGC CACTACATCT GGCTAAATTT TTGTAGAGAT   120

AGGGTTTCAT CATGTTGCCC TGGCTGGTCT CAAACTCCTG ACCTCAAGCA ATGTGCCCAC   180

CTCAGCCTCC CAAAGTGCTG GGATTACAGG CATAAGCCAC CATGCCCAGT CCATNTTTAA   240

TCTTTCCTAC CACATTCTTA CCACACTTTC TTTTATGTTT AGATACATAA ATGCTTACCA   300

TTATGATACA ATTGCCCACA GTATTAAGAC AGTAACATGC TGCACAGGTT TGTAGCCTAG   360

GAACAGTAGG CAATACCACA TAGCTTAGGT GTGTGGTAGA CTATACCATC TAGGTTTGTG   420

TAAGTTACAC TTTATGCTGT TTACACAATG ACAAAACCAT CTAATGATGC ATTTCTCAGA   480

ATGTATCCTT GTCAGTAAGC TATGATGTAC AGGGAACACT GCCCAAGGAC ACAGATATTG   540

TACCTGT                                                             547

(2) INFORMATION FOR SEQ ID NO:159:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (xi) SEQUENCE DESCRIPTION: SEQ ID NO:159:

GCTCCTCTTG CCTTACCAAC TCACCCAGTA TGTCAGCAAT TTTATCRGCT TTACCTACGA    60

AACAGCCTGT ATCCAAACAC TTAACACACT CACCTGAAAA GTTCAGGCAA CAATCGCCTT   120

CTCATGGGTC TCTCTGCTCC AGTTCTGAAC CTTTCTCTTT TCCTAGAACA TGCATTTARG   180

TCGATAGAAG TTCCTCTCAG TGC                                           203

(2) INFORMATION FOR SEQ ID NO:160:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO:160:

TGTAAGTCGA GCAGTGTGAT GGGTGGAACA GGGTTGTAAG CAGTAATTGC AAACTGTATT    60

TAAACAATAA TAATAATATT TAGCATTTAT AGAGCACTTT ATATCTTCAA AGTACTTGCA   120

AACATTAYCT AATTAAATAC CCTCTCTGAT TATAATCTGG ATACAAATGC ACTTAAACTC   180

AGGACAGGGT CATGAGARAA GTATGCATTT GAAAGTTGGT GCTAGCTATG CTTTAAAAAC      240

CTATACAATG ATGGGRAAGT TAGAGTTCAG ATTCTGTTGG ACTGTTTTTG TGCATTTCAG      300

TTCAGCCTGA TGGCAGAATT AGATCATATC TGCACTCGAT GACTYTGCTT GATAACTTAT     360

CACTGAAATC TGAGTGTTGA TCATCACACT GCTCGACTTA CA                        402

(2) INFORMATION FOR SEQ ID NO:161:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (xi) SEQUENCE DESCRIPTION: SEQ ID NO:161:

AGCATGTTGA GCCCAGACAC TGACCAGGAG AAAAACCAAC CAATAGAAAC ACGCCCAGAC      60

ACTGACCAGG AGAAAAACCA ACCAATAAAA ACAGGCCCGG ACATAAGACA AATAATAAAA     120

TTAGCGGACA AGGACATGAA AACAGCTATT GTAAGAGCGG ATATAGTGGT GTGTGTCTGG     180

GCTCAACATG CTA                                                        193

(2) INFORMATION FOR SEQ ID NO:162:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (xi) SEQUENCE DESCRIPTION: SEQ ID NO:162:

TGTTGAGCCC AGACACTGAC CAGGAGAAAA ACCAACCAAT AAAAACAGGC CCGGACATAA      60

GACAAATAAT AAAATTAGCG GACAAGGACA TGAAAACAGC TATTGTAAGA GCGGATATAG     120

TGGTGTGTGT CTGGGCTCAA CATGCTA                                         147

(2) INFORMATION FOR SEQ ID NO:163:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:163:

TAGCATGTTG AGCCCAGACA CAAATCTTTC CTTAAGCAAT AAATCATTTC TGCATATGTT      60

TTTAAAACCA CAGCTAAGCC ATGATTATTC AAAAGGACTA TTGTATTGGG TATTTTGATT     120

TGGGTTCTTA TCTCCCTCAC ATTATCTTCA TTTCTATCAT TGACCTCTTA TCCCAGAGAC     180

TCTCAAACTT TTATGTTATA CAAATCACAT TCTGTCTCAA AAAATATCTC ACCCACTTCT     240

CTTCTGTTTC TGCGTGTGTA TGTGTGTGTG TGTGTGTCTG GGCTCAACAT GCTA           294

(2) INFORMATION FOR SEQ ID NO:164:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (xi) SEQUENCE DESCRIPTION: SEQ ID NO:164:

CGGGATTGGC TTTGAGCTGC AGATGCTGCC TGTGACCGCA CCCGGCGTGG AACAGAAAGC      60

```
CACCTGGCTG CAAGTGCGCC AGAGCCGCCC TGACTACGTG CTGCTGTGGG GCTGGGGCGT      120

GATGAACTCC ACCGCCCTGA AGGAAGCCCA GGCCACCGGA TACCCCCGCG ACAAGATGTA      180

CGGCGTGTGG TGGGCCGGTG CGGAGCCCGA TGTGCGTGAC GTGGGCGAAG GCGCCAAGGG      240

CTACAACGCG CTGGCTCTGA ACGGCTACGG CACGCAGTCC AAGGTGATCC ANGACATCCT      300

GAAACACGTG CACGACAAGG GCCAGGGCAC GGGGCCCAAA GACGAAGTGG GCTCGGTGCT      360

GTACACCCGC GGCGTGATCA TCCAGATGCT GGACAAGGTG TCAATCACTA AT              412

(2) INFORMATION FOR SEQ ID NO:165:

(i) SEQUENCE CHARACTERISTICS:
        (A) LENGTH: 361 base pairs
        (B) TYPE: nucleic acid
        (C) STRANDEDNESS: single
        (D) TOPOLOGY: linear (xi) SEQUENCE DESCRIPTION: SEQ ID NO:165:

TTGACACCTT GTCCAGCATC TGCATCTGAT GAGAGCCTCA GATGGCTACC ACTAATGGCA       60

GAAGGCAAAG GAGAACAGGC ATTGTATGGC AAGAAAGGAA GAAAGAGAGA GGGGAGAAAG      120

GTGCTAGGTT CTTTTCAACA ACCAGTTCTT GATGGAACTG AGAGTAAGAG CTCAAGGCCA      180

GGTGTGGTGA CTCCAACCAG TAATCCCAAC ATTTTAGGAG GCTGAGGCAG GCAGATGTCT      240

TGACCCCATG AGTTTGTGAC CAGCCTGAAC AACATCATGA GACTCCATCT CTACAATAAT      300

TACAAAAATT AATCAGGCAT TGTGGTATGC CCTGTAGTCC CAGATGCTGG ACAAGGTGTC      360

A                                                                     361

(2) INFORMATION FOR SEQ ID NO:166:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (xi) SEQUENCE DESCRIPTION: SEQ ID NO:166:

TWGACTGACT CATGTCCCCT ACACCCAACT ATCTTCTCCA GGTGGCCAGG CATGATAGAA       60

TCTGATCCTG ACTTAGGGGA ATATTTTCTT TTTACTTCCC ATCTTGATTC CCTGCCGGTG      120

AGTTTCCTGG TTCAGGGTAA GAAAGGAGCT CAGGCCAAAG TAATGAACAA ATCCATCCTC      180

ACAGACGTAC AGAATAAGAG AACWTGGACW TAGCCAGCAG AACMCAAKTG AAAMCAGAAC      240

MCTTAMCTAG GATRACAAMC MCRRARATAR KTGCYCMCMC WTATAATAGA AACCAAACTT      300

GTATCTAATT AAATATTTAT CCACYGTCAG GGCATTAGTG GTTTTGATAA ATACGCTTTG      360

GCTAGGATTC CTGAGGTTAG AATGGAARAA CAATTGCAMC GAGGGTAGGG GACATGAGTC      420

AKTCTAA                                                               427

(2) INFORMATION FOR SEQ ID NO:167:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (xi) SEQUENCE DESCRIPTION: SEQ ID NO:167:

AACGTCGCAT GCTCCCGGCC GCCATGGCCG CGGGATAGAC TGACTCATGT CCCCTAAGAT       60

AGAGGAGACA CCTGCTAGGT GTAAGGAGAA GATGGTTAGG TCTACGGAGG CTCCAGGGTG      120
```

| | | |
|---|---|---|
| GGAGTAGTTC CCTGCTAAGG GAGGGTAGAC TGTTCAACCT GTTCCTGCTC CGGCCTCCAC | 180 |
| TATAGCAGAT GCGAGCAGGA GTAGGAGAGA GGGAGGTAAG AGTCAGAAGC TTATGTTGTT | 240 |
| TATGCGGGGA AACGCCRTAT CGGGGGCAGC CRAGTTATTA GGGGACANTR TAGWYARTCW | 300 |
| AGNTAGCATC CAAAGCGNGG GAGTTNTCCC ATATGGTTGG ACCTGCAGGC GGCCGCATTA | 360 |
| GTGATTAGCA TGTGAGCCCC AGACACGCAT AGCAACAAGG ACCTAAACTC AGATCCTGTG | 420 |
| CTGATTACTT AACATGAATT ATTGTATTTA TTTAACAACT TTGAGTTATG AGGCATATTA | 480 |
| TTAGGTCCAT ATTACCTGGA | 500 |

(2) INFORMATION FOR SEQ ID NO:168:

(i) SEQUENCE CHARACTERISTICS:
        (A) LENGTH: 358 base pairs
        (B) TYPE: nucleic acid
        (C) STRANDEDNESS: single
        (D) TOPOLOGY: linear (xi) SEQUENCE DESCRIPTION: SEQ ID NO:168:

| | |
|---|---|
| TTCATCGCTC GGTGACTCAA GCCTGTAATC CCAGAACTTT GGGAGGCCGA GGGGAGCAGA | 60 |
| TCACCTGAGG TTGGGAGTTT GAGACCAGCC TGGCCAACAT GGTGACAACC CGTCTCTGCT | 120 |
| AAAAATACAA AAATTAGCCA AGCATGGTGG CATGCACTTG TAATCCCAGC TACTCGGGAG | 180 |
| GCTGAGGCAG GAGAATCACT TGAGGCCAGG AGGCAGAGGT TGCAGTGAGG CAGAGGTTGA | 240 |
| GATCATGCCA CTGCACTCCA GCCTGGGCAA CAGAGTAAGA CTCCATCTCA AAAAAAAAA | 300 |
| AAAAAAAGAA TGATCAGAGC CACAAATACA GAAAACCTTG AGTCACCGAG CGATGAAA | 358 |

(2) INFORMATION FOR SEQ ID NO:169:

(i) SEQUENCE CHARACTERISTICS:
        (A) LENGTH: 1265 base pairs
        (B) TYPE: nucleic acid
        (C) STRANDEDNESS: single
        (D) TOPOLOGY: linear (xi) SEQUENCE DESCRIPTION: SEQ ID NO:169:

| | |
|---|---|
| TTCTGTCCAC ACCAATCTTA GAGCTCTGAA AGAATTTGTC TTTAAATATC TTTTAATAGT | 60 |
| AACATGTATT TTATGGACCA AATTGACATT TTCGACTATT TTTTCCCAAA AAAGTCAGG | 120 |
| TGAATTTCAG CACACTGAGT TGGGAATTTC TTATCCCAGA AGWCGGCACG AGCAATTTCA | 180 |
| TATTTATTTA AGATTGATTC CATACTCCGT TTTCAAGGAG AATCCCTGCA GTCTCCTTAA | 240 |
| AGGTAGAACA AATACTTTCT ATTTTTTTTT CACCATTGTG GGATTGGACT TTAAGAGGTG | 300 |
| ACTCTAAAAA AACAGAGAAC AAATATGTCT CAGTTGTATT AAGCACGGAC CCATATTATC | 360 |
| ATATTCACTT AAAAAAATGA TTTCCTGTGC ACCTTTTGGC AACTTCTCTT TTCAATGTAG | 420 |
| GGAAAAACTT AGTCACCCTG AAAACCCACA AATAAATAA AACTTGTAGA TGTGGGCAGA | 480 |
| ARGTTTGGGG GTGGACATTG TATGTGTTTA AATTAAACCC TGTATCACTG AGAAGCTGTT | 540 |
| GTATGGGTCA GAGAAAATGA ATGCTTAGAA GCTGTTCACA TCTTCAAGAG CAGAAGCAAA | 600 |
| CCACATGTCT CAGCTATATT ATTATTTATT TTTTATGCAT AAAGTGAATC ATTTCTTCTG | 660 |
| TATTAATTTC CAAAGGGTTT TACCCTCTAT TTAAATGCTT TGAAAAACAG TGCATTGACA | 720 |
| ATGGGTTGAT ATTTTTCTTT AAAAGAAAAA TATAATTATG AAAGCCAAGA TAATCTGAAG | 780 |
| CCTGTTTTAT TTTAAAACTT TTTATGTTCT GTGGTTGATG TTGTTTGTTT GTTTGTTTCT | 840 |
| ATTTTGTTGG TTTTTTACTT TGTTTTTTGT TTGTTTTGT TTTGGTTTDG CATACTACAT | 900 |
| GCAGTTTCTT TAACCAATGT CTGTTTGGCT AATGTAATTA AAGTTGTTAA TTTATATGAG | 960 |

```
TGCATTTCAA CTATGTCAAT GGTTTCTTAA TATTTATTGT GTAGAAGTAC TGGTAATTTT     1020

TTTATTTACA ATATGTTTAA AGAGATAACA GTTTGATATG TTTTCATGTG TTTATAGCAG     1080

AAGTTATTTA TTTCTATGGC ATTCCAGCGG ATATTTTGGT GTTTGCGAGG CATGCAGTCA     1140

ATATTTTGTA CAGTTAGTGG ACAGTATTCA GCAACGCCTG ATAGCTTCTT TGGCCTTATG     1200

TTAAATAAAA AGACCTGTTT GGGATGTAAA AAAAAAAAAA AAAAAAAAAA AAAAAAAAA     1260

AAAAA                                                                 1265

(2) INFORMATION FOR SEQ ID NO:170:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO:170:

TGTAAGTCGA GCAGTGTGAT GACGATATTC TTCTTATTAA TGTGGTAATT GAACAAATGA       60

TCTGTGATAC TGATCCTGAG CTAGGAGGCG CTGTTCAGTT AATGGGACTT CTTCGTACTC      120

TAATTGATCC AGAGAACATG CTGGCTACAA CTAATAAAAC CGAAAAAAGT GAATTTCTAA      180

ATTTTTTCTA CAACCATTGT ATGCATGTTC TCACAGCACC ACTTTTGACC AATACTTCAG      240

AAGACAAATG TGAAAAGGAT AATATAGTTG GATCAAACAA AAACAACACA ATTTGTCCCG      300

ATAATTATCA AACAGCACAG CTACTTGCCT TAATTTTAGA GTTACTCACA TTTTGTGTGG      360

AACATCACAC TGCTCGACTT ACA                                              383

(2) INFORMATION FOR SEQ ID NO:171:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO:171:

TGGGCACCTT CAATATCGCA AGTTAAAAAT AATGTTGAGT TTATTATACT TTTGACCTGT       60

TTAGCTCAAC AGGGTGAAGG CATGTAAAGA ATGTGGACTT CTGAGGAATT TTCTTTTAAA      120

AAGAACATAA TGAAGTAACA TTTTAATTAC TCAAGGACTA CTTTTGGTTG AAGTTTATAA      180

TCTAGATACC TCTACTTTTT GTTTTTGCTG TTCGACAGTT CACAAAGACC TTCAGCAATT      240

TACAGGGTAA AATCGTTGAA GTAGTGGAGG TGAAACTGAA ATTTAAAATT ATTCTGTAAA      300

TACTATAGGG AAAGAGGCTG AGCTTAGAAT CTTTTGGTTG TTCATGTGTT CTGTGCTCTT      360

ATCATCACAC TGCTCGACTT ACA                                              383

(2) INFORMATION FOR SEQ ID NO:172:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (xi) SEQUENCE DESCRIPTION: SEQ ID NO:172:

TCGGGTGATG CCTCCTCAGG CTTGTCGTTA GTGTACACAG AGCTGCTCAT GAAGCGACAG       60

CGGCTGCCCC TGGCACTTCA GAACCTCTTC CTCTACACTT TTGGTGCGCT TCTGAATCTA      120

GGTCTGCATG CTGGCGGCGG CTCTGGCCCA GGCCTCCTGG AAAGTTTCTC AGGATGGGCA      180
```

```
GCACTCGTGG TGCTGAGCCA GGCACTAAAT GGACTGCTCA TGTCTGCTGT CATGGAGCAT      240

GGCAGCAGCA TCACACGCCT CTTTGTGGTG TCCTGCTCGC TGGTGGTCAA CGCCGTGCTC      300

TCAGCAGTCC TGCTACGGCT GCAGCTCACA GCCGCCTTCT TCCTGGCCAC ATTGCTCATT      360

GGCCTGGCCA TGCGCCTGTA CTATGGCAGC CGCTAGTCCC TGACAACTTC CACCCTGATT      420

CCGGACCCTG TAGATTGGGC GCCACCACCA GATCCCCCTC CCAGGCCTTC CTCCCTCTCC      480

CATCAGCGGC CCTGTAACAA GTGCCTTGTG AGAAAAGCTG GAGAAGTGAG GGCAGCCAGG      540

TTATTCTCTG GAGGTTGGTG GATGAAGGGG TACCCCTAGG AGATGTGAAG TGTGGGTTTG      600

GTTAAGGAAA TGCTTACCAT CCCCCACCCC CAACCAAGTT NTTCCAGACT AAAGAATTAA      660

GGTAACATCA ATACCTAGGC CTGAGGAGGC ATCACCCGA                             699

(2) INFORMATION FOR SEQ ID NO:173:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (xi) SEQUENCE DESCRIPTION: SEQ ID NO:173:

TCGGGTGATG CCTCCTCAGG CCAGATCAAA CTTGGGGTTG AAAACTGTGC AAAGAAATCA       60

ATGTCGGAGA AAGAATTTTG CAAAAGAAAA ATGCCTAATC AGTACTAATT TAATAGGTCA      120

CATTAGCAGT GGAAGAAGAA ATGTTGATAT TTTATGTCAG CTATTTTATA ATCACCAGAG      180

TGCTTAGCTT CATGTAAGCC ATCTCGTATT CATTAGAAAT AAGAACAATT TTATTCGTCG      240

GAAAGAACTT TTCAATTTAT AGCATCTTAA TTGCTCAGGA TTTTAAATTT TGATAAAGAA      300

AGCTCCACTT TTGGCAGGAG TAGGGGGCAG GGAGAGAGGA GGCTCCATCC ACAAGGACAG      360

AGACACCAGG GCCAGTAGGG TAGCTGGTGG CTGGATCAGT CACAACGGAC TGACTTATGC      420

CATGAGAAGA AACAACCTCC AAATCTCAGT TGCTTAATAC AACACAAGCT CATTTCTTGC      480

TCACGTTACA TGTCCTATGT AGATCAACAG CAGGTGACTC AGGGACCCAG GCTCCATCTC      540

CATATGAGCT TCCATAGTCA CCAGGACACG GGCTCTGAAA GTGTCCTCCA TGCAGGGACA      600

CATGCCTCTT CCTTTCATTG GGCAGAGCAA GTCACTTATG GCCAGAAGTC ACACTGCAGG      660

GCAGTGCCAT CCTGCTGTAT GCCTGAGGAG GCATCACCCG A                         701

(2) INFORMATION FOR SEQ ID NO:174:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (xi) SEQUENCE DESCRIPTION: SEQ ID NO:174:

TCGGGTGATG CCTCCTCANG CCCCTAAATC AGAGTCCAGG GTCAGAGCCA CAGGAGACAG       60

GGAAAGACAT AGATTTTAAC CGGCCCCCTT CAGGAGATTC TGAGGCTCAG TTCACTTTGT      120

TGCAGTTTGA ACAGAGGCAG CAAGGCTAGT GGTTAGGGGC ACGGTCTCTA AAGCTGCACT      180

GCCTGGATCT GCCTCCCAGC TCTGCCAGGA ACCAGCTGCG TGGCCTTGAG CTGCTGACAC      240

GCAGAAAGCC CCCTGTGGAC CCAGTCTCCT CGTCTGTAAG ATGAGGACAG GACTCTAGGA      300

ACCCTTTCCC TTGGTTTGGC CTCACTTTCA CAGGCTCCCA TCTTGAACTC TATCTACTCT      360

TTTCCTGAAA CCTTGTAAAA GAAAAAAGTG CTAGCCTGGG CAACATGGCA AAACCCTGTC      420
```

```
TCTACAAAAA ATACAAAAAT TAGTTGGGTG TGGTGGCATG TGCCTGTAGT CCCAGCCACT    480

TGGGAGGTGC TGAGGTGGGA GGATCACTTG AGCCCGGGAG GTGGAGGTTG CAGTGAGCCA    540

AGATCATGCC ACTGCACTCC AGCCTGAGTA ATAGAGTAAG ACTCTGTCTC AAAAACAACA    600

ACAACAACAG TGAGTGTGCC TCTGTTTCCG GGTTGGATGG GGCACCACAT TTATGCATCT    660

CTCAGATTTG GACGCTGCAG CCTGAGGAGG CATCACCCGA                          700
```

(2) INFORMATION FOR SEQ ID NO:175:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (xi) SEQUENCE DESCRIPTION: SEQ ID NO:175:

```
TATAGGGCGA ATTGGGCCCG AGTTGCATGN TCCCGGCCGC CATGGCCGCG GGATTCGGGT     60

GATGCCTCCT CAGGCTTGTC TGCCACAAGC TACTTCTCTG AGCTCAGAAA GTGCCCCTTG    120

ATGAGGGAAA ATGTCCTACT GCACTGCGAA TTTCTCAGTT CCATTTTACC TCCCAGTCCT    180

CCTTCTAAAC CAGTTAATAA ATTCATTCCA CAAGTATTTA CTGATTACCT GCTTGTGCCA    240

GGGACTATTC TCAGGCTGAA GAAGGTGGGA GGGGAGGGCG GAACCTGAGG AGCCACCTGA    300

GCCAGCTTTA TATTTCAACC ATGGCTGGCC CATCTGAGAG CATCTCCCCA CTCTCGCCAA    360

CCTATCGGGG CATAGCCCAG GGATGCCCCC AGGCGGCCCA GGTTAGATGC GTCCCTTTGG    420

CTTGTCAGTG ATGACATACA CCTTAGCTGC TTAGCTGGTG CTGGCCTGAG GAGGCATCAC    480

CCGA                                                                484
```

(2) INFORMATION FOR SEQ ID NO:176:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO:176:

```
TCGGGTGATG CCTCCTCAGG GCTCAAGGGA TGAGAAGTGA CTTCTTTCTG GAGGGACCGT     60

TCATGCCACC CAGGATGAAA ATGGATAGGG ACCCACTTGG AGGACTTGCT GATATGTTTG    120

GACAAATGCC AGGTAGCGGA ATTGGTACTG GTCCAGGAGT TATCCAGGAT AGATTTTCAC    180

CCACCATGGG ACGTCATCGT TCAAATCAAC TCTTCAATGG CCATGGGGGA CACATCATGC    240

CTCCCACACA ATCGCAGTTT GGAGAGATGG GAGGCAAGTT TATGAAAAGC CAGGGGCTAA    300

GCCAGCTCTA CCATAACCAG AGTCAGGGAC TCTTATCCCA GCTGCAAGGA CAGTCGAAGG    360

ATATGCCACC TCGGTTTTCT AAGAAAGGAC AGCTTAATGC AGATGAGATT AGCCTGAGGA    420

GGCATCACCC GA                                                       432
```

(2) INFORMATION FOR SEQ ID NO:177:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (xi) SEQUENCE DESCRIPTION: SEQ ID NO:177:

```
TAGCATGTTG AGCCCAGACA CAGTAGCATT TGTGCCAATT TCTGGTTGGA ATGGTGACAA     60
```

```
CATGCTGGAG CCAAGTGCTA ACATGCCTTG GTTCAAGGGA TGGAAAGTCA CCCGTAAGGA      120

TGGCAATGCC AGTGGAACCA CGCTGCTTGA GGCTCTGGAC TGCATCCTAC CACCAACTCG      180

CCCAACTGAC AAGCCCTTGC GCCTGCCTCT CCAGGATGTC TACAAAATTG GTGGTATTGG      240

TACTGTTCCT GTTGGCCGAG TGGAGACTGG TGTTCTCAAA CCCGGTATGG TGGTCACCTT      300

TGCTCCAGTC AACGTTACAA CGGAAGTAAA ATCTGTCGAA ATGCACCATG AAGCTTTGAG      360

TGAAGCTCTT CCTGGGGACA ATGTGGGCTT CAATGTCAAG AATGTGTCTG TCAAGGATGT      420

TCGTCGTGGC AACGTTGCTG GTGACAGCAA AAATGACCCA CCAATGGAAG CAGCTGGCTT      480

CACTGCTCAG GTGATTATCC TGAACCATCC AGGCCAAATA AGTGCCGGCT ATGCCCCTGT      540

ATTGGATTGC CACACGGCTC ACATTGCATG CAAGTTTGCT GAGCTGAAGG AAAAGATTGA      600

TCGCCGTTCT GGTAAAAAGC TGGAAGATGG CCCTAAATTC TTGAAGTCTG GTGATGCTGC      660

CATTGTTGAT ATGGTTCCTG GCAAGCCCAT GTGTGTTGAG AGCTTCTCAG ACTATCCACC      720

TTTGGGTCGC TTTGCTGTTC GTGATATGAG ACAGACAGTT GCGGTGGGTG TCTGGGCTCA      780

ACATGCTA                                                              788

(2) INFORMATION FOR SEQ ID NO:178:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (xi) SEQUENCE DESCRIPTION: SEQ ID NO:178:

TAGCATGTTG AGCCCAGACA CCTGTGTTTC TGGGAGCTCT GGCAGTGGCG GATTCATAGG       60

CACTTGGGCT GCACTTTGAA TGACACACTT GGCTTTATTA GATTCACTAG TTTTTAAAAA      120

ATTGTTGTTC GTTTCTTTTC ATTAAAGGTT TAATCAGACA GATCAGACAG CATAATTTTG      180

TATTTAATGA CAGAAACGTT GGTACATTTC TTCATGAATG AGCTTGCATT CTGAAGCAAG      240

AGCCTACAAA AGGCACTTGT TATAAATGAA AGTTCTGGCT CTAGAGGCCA GTACTCTGGA      300

GTTTCAGAGC AGCCAGTGAT TGTTCCAGTC AGTGATGCCT AGTTATATAG AGGAGGAGTA      360

CACTGTGCAC TCTTCTAGGT GTAAGGGTAT GCAACTTTGG ATCTTAAAAT TCTGTACACA      420

TACACACTTT ATATATATGT ATGTATGTAT GAAAACATGA AATTAGTTTG TCAAATATGT      480

GTGTGTTTAG TATTTTAGCT TAGTGCAACT ATTTCCACAT TATTTATTAA ATTGATCTAA      540

GACACTTTCT TGTTGACACC TTGAATATTA ATGTTCAAGG GTGCAATGTG TATTCCTTTA      600

GATTGTTAAA GCTTAATTAC TATGATTGT AGTAAATTAA CTTTTAAAAT GTATTTGAGC       660

CCTTCTGTAG TGTCGTAGGG CTCTTACAGG GTGGGAAAGA TTTTAATTTT CCAGTTGCTA      720

ATTGAACAGT ATGGCCTCAT TATATATTTT GATTTATAGG AGTTTGTGTC TGGGCTCAAC      780

ATGCTA                                                                786

(2) INFORMATION FOR SEQ ID NO:179:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (xi) SEQUENCE DESCRIPTION: SEQ ID NO:179:

TAGCATGTTG AGCCCAGACA CTGGTTACAA GACCAGACCT GCTTCCTCCA TATGTAAACA       60

GCTTTTAAAA AGCCAGTGAA CCTTTTTAAT ACTTTGGCAA CCTTCTTTCA CAGGCAAAGA      120
```

ACACCCCCAT CCGCCCCTTG TTTGGAGTGC AGAGTTTGGC TTTGGTTCTT TGCCTTGCCT        180

GGAGTATACT TCTAATTCCT GTTGTCCTGC ACAAGCTGAA TACCGAGCTA CCCACCGCCA        240

CCCAGGCCAG GTTTCCACTC ATTTATTACT TTATGTTTCT GTTCCATTGC TGGTCCACAG        300

AAATAAGTTT TCCTTTGGAG GAATGTGATT ATACCCCTTT AATTTCCTCC TTTTGCTTTT        360

TTTTAATATC ATTGGTATGT GTTTGGCCCA GAGGAAACTG AAATTCACCA TCATCTTGAC        420

TGGCAATCCC ATTACCATGC TTTTTTTAAA AAACGTAATT TTTCTTGCCT TACATTGGCA        480

GAGTAGCCCT TCCTGGCTAC TGGCTTAATG TAGTCACTCA GTTTCTAGGT GGCATTAGGC        540

ATGAGACCTG AAGCACAGAC TGTCTTACCA CAAAAGGTGA CAAGATCTCA AACCTTAGCC        600

AAAGGGCTAT GTCAGGTTTC AATGCTATCT GCTTCTGTTC CTGCTCACTG TTCTGGATTT        660

TGTCCTTCTT CATCCCTAGC ACCAGAATTT CCCAGTCTCC CTCCCTACCT TCCCTTGTTT        720

TAATTCTAAT CTATCAGCAA AATAACTTTT CAAATGTTTT AACCGGTATC TCCATGTGTC        780

TGGGCTCAAC ATGCTA                                                       796

(2) INFORMATION FOR SEQ ID NO:180:

(i) SEQUENCE CHARACTERISTICS:
        (A) LENGTH: 488 base pairs
        (B) TYPE: nucleic acid
        (C) STRANDEDNESS: single
        (D) TOPOLOGY: linear (xi) SEQUENCE DESCRIPTION: SEQ ID NO:180:

GGATGTGCTG CAAGGCGATT AAGTTGGGTA ACGCCAGGGT TTTCCCAGTC ACGACGTTGT         60

AAAACGACGG CCAGTGAATT GTAATACGAC TCACTATAGG GCGAATTGGG CCCGACGTCG        120

CATGCTCCCG GCCGCCATGG CCGCGGGATA GCATGTTGAG CCCAGACACC TGCAGGTCAT        180

TTGGAGAGAT TTTTCACGTT ACCAGCTTGA TGGTCTTTTT CAGGAGGAGA GACACTGAGC        240

ACTCCCAAGG TGAGGTTGAA GATTTCCTCT AGATAGCCGG ATAAGAAGAC TAGGAGGGAT        300

GCCTAGAAAA TGATTAGCAT GCAAATTTCT ACCTGCCATT TCAGAACTGT GTGTCAGCCC        360

ACATTCAGCT GCTTCTTGTG AACTGAAAAG AGAGAGGTAT TGAGACTTTT CTGATGGCCG        420

CTCTAACATT GTAACACAGT AATCTGTGTG TGTGTGGGTG TGTGTGTGTG TCTGGGCTCA        480

ACATGCTA                                                                488

(2) INFORMATION FOR SEQ ID NO:181:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO:181:

TAGCATGTTG AGCCCAGACA CGGCGACGGT ACCTGATGAG TGGGGTGATG GCACCTGTGA         60

AAAGGAGGAA CGTCATCCCC CATGATATTG GGGACCCAGA TGATGAACCA TGGCTCCGCG        120

TCAATGCATA TTTAATCCAT GATACTGCTG ATTGGAAGGA CCTGAACCTG AAGTTTGTGC        180

TGCAGGTTTA TCGGGACTAT TACCTCACGG GTGATCAAAA CTTCCTGAAG GACATGTGGC        240

CTGTGTGTCT AGTAAGGGAT GCACATGCAG TGGCCAGTGT GCCAGGGGTA TGGTTGGTGT        300

CTGGGCTCAA CATGCTA                                                      317

(2) INFORMATION FOR SEQ ID NO:182:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:182:

TAGCATGTTG AGCCCAGACA CTGGCTGTTA GCCAAATCCT CTCTCAGCTG CTCCCTGTGG    60

TTTGGTGACT CAGGATTACA GAGGCATCCT GTTTCAGGGA ACAAAAAGAT TTTAGCTGCC   120

AGCAGAGAGC ACCACATACA TTAGAATGGT AAGGACTGCC ACCTCCTTCA AGAACAGGAG   180

TGAGGGTGGT GGTGAATGGG AATGGAAGCC TGCATTCCCT GATGCATTTG TGCTCTCTCA   240

AATCCTGTCT TAGTCTTAGG AAAGGAAGTA AAGTTTCAAG GACGGTTCCG AACTGCTTTT   300

TGTGTCTGGG CTCAACATGC TATCCCGCGG CCATGGCGGC CGGGAGCATG CGACGTCGGG   360

CCCAATTCGC CCTATAGTGA GTCGTATTAC AATTCACTGG CCGTCGTTTT ACAACGTCGT   420

GACTGGGAAA ACCCTGGCGT TACCCAACTT AATCGCCTTG CAGCACATCC CCCTTTCCCA   480

GCTGGCGTAA TANCGAAAAG GCCCGCA                                      507

(2) INFORMATION FOR SEQ ID NO:183:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (xi) SEQUENCE DESCRIPTION: SEQ ID NO:183:

GATTTACGCT GCAACACTGT GGAGGTAGCC CTGGAGCAAG GCAGGCATGG ATGCTTCTGC    60

AATCCCCAAA TGGAGCCTGG TATTTCAGCC AGGAATCTGA GCAGAGCCCC CTCTAATTGT   120

AGCAATGATA AGTTATTCTC TTTGTTCTTC AACCTTCCAA TAGCCTTGAG CTTCCAGGGG   180

AGTGTCGTTA ATCATTACAG CCTGGTCTCC ACAGTGTTGC AGCGTAA                227

(2) INFORMATION FOR SEQ ID NO:184:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (xi) SEQUENCE DESCRIPTION: SEQ ID NO:184:

TTACGCTGCA ACACTGTGGA GCAGATTAAC ATCAGACTTT TCTATCAACA TGACTGGGGT    60

TACTAAAAAG ACAACAAATC AATGGCTTCA AAAGTCTAAG GAATAATTTC GATACTTCAA   120

CTTTATAAAA CCTGACAAAA CTATCAATCA AGCATAAAGA CAGATGAAGA ACATTTCCAG   180

ATTTTGGCCA ATCAGATATT TTACCTCCAC AGTGTTGCAG CGTAA                  225

(2) INFORMATION FOR SEQ ID NO:185:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (xi) SEQUENCE DESCRIPTION: SEQ ID NO:185:

GGCCCGACGT CGCATGCTCC CGGCCGCCAT GGCCGCGGGA TTCGTTAGGG TCTCTATCCA    60

CTGGGACCCA TAGGCTAGTC AGAGTATTTA GAGTTGAGTT CCTTTCTGCT TCCCAGAATT   120

```
TGAAAGAAAA GGAGTGAGGT GATAGAGCTG AGAGATCAGA TTTGCCTCTG AAGCCTGTTC      180

AAGATGTATG TGCTCAGACC CCACCACTGG GGCCTGTGGG TGAGGTCCTG GGCATCTATT      240

TGAATGAATT GCTGAAGGGG AGCACTATGC CAAGGAAGGG GAACCCATCC TGGCACTGGC      300

ACAGGGGTCA CCTTATCCAG TGCTCAGTGC TTCTTTGCTG CTACCTGGTT TTCTCTCATA      360

TGTGAGGGGC AGGTAAGAAG AAGTGCCCRG TGTTGTGCGA GTTTTAGAAC ATCTACCAGT      420

AAGTGGGGAA GTTTCACAAA GCAGCAGCTT TGTTTTGTGT ATTTTCACCT TCAGTTAGAA      480

GAGGAAGGCT GTGAGATGAA TGTTAGTTGA GTGGAAAAGA CGGGTAAGCT TAGTGGATAG      540

AGACCCTAAC GAATCACTAG TGCGGCCGCC TTGCAGGTCG ACCATATGGG AGAGCTC        597
```

(2) INFORMATION FOR SEQ ID NO:186:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (xi) SEQUENCE DESCRIPTION: SEQ ID NO:186:

```
GGCCCGAAGT TGCATGTTCC CGGCCGCCAT GGCCGCGGGA TTCGTTAGGG TCTCTATCCA       60

CTACCTAAAA AATCCCAAAC ATATAACTGA ACTCCTCACA CCCAATTGGA CCAATCCATC      120

ACCCCAGAGG CCTACAGATC CTCCTTTGAT ACATAAGAAA ATTTCCCCAA ACTACCTAAC      180

TATATCATTT TGCAAGATTT GTTTTACCAA ATTTTGATGG CCTTTCTGAG CTTGTCAGTG      240

TGAACCACTA TTACGAACGA TCGGATATTA ACTGCCCCTC ACCGTCCAGG TGTAGCTGGC      300

AACATCAAGT GCAGTAAATA TTCATTAAGT TTTCACCTAC TAAGGTGCTT AAACACCCTA      360

GGGTGCCATG TCGGTAGCAG ATCTTTTGAT TTGTTTTTAT TTCCCATAAG GGTCCTGTTC      420

AAGGTCAATC ATACATGTAG TGTGAGCAGC TAGTCACTAT CGCATGACTT GGAGGGTGAT      480

AATAGAGGCC TCCTTTGCTG TTAAAGAACT CTTGTCCCAG CCTGTCAAAG TGGATAGAGA      540

CCCTAACGAA TCACTAGTGC GGCCGCCTGC AGGTCGACCA TATGGGAGAG CTCCCAA        597
```

(2) INFORMATION FOR SEQ ID NO:187:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (xi) SEQUENCE DESCRIPTION: SEQ ID NO:187:

```
TCGTTAGGGT CTCTATCCAC TTGCAGGTAA AATCCAATCC TGTGTATATC TTATAGTCTT       60

CCATATGTAG TGGTTCAAGA GACTGCAGTT CCAGAAAGAC TAGCCGAGCC CATCCATGTC      120

TTCCACTTAA CCCTGCTTTG GGTTACACAT CTTAACTTTT CTGTTCAAGT TTCTCTGTGT      180

AGTTTATAGC ATGAGTATTG GGAWAATGCC CTGAAACCTG ACATGAGATC TGGGAAACAC      240

AAACTTACTC AATAAGAATT TCTCCCATAT TTTTATGATG GAAAAATTTC ACATGCACAG      300

AGGAGTGGAT AGAGACCCTA ACGA                                             324
```

(2) INFORMATION FOR SEQ ID NO:188:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (xi) SEQUENCE DESCRIPTION: SEQ ID NO:188:

| | | |
|---|---|---|
| GCGCGGGGAT TCGGGGTGAT ACCTCCTCAT GCCAAAATAC AACGTNTAAT TTCACAACTT | 60 |
| GCCTTCCAAT TTACGCATTT TCAATTTGCT CTCCCCATTT GTTGAGTCAC AACAAACACC | 120 |
| ATTGCCCAGA AACATGTATT ACCTAACATG CACATACTCT TAAAACTACT CATCCCTT | 178 |

(2) INFORMATION FOR SEQ ID NO:189:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (xi) SEQUENCE DESCRIPTION: SEQ ID NO:189:

| | |
|---|---|
| TGACACCTTG TCCAGCATCT GACACAGTCT TGGCTCTTGG AAAATATTGG ATAAATGAAA | 60 |
| ATGAATTTCT TTAGCAAGTG GTATAAGCTG AGAATATACG TATCACATAT CCTCATTCTA | 120 |
| AGACACATTC AGTGTCCCTG AAATTAGAAT AGGACTTACA ATAAGTGTGT TCACTTTCTC | 180 |
| AATAGCTGTT ATTCAATTGA TGGTAGGCCT TAAAAGTCAA AGAAATGAGA GGGCATGTGA | 240 |
| AAAAAAGCTC AACATCACTG ATCATTAGAA AACTTCCATT CAAACCCCCA ATGAGATACC | 300 |
| ATCTCATACC AGTCAGAATG GCTATTATTA AAAAGTCAAA AATAACAGA TGCTGGACAA | 360 |
| GGTGTCA | 367 |

(2) INFORMATION FOR SEQ ID NO:190:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (xi) SEQUENCE DESCRIPTION: SEQ ID NO:190:

| | |
|---|---|
| GACACCTTGT CCAGCATCTG ACAACGCTAA CAGCCTGAGG AGATCTTTAT TTATTTATTT | 60 |
| AGTTTTTACT CTGGCTAGGC AGATGGTGGC TAAAACATTC ATTTACCCAT TTATTCATTT | 120 |
| AATTGTTCCT GCAAGGCCTA TGGATAGAGT ATTGTCCAGC ACTGCTCTGG AAGCTAGGAG | 180 |
| CATGGGGATG AACAAGATAG GCTACATCCT GTTCCCACAG AACTTCCACT TTAGTCTGGG | 240 |
| AAACAGATGA TATATACAAA TATATAAATG AATTCAGGTA GTTTTAAGTA CGAAAAGAAT | 300 |
| AAGAAAGCAG AGTCATGATT TANAATGCTG GAAACAGGGG CTATTGCTTG AGATATTGAA | 360 |
| GGTGCCCAA | 369 |

(2) INFORMATION FOR SEQ ID NO:191:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (xi) SEQUENCE DESCRIPTION: SEQ ID NO:191:

| | |
|---|---|
| TGACACCTTG TCCAGCATCT GCACAGGGAA AAGAAACTAT TATCAGAGTG AACAGGCAAC | 60 |
| CTACAGAATG GGAGAAAATT TTTGCAATCT ATCCATCTGA CAAAGGGCTA ATATCCAGAA | 120 |
| TCTACAAAGA ACTTATACAA ATTTACAAGA AACAAACAAA CAAACAACTC CTCAAAAAGT | 180 |
| GGGTGAAGGA TGTGAACAGA CACTTCTCAA AAGAAGACAT TTATGGGGCC AACAAACATA | 240 |
| TGAAAAAAAG CTCATCATCA CTGGTCACTA GATAAATGCA AATCAAAACC ACAATGAGAT | 300 |

```
ACCATCTCAT TCCAGTTAGA ATGGCAATCA TTAAAAAGTC AGGAAACAAC AGATGCTGGA    360

CAAGGTGTC                                                           369
```

(2) INFORMATION FOR SEQ ID NO:192:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (xi) SEQUENCE DESCRIPTION: SEQ ID NO:192:

```
TGACGCTTGG CCACTTGACA CTTCATCTTT GCACAGAAAA ACTTCTTTAC AGATTTAATT     60

CAAGACTGGT CTAGTGACAG TCCTCCAGAC ATTTTTTCAT TTGTTCCATA TACGTGGAAT    120

TTTAAAATCA TGTTTCATCA GTTTGAAATG ATTTGGGCTG CTAATCAACA CAATTGGATC    180

GACTGTTCTA CTAAACAACA GGAAAATGTG TATCTGGCAG CCTGTGGAGA AACACTAAAC    240

ATTGATTTTT CTTTGCCTTT TACGGACTTT GTTCCAGCTA CATGTAATAC CAAGTTCTCT    300

TTAAGAGGAG AAGATGTTGA TCTTCATTTG TTTCTACCAG ACTGCCACCC TAGTAAATAT    360

TCTTTATTTA TGCTGGTAAA AAATTGCCAT CCAAATAAGA TGATTCATGA TACTGGTATT    420

CCTGCTGAGT GTCAAGTGGC CAAGCGTCA                                     449
```

(2) INFORMATION FOR SEQ ID NO:193:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO:193:

```
TGACGCTTGG CCACTTGACA CCAGGGATGT AKCAGTTGAA TATAATCCTG CAATTGTACA     60

TATTGGCAAT TTCCCATCAA ACATTCTAGA AAGAGACAAC CAGGATTGCT AGGCCATAAA    120

AGCTGCAATA AATAACTGGT AATTGCAGTA ATCATTTCAG GCCAATTCAA TCCAGTTTGG    180

CTCAGAGGTG CCTTTGGCTG AGAGAAGAGG TGAGATATAA TGTGTTTTCT TGCAACTTCT    240

TGGAAGAATA ACTCCACAAT AGTCTGAGGA CTAGATACAA ACCTATTTGC CATTAAAGCA    300

CCAGAGTCTG TTAATTCCAG TACTGATAAG TGTTGGAGAT TAGACTCCAG TGTGTCAAGT    360

GGCCAAGCGT CA                                                       372
```

(2) INFORMATION FOR SEQ ID NO:194:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (xi) SEQUENCE DESCRIPTION: SEQ ID NO:194:

```
TGACGCTTGG CCACTTGACA CTTATGTAGA ATCCATCGTG GGCTGATGCA AGCCCTTTAT     60

TTAGGCTTAG TGTTGTGGGC ACCTTCAATA TCACACTAGA GACAAACGCC ACAAGATCTG    120

CAGAAACATT CAGTTCTGAN CACTCGAATG GCAGGATAAC TTTTTGTGTT GTAATCCTTC    180

ACATATACAA AAACAAACTC TGCANTCTCA CGTTACAAAA AAACGTACTG CTGTAAAATA    240

TTAAGAAGGG GTAAAGGATA CCATCTATAA CAAAGTAACT TACAACTAGT GTCAAGTGGC    300

CAAGCGTCA                                                           309
```

(2) INFORMATION FOR SEQ ID NO:195:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (xi) SEQUENCE DESCRIPTION: SEQ ID NO:195:

| | | | | | |
|---|---|---|---|---|---|
| TGACGCTTGG | CCACTTGACA | CCCAATCTCG | CACTTCATCC | TCCCAGCACC | TGATGAAGTA | 60 |
| GGACTGCAAC | TATCCCCACT | TCCCAGATGA | GGGGACCAAN | GTACACATTA | GGACCCGGAT | 120 |
| GGGAGCACAG | ATTTGTCCGA | TCCCAGACTC | CAAGCACTCA | GCGTCACTCC | AGGACAGCGG | 180 |
| CTTTCAGATA | AGGTCACAAA | CATGAATGGC | TCCGACAACC | GGAGTCAGTC | CGTGCTGAGT | 240 |
| TAAGGCAATG | GTGACACGGA | TGCACGTGTN | ACCTGTAATG | GTTCATCGTA | AGTGTCAAGT | 300 |
| GGCCAAGCGT | CA | | | | | 312 |

(2) INFORMATION FOR SEQ ID NO:196:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (xi) SEQUENCE DESCRIPTION: SEQ ID NO:196:

| | | | | | |
|---|---|---|---|---|---|
| TGTATCGACG | TAGTGGTCTC | CTCAGCCATG | CAGAACTGTG | ACTCAATTAA | ACCTCTTTCC | 60 |
| TTTATGAATT | ACCCAATCTC | GGGTAGTGTC | TTTATAGTAG | TGTGAGAATG | GACTAATACA | 120 |
| AGTACATTTT | ACTTAGTAAT | AATAATAAAC | AAATATATTA | CATTTTGTG | TATTTACTAC | 180 |
| ACCATATTTT | TTATTGTTAT | TGTAGTGTAC | ACCTTCTACT | TATTAAAAGA | AATAGGCCCG | 240 |
| AGGCGGGCAG | ATCACGAGGT | CAGGAGATGG | AGACCACTAC | GTCGATAC | | 288 |

(2) INFORMATION FOR SEQ ID NO:197:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (xi) SEQUENCE DESCRIPTION: SEQ ID NO:197:

| | | | | | |
|---|---|---|---|---|---|
| TTGGGCACCT | TCAATATCAT | GACAGGTGAT | GTGATAACCA | AGAAGGCTAC | TAAGTGATTA | 60 |
| ATGGGTGGGT | AATGTATACA | GAGTAGGTAC | ACTGGACAGA | GGGGTAATTC | ATAGCCAAGG | 120 |
| CAGGAGAAGC | AGAATGGCAA | ACATTTCAT | CACACTACTC | AGGATAGCAT | GCAGTTTAAA | 180 |
| ACCTATAAGT | AGTTTATTTT | TGGAATTTTC | CACTTAATAT | TTTCAGACTG | CAGGTAACTA | 240 |
| AACTGTGGAA | CACAAGAACA | TAGATAAGGG | GAGACCACTA | CGTCGATAC | | 289 |

(2) INFORMATION FOR SEQ ID NO:198:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (xi) SEQUENCE DESCRIPTION: SEQ ID NO:198:

| | | | | | |
|---|---|---|---|---|---|
| GTATCGACGT | AGTGGTCTCC | CAAGCAGTGG | GAAGAAAACG | TGAACCAATT | AAAATGTATC | 60 |

-continued

```
AGATACCCCA AAGAAAGGCG CTTGAGTAAA GATTCCAAGT GGGTCACAAT CTCAGATCTT    120

AAAATTCAGG CTGTCAAAGA GATTTGCTAT GAGGTTGCTC TCAATGACTT CAGGCACAGT    180

CGGCAGGAGA TTGAAGCCCT GGCCATTGTC AAGATGAAGG AGCTTTGTGC CATGTATGGC    240

AAGAAAGACC CCAATGAGCG GGACTCCTGG AGACCACTAC GTCGATAC                 288
```

(2) INFORMATION FOR SEQ ID NO:199:

(i) SEQUENCE CHARACTERISTICS:
        (A) LENGTH: 1027 base pairs
        (B) TYPE: nucleic acid
        (C) STRANDEDNESS: single
        (D) TOPOLOGY: linear (xi) SEQUENCE DESCRIPTION: SEQ ID NO:199:

```
GCTTTTTGGG AAAAACNCAA NTGGGGGAAA GGGGGNTTNN TNGCAAGGGG ATAAAGGGGG     60

AANCCCAGGG TTTCCCCATT CAGGGAGGTG TAAAAAGNCG GCCAGGGGAT TGTAANAGGA    120

TTCAATAATA GGGGGAATGG GCCCNGAAGT TGCAAGGTTC CNGCCCGCCA TGNCCGCGGG    180

ATTTAGTGAC ATTACGACGS TGGTAATAAA GTGGGSCCAA WAAATATTTG TGATGTGATT    240

TTTSGACCAG TGAACCCATT GWACAGGACC TCATTTCCTY TGAGATGRTA GCCATAATCA    300

GATAAAAGRT TAGAAGTYTT TCTGCACGTT AACAGCATCA TTAAATGGAG TGGCATCACC    360

AATTTCACCC TTTGTTAGCC GATACCTTCC CCTTGAAGGC ATTCAATTAA GTGACCAATC    420

GTCATACGAG AGGGGATGGC ATGGGGATTG ATGATGATAT CAGGGGTGAT ACCTTCACAG    480

GTGAAAGGCA TATCCTCTTG TCTATACTGA ATACCACAAG TACCCTTTTG ACCATGTCGA    540

CTAGCAAATT TGTCTCCAAT CTGTGTWATC CCTAACAGAG CGTACCCTTA TTTTACAAAA    600

TTTATATCCT TCCTGATTGA GAGTTACCAT AACCTGATCC ACAATGCCCG TCTCGCTWGT    660

TCTGAGAAAA GTGCTACAGT CTCTCTTGGT ATAGCGTCTA TTGGTGCTCT CCAATTCATC    720

TTCATTTTTC AGGCAAGGTG AACTGTTTTG CCTATAATAA CMTCATCTCC TGATACMCGA    780

AACCCCKGGA RCTATCAAAC CATCATCATC CAGCGTTCKT WATGTYMCTA AATCCCTATT    840

GCGGCCGCCT GCAGGTCAAC ATATNGGAAA ACCCCCCACC CCTTNGGAGC NTACCTTGAA    900

TTTTCCATAT GTCCCNTAAA TTANCTNGNC TTANCCTGGC CNTAACCTNT TCCGGTTTAA    960

ATTGTTTCCG CCCCCNTTCC CCNCCTTNNA ACCGGAAACC TTAATTTTNA ACCNGGGGTT   1020

CCTATCC                                                             1027
```

(2) INFORMATION FOR SEQ ID NO:200:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (xi) SEQUENCE DESCRIPTION: SEQ ID NO:200:

```
AGTGACATTA CGACGCTGGC CATCTTGAAT CCTAGGGCAT GAAGTTGCCC CAAAGTTCAG     60

CACTTGGTTA AGCCTGATCC CTCTGGTTTA TCACAAAGAA TAGGATGGGA TAAAGAAAGT    120

GGACACTTAA ATAAGCTATA AATTATATGG TCCTTGTCTA GCAGGAGACA ACTGCACAGG    180

TATACTACCA GCGTCGTAAT GTCACTA                                        207
```

(2) INFORMATION FOR SEQ ID NO:201:

(i) SEQUENCE CHARACTERISTICS:
        (A) LENGTH: 209 base pairs

```
    (B) TYPE: nucleic acid
    (C) STRANDEDNESS: single
    (D) TOPOLOGY: linear (xi) SEQUENCE DESCRIPTION: SEQ ID NO:201:

TGGGCACCTT CAATATCTAT TAAAAGCACA AATACTGAAG AACACACCAA GACTATCAAT      60

GAGGTTACAT CTGGAGTCCT CGATATATCA GGAAAAAATG AAGTGAACAT TCACAGAGTT     120

TTACTTCTTT GGGAACTCAA ATGCTAGAAA AGAAAAGGGT GCCCTCTTTC TCTGGCTTCC     180

TGGTCCTATC AGCGTCGTA ATGTCACTA                                        209

(2) INFORMATION FOR SEQ ID NO:202:

(i) SEQUENCE CHARACTERISTICS:
        (A) LENGTH: 349 base pairs
        (B) TYPE: nucleic acid
        (C) STRANDEDNESS: single
        (D) TOPOLOGY: linear (xi) SEQUENCE DESCRIPTION: SEQ ID NO:202:

NTACGCTGCA ACACTGTGGA GCCACTGGTT TTTATTCCCG GCAGGTTATC CAGCAAACAG      60

TCACTGAACA CACCGAAGAC CGTGGTATGG TAACCGTTCA CAGTAATCGT TCCAGTCGTC     120

TGCGGGACCC CGACGAGCGT CACTGGGTAC AGACCAGATT CAGCCGGAAG AGAAAGCGCC     180

GCAGGGAGAG ACTCGAACTC CACTCCGCTG GTGAGCAGCC CCATGTTTTC AACTCGAAGT     240

TCAAACGGCA TTGGGTTATA TACCATCAGC TGAACTTCAC ACACATCTCC TTGAACCCAC     300

TGGAAATCTA TTTTCTTGTT CCGCTCTTCT CCACAGTGTT GCAGCGTAA                349

(2) INFORMATION FOR SEQ ID NO:203:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (xi) SEQUENCE DESCRIPTION: SEQ ID NO:203:

TGCTCCTCTT GCCTTACCAA CCCAAAGCCC ACTGTGAAAT ATGAAGTGAA TGACAAAATT      60

CAGTTTTCAA CGCAATATAG TATAGTTTAT CTGATTCTTT TGATCTCCAG GACACTTTAA     120

ACAACTGCTA CCACCACCAC CAACCTAGGG ATTTAGGATT CTCCACAGAC CAGAAATTAT     180

TTCTCCTTTG AGTTTCAGGC TCCTCTGGGA CTCCTGTTCA TCAATGGGTG GTAAATGGCT     240

A                                                                    241

(2) INFORMATION FOR SEQ ID NO:204:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (xi) SEQUENCE DESCRIPTION: SEQ ID NO:204:

TAGCCATTTA CCACCCATCT GCAAACCSWG ACMWWCARGR CYWGWACKYA GGCGATTTGA      60

AGTACTGGTA ATGCTCTGAT CATGTTAGTT ACATAAGTGT GGTCAGTTTA CAAAAATTCA     120

CAGAACTAAA TACTCAATGC TATGTGTTCA TGTCTGTGTT TATGTGTGTG TAATGTTTCA     180

ATTAAGTTTT TTTAAAAAAA AGAGATGATT TCCAAATAAG AAAGCCGTGT TGGTAAGGCA     240

AGAGGAGC                                                             248
```

(2) INFORMATION FOR SEQ ID NO:205:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (xi) SEQUENCE DESCRIPTION: SEQ ID NO:205:

```
TACGCTGCAA CACTGTGGAG CCATTCATAC AGGTCCCTAA TTAAGGAACA AGTGATTATG      60

CTACCTTTGC ACGGTTAGGG TACCGCGGCC GTTAAACATG TGTCACTGGG CAGGCGGTGC     120

CTCTAATACT GGTGATGCTA GAGGTGATGT TTTTGGTAAA CAGGCGGGGT AAGATTTGCC     180

GAGTTCCTTT TACTTTTTTT AACCTTTCCT TATGAGCATG CCTGTGTTGG GTTGACAGTG     240

GGGGTAATAA TGACTTGTTG GTTGATTGTA GATATTGGGC TGTTAATTGT CAGTTCAGTG     300

TTTTAATCTG ACGCAGGCTT ATGCGGAGGA GAATGTTTTC ATGTTACTTA TACTAACATT     360

AGTTCTTCTA TAGGGTGATA GATTGGTCCA ATTGGGTGTG AGGAGTTCAG TTATATGTTT     420

GGGATTTTTT AGGTAGTGGG TGTTGANCTT GAACGCTTTC TTAATTGGTG GCTGCTTTTA     480

RGCCTACTAT GGGTGGTAAA TGGCT                                          505
```

(2) INFORMATION FOR SEQ ID NO:206:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (xi) SEQUENCE DESCRIPTION: SEQ ID NO:206:

```
TAGACTGACT CATGTCCCCT ACCAAAGCCC ATGTAAGGAG CTGAGTTCTT AAAGACTGAA      60

GACAGACTAT TCTCTGGAGA AAAATAAAAT GGAAATTGTA CTTTAAAAAA AAAAAAAATC     120

GGCCGGGCAT GGTAGCACAC ACCTGTAATC CCAGCTACTA GGGGACATGA GTCAGTCTA     179
```

(2) INFORMATION FOR SEQ ID NO:207:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (xi) SEQUENCE DESCRIPTION: SEQ ID NO:207:

```
AGACTGACTC ATGTCCCCTA CCCCACCTTC TGCTGTGCTG CCGTGTTCCT AACAGGTCAC      60

AGACTGGTAC TGGTCAGTGG CCTGGGGGTT GGGGACCTCT ATTATATGGG ATACAAATTT     120

AGGAGTTGGA ATTGACACGA TTTAGTGACT GATGGGATAT GGGTGGTAAA TGGCTA        176
```

(2) INFORMATION FOR SEQ ID NO:208:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO:208:

```
AGACTGACTC ATGTCCCCTA TTTAACAGGG TCTCTAGTGC TGTGAAAAAA AAAAATGCTG      60

AACATTGCAT ATAACTTATA TTGTAAGAAA TACTGTACAA TGACTTTATT GCATCTGGGT     120

AGCTGTAAGG CATGAAGGAT GCCAAGAAGT TTAAGGAATA TGGGTGGTAA ATGGCTAGGG     180
```

GACATGAGTC AGTCTA                                                             196

(2) INFORMATION FOR SEQ ID NO:209:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO:209:

GACGCTTGGC CACTTGACAC CTTTTATTTT TTAAGGATTC TTAAGTCATT TANGTNACTT        60

TGTAAGTTTT TCCTGTGCCC CCATAAGAAT GATAGCTTTA AAAATTATGC TGGGGTAGCA       120

AAGAAGATAC TTCTAGCTTT AGAATGTGTA GGTATAGCCA GGATTCTTGT GAGGAGGGGT       180

GATTTAGAGC AAATTTCTTA TTCTCCTTGC CTCATCTGTA ACATGGGGAT AATAATAGAA       240

CTGGCTTGAC AAGGTTGGAA TTAGTATTAC ATGGTAAATA CATGTAAAAT GTTTAGAATG       300

GTGCCAAGTA TCTAGGAAGT ACTTGGGCAT GGGTGGTAAA TGGCT                       345

(2) INFORMATION FOR SEQ ID NO:210:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (xi) SEQUENCE DESCRIPTION: SEQ ID NO:210:

GACGCTTGGC CACTTGACAC TAGAGTAGGG TTTGGCCAAC TTTTTCTATA AAGGACCAGA        60

GAGTAAATAT TTCAGGCTTT GTGGGTTGTG CAGTCTCTCT TGCAACTACT CAGCTCTGCC       120

ATTGTAGCAT AGAAATCAGC CATAGACAGG ACAGAAATGA ATGGGTGGTA AATGGCTA         178

(2) INFORMATION FOR SEQ ID NO:211:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO:211:

TGGGCACCTT CAATATCTAT CCAGCGCATC TAAATTCGCT TTTTTCTTGA TTAAAAATTT        60

CACCACTTGC TGTTTTTGCT CATGTATACC AAGTAGCAGT GGTGTGAGGC CATGCTTGTT       120

TTTTGATTCG ATATCAGCAC CGTATAAGAG CAGTGCTTTG GCCATTAATT TATCTTCATT       180

GTAGACAGCA TAGTGTAGAG TGGTATCTCC ATACTCATCT GGAATATTTG GATCAGTGCC       240

ATGTTCCAGC AACATTAACG CACATTCATC TTCCTGGCAT TGTACGGCCT TTGTCAGAGC       300

TGTCCTCTTT TTGTTGTCAA GGACATTAAG TTGACATCGT CTGTCCAGCA CGAGTTTTAC       360

TACTTCTGAA TTCCCATTGG CAGAGGCCAG ATGTAGAGCA GTCCTCTTTT GCTTGTCCCT       420

CTTGTTCACA TCAGTGTCCC TGAGCATAAC GGAA                                   454

(2) INFORMATION FOR SEQ ID NO:212:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (xi) SEQUENCE DESCRIPTION: SEQ ID NO:212:

```
TCCGTTATGC CACCCAGAAA ACCTACTGGA GTTACTTATT AACATCAAGG CTGGAACCTA      60

TTTGCCTCAG TCCTATCTGA TTCATGAGCA CATGGTTATT ACTGATCGCA TTGAAAACAT     120

TGATCACCTG GGTTTCTTTA TTTATCGACT GTGTCATGAC AAGGAAACTT ACAAACTGCA     180

ACGCAGAGAA ACTATTAAAG GTATTCAGAA ACGTGAAGCC AGCAATTGTT TCGCAATTCG     240

GCATTTTGAA AACAAATTTG CCGTGGAAAC TTTAATTTGT TCTTGAACAG TCAAGAAAAA     300

CATTATTGAG GAAAATTAAT ATCACAGCAT AACGGAA                              337
```

(2) INFORMATION FOR SEQ ID NO:213:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (xi) SEQUENCE DESCRIPTION: SEQ ID NO:213:

```
TCGGGTGATG CCTCCTCAGG CATCTTCCAT CCATCTCTTC AAGATTAGCT GTCCCAAATG      60

TTTTTCCTTC TCTTCTTTAC TGATAAATTT GGACTCCTTC TTGACACTGA TGACAGCTTT     120

AGTATCCTTC TTGTCACCTT GCAGACTTTA AACATAAAAA TACTCATTGG TTTTAAAAGG     180

AAAAAAGTAT ACATTAGCAC TATTAAGCTT GGCCTTGAAA CATTTTCTAT CTTTTATTAA     240

ATGTCGGTTA GCTGAACAGA ATTCATTTTA CAATGCAGAG TGAGAAAAGA AGGGAGCTAT     300

ATGCATTTGA GAATGCAAGC ATTGTCAAAT AAACATTTTA AATGCTTTCT TAAAGTGAGC     360

ACATACAGAA ATACATTAAG ATATTAGAAA GTGTTTTTGC TTGTGTACTA CTAATTAGGG     420

AAGCACCTTG TATAGTTCCT CTTCTAAAAT TGAAGTAGAT TTTAAAAACC CATGTAATTT     480

AATTGAGCTC TCAGTTCAGA TTTTAGGAGA ATTTTAACAG GGATTGGTT TTGTCTAAAT      540

TTTGTCAATT TNTTTAGTTA ATCTGTATAA TTTTATAAAT GTCAAACTGT ATTTAGTCCG     600

TTTTCATGCT GCTATGAAAG AAATACCCAN GACAGGGTTA TTTATAAANG GAAAGANGTT     660

AATTTGACTC CCAGTTCACA GGCCTGAGGA NGNATCNCCC GAAATCCTTA TTGCG          715
```

(2) INFORMATION FOR SEQ ID NO:214:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO:214:

```
GGTAANGNGC ATACNTCGGT GCTCCGGCCG CCGGAGTCGG GGGATTCGGG TGATGCCTCC      60

TCAGGCCCAC TTGGGCCTGC TTTTCCCAAA TGGCAGCTCC TCTGGACATG CCATTCCTTC     120

TCCCACCTGC CTGATTCTTC ATATGTTGGG TGTCCCTGTT TTTCTGGTGC TATTTCCTGA     180

CTGCTGTTCA GCTGCCACTG TCCTGCAAAG CCTGCCTTTT TAAATGCCTC ACCATTCCTT     240

CATTTGTTTC TTAAATATGG GAAGTGAAAG TGCCACCTGA GGCCGGGCAC AGTGGCTCAC     300

GCCTGTAATC CCAGCACTTT GGGAGCCTGA GGAGGCATCA CCCGA                     345
```

(2) INFORMATION FOR SEQ ID NO:215:

(i) SEQUENCE CHARACTERISTICS:
        (A) LENGTH: 429 base pairs
        (B) TYPE: nucleic acid
        (C) STRANDEDNESS: single (D) TOPOLOGY: linear (xi) SEQUENCE DESCRIPTION: SEQ ID NO:215:

GGTGATGCCT CCTCAGGCGA AGCTCAGGGA GGACAGAAAC CTCCCGTGGA GCAGAAGGGC    60

AAAAGCTCGC TTGATCTTGA TTTTCAGTAC GAATACAGAC CGTGAAAGCG GGGCCTCACG   120

ATCCTTCTGA CCTTTTGGGT TTTAAGCAGG AGGTGTCAGA AAAGTTACCA CAGGGATAAC   180

TGGCTTGTGG CGGCCAAGCG TTCATAGCGA CGTCGCTTTT TGATCCTTCG ATGTCGGCTC   240

TTCCTATCAT TGTGAAGCAG AATTCACCAA GCGTTGGATT GTTCACCCAC TAATAGGGAA   300

CGTGAGCTGG GTTTAGACCG TCGTGAGACA GGTTAGTTTT ACCCTACTGA TGATGTGTKG   360

TTGCCATGGT AATCCTGCTC AGTACGAGAG GAACCGCAGG TTCASACATT TGGTGTATGT   420

GCTTGCCTT                                                           429

(2) INFORMATION FOR SEQ ID NO:216:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (xi) SEQUENCE DESCRIPTION: SEQ ID NO:216:

TGACACCTAT GTCCNGCATC TGTTCACAGT TTCCACAAAT AGCCAGCCTT TGGCCACCTC    60

TCTGTCCTGA GGTATACAAG TATATCAGGA GGTGTATACC TTCTCTTCTC TTCCCCACCA   120

AAGAGAACAT GCAGGCTCTG GAAGCTGTCT TAGGAGCCTT TGGGCTCAGA ATTTCAGAGT   180

CTTGGGTACC TTGGATGTGG TCTGGAAGGA GAAACATTGG CTCTGGATAA GGAGTACAGC   240

CGGAGGAGGG TCACAGAGCC CTCAGCTCAA GCCCCTGTGC CTTAGTCTAA AAGCAGCTTT   300

GGATGAGGAA GCAGGTTAAG TAACATACGT AAGCGTACAC AGGTAGAAAG TGCTGGGAGT   360

CAGAATTGCA CAGTGTGTAG GAGTAGTACC TCAATCAATG AGGGCAAATC AACTGAAAGA   420

AGAAGACCNA TTAATGAATT GCTTANGGGG AAGGATCAAG GCTATCATGG AGATCTTTCT   480

AGGAAGATTA TTGTTTANAA TTATGAAAGG ANTAGGGCAG GGACAGGGCC AGAAGTANAA   540

GANAACATTG CCTATANCCC TTGTCTTGCA CCCAGATGCT GGACAAGGTG TCA          593

(2) INFORMATION FOR SEQ ID NO:217:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (xi) SEQUENCE DESCRIPTION: SEQ ID NO:217:

TGACACCTTG TCCAGCATCT GACGTGAAGA TGAGCAGCTC AGAGGAGGTG TCCTGGATTT    60

CCTGGTTCTG TGGGCTCCGT GGCAATGAAT TCTTCTGTGA AGTGGATGAA GACTACATCC   120

AGGACAAATT TAATCTTACT GGACTCAATG AGCAGGTCCC TCACTATCGA CAAGCTCTAG   180

ACATGATCTT GGACCTGGAG CCTGATGAAG AACTGGAAGA CAACCCCAAC CAGAGTGACC   240

TGATTGAGCA GGCAGCCGAG ATGCTTTATG GATTGATCCA CGCCCGCTAC ATCCTTACCA   300

ACCGTGGCAT CGCCCAGATG CTGGACAAGG TGTCA                              335

(2) INFORMATION FOR SEQ ID NO:218:

(i) SEQUENCE CHARACTERISTICS:
        (A) LENGTH: 248 base pairs (B) TYPE: nucleic acid
          (C) STRANDEDNESS: single
          (D) TOPOLOGY: linear (xi) SEQUENCE DESCRIPTION: SEQ ID NO:218:

TACGTACTGG TCTTGAAGGT CTTAGGTAGA GAAAAAATGT GAATATTTAA TCAAAGACTA      60

TGTATGAAAT GGGACTGTAA GTACAGAGGG AAGGGTGGCC CTTATCGCCA GAAGTTGGTA     120

GATGCGTCCC CGTCATGAAA TGTTGTGTCA CTGCCCGACA TTTGCCGAAT TACTGAAATT     180

CCGTAGAATT AGTGCAAATT CTAACGTTGT TCATCTAAGA TTATGGTTCC ATGTTTCTAG     240

TACTTTTA                                                              248

(2) INFORMATION FOR SEQ ID NO:219:

(i) SEQUENCE CHARACTERISTICS:
          (A) LENGTH: 530 base pairs
          (B) TYPE: nucleic acid
          (C) STRANDEDNESS: single
          (D) TOPOLOGY: linear (xi) SEQUENCE DESCRIPTION: SEQ ID NO:219:

TGACGCTTGG CCACTTGACA CAAGTAGGGG ATAAGGACAA AGACCCATNA GGTGGCCTGT      60

CAGCCTTTTG TTACTGTTGC TTCCCTGTCA CCACGGCCCC CTCTGTAGGG GTGTGCTGTG     120

CTCTGTGGAC ATTGGTGCAT TTTCACACAT ACCATTCTCT TTCTGCTTCA CAGCAGTCCT     180

GAGGCGGGAG CACACAGGAC TACCTTGTCA GATGANGATA ATGATGTCTG GCCAACTCAC     240

CCCCCAACCT TCTCACTAGT TATANGAAGA GCCANGCCTA NAACCTTCTA TCCTGNCCCC     300

TTGCCCTATG ACCTCATCCC TGTTCCATGC CCTATTCTGA TTTCTGGTGA ACTTTGGAGC     360

AGCCTGGTTT NTCCTCCTCA CTCCAGCCTC TCTCCATACC ATGGTANGGG GGTGCTGTTC     420

CACNCAAANG GTCAGGTGTG TCTGGGGAAT CCTNANANCT GCCNGGAGTT TCCNANGCAT     480

TCTTAAAAAC CTTCTTGCCT AATCANATNG TGTCCAGTGG CCAACCNTCN                530

(2) INFORMATION FOR SEQ ID NO:220:

(i) SEQUENCE CHARACTERISTICS:
          (A) LENGTH: 531 base pairs
          (B) TYPE: nucleic acid
          (C) STRANDEDNESS: single
          (D) TOPOLOGY: linear (xi) SEQUENCE DESCRIPTION: SEQ ID NO:220:

TGACGCTTGG CCACTTGACA CTAAATAGCA TCTTCTAAAG GCCTGATTCA GAGTTGTGGA      60

AAATTCTCCC AGTGTCAGGG ATTGTCAGGA ACAGGGCTGC TCCTGTGCTC ACTTTACCTG     120

CTGTGTTTCT GCTGGAAAAG GAGGGAAGAG GAATGGCTGA TTTTTACCTA ATGTCTCCCA     180

GTTTTTCATA TTCTTCTTGG ATCCTCTTCT CTGACAACTG TTCCCTTTTG GTCTTCTTCT     240

TCTTGCTCAG AGAGCAGGTC TCTTTAAAAC TGAGAAGGGA GAATGAGCAA ATGATTAAAG     300

AAAACACACT TCTGAGGCCC AGAGATCAAA TATTAGGTAA ATACTAAACC GCTTGCCTGC     360

TGTGGTCACT TTTCTCCTCT TTCACATGCT CTATCCCTCT ATCCCCCACC TATTCATATG     420

GCTTTTATCT GCCAAGTTAT CCGGCCTCTC ATCAACCTTC TCCCCTAGCC TACTGGGGA      480

TATCCATCTG GGTCTGTCTC TGGTGTATTG GTGTCAAGTG GCCAAGCGTC A              531

(2) INFORMATION FOR SEQ ID NO:221:

(i) SEQUENCE CHARACTERISTICS:
          (A) LENGTH: 530 base pairs (B) TYPE: nucleic acid
        (C) STRANDEDNESS: single
        (D) TOPOLOGY: linear (xi) SEQUENCE DESCRIPTION: SEQ ID NO:221:

| | | |
|---|---|---|
| ATTGACGCTT GGCCACTTGA CACCCGCCTG CCTGCAATAC TGGGGCAAGG GCCTTCACTG | 60 |
| CTTTCCTGCC ACCAGCTGCC ACTGCACACA GAGATCAGAA ATGCTACCAA CCAAGACTGT | 120 |
| TGGTCCTCAG CCTCTCTGAG GAGAAAGAGC AGAAGCCTGG AAGTCAGAAG AGAAGCTAGA | 180 |
| TCGGCTACGG CCTTGGCAGC CAGCTTCCCC ACCTGTGGCA ATAAAGTCGT GCATGGCTTA | 240 |
| ACAATGGGGG CACCTCCTGA GAAACACATT GTTAGGCAAT TCGGCGTGTG TTCATCAGAG | 300 |
| CATATTTACA CAAACCTCGA TAGTGCAGCC TACTATCCAC TATTGCTCCT ACGCTGCAAA | 360 |
| CCTGAACAGC ATGGGACTGT ACTGAATACT GGAAGCAGCT GGTGATGGTA CTTATTTGTG | 420 |
| TATCTAAACA CAGAGAAGGT ACAGTAAGAA TATGGTATCA TAAACTTACA GGGACCGCCA | 480 |
| TCCTATATGC AGTCTGTTGT GACCAAAATG TGTCAAGTGG CCAAGCGTCA | 530 |

(2) INFORMATION FOR SEQ ID NO:222:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO:222:

| | | |
|---|---|---|
| TGTATCGACG TAGTGGTCTC CGGGCTACTA GGCCGTTGTG TGCTGGTAGT ACCTGGTTCA | 60 |
| CTGAAAGGCG CATCTCCCTC CCCGCGTCGC CCTGAAGCAG GGGGAGGACT TCGCCCAGCC | 120 |
| AAGGCAGTTG TATGAGTTTT AGCTGCGGCA CTTCGAGACC TCTGAGCCCA CCTCCTTCAG | 180 |
| GAGCCTTCCC CGATTAAGGA AGCCAGGGTA AGGATTCCTT CCTCCCCCAG ACACCACGAA | 240 |
| CAAACCACCA CCCCCCCTAT TCTGGCAGCC CATATACATC AGAACGAAAC AAAAATAACA | 300 |
| AATAAACNAA AACCAAAAAA AAAAGAGAAG GGGAAATGTA TATGTCTGTC CATCCTGTTG | 360 |
| CTTTAGCCTG TCAGCTCCTA NAGGGCAGGG ACCGTGTCTT CCGAATGGTC TGTGCAGCGC | 420 |
| CGACTGCGGG AAGTATCGGA GGAGGAAGCA GAGTCAGCAG AAGTTGAACG GTGGGCCCGG | 480 |
| CGGCTCTTGG GGGCTGGTGT TGTACTTCGA GACCGCTTTC GCTTTTTGTC TTAGATTTAC | 540 |
| GTTTGCTCTT TGGAGTGGGA NACCACTACN TCNATACA | 578 |

(2) INFORMATION FOR SEQ ID NO:223:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO:223:

| | | |
|---|---|---|
| TGTATCGACG TAGTGGTCTC CTCTTGCAAA GGACTGGCTG GTGAATGGTT TCCCTGAATT | 60 |
| ATGGACTTAC CCTAAACATA TCTTATCATC ATTACCAGTT GCAAAATATT AGAATGTGTT | 120 |
| GTCACTGTTT CATTTGATTC CTAGAAGGTT AGTCTTAGAT ATGTTACTTT AACCTGTATG | 180 |
| CTGTAGTGCT TTGAATGCAT TTTTTGTTTG CATTTTTGTT TGCCCAACCT GTCAATTATA | 240 |
| GCTGCTTAGG TCTGGACTGT CCTGGATAAA GCTGTTAAAA TATTCACCAG TCCAGCCATC | 300 |
| TTACAAGCTA ATTAAGTCAA CTAAATGCTT CCTTGTTTTG CCAGACTTGT TATGTCAATC | 360 |
| CTCAATTTCT GGGTTCATTT TGGGTGCCCT AAATCTTAGG GTGTGACTTT CTTAGCATCC | 420 |

```
TGTAACATCC ATTCCCAAGC AAGCACAACT TCACATAATA CTTTCCAGAA GTTCATTGCT        480

GAAGCCTTTC CTTCACCCAG CGGAGCAACT TGATTTTCTA CAACTTCCCT CATCAGAGCC        540

ACAAGAGTAT GGGATATGGA GACCACTACG TCGATACA                                578
```

(2) INFORMATION FOR SEQ ID NO:224:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO:224:

```
TGTATCGACG TANTGGTCTC CCAAGGTGCT GGGATTGCAG GCATGAGCCA CCACTCCCAG         60

GTGGATCTTT TTCTTTATAC TTACTTCATT AGGTTTCTGT TATTCAAGAA GTGTAGTGGT        120

AAAAGTCTTT TCAATCTACA TGGTTAAATA ATGATAGCCT GGGAAATAAA TAGAAATTTT        180

TTCTTTCATC TTTAGGTTGA ATAAAGAAAC AGAAAAAATA GAACATACTG AAAATAATCT        240

AAGTTCCAAC CATAGAAGAA CTGCAGAAGA AATGAAGAAA GTGATGATGA TTTAGATTTT        300

GATATTGATT TAGAAGACAC AGGAGGAGAC CACTACGTCG ATACA                       345
```

(2) INFORMATION FOR SEQ ID NO:225:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (xi) SEQUENCE DESCRIPTION: SEQ ID NO:225:

```
TGTATCGACG TAGTGGTCTC CAAACTGAGG TATGTGTGCC ACTAGCACAC AAAGCCTTCC         60

AACAGGGACG CAGGCACAGG CAGTTTAAAG GGAATCTGTT TCTAAATTAA TTTCCACCTT        120

CTCTAAGTAT TCTTTCCTAA AACTGATCAA GGTGTGAAGC CTGTGCTCTT TCCCAACTCC        180

CCTTTGACAA CAGCCTTCAA CTAACACAAG AAAAGGCATG TCTGACACTC TTCCTGAGTC        240

TGACTCTGAT ACGTTGTTCT GATGTCTAAA GAGCTCCAGA ACACCAAAGG GACAATTCAG        300

AATGCTGGTG TATAACAGAC TCCAATGGAG ACCACTACGT CGATACA                     347
```

(2) INFORMATION FOR SEQ ID NO:226:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (xi) SEQUENCE DESCRIPTION: SEQ ID NO:226:

```
AGGNGNGGGA NTGTATCGAC GTAGTGGTCT CCCAACAGTC TGTCATTCAG TCTGCAGGTG         60

TCAGTGTTTT GGACAATGAG GCACCATTGT CACTTATTGA CTCCTCAGCT CTAAATGCTG        120

AAATTAAATC TTGTCATGAC AAGTCTGGAA TTCCTGATGA GGTTTTACAA AGTATTTTGG        180

ATCAATACTC CAACAAATCA GAAAGCCAGA AAGAGGATCC TTTCAATATT GCAGAACCAC        240

GAGTGGATTT ACACACCTCA GGAGACCACT ACGTCGATAC A                           281
```

(2) INFORMATION FOR SEQ ID NO:227:

(i) SEQUENCE CHARACTERISTICS:
        (A) LENGTH: 3646 base pairs (B) TYPE: nucleic acid
(C) STRANDEDNESS: single
(D) TOPOLOGY: linear (xi) SEQUENCE DESCRIPTION: SEQ ID NO:227:

| | | | | | |
|---|---|---|---|---|---|
| GGGAAACACT | TCCTCCCAGC | CTTGTAAGGG | TTGGAGCCCT | CTCCAGTATA | TGCTGCAGAA | 60 |
| TTTTTCTCTC | GGTTTCTCAG | AGGATTATGG | AGTCCGCCTT | AAAAAAGGCA | AGCTCTGGAC | 120 |
| ACTCTGCAAA | GTAGAATGGC | CAAAGTTTGG | AGTTGAGTGG | CCCCTTGAAG | GGTCACTGAA | 180 |
| CCTCACAATT | GTTCAAGCTG | TGTGGCGGGT | TGTTACTGAA | ACTCCCGGCC | TCCCTGATCA | 240 |
| GTTTCCCTAC | ATTGATCAAT | GGCTGAGTTT | GGTCAGGAGC | ACCCCTTCCG | TGGCTCCACT | 300 |
| CATGCACCAT | TCATAATTTT | ACCTCCAAGG | TCCTCCTGAG | CCAGACCGTG | TTTTCGCCTC | 360 |
| GACCCTCAGC | CGGTTCGGCT | CGCCCTGTAC | TGCCTCTCTC | TGAAGAAGAG | GAGAGTCTCC | 420 |
| CTCACCCAGT | CCCACCGCCT | TAAAACCAGC | CTACTCCCTT | AGGGTCATCC | CATGTCTCCT | 480 |
| CGGCTATGTC | CCCTGTAGGC | TCATCACCCA | TTGCCTCTTG | GTTGCAACCG | TGGTGGGAGG | 540 |
| AAGTAGCCCC | TCTACTACCA | CTGAGAGAGG | CACAAGTCCC | TCTGGGTGAT | GAGTGCTCCA | 600 |
| CCCCCTTCCT | GGTTTATGTC | CCTTCTTTCT | ACTTCTGACT | TGTATAATTG | GAAAACCCAT | 660 |
| AATCCTCCCT | TCTCTGAAAA | GCCCCAGGCT | TTGACCTCAC | TGATGGAGTC | TGTACTCTGG | 720 |
| ACACATTGGC | CCACCTGGGA | TGACTGTCAA | CAGCTCCTTT | TGACCCTTTT | CACCTCTGAA | 780 |
| GAGAGGGAAA | GTATCCAAAG | AGAGGCCAAA | AAGTACAACC | TCACATCAAC | CAATAGGCCG | 840 |
| GAGGAGGAAG | CTAGAGGAAT | AGTGATTAGA | GACCCAATTG | GACCTAATT | GGGACCCAAA | 900 |
| TTTCTCAAGT | GGAGGGAGAA | CTTTTGACGA | TTTCCACCGG | TATCTCCTCG | TGGGTATTCA | 960 |
| GGGAGCTGCT | CAGAAACCTA | TAAACTTGTC | TAAGGCGACT | GAAGTCGTCC | AGGGGCATGA | 1020 |
| TGAGTCACCA | GGAGTGTTTT | TAGAGCACCT | CCAGGAGGCT | TATCAGATTT | ACACCCCTTT | 1080 |
| TGACCTGGCA | GCCCCCGAAA | ATAGCCATGC | TCTTAATTTG | GCATTTGTGG | CTCAGGCAGC | 1140 |
| CCCAGATAGT | AAAAGGAAAC | TCCAAAAACT | AGAGGGATTT | TGCTGGAATG | AATACCAGTC | 1200 |
| AGCTTTTAGA | GATAGCCTAA | AAGGTTTTTG | ACAGTCAAGA | GGTTGAAAAA | CAAAAACAAG | 1260 |
| CAGCTCAGGC | AGCTGAAAAA | AGCCACTGAT | AAAGCATCCT | GGAGTATCAG | AGTTTACTGT | 1320 |
| TAGATCAGCC | TCATTTGACT | TCCCCTCCCA | CATGGTGTTT | AAATCCAGCT | ACACTACTTC | 1380 |
| CTGACTCAAA | CTCCACTATT | CCTGTTCATG | ACTGTCAGGA | ACTGTTGGAA | ACTACTGAAA | 1440 |
| CTGGCCGACC | TGATCTTCAA | AATGTGCCCC | TAGGAAAGGT | GGATGCCACC | ATGTTCACAG | 1500 |
| ACAGTAGCAG | CTTCCTCGAG | AAGGGACTAC | GAAAGGCCGG | TGCAGCTGTT | ACCATGGAGA | 1560 |
| CAGATGTGTT | GTGGGCTCAG | GCTTTACCAG | CAAACACCTC | AGCACAAAAG | CTGAATTGA | 1620 |
| TCGCCCTCAC | TCAGGCTCTC | CGATGGGGTA | AGGATATTAA | CGTTAACACT | GACAGCAGGT | 1680 |
| ACGCCTTTGC | TACTGTGCAT | GTACGTGGAG | CCATCTACCA | GGAGCGTGGG | CTACTCACCT | 1740 |
| CAGCAGGTGG | CTGTAATCCA | CTGTAAAGGA | CATCAAAAGG | AAAACACGGC | TGTTGCCCGT | 1800 |
| GGTAACCAGA | AAGCTGATTC | AGCAGCTCAA | GATGCAGTGT | GACTTTCAGT | CACGCCTCTA | 1860 |
| AACTTGCTGC | CCACAGTCTC | CTTTCCACAG | CCAGATCTGC | CTGACAATCC | CGCATACTCA | 1920 |
| ACAGAAGAAG | AAAACTGGCC | TCAGAACTCA | GAGCCAATAA | AAATCAGGAA | GGTTGGTGGA | 1980 |
| TTCTTCCTGA | CTCTAGAATC | TTCATACCCC | GAACTCTTGG | GAAAACTTTA | ATCAGTCACC | 2040 |
| TACAGTCTAC | CACCCATTTA | GGAGGAGCAA | AGCTACCTCA | GCTCCTCCGG | AGCCGTTTTA | 2100 |
| AGATCCCCCA | TCTTCAAAGC | CTAACAGATC | AAGCAGCTCT | CCGGTGCACA | ACCTGCGCCC | 2160 |
| AGGTAAATGC | CAAAAAAGGT | CCTAAACCCA | GCCCAGGCCA | CCGTCTCCAA | GAAAACTCAC | 2220 |

```
CAGGAGAAAA GTGGGAAATT GACTTTACAG AAGTAAAACC ACACCGGGCT GGGTACAAAT      2280

ACCTTCTAGT ACTGGTAGAC ACCTTCTCTG GATGGACTGA AGCATTTGCT ACCAAAAACG      2340

AAACTGTCAA TATGGTAGTT AAGTTTTTAC TCAATGAAAT CATCCCTCGA CATGGGCTGC      2400

CTGTTTGCCA TAGGGTCTGA TAATGGACCG GCCTTCGCCT TGTCTATAGT TTAGTCAGTC      2460

AGTAAGGCGT TAAACATTCA ATGGAAGCTC CATTGTGCCT ATCGACCCCA GAGCTCTGGG      2520

CAAGTAGAAC GCATGAACTG CACCCTAAAA AACACTCTTA CAAAATTAAT CTTAGAAACC      2580

GGTGTAAATT GTGTAAGTCT CCTTCCTTTA GCCCTACTTA GAGTAAGGTG CACCCCTTAC      2640

TGGGCTGGGT TCTTACCTTT TGAAATCATG TATGGGAGGG TGCTGCCTAT CTTGCCTAAG      2700

CTAAGAGATG CCCAATTGGC AAAAATATCA CAAACTAATT TATTACAGTA CCTACAGTCT      2760

CCCCAACAGG TACAAGATAT CATCCTGCCA CTTGTTCGAG GAACCCATCC CAATCCAATT      2820

CCTGAACAGA CAGGGCCCTG CCATTCATTC CCGCCAGGTG ACCTGTTGTT TGTTAAAAAG      2880

TTCCAGAGAG AAGGACTCCC TCCTGCTTGG AAGAGACCTC ACACCGTCAT CACGATGCCA      2940

ACGGCTCTGA AGGTGGATGG CATTCCTGCG TGGATTCATC ACTCCCGCAT CAAAAAGGCC      3000

AACAGAGCCC AACTAGAAAC ATGGGTCCCC AGGGCTGGGT CAGGCCCCTT AAAACTGCAC      3060

CTAAGTTGGG TGAAGCCATT AGATTAATTC TTTTTCTTAA TTTTGTAAAA CAATGCATAG      3120

CTTCTGTCAA ACTTATGTAT CTTAAGACTC AATATAACCC CCTTGTTATA ACTGAGGAAT      3180

CAATGATTTG ATTCCCCCAA AAACACAAGT GGGGAATGTA GTGTCCAACC TGGTTTTTAC      3240

TAACCCTGTT TTTAGACTCT CCCTTTCCTT TAATCACTCA GCTTGTTTCC ACCTGAATTG      3300

ACTCTCCCTT AGCTAAGAGC GCCAGATGGA CTCCATCTTG GCTCTTTCAC TGGCAGCCGC      3360

TTCCTCAAGG ACTTAACTTG TGCAAGCTGA CTCCCAGCAC ATCCAAGAAT GCAATTAACT      3420

GATAAGATAC TGTGGCAAGC TATATCCGCA GTTCCCAGGA ATTCGTCCAA TTGATCACAG      3480

CCCCTCTACC CTTCAGCAAC CACCACCCTG ATCAGTCAGC AGCCATCAGC ACCGAGGCAA      3540

GGCCCTCCAC CAGCAAAAAG ATTCTGACTC ACTGAAGACT TGGATGATCA TTAGTATTTT      3600

TAGCAGTAAA GTTTTTTTTT CTTTTTCTTT CTTTTTTTCT CGTGCC                    3646
```

(2) INFORMATION FOR SEQ ID NO:228:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:228:

```
TAAGAGGGTA CAAGATCTAA GCACAGCCGT CAATGCAGAA CACAGAACGT AGCCTGGTAA       60

GTGTGTTAAG AGTGGGAATT TTTGGAGTAC AGAGTAAGGC ACCTAACCCT AGCTGGGGTT      120

TGGTGACGGT CCCAGATGGC TTACAGAAGA AAGTGTCCTG AGATGAGTTT TTAAGAATGA      180

ATAAGGATAG ACACAAGTGA GGACTGACTT GGCAGTGGTG AATGGTGGGT GGCAAAAAAC      240

TTCGCATGTA TGGAAACTGC ACGTACAGGA ATGAAGAATG AGACTGTGTG GTGTTTAATG      300

AGCTGCAAAT ACTAATTTTA TCCTGAAAGT TTTGAAGAGT TAACTAAAAA GTATTTTTTA      360

GTAAGGAAAT AACCCTACAT TTCAGGGTTA TTGTTTGTTT ANATATTGAA GGTGCCCAA       419
```

(2) INFORMATION FOR SEQ ID NO:229:

(i) SEQUENCE CHARACTERISTICS:
        (A) LENGTH: 148 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:229:

```
AAGAGGGTAC CTGTATGTAG CCATGGTGGC AATGAGAGAC TGATTACTAC CTGCTGGAGA      60

TTGTTTAAGT GAGTTAATAT ATTAAGGATA AAGGGAGCCA GGTTTTTTGA CTGTTGGAGA     120

AGGAAATTAC AGATATTGAA GGTCCCAA                                       148
```

(2) INFORMATION FOR SEQ ID NO:230:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens (xi) SEQUENCE DESCRIPTION: SEQ ID NO:230:

```
TAAGAGGGTA CMAAAAAAAA AAAATAGAAC GAATGAGTAA GACCTACTAT TTGATAGTAC      60

AACAGGGTGA CTATAGTCAA TGATAACTTA ATTATACATT TAACATAGAG TGTAATTGGA     120

TTGTTTGTAA CTCGAAGGAT AAATGCTTGA GAGGATGGAT ACCCCATTCT CCATGATGTA     180

CTTATTTCAC ATTACATGCC TGTATCAAAG CATCTCATAT ACCCTATAAA TATGTACACC     240

TACTATGTAC CCTCTTA                                                    257
```

(2) INFORMATION FOR SEQ ID NO:231:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:231:

```
TAAGAGGGTA CGGGTATTTG CTGATGGGAT TTTTTTTTCT TTCTTTTTCT TTGGAAAACA      60

AAATGAAAGC CAGAACAAAA TTATTGAACA AAAGACAGGG ACTAAATCTG GAGAAATGAA     120

GTCCCCTCAC CTGACTGCCA TTTCATTCTA TCTGACCTTC CAGTCTAGGT TAGGAGAATA     180

GGGGGTGGAG GGGATTAATC TGATACAGGT ATATTTAAAG CAACTCTGCA TGTGTGCCAG     240

AAGTCCATGG TACCCTCTTA                                                260
```

(2) INFORMATION FOR SEQ ID NO:232:

(i) SEQUENCE CHARACTERISTICS:
        (A) LENGTH: 596 base pairs

```
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:232:

TGCTCCTCTT GCCTTACCAA CCACAAATTA GAACCATAAT GAGATGTCAC CTCATACCTG      60

GTGGGATTAA CATTATTTAA AAAATCAGAA GTATTGACAA GGATGTGAAG AAATTAGAAC     120

ATCTGTGCAC TGTTGGTGGG AATGTAAAAA AGGTGTGGCC ACTATGGGTA ACAGCATGAA     180

GGTTCCTCAA AAAAAATTTT TTTTAATCTA CTCTATGATC GATCTTGAGG TTGTTTATGC     240

AAAAGAACTG AAATCAGGAT TTTGAGGAAA TATTCACATT CCCACATCCA TTTCTGCTTT     300

ATTCATAATA CTCAAGAGAT GGAAACAACC TAAATGTCCA TCCCGGGATG AATGGATAAA     360

CACAGTGTGG TATATGCATA CAATGGAATA TTATTTAGTC TTTAAAAGA AAAATTCTAT      420

CATATACTAC AACTTANATN AACCTTGAGG ACACAATGCT NAGTGAAATA AGCCACGGAA     480

GGACGAATAC TGCATTATTC CCTTATATGA AGTATCTAAA GTGGTCAAAC TCTTANAGCA     540

NAAAGTAAAA ATGGGTGGTT GCCANACAGT TGGTTAGGCN AGAAGANAAN CCTANT        596

(2) INFORMATION FOR SEQ ID NO:233:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:233:

TCTTCTGAAG ACCTTTCGCG ACTCTTAAGC TCGTGGTTGG TAAGGCAAGA GGAGCGTTGG      60

TAAGGCAAGA GGAGCGTTGG TAAGGCAAGA GGAGCA                               96

(2) INFORMATION FOR SEQ ID NO:234:

(i) SEQUENCE CHARACTERISTICS:
        (A) LENGTH: 313 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:234:

TGTAAGTCGA GCAGTGTGAT GATAAAACTT GAATGGATCA ATAGTTGCTT CTTATGGATG      60

AGCAAAGAAA GTAGTTTCTT GTGATGGAAT CTGCTCCTGG CAAAAATGCT GTGAACGTTG     120

TTGAAAAGAC AACAAAGAGT TTAGAGTAGT ACATAAATTT AGAATAGTAC ATAAACTTAG     180

AATAGTACAT AAACTTAGTA CATAAATAAT GCACGAAGCA GGGGCAGGGC TTGAGAGAAT     240

TGACTTCAAT TTGGAAAGAG TATCTACTGT AGGTTAGATG CTCTCAAACA GCATCACACT     300

GCTCGACTTA CAA                                                        313
```

(2) INFORMATION FOR SEQ ID NO:235:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:235:

```
AACGAGGACA GATCCTTAAA AAGAATGTTG AGTGAAAAAA GTAGAAAATA AGATAATCTC      60

CAAAGTCCAG TAGCATTATT TAAACATTTT TAAAAAATAC ACTGATAAAA ATTTTGTACA     120

TTTCCCAAAA ATACATATGG AAGCACAGCA GCATGAATGC CTATGGGRTT GAGGATAGGG     180

GTTGGGAGTA GGGATGGGGA TAAAGGGGGA AAATAAAACC AGAGAGGAGT CTTACACATT     240

TCATGAACCA AGGAGTATAA TTATTTCAAC TATTTGTACC WGAAGTCCAG AAAGAGTGGA     300

GGCAGAAGGG GGAGAAGAGG GCGAAGAAAC GTTTTTGGGA GAGGGGTCCC ASAAGAGAGA     360

TTTTCGCGAT GTGGCGCTAC ATACGTTTTT CCAGGATGCC TTAAGCTCTG CACCCTATTT     420

TTCTCATCAC TAATATTAGA TTAAACCCTT TGAAGACAGC GTCTGTGGTT TCTCTACTTC     480

AGCTTTCCCT CCGTGTCTTG CACACAGTAG CTGTTTTACA AGGGTTGAAC TGACTGAAGT     540

GAGATTATTC                                                           550
```

(2) INFORMATION FOR SEQ ID NO:236:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:236:

```
TAGACTGACT CATGTCCCCT ACCAGAGTAG CTAGAATTAA TAGCACAAGC CTCTACACCC      60

AGGAACTCAC TATTGAATAC ATAAATGGAA TTTATTCAGC CTTAAAAAGT TTGGAAGGAA     120

ATTCTGACAT ATGCTAAAAC ATGGATGAAC CTTGAAGACT TTATGATAAG TAAAAGAAGC     180

CAGTCATAAA AGGAAAAATA TTGCATGATT CCACTTATAT GAGGTACCTA GAGTAGTCAA     240

TTTCATAGAA ACACAAAATA GAATGGTGTT TGCCAGGGCT TTTGAGGAAA AGGGAATGAC     300

AAGTTAGGGG ACATGAGTCA GTCTA                                          325
```

(2) INFORMATION FOR SEQ ID NO:237:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:237:

```
TAGACTGACT CATGTCCCCT ATCTACTCAA CATTTCCACT TGAAGTCTGA TAGGCATCTC        60

AGACTTATCT TGTCCCAAAG CAAACTCTTT ATTTCTTTTC ATCCTAGTCT TTATTTCTTG       120

TGCTGTCTTA CCCATCTCAA AAGAGTGCCA AAATCCACCA AGTTGCTGAA ACAGAAATCT       180

AAGAAATATC CTTGATTCTT CTTTTTCCCA TCTACTTCAC TTCTAATTCA TTAGTAAATA       240

ATCTGTTTCA GAAAACCAAA CACCTCATGT TCTCACTCAT AAGGGGGAGT TGAACAATGA       300

GAACACACAG ACACAGGGAG GGGAACATCA CACACCACGG CCCGTCAGGG AGTANGGGAC       360

ATGAGTCAGT CTA                                                         373

(2) INFORMATION FOR SEQ ID NO:238:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:238:

TAGACTGACT CATGTCCCCT ATAATGCTCC CAGGCATCAG AAAGCATCTC AAACTGGAGC        60

TGACACCATG GCAGAGGTTT CAGGTAAGTC ACAAAAGGGG TCCTAAAGAA TTTGCCCTCA       120

ATATCAGAGT GATTAGAAGA AGTGGACAGA GCTACCCAAG TTAAACATAT GCGAGATAAA       180

AAAAATATGG CACTTGTGAA CACACACTAC AGGAGGAAAA TAAGGAACAT AATAGCATAT       240

TGTGCTATTA TGATGATGAA GAACCTCTCT ANAAGAAAAC ATAACCAAAG AAACAAAGAA       300

AATTCCTGCN AATGTTTAAT GCTATAGAAG AAATTAACAA AACATATAT TCAATGAATT        360

CAGAAAAGTT AGCAGGTCAN AAGAAAACAA ATCAAAGACC AGAATAATCC CATTTTAGAT       420

TGTCGAGTAA ACTANAACAG AAAGAATACC ACTGGAAATT GAATTCCTAC GTANGGGACA       480

TGANTCANTC TA                                                          492

(2) INFORMATION FOR SEQ ID NO:239:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:239:

TGGAAAGTAT TTAATGATGG GCAACTTGCT GTTTACTTCC TACATATCCC ATCATCTTCT        60

GTATTTTTTT AAATAACTTT TTTTTGGATT TTTAAAGTAA CCTTATTCTG AGAGGTAACA       120

TGGATTACAT ACTTCTAAGC CATTAGGAGA CTCTATGTTA AACCAAAAGG AAATGTTACT       180

AGATCTTCAT TTGATCAATA GGATGTGATA ATCATCATCT TTCTGCTCTA ATGGAAAAGT       240

ACTANAAACA TGGAACCATA ATCTTAGATG AACAACGTTA GAATTTGCAC TAATTCTACG       300

GAATTTCAGT AATTCGGCAA ATGTCGGGCA GTGCACAAC ATTTCATGAC GGGGACGCAT        360

CTACCAACTT CTGGCGATAA GGGCCACCCT TCCCTCTGTA CTTACAGTCC CATTTCATAC       420
```

| ACAGTCTTTG ATTAAATATT CACATTTTTT CTCTACCTAA AGACCTTCAA GACCAGTACG | 480 |
| TA | 482 |

(2) INFORMATION FOR SEQ ID NO:240:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:240:

| TGTATCGACG TAGTGGTCTC CCCATGTGAT AGTCTGAAAT ATAGCCTCAT GGGATGAGAG | 60 |
| GCTGTGCCCC AGCCCGACAC CCGTAAAGGG TCTGTGCTGA GGTGGATTAG TAAAAGAGGA | 120 |
| AAGCCTTGCA GTTGAGATAG AGGAAGGGCA CTGTCTCCTG CCTGCCCCTG GAACTGAAT | 180 |
| GTCTCGGTAT AAAACCCGAT TGTACATTTG TTCAATTCTG AGATAGGAGA AAAACCACCC | 240 |
| TATGGCGGGA GGCGAGACAT GTTGGCAGCA ATGCTGCCTT GTTATGCTTT ACTCCACAGA | 300 |
| TGTTTGGGCG GAGGGAAACA TAAATCTGGC CTACGTGCAC ATCCAGGCAT AGTACCTCCC | 360 |
| TTTGAACTTA ATTATGACAC AGATTCCTTT GCTCACATGT TTTTTTGCTG ACCTTCTCCT | 420 |
| TATTATCACC CTGCTCTCCT ACCGCATTCC TTGTGCTGAG ATAATGAAAA TAATATCAAT | 480 |
| AAAAACTTGA NGGAACTCGG AGACCACTAC GTCGATACA | 519 |

(2) INFORMATION FOR SEQ ID NO:241:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:241:

| TGTATCGACG TAGTGGTCTC CACTCCCGCC TTGACGGGGC TGCTATCTGC CTTCCAGGCC | 60 |
| ACTGTCACGG CTCCCGGGTA GAAGTCACTT ATGAGACACA CCAGTGTGGC CTTGTTGGCT | 120 |
| TGAAGCTCCT CAGAGGAGGG TGGGAACAGA GTGACCGAGG GGGCAGCCTT GGGCTGACCT | 180 |
| AGGACGGTCA GCTTGGTCCC TCCGCCAAAC ACGAGAGTGC TGCTGCTTGT ATATGAGCTG | 240 |
| CAGTAATAAT CAGCCTCGTC CTCAGCCTGG AGCCCAGAGA TGGTCAGGGA GGCCGTGTTG | 300 |
| CCANACTTGG AGCCAGAGAA GCGATTAGAA ACCCCTGAGG GCCGATTACC GACCTCATAA | 360 |
| ATCATGAATT TGGGGCTTT GCCTGGGTGC TGTTGGTACC ANGAGACATT ATTATAACCA | 420 |
| CCAACGTCAC TGCTGGTTCC ANTGCAGGGA AAATGGTTGA TCNAACTGTC CAAGAAAACC | 480 |
| ACTACGTCCA TACCAATCCA CTAATTGCCN GCCGCCTGCA GGTTCAACCA TATTGGGGAA | 540 |
| NAACTCCCCN CCGCCGTTTG GGATTGNCAT NAACCTTTGA AATTTTTTCC TATTANTTGT | 600 |
| CCCCCTAAAA TAAACCNTTG GGCNTTAATC CATTGGGTCC ATANCTTNTT TNCCCGGTTT | 660 |
| TTAAAANTTG TTTATCCCGC CNCCCNATTT CCCCCCCAAC TTTCCAAAAC CCGAAACCNT | 720 |
| TNAAATTTNT TNAAACCCTG GGGGGTTCCC NNAATTNNAN TTNAANCTNC C | 771 |

(2) INFORMATION FOR SEQ ID NO:242:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:242:

```
TGGGCACCTT CAATATCGGG CTCATCGATA ACATCACGCT GCTGATGCTG CTGTTGCTGG      60

TCCTCTCTAG GAACCTCTGG ATTTTCAAAT TCTTTGAGGA ATTCATCCAA ATTATCTGCC     120

TCTCCTCCTT TCCTCCTTTT TCTAAGGTCT TCTGGTACAA GCGGTCA                   167
```

(2) INFORMATION FOR SEQ ID NO:243:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:243:

```
TTGGGCACCT TCAATATCTA CTGATCTAAA TAGTGTGGTT TGAGGCCTCT TGTTCCTGGC      60

TAAAAATCCT TGGCAAGAGT CAATCTCCAC TTTACAATAG AGGTAAAAAT CTTACAATGG     120

ATATTCTTGA CAAAGCTAGC ATAGAGACAG CAATTTTACA CAAGGTATTT TTCACCTGTT     180

TAATAACAGT GGTTTTCCTA CACCCATAGG GTGCCACCAA GGGAGGAGTG CACAGTTGCA     240

GAAACAAATT AAGATACTGA AGACAACACT ACTTACCATT TCCCGTATAG CTAACCACCA     300

GTTCAACTGT ACATGTATGT TCTTATGGGC AATCAAGA                             338
```

(2) INFORMATION FOR SEQ ID NO:244:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:244:

```
TTTTTGGCTC CCATACAGCA CACTCTCATG GGAAATGTCT GTTCTAAGGT CAACCCATAA      60

TGCAAAAATC ATCAATATAC TTGAAGATCC CCGTGTAAGG TACAATGTAT TTAATATTAT     120

CACTGATACA ATTGATCCAA TACCAGTTTT AGTCTGGCAT TGAATCAAAT CACTGTTTTT     180

GTTGTATAAA AAGAGAAATA TTTAGCTTAT ATTTAAGTAC CATATTGTAA GAAAAAAGAT     240

GCTTATCTTT ACATGCTAAA ATCATGATCT GTACATTGGT GCAGTGAATA TTACTGTAAA     300

AGGGAAGAAG GAATGAAGAC GAGCTAAGGA TATTGAAGGT GCCCAA                    346
```

(2) INFORMATION FOR SEQ ID NO:245:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:245:

```
ACCAATCCCA CACGGATACT GAGGGACAAG TATATCATCC CATTTCATCC CTACAGCAGC    60

AACTTCATGA GGCAGGAGTT ATTAGTCCCA TTTTACAGAA GAGGAAACTG AGACTTAGGG   120

AGATCAAGTA ATTTGCCCAG GTCGCACAAT TAGTGATAGA GCCAGGGCTT GAAGCGACGT   180

CTGTCTTAAG CCAATGACCC CTGCAGATTA TTAGAGCAAC TGTTCTCCAC AACAGTGTAA   240

GCCTCTTGCT ANAAGCTCAG GTCCACAAGG GCAGAGATTT TTGTCTGTTT TGCTCATTGC   300

TCCTTCCCCA TTGCTTAGAG CAGGGTCTGC CACGAANCAG GTTCTCAATG CATAGTTATT   360

AAATGTATAT AAGAGCAAAC ATATGTTACA GAGAACTTTC TGTATGCTTG TCACTTACAT   420

GAATCACCTG TGANATGGGT ATGCTTGTTC CCCANTGTTG CAGATNAAGA TATTGAANGT   480

GCCCAAATCA CTANTTGCGG GCGCCTGCAN GTCCANCATA T                       521
```

(2) INFORMATION FOR SEQ ID NO:246:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:246:

```
TGGAACCAAT CCAAATACCC ATCAATGATA GACTGGATAA AGAAAATTTG GCACATGTTC    60

ACCATGAAAT ACTATGCAGC CATAAAAAAG GATGAGTTCA TATCCTTTGC AGGGACATGG   120

ATGAAGCTGG AGACCATCAT TCTCAGCAAA CTAACAAGGG AACAGAAAAC CAAACACTGC   180

ATGTTCTCAC TCTTAAGTGG GAGCTGAACA ATGAGAACAC ATGGACACAG GGAGGGGAAC   240

ATCACACAGT GGGGCCTGCT GGTGGGTAGG GGTCTAGGGG AGGGATAGCA TTAGGAGAAA   300

TACCTAATGT AGATGACGGG TTGATGGGTG CAGCAAACCA CCATGACACG TGTATACCTA   360

TGTAACAAAC CTGCATGTTC TGCACATGTA CCCCAGAACT TAAAGTGTTA ATAAAAAAAT   420

TAAGAAAAAA GTTAAGTATG TCATAGATAC ATAAAATATT GTANATATTG AAGGTGCCCA   480

AA                                                                  482
```

(2) INFORMATION FOR SEQ ID NO:247:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:247:

```
TTCGATACAG GCACAGAGTA AGCAGAAAAA TGGCTGTGGT TTAACCAAGT GAGTACAGTT    60

AAGTGAGAGA GGGGCAGAGA AGACAAGGGC ATATGCAGGG GGTGATTATA ACAGGTGGTT   120

GTGCTGGGAA GTGAGGGTAC TCGGGGATGA GGAACAGTGA AAAAGTGGCA AAAAGTGGTA   180

AGATCAGTGA ATTGTACTTC TCCAGAATTT GATTTCTGGN GGAGTCAAAT AACTATCCAG   240

TTTGGGGTAT CATANGGCAA CAGTTGAGGT ATAGGAGGTA GAAGTCNCAG TGGGATAATT   300

GAGGTTATGA ANGGTTTGGT ACTGACTGGT ACTGACAANG TCTGGGTTAT GACCATGGGA   360

ATGAATGACT GTANAAGCGT ANAGGATGAA ACTATTCCAC GANAAAGGGG TCCNAAAACT   420

AAAAANNNAA GNNNNNGGGG AATATTATTT ATGTGGATAT TGAANGTGCC CAAA         474
```

(2) INFORMATION FOR SEQ ID NO:248:

(i) SEQUENCE CHARACTERISTICS:
       (A) LENGTH: 355 base pairs
       (B) TYPE: nucleic acid
       (C) STRANDEDNESS: single
       (D) TOPOLOGY: linear (xi) SEQUENCE DESCRIPTION: SEQ ID NO:248:

```
TTCGATACAG GCAAACATGA ACTGCAGGAG GGTGGTGACG ATCATGATGT TGCCGATGGT    60

CCGGATGGNC ACGAAGACGC ACTGGANCAC GTGCTTACGT CCTTTTGCTC TGTTGATGGC   120

CCTGAGGGGA CGCAGGACCC TTATGACCCT CAGAATCTTC ACAACGGGAG ATGGCACTGG   180

ATTGANTCCC ANTGACACCA GAGACACCCC AACCACCAGN ATATCANTAT ATTGATGTAG   240

TTCCTGTAGA NGGCCCCCTT GTGGAGGAAA GCTCCATNAG TTGGTCATCT TCAACAGGAT   300

CTCAACAGTT TCCGATGGCT GTGATGGGCA TAGTCATANT TAACCNTGTN TCGAA        355
```

(2) INFORMATION FOR SEQ ID NO:249:

(i) SEQUENCE CHARACTERISTICS:
       (A) LENGTH: 434 base pairs
       (B) TYPE: nucleic acid
       (C) STRANDEDNESS: single
       (D) TOPOLOGY: linear (xi) SEQUENCE DESCRIPTION: SEQ ID NO:249:

```
TTGGATTGGT CCTCCAGGAG AACAAGGGGA AAAAGGTGAC CGAGGGCTCC CTGGAACTCA    60

AGGATCTCCA GGAGCAAAAG GGGATGGGGG AATTCCTGGT CCTGCTGGTC CCTTAGGTCC   120

ACCTGGTCCT CCAGGCTTAC CAGGTCCTCA AGGCCCAAAG GGTAACAAAG GCTCTACTGG   180

ACCCGCTGGC CAGAAAGGTG ACAGTGGTCT TCCAGGGCCT CCTGGGCCTC CAGGTCCACC   240

TGGTGAAGTC ATTCAGCCTT TACCAATCTT GTCCTCCAAA AAAACGAGAA GACATACTGA   300

AGGCATGCAA GCAGATGCAG ATGATAATAT TCTTGATTAC TCGGATGGAA TGGAAGAAAT   360

ATTTGGTTCC CTCAATTCCC TGAAACAAGA CATCGAGCAT ATGAAATTTC CAATGGGTAC   420

TCAGACCAAT CCAA                                                    434
```

(2) INFORMATION FOR SEQ ID NO:250:

(i) SEQUENCE CHARACTERISTICS:
       (A) LENGTH: 430 base pairs
       (B) TYPE: nucleic acid
       (C) STRANDEDNESS: single
       (D) TOPOLOGY: linear (xi) SEQUENCE DESCRIPTION: SEQ ID NO:250:

```
TGGATTGGTC ACATGGCAGA GACAGGATTC CAAGGCAGTG AGAGGAGGAT ACAATGCTTC    60
TCACTAGTTA TTATTATTTA TTTTATTTTT GAGATGAAGT CTCGCTTTGT CTCCCAGGCT   120
GGAGAGCGGT GGTGCGATCT TGGCTCTCTG CAACCCCCGC CTCAAGCAAT TCTCCTGTCT   180
TAGCCTCGCG GGTAGATGGA ATTACAGGCG CCCACCGCCA TGCCCAACTA ATTTTTTTGT   240
GTCTTCAGTA GAGACAGGGT TTCGCCATGT TGGGCAGGCT GGTCTTGAAC TCCTGACCTC   300
NAGTGATCTG CCCTCCTCGG CCTCACAAAG TGCTGGAATT ACAGGCATGG GCTGCTGCAC   360
CCAGTCAACT TCTCACTAGT TATGGCCTTA TCATTTTCAC CACATTCTAT TGGCCCAAAA   420
AAAAAAAAN                                                            430
```

(2) INFORMATION FOR SEQ ID NO:251:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (xi) SEQUENCE DESCRIPTION: SEQ ID NO:251:

```
TGGTACTCCA CCATYATGGG GTCAACCGCC ATCCTCGCCC TCCTCCTGGC TGTTCTCCAA    60
GGAGTCTGTG CCGAGGTGCA GCTGRTGCAG TCTGGAGCAG AGGTGAAAAA GTCCGGGGAG   120
TCTCTGAAGA TCTCCTGTAA GGGTTCTGGA TACACCTTTA AGATCTACTG GATCGCCTGG   180
GTGCGCCAGT TGCCCGGGAA AGGCCTGGAG TGGATGGGGC TCATCTTTCC TGATGACTCT   240
GATACCAGAT ACAGCCCGTC CTTCCAAGGC CAGGTCACCA TCTCAGTCGA TAAGTCCATC   300
AGCACCGCCT ATCTGCAGTG GAGTACCAA                                      329
```

(2) INFORMATION FOR SEQ ID NO:252:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (xi) SEQUENCE DESCRIPTION: SEQ ID NO:252:

```
TGGTACTCCA CTCAGCCCAA CCTTAATTAA GAATTAAGAG GGAACCTATT ACTATTCTCC    60
CAGGCTCCTC TGCTCTAACC AGGCTTCTGG GACAGTATTA GAAAAGGATG TCTCAACAAG   120
TATGTAGATC CTGTACTGGC CTAAGAAGTT AAACTGAGAA TAGCATAAAT CAGACCAAAC   180
TTAATGGTCG TTGAGACTTG TGTCCTGGAG CAGCTGGGAT AGGAAAACTT TTGGGCAGCA   240
AGAGGAAGAA CTGCCTGGAA GGGGGCATCA TGTTAAAAAT TACAAGGGGA ACCCACACCA   300
GGCCCCCTTC CCAGCTCTCA GCCTAGAGTA TTAGCATTTC TCAGCTAGAG ACTCACAACT   360
TCCTTGCTTA GAATGTGCCA CCGGGGGGAG TCCCTGTGGG TGATGAGGCT CTCAAGAGTG   420
AGAGTGGCAT CCTATCTTCT GTGTGCCCAC AGGAGCCTGG CCCGAGACTT AGCAGGTGAA   480
GTTTCTGGTC CAGGCTTTGC CCTTGACTCA CTATGTGACC TCTGGTGGAG TACCAA        536
```

(2) INFORMATION FOR SEQ ID NO:253:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:253:

```
NTGTTGCGAT CCCAGTAACT CGGGAAGCTG AGGCGGGAGG ATCACCTGAG CTCAGGAGGT        60

TGAGGCCGCA GTGAGCCGGG ACCACGCCAC TACACTCCAG CCTGGGGCAT AGAGTGAGAC       120

CCTCCAAGAC AGAAAAGAAA AGAAAGGAAG GGAAAGGGAA AGGGAAAAGG AAAAGGAAAA       180

GGAAAAGGAA AAGGAAAAGA CAAGACAAAA CAAGACTTGA ATTTGGATCT CCTGACTTCA       240

ATTTTATGTT CTTTCTACAC CACAATTCCT CTGCTTACTA AGATGATAAT TTAGAAACCC       300

CTCGTTCCAT TCTTTACAGC AAGCTGGAAG TTTGGTCAAG TAATTACAAT AATAGTAACA       360

AATTTGAATA TTATATGCCA GGTGTTTTTC ATTCCTGCTC TCACTTAATT CTCACCACTC       420

TGATATAAAT ACAATTGCTG CCGGGTGTGG TGGCTCATGC CTGTAATCCC GGCACTTTGG       480

GAGACCGAGG TGGGCGGATS GCAACAA                                          507
```

(2) INFORMATION FOR SEQ ID NO:254:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (xi) SEQUENCE DESCRIPTION: SEQ ID NO:254:

```
TTGGATTGGT CACTGTGAGG AAGCCAAATC GGATCCGAGA GTCTTTTTCT AAAGGCCAGT        60

ACTGGCCACA CTTTCTCCTG CCGCCTTCCT CAAAGCTGAA GACACACAGA GCAAGGCGCT       120

TCTGTTTTAC TCCCCAATGG TAACTCCAAA CCATAGATGG TTAGCTNCCC TGCTCATCTT       180

TCCACATCCC TGCTATTCAG TATAGTCCGT GGACCAATCC AA                         222
```

(2) INFORMATION FOR SEQ ID NO:255:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (xi) SEQUENCE DESCRIPTION: SEQ ID NO:255:

```
TGTTGCGATC CATAAATGCT GAAATGGAAA TAAACAACAT GATGAGGGAG GATTAAGTTG        60

GGGAGGGAGC ACATTAAGGT GGCCATGAAG TTTGTTGGAA GAAGTGACTT TTGAACAAGG       120

CCTTGGTGTT AAGAGCTGAT GAGAGTGTCC CAGACAGAGG GGCCACTGGT ACAATAGACG       180

AGATGGGAGA GGGCTTGGAA GGTGTGCGAA ATAGGAAGGA GTTTGTTCTG GTATGAGTCT       240

AGTGAACACA GAGGCGAGAG GCCCTGGTGG GTGCAGCTGG AGAGTTATGC AGAATAACAT       300

TAGGCCCTGT GGGGGACTGT AGACTGTCAG CAATAATCCA CAGTTTGGAT TTTATTCTAA       360

GAGTGATGGG AAGCCGTGGA AAGGGGTTA AGCAAGGAGT GAAATTATCA GATTTACAGT       420

GATAAAAATA AATTGGTCTG GCTACTGGGG AAAAAAAAAA AAA                        463
```

(2) INFORMATION FOR SEQ ID NO:256:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (xi) SEQUENCE DESCRIPTION: SEQ ID NO:256:

```
TTGGATTGGT CAACCTGCTC AACTCTACYT TTCCTCCTTC TTCCTAAAAA ATTAATGAAT        60
```

```
CCAATACATT AATGCCAAAA CCCTTGGGTT TTATCAATAT TTCTGTTAAA AAGTATTATC     120

CAGAACTGGA CATAATACTA CATAATAATA CATAACAACC CCTTCATCTG GATGCAAACA     180

TCTATTAATA TAGCTTAAGA TCACTTTCAC TTTACAGAAG CAACATCCTG TTGATGTTAT     240

TTTGATGTTT GGACCAATCC AA                                              262

(2) INFORMATION FOR SEQ ID NO:257:

(i) SEQUENCE CHARACTERISTICS:
          (A) LENGTH: 461 base pairs
          (B) TYPE: nucleic acid
          (C) STRANDEDNESS: single
          (D) TOPOLOGY: linear (xi) SEQUENCE DESCRIPTION: SEQ ID NO:257:

GNGGNNNNNN NNNCAATTCG ACTCNGTTCC CNTGGTANCC GGTCGACATG GCCGCGGGAT      60

TACCGCTTGT NNCTGGGGGT GTATGGGGGA CTATGACCGC TTGTAGCTGG GGGTGTATGG     120

GGGACTATGA CCGCTTGTAG MTGGKGGTGT ATGGGGGACT ATGACCGCTT GTCGGGTGGT     180

CGGATAAACC GACGCAAGGG ACGTGATCGA AGCTGCGTTC CCGCTCTTTC GCATCGGTAG     240

GGATCATGGA CAGCAATATC CGCATTCGYC TGAAGGCGTT CGACCATCGC GTGCTCGATC     300

AGGCGACCGG CGACATCGCC GACACCGCAC GCCGTACCGG CGCGCTCATC CGCGGTCCGA     360

TCCCGCTTCC CACGCGCATC GAGAAGTTCA CGGTCAACCG TGGCCCGCAC GTCGACAAGA     420

AGTCGCGCGA GCAGTTCGAG GTGCGTACCT ACAAGCGGTC A                         461

(2) INFORMATION FOR SEQ ID NO:258:

(i) SEQUENCE CHARACTERISTICS:
          (A) LENGTH: 332 base pairs
          (B) TYPE: nucleic acid
          (C) STRANDEDNESS: single
          (D) TOPOLOGY: linear (xi) SEQUENCE DESCRIPTION: SEQ ID NO:258:

TGACCGCTTG TAGCTGGGGG TGTATGGGGG ACTACGACCG CTTGTAGCTG GGGGTGTATG      60

GGGGACTATG ACCGCTTGTA GCTGGGGGTG TATGGGGGAC TATGACCGCT TGTAGCTGGG     120

GGTGTATGGG GGACTAGGAC CGCTTGTAGC TGGGGGTGTA TGGGGACTA TGACCGCTTG      180

TAGCTGGGGG TGTATGGGGG ACTACGACCG CTTGTAGCTG GGGGTGTATG GGGACTATG      240

ACCGCTTGTA NCTGGGGTG TATGGGGGAC TATGACCGCT TGTGCTGCCT GGGGGATGGG     300

AGGAGAGTTG TGGTTGGGGA AAAAAAAAAA AA                                   332

(2) INFORMATION FOR SEQ ID NO:259:

(i) SEQUENCE CHARACTERISTICS:
          (A) LENGTH: 291 base pairs
          (B) TYPE: nucleic acid
          (C) STRANDEDNESS: single
          (D) TOPOLOGY: linear (xi) SEQUENCE DESCRIPTION: SEQ ID NO:259:

TACCGCTTGT GACCGCTTGT GACCGCTTGT GACCGCTTGT GACCGCTTGT GACCGCTTGT      60

GACCGCTTGT GACCGCTTGT GACCGCTTGT GACCGCTTGT GACCGCTTGT GACCGCTTGT     120

GACCGCTTGT GACCGCTTGT NACNGGGGGT GTCTGGGGGA CTATGANNGA NTGTNACTGG     180

GGGTGTCTGG GGGNCTATGA NNGANTGTNA CNGGGGGTGT CTGGGGGACT ATGANNGACT     240

GTGCNNCCTG GGGGATCNGA GGAGANTNGN GGNTAGNGAT GGTTNGGGAN A              291
```

(2) INFORMATION FOR SEQ ID NO:260:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (xi) SEQUENCE DESCRIPTION: SEQ ID NO:260:

```
TAAGAGGGTA CTGGTTAAAA TACAGGAAAT CTGGGGTAAT GAGGCAGAGA ACCAGGATAC    60

TTTGAGGTCA GGGATGAAAA CTAGAATTTT TTTCTTTTTT TTTGCCTGAG AAACTTGCTG   120

CTCTGAAGAG GCCCATGTAT TAATTGCTTT GATCTTCCTT TTCTTACAGC CCTTTCAAGG   180

GCAGAGCCCT CCTTATCCTG AAGGAATCTT ATCCTTAGCT ATAGTATGTA CCCTCTTA     238
```

(2) INFORMATION FOR SEQ ID NO:261:

(i) SEQUENCE CHARACTERISTICS:
        (A) LENGTH: 746 base pairs
        (B) TYPE: nucleic acid
        (C) STRANDEDNESS: single
        (D) TOPOLOGY: linear (xi) SEQUENCE DESCRIPTION: SEQ ID NO:261:

```
TTGGGCACCT TCAATATCAA TAGCTAACAT TTATTGAGTG TTTATCGTAT CATAAAACAC    60

TGTTCTAAGC CTTTAAACGT ACTAATTCAT TTAATGCTCA TAATCACTTT AGAAGGTGGG   120

TACTAGTATT AGTCTCATTT ACAGATGCAA CATGCAGGCA CAGAGAGGTT AATTAACTTG   180

CCCAAGGTAA CACAGCTAAG AAATAGAAAA AATATTGAAT CTGGAAAGTT GGGCTTCTGG   240

GTAACCCACA GAGTCTTCAA TGAGCCTGGG GCCTCACTCA GTTTGCTTTT ACAAAGCGAA   300

TGAGTAACAT CACTTAATTC AGTGAGTAGG CCAAATGGAG GTCAGCTACG AGTTTCTGCT   360

GTTCTTGCAG TGGACTGACA GATGTTTACA ACGTCTGGCC ATCAGTWAAT GGACTGATTA   420

TCATTGGGAW GTGGGTGGGC TGAATGTTGG CCAGTGAAGT TTATTCAWGC CATATTTTTA   480

TGTTTAGGAT GACTTTTGGC TGGTCCTAGG GCAAGCTCTG TCTGSCACGG AACACAGAAT   540

WACACAGGGA CCCCCTCAAT TTCTGGTGTG GCTAGAACCA TGAACCACTG GTTGGGGGAA   600

CAAGCGGTCA AAACCTAAGT GCGGCCGGCT GGCAGGGTCC ACCCATATGG GGAAAACTCC   660

CNACGCGTTT GGAATGCCTN AGCTNGAATT ATTCTAANAG TTGTCCNCNT AAAATTAGCC   720

TGGGCGTTAA TCANGGGTCN NAAGCC                                        746
```

(2) INFORMATION FOR SEQ ID NO:262:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (xi) SEQUENCE DESCRIPTION: SEQ ID NO:262:

```
TGACCGCTTG TCATCTCACA TGGGGTCCTG CACGCTTTTG CCTTTGTAGG AAACCTGACA    60

TTTGTCTGTT TCTTCTTTCT CTTTTCCTTC CCATATCCTC CTAATTTACG TTTGACTTGT   120

TTGCTGAGGA GGCAGGAGCT AGAGACTGCT GTGAGCTCAT AGGGGTGGGA AGTTTATCCT   180

TCAAGTCCCG CCCACTCATC ACTGCTTCTC ACCTTCCCCT GACCAGGCTT ACAAGTGGGT   240

TCTTGCCTGC TTTCCCTTTG GACCCAACAA GCCCCTGTAA TGAGTGTGCA TGACTCTGAC   300

AGCTGTGGAC TCAGGGTCCT TGGCTACAGC TGCCATGTAA AATATCTCAT CCAGTTCTCG   360
```

```
CAAATTGTTA AAATAACCAC ATTTCTTAGA TTCCAGTACC CAAATCATGT CTTTACGAAC      420

TGCTCCTCAC ACCCAGAAGT GGCACAATAA TTCTTGGGGA ATTATTACTT TTTTTTTTCT      480

CTCTNTTNNC GNNNGNNNNG GNNNGNCCAG GAATTACCAC NTTGGAAGAC CTGGCCNGAA      540

TTTATTATAN AGGGGAGCCG ATTNTTTTTC CTAACACAAA GCGGGTCA                   588

(2) INFORMATION FOR SEQ ID NO:263:

(i) SEQUENCE CHARACTERISTICS:
        (A) LENGTH: 730 base pairs
        (B) TYPE: nucleic acid
        (C) STRANDEDNESS: single
        (D) TOPOLOGY: linear (xi) SEQUENCE DESCRIPTION: SEQ ID NO:263:

TTTTTTTTTT TTTGGCCTGA GCAACTGAAA TTATGAAATT TCCATATACT CAAAAGAGTA       60

AGACTGCAAA AAGATTAAAT GTAAAAGTTG TCTTGTATAC AGTAATGTTT AAGATACCTA      120

TTANATTTAT AAATGGAAAA TTAGGGCATT TGGATATACA AGTTGAAAAT TCAGGAGTGA      180

GGTTGGGCTG GCTGGGTATA TACTGAAAAC TGTCAGTACA CAGATGACAT CTAAAACCAC      240

AAATCTGGTT TTATTTTAGC AGTGATATGT GTCACTCCCA CAAAAGCCTT CCCAATTGGC      300

CTCAGCATAC ACAACAAGTC ACCTCCCCAC AGCCCTCTAC ACATAAACAA ATTCCTTAGT      360

TTAGTTCAGG AGGAAATGCG CCCTTTTCCT TCCGCTCTAG GTGACCGCAA GGCCCAGTTC      420

TCGTCACCAA GATGTTAAGG GAAGTCTGCC AAAGAGGCAT CTGAAAGGAA ATAAGGGGAA      480

TGGGAGTGAC CACAAAGGAA AGCCAAGGAN AAACTTTGGA GACCGTTTCT AGANCCCTGG      540

CATTTCACAA CAAAACTCNG GAACAAACCT TGTCTCATCA ATCATTTAAG CCCTTCGTTT      600

GGANNAGACT TTCTGAACTG GGCGCTGAAC ATAANCCTCA TTGAATGTCT TCACAGTCTC      660

CCAGCTGAAG GCACACCTTG GGCCAGAAGG GGAATCTTCC AGGTCCTCAA NACAGGGCTC      720

GCCCTTTGNC                                                             730

(2) INFORMATION FOR SEQ ID NO:264:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (xi) SEQUENCE DESCRIPTION: SEQ ID NO:264:

TTTTTTTTTT TTTGGCCAGT ATGATAGTCT CTACCACTAT ATTGAAGCTC TTAGGTCATT       60

TACACTTAAT GTGGTTATAG ATGCTGTTGA GCTTACTTCT ACCACCTTGC TATTTCTCCC      120

GTCTCTTTTT TGTTCCTTTT CTCTTCTTTT CCTCCCTTAT TTTATAATTG AATTTTTTAG      180

GATTCTATTT TATATAGATT TATCAGCTAT AACACTTTGT ATTCTTTTGT TTTGTGGTTC      240

TTCTGTCATT TCAATGTGCA TCTTAAACTC ATCACAATCT ATTTTCAAAT AATATCATAT      300

AACCTTACAT ATAATGTAAG AATCTACCAC CATATATTTC CATTTCTCCC TTCCATCCTA      360

TGTNTGTCAT ATTTTTTCCT TTATATATGT TTTAAAGACA TAATAGTATA TGGGAGGTTT      420

TTGCTTAAAA TGTGATCAAT ATTCCTTCAA NGAAACGTAA AAATTCAAAA TAAATNTCTG      480

TTTATTCTCA AATNNACCTA ATATTTCCTA CCATNTCTNA TACNTTTCAA GAATCTGAAG      540

GCATTGGTTT TTTCCGGCTT AAGAACCTCC TCTAAAGCAC TCTAAGCAGA ATTAAGTCTT      600

CTGGGAGAGG AATTCTCCCA AGCTTGGGCC TTNANNTGTA CTCCNTNANG GTTAAANTTT      660
```

```
GGCCGGGAAA TAGAAATTCC AAGTTAACAG GNTANTTTTT NTTTTTNTTN TCNCC            715

(2) INFORMATION FOR SEQ ID NO:265:

(i) SEQUENCE CHARACTERISTICS:
         (A) LENGTH: 152 base pairs
         (B) TYPE: nucleic acid
         (C) STRANDEDNESS: single
         (D) TOPOLOGY: linear (xi) SEQUENCE DESCRIPTION: SEQ ID NO:265:

TTTTTTTTTT TTTCCCAACA CAAAGCACCA TTATCTTTCC TCACAATTTT CAACATAGTT       60

TGATTCCCAT GAAGAGGTTA TGATTTCTAA AGAAAACATG GCTACTATAC TATCAATCAG     120

GGTTAAATCT TTTTTTTTTG AGACGGAGTT TA                                  152

(2) INFORMATION FOR SEQ ID NO:266:

(i) SEQUENCE CHARACTERISTICS:
         (A) LENGTH: 193 base pairs
         (B) TYPE: nucleic acid
         (C) STRANDEDNESS: single
         (D) TOPOLOGY: linear (xi) SEQUENCE DESCRIPTION: SEQ ID NO:266:

TAAACTCCGT CCCCTTCTTA ATCAATATGG AGGCTACCCA CTCCACATTA CCTTCTTTTC      60

AAGGGACTGT TTCCGTAACT GTTGTGGGTA TTCACGACCA GGCTTCTAAA CCTCTTAAAA   120

CTCCCCAATT CTGGTGCCAA CTTGGACAAC ATGCTTTTTT TTTTTTTTT TTTTTTTTTN    180

GAGACGGAGT TTA                                                      193

(2) INFORMATION FOR SEQ ID NO:267:

(i) SEQUENCE CHARACTERISTICS:
         (A) LENGTH: 460 base pairs
         (B) TYPE: nucleic acid
         (C) STRANDEDNESS: single
         (D) TOPOLOGY: linear (xi) SEQUENCE DESCRIPTION: SEQ ID NO:267:

TGTTGCGATC CCTTAAGCAT GGGTGCTATT AAAAAAATGG TGGAGAAGAA AATACCTGGA      60

ATTTACGTCT TATCTTTAGA GATTGGGAAG ACCCTGATGG AGGACGTGGA GAACAGCTTC    120

TTCTTGAATG TCAATTCCCA AGTAACAACA GTGTGTCAGG CACTTGCTAA GGATCCTAAA    180

TTGCAGCAAG GCTACAATGC TATGGGATTC TCCCAGGGAG GCCAATTTCT GAGGGCAGTG    240

GCTCAGAGAT GCCCTTCACC TCCCATGATC AATCTGATCT CGGTTGGGGG ACAACATCAA    300

GGTGTTTTTG GACTCCCTCG ATGCCCAGGA GAGAGCTCTC ACATCTGTGA CTTCATCCGA    360

AAAACACTGA ATGCTGGGGC GTACTCCAAA GTTGTTCAGG AACGCCTCGT GCAAGCCGAA    420

TACTGGCATG ACCCATAAAA GGAGGATGTG GATCGCAACA                          460

(2) INFORMATION FOR SEQ ID NO:268:

(i) SEQUENCE CHARACTERISTICS:
         (A) LENGTH: 533 base pairs
         (B) TYPE: nucleic acid
         (C) STRANDEDNESS: single
         (D) TOPOLOGY: linear (xi) SEQUENCE DESCRIPTION: SEQ ID NO:268:

TGTTGCGATC CGTTGATAGA ATAGCGACGT GGTAATGAGT GCATGGCACG CCTCCGACTT      60

ACCTTCGCCC GTGGGACCCC CGAGTACGTC TACGGCGTCG TCACTTAGAG TACCCTCTGG    120
```

```
ACGCCCGGGC GCGTTCGATT TACCGGAAGC GCGAGCTGCA GTGGGCTTGC GCCCCCGGCC    180

AAATTCTTTG GGGGGTTTAA GGCCGCGGGG AATTTGAGGT ATCTCTATCA GTATGTAGCC    240

AAGTTGGAAC AGTCGCCATT CCCGAAATCG CTTTCTTTGA ATCCGCACCG CCTCCAGCAT    300

TGCCTCATTC ATCAACCTGA AGGCACGCAT AAGTGACGGT TGTGTCTTCA GCAGCTCCAC    360

TCCATAACTA GCGCGCTCGA CCTCGTCTTC GTACGCGCCA GGTCCGTGCG TGCGAATTCC    420

CAACTCCGGT GAGTTGCGCA TTTCAAGTTN CGAAACTGTT CGCCTCCACN ATTTGGCATG    480

TTCACGCATG ACACGGAATA AACTCGTCCA GTACCGGGAA TGGGATCGCA ACA          533
```

(2) INFORMATION FOR SEQ ID NO:269:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:269:

```
TTTTTTTTTT TTCGCCTGAA TTAGCTACAG ATCCTCCTCA CAAGCGGTCA               50
```

(2) INFORMATION FOR SEQ ID NO:270:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (xi) SEQUENCE DESCRIPTION: SEQ ID NO:270:

```
TGTTGCGATC CAAATAACCC ACCAGCTTCT TGCACACTTC GCAGAAGCCA CCGTCCTTTG    60

GCTGAGTCAC GTGAACGGTC AGTGCAAGCA GCCGCGTGCC AGAGCAGAGG TGCAGCATGC    120

TGCACACCAG CTCAGGGCTG ACCTCCTCCA GCAGGATGGA CAGGATGGAG CTGCCGTACG    180

TGTCCACCAC CTCCTGGCAC TCTTCCGACA GGGACTTCGG CAGCTTCGAG CACATTTTGT    240

CAAAAGCGTC GAGTATTTCT TTCTCAGTCT TGTTGTTGTC AATCAGCTTG GTCACCTCCT    300

TCACCAGGAA TTCACACACC TCACAGTAAA CATCAGACTT TGCTGGGACC TCGTGCTTCT    360

TAATGGGCTC CACCAGTTCC AGGGCAGGGA TGACATTCTT GGAGGCCACT TTGGCGGGGA    420

CCAGAGTCTG CATGGGCATC TCTTTCACCT CATCACAGAA CCCAACCAGC GCACAGATCT    480

CCTTGGGTTG CATGTGCATC ATCATCTGGG ATCGCAACA                          519
```

(2) INFORMATION FOR SEQ ID NO:271:

(i) SEQUENCE CHARACTERISTICS:
        (A) LENGTH: 457 base pairs
        (B) TYPE: nucleic acid
        (C) STRANDEDNESS: single
        (D) TOPOLOGY: linear (xi) SEQUENCE DESCRIPTION: SEQ ID NO:271:

```
TTTTTTTTTT TTCGGGCGGC GACCGGACGT GCACTCCTCC AGTAGCGGCT GCACGTCGTG    60

CCAATGGCCC GCTATGAGGA GGTGAGCGTG TCCGGCTTCG AGGAGTTCCA CCGGGCCGTG    120

GAACAGCACA ATGGCAAGAC CATTTTCGCC TACTTTACGG GTTCTAAGGA CGCCGGGGGG    180

AAAAGCTGGT GCCCCGACTG CGTGCAGGCT GAACCAGTCG TACGAGAGGG GCTGAAGCAC    240

ATTAGTGAAG GATGTGTGTT CATCTACTGC CAAGTAGGAG AAGAGCCTTA TTGGAAAGAT    300

CCAAATAATG ACTTCAGAAA AAACTTGAAA GTAACAGCAG TGCCTACACT ACTTAAGTAT    360
```

```
GGAACACCTC AAAAACTGGT AGAATCTGAG TGTCTTCAGG CCAACCTGGT GGAAATGTTG      420

TTCTCTGAAG ATTAAGATTT TAGGATGGCA ATCAAGA                              457
```

(2) INFORMATION FOR SEQ ID NO:272:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (xi) SEQUENCE DESCRIPTION: SEQ ID NO:272:

```
TTTTTTTTTT TTGGGCAACA ACCTGAATAC CTTTTCAAGG CTCTGGCTTG GGCTCAAGCC       60

CGCAGGGGAA ATGCAACTGG CCAGGTCACA GGGCAATCAA GA                        102
```

(2) INFORMATION FOR SEQ ID NO:273:

(i) SEQUENCE CHARACTERISTICS:
        (A) LENGTH: 455 base pairs
        (B) TYPE: nucleic acid
        (C) STRANDEDNESS: single
        (D) TOPOLOGY: linear (xi) SEQUENCE DESCRIPTION: SEQ ID NO:273:

```
TTTTTTTTTT TTGGCAATCA ACAGGTTTAA GTCTTCGGCC GAAGTTAATC TCGTGTTTTT       60

GGCAATCAAC AGGTTTAAGT CTTCGGCCGA AGTTAATCTC GTGTTTTTGG CAATCAACAG      120

GTTTAAGTCT TCGGCCGAAG TTAATCTCGT GTTTTTGGCA ATCAACAGGT TTAAGTCTTC      180

GGCCGAAGTT AATCTCGTGT TTTTGGCAAT CAACAGGTTT AAGTCTTCGG CCGAAGTTAA      240

TCTCGTGTTT TTGGCAATCA ACAGGTTTAA GTCTTCGGCC GAAGTTAATC TCGTGTTTTT      300

GGCAATCAAG AGGTTTAAGT CTTCGGCCGA AGTTAATCTC GTGTTTTTGG CAATCAACAG      360

GTTTAAGTCT TCGGCCGAAN TTAATCTCGT GTTTTTGGCA ATCAACAGGT TTAANTCTTC      420

GGCCGAAGTT AATCTCGTGT TTTTGGCAAT CAANA                                455
```

(2) INFORMATION FOR SEQ ID NO:274:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (xi) SEQUENCE DESCRIPTION: SEQ ID NO:274:

```
TTTTTTTTTT TTGGCCAATA CCCTTGATGA ACATCAATGT GAAAATCCTC GGTAAAATAC       60

TGGCAAACCA AATCCAGCAG CACATCAAAA AGCTTATCCA CCATGATCAA GTGGGCTTCA      120

TCCCTGGGAT GCAAGGCTGG TTCAACATAA GAAAATCAAT AAATGTAATC CATCACATAA      180

ACAGAACCAA AGACAAAAAC CACATGATTA TCTCAATAGA TGCAGAAAAG GCCTTGGACA      240

AATTCAACAG CCCTTCATGC TAAACACTCT TAATAAACTA GATATTGATG GAATGTATCT      300

CAAAATAATA AGAGCTATTT ATGACAAACC CACAGCCAAT ATCATACTGA ATGGGCAAAG      360

ACTGGAAGCA TTCCCTTTGA AAACTGGCAC AAGACAAGGA TGCCCTCTCT CACCGCTCCT      420

ATTCAACATA GTATTGGAAG TTCTGGCCAG GGCAATCAAG A                         461
```

(2) INFORMATION FOR SEQ ID NO:275:

(i) SEQUENCE CHARACTERISTICS:
        (A) LENGTH: 729 base pairs

```
        (B) TYPE: nucleic acid
        (C) STRANDEDNESS: single
        (D) TOPOLOGY: linear (xi) SEQUENCE DESCRIPTION: SEQ ID NO:275:

TTTTTTTTTT TTGGCCAACA CCAAGTCTTC CACGTGGGAG GTTTTATTAT GTTTTACAAC      60

CATGAAAACA TAGGAAGGTG GCTGTTACAG CAAACATTTC AGATAGACGA ATCGGCCAAG     120

CTCCCCAAAC CCCACCTTCA CAGCCTCTTC CACACGTCTC CCANAGATTG TTGTCCTTCA     180

CTTGCAAATT CANGGATGTT GGAAGTNGAC ATTTNNAGTN GCNGGAACCC CATCAGTGAA     240

NCANTAAGCA GAANTACGAT GACTTTGANA NACANCTGAT GAAGAACACN CTACNGANAA     300

CCCTTTCTNT CGTGTTANGA TCTCNNGTCC NTCACTAATG CGGCCCCCTG CNGGTCCACC     360

ATTTGGGAGA ACTCCCCCCN CGTTGGATCC CCCCTTGAGT NTCCCATTCT NGTCCCCCAN     420

ACCNGNCTTG NGNGNCANTN CNNCCTCNCA CCNTGTTTCC CTGNNGTNAA AATNNGTTTT     480

NCCGCCNCCC NAATTCCCAC CCNAATCACA GCGAANCCNG AAGGCCTTCN NAAGTGTTTA     540

ANGCCCNGNG GTTTCCTCNT NTANTTGCAG CCTACCCTCC CNCTTNNNNT TNCGNGTTGG     600

TCGCGCCCTG GNCNCGCCTN GTTCCTCTTT NNGGNNACAA CCTNGNTCNN NGGCNCNTCN     660

NNNCTNTTCC TNNNACTAGC TNGCCTNTCC NCNCCGNGGN NCANNGCACA TTNCNCNNAC     720

TNTGTNNCC                                                            729

(2) INFORMATION FOR SEQ ID NO:276:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (xi) SEQUENCE DESCRIPTION: SEQ ID NO:276:

TGACCTGACA TGTAGTAGAT ACTTAATAAA TATTTGTGGA ATGAATGGAT GAAGTGGAGT      60

TACAGAGAAA AATAGAAAAG TACAAATTGT TGTCAGTGTT TTGAAGGAAA ATTATGATCT     120

TTCCCAAAGT TCTGACTTCA TTCTAAGACA GGGTTAGTAT CTCCATACAT AATTTTACTT     180

GCTTTTGAAA ATCAAATGAG ATAATCTATT TAGATTGATA ATTTATTTAG ACTGGCTATA     240

AACTATTAAG TGCTAGCAAA TATACATTTT AATCTCATTT TCCACCTCTT GTGATATAGC     300

TATGTAGGTG TTGACTTTAA TGGATGTCAG GTCAATCCC                            339

(2) INFORMATION FOR SEQ ID NO:277:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (xi) SEQUENCE DESCRIPTION: SEQ ID NO:277:

TGACCTGACA TCCATAACAA AATCTTTCTC CATTATATTC TTCTAGGGGA ATTTCTTGAA      60

AAGCATCCAA AGGAAACAAA TGATGGTAAG ACCGTGCCAA GTGGGGAGCA GACACCAAAG     120

TAAGACCACA GATTTTACAT TCAACAGGTA GCTCACAGTA CTTTGCCCGA CACTGTGGGC     180

AGAAATAGCC TCCTAATGTA AGCCCTGGCT CAGTATTGCC ATCCAAATGC GCCATGCTGA     240

AAGAGGGTTT TGCATCCTGG TCAGATNAAG AAGCAATGGT GTGCTGAGGA AATCCCATAC     300

GAATAAGTGA GCATTCAGAA CTTGAGCTAG CAGGAGGAGG ACTAAGATGA TGTGTGAGCA     360

ACTCTTTGTA ATGGCTTTCA TCTAAAATAA CATGGTACGT GCCACCAGTT TCACGAGCAA     420
```

```
GTACAGTGCA AACGCGAACT TCTGCAGACA ATCCAATAAC AGATACTCTA ATTTTAGCTG      480

CCTTTAGGGT CTTGATTAAA TCATAAATAT TAGATGGATC GCAAGTTGTA AGGNTGCTAA      540

AAGATGATTA GTACTTCTCG ACTTGTATGT CCAGGCATGT TGTTTTAAAN TCTGCCTTAG      600

NCCCTGCTTA GGGGAATTTT TAAAGAAGAT GGCTCTCCAT GTTCANGGTC AATCACNAAT      660

TGCC                                                                   664
```

(2) INFORMATION FOR SEQ ID NO:278:

(i) SEQUENCE CHARACTERISTICS:
        (A) LENGTH: 452 base pairs
        (B) TYPE: nucleic acid
        (C) STRANDEDNESS: single
        (D) TOPOLOGY: linear (xi) SEQUENCE DESCRIPTION: SEQ ID NO:278:

```
TGACCTGACA TTGAGGAAGA GCACACACCT CTGAAATTCC TTAGGTTCAG AAGGGCATTT       60

GACACAGAGT GGGCCTCTGA TAATTCATGA AATGCATTCT GAAGTCATCC AGAATGGAGG      120

CTGCAATCTG CTGTGCTTTG GGGGTTGCCT CACTGTGCTC CTGGATATCA CACAAAAGCT      180

GCAATCCTTC TTCTTCAACT AACATTTTGC AGTATTTGCT GGGATTTTTA CTGCAGACAT      240

GATACATAGC CCATAGTGCC CAGAGCTGAA CCTCTGGTTG AGAGAAGTTG CCAAGGAGCG      300

GGAAAAATGT CTTGAAAGAT CTATAGGTCA CCAATGCTGT CATCTTACAA CTTGAACTTG      360

GCCAATTCTG TATGGTTGCA TGCAGATCTT GGAGAAGAGT ACGCCTCTGG AAGTCACGGG      420

ATATCCAAAN CTGTCTGTCA GATGTCAGGT CA                                    452
```

(2) INFORMATION FOR SEQ ID NO:279:

(i) SEQUENCE CHARACTERISTICS:
        (A) LENGTH: 274 base pairs
        (B) TYPE: nucleic acid
        (C) STRANDEDNESS: single
        (D) TOPOLOGY: linear (xi) SEQUENCE DESCRIPTION: SEQ ID NO:279:

```
TTTTTTTTTT TTCGGCAAGG CAAATTTACT TCTGCAAAAG GGTGCTGCTT GCACTTTTGG       60

CCACTGCGAG AGCACACCAA ACAAAGTAGG GAAGGGGTTT TTATCCCTAA CGCGGTTATT      120

CCCTGGTTCT GTGTCGTGTC CCCATTGGCT GGAGTCAGAC TGCACAATCT ACACTGACCC      180

AACTGGCTAC TGTTTAAAAT TGAATATGAA TAATTAGGTA GGAAGGGGGA GGCTGTTTGT      240

TACGGTACAA GACGTGTTTG GGCATGTCAG GTCA                                  274
```

(2) INFORMATION FOR SEQ ID NO:280:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO:280:

```
TACCTGACAT GGAGAAATAA CTTGTAGTAT TTTGCGTGCA ATGGAATACT ATATGAGGGT       60

GAAAATGAAT GAACTAGCAA TGCGTGTATC AACATGAATA AATCCCCAAA ACATAATAAT      120

GTTGAATGGA AAAGGTGAGT TTCAGAAGGA TATATATGCC CTCTAAATCC ATTTATGTAA      180

ACCTTTAAAA AACTACATTA TTTATGGTCA TAAGTCCATC CAGAAAATAT TTAAAAACCT      240

ACATGGGATT GATAACTACT GATGTCAGGT CA                                    272
```

(2) INFORMATION FOR SEQ ID NO:281:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (xi) SEQUENCE DESCRIPTION: SEQ ID NO:281:

```
TTTTTTTTTT TTGGCCAATA GCATGATTTA AACATTGGAA AAAGTCAAAT GAGCAATGCG    60

AATTTTTATG TTCTCTTGAA TAATCAAAAG AGTAGGCAAC ATTGGTTCCT CATTCTTGAA   120

TAGCATTAAT CAGAAAATAT TGCATAGCCT CTAGCCTCCT TAGAGTAGGT GTGCTCTCTC   180

AAATATATCA TAGTCCCACA GTTTATTTCA TGTATATTTT CTGCCTGAAT CACATAGACA   240

TTTGAATTTG CAACGCCTGA TGTAAATATA TAAATTCTTA CCAATCAGAA ACATAGCAAG   300

AAATTCAGGG ACTTGGTCAT YATCAGGGTA TGACAGCANA TCCCTGTARA AACACTGATA   360

CACACTCACA CACGTATGCA ACGTGGAGAT GTCGCYTTWW KKKTWYWCWM RMRYCRWCGN   420

AATCACTTAN N                                                       431
```

(2) INFORMATION FOR SEQ ID NO:282:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO:282:

```
ATTCGATTCG ATGCTTGAGC CCAGGAGTTC AAGACTGCAG TGAGCCACTG CACTTCAGGC    60

TGGACAACAG AGCGAGTCCC TGTGCCAAAA AAAAAAAA                           98
```

(2) INFORMATION FOR SEQ ID NO:283:

(i) SEQUENCE CHARACTERISTICS:
        (A) LENGTH: 764 base pairs
        (B) TYPE: nucleic acid
        (C) STRANDEDNESS: single
        (D) TOPOLOGY: linear (xi) SEQUENCE DESCRIPTION: SEQ ID NO:283:

```
TTTTTTTTTT TTCGCAAGCA CGTGCACTTT ATTGAATGAC ACTGTAGACA GGTGTGTGGG    60

TATAAACTGC TGTATCTAGG GGCAGGACCA AGGGGGCAGG GGCAACAGCC CCAGCGTGCA   120

GGGCCASCAT TGCACAGTGG ASTGCAAAGG TTGCAGGCTA TGGGCGGCTA CTAVTAACCC   180

CGTTTTTCCT GTATTATCTG TAACATAATA TGGTAGACTG TCACAGAGCC GAATWCCART   240

HACASGATGA ATCCAAWGGT CAYGAGGATG CCCASAATCA GGGCCCASAT STTCAGGCAC   300

TTGGCGGTGG GGGCATASGC CTGKGCCCCG GTCACGTCSC CAACCWTCTY CCTGTCCCTA   360

CMCTTGAWTC CNCNCCTTNN NNTNCCNTNA TNTGCCCGCC CNCCTCCTNG NGTCAACCNG   420

NATCTGCACT ANCTCCCTCN CCCCTTNTGG ANTCTCNTCC TTCAANTAAN NTTATCCTTN   480

ACNCCCCCCT CNCCTTTCCC CTNCCNCCCN TNATCCCNGN NCCNCTATCA NTCNTNCCCT   540

CNCTNTNCTN CNNATCGTTC CNCCTNNTAA CTACNCTTTN NACNANNCCT CACTNATNCC   600

NGNNANTTCT TTCCTTCCCT CCCNACGCNN TGCGTGCGCC CGTCTNGCCT NNNCTNCGNA   660

CCCNNACTTT ATTTACCTTT NCACCCTAGC NCTCTACTTN ACCCANCCNC TCCTACCTCC   720

NGGNCCACCC NNCCCTNATC NCTNNCTCTN TCNNCTCNTT CCCC                   764
```

(2) INFORMATION FOR SEQ ID NO:284:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (xi) SEQUENCE DESCRIPTION: SEQ ID NO:284:

```
CAAGTGTAGG CACAGTGATG AAAGCCTGGA GCAAACACAA TCTGTGGGTA ATTAACGTTT      60

ATTTCTCCCC TTCCAGGAAC GTCTTGCATG GATGATCAAA GATCAGCTCC TGGTCAACAT     120

AAATAAGCTA GTTTAAGATA CGTTCCCCTA CACTTGA                              157
```

(2) INFORMATION FOR SEQ ID NO:285:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (xi) SEQUENCE DESCRIPTION: SEQ ID NO:285:

```
ATTCGATTGT ACTCAGACAA CAATATGCTA AGTGGAAGAA GTCAGTCACA AAAGACCACA      60

TACTGTATGA CTTCATTTAC ATTAAGTGTC CAGAATAGGC AAATCCGTAG AGACAGAAAG     120

TAGATGAGCA GCTGCCTAGG TCTGAGTACA                                      150
```

(2) INFORMATION FOR SEQ ID NO:286:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (xi) SEQUENCE DESCRIPTION: SEQ ID NO:286:

```
ATTCGATTTT TTTTTTTTTG GCCATGATGA AATTCTTACT CCCTCAGATT TTTTGTCTGG      60

ATAAATGCAA GTCTCACCAC CAGATGTGAA ATTACAGTAA ACTTTGAAGG AATCTCCTGA     120

GCAACCTTGG TTAGGATCAA TCCAATATTC ACCATCTGGG AAGTCAGGAT GGCTGAGTTG     180

CAGGTCTTTA CAAGTTCGGG CTGGATTGGT CTGAGTACA                            219
```

(2) INFORMATION FOR SEQ ID NO:287:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO:287:

```
ATTCGATTCT TGAGGCTACC AGGAGCTAGG AGAAGAGGCA TGGAACAAAT TTTCCCTCAT      60

ATCCATACTC AGAAGGAACC AACCCTGCTG ACACCTTAAT TTCAGCTTCT GGCCTCTAGA     120

ACTGTGAGAG AGTACATTTC TCTTGGTTTA AGCCAAGAGA ATCTGTCTTT TGGTACTTTA     180

TATCATAGCC TCAAGA                                                     196
```

(2) INFORMATION FOR SEQ ID NO:288:

(i) SEQUENCE CHARACTERISTICS:
        (A) LENGTH: 199 base pairs
        (B) TYPE: nucleic acid (C) STRANDEDNESS: single
        (D) TOPOLOGY: linear (xi) SEQUENCE DESCRIPTION: SEQ ID NO:288:

ATTCGATTTC AGTCCAGTCC CAGAACCCAC ATTGTCAATT ACTACTCTGT ARAAGATTCA        60

TTTGTTGAAA TTCATTGAGT AAAACATTTA TGATCCCTTA ATATATGCCA ATTACCATGC       120

TAGGTACTGA AGATTCAAGT GACCGAGATG CTAGCCCTTG GGTTCAAGTG ATCCCTCTCC       180

CAGAGTGCAC TGGACTGAA                                                    199

(2) INFORMATION FOR SEQ ID NO:289:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (xi) SEQUENCE DESCRIPTION: SEQ ID NO:289:

ATTCGATTCT TGAGGCTACA AACCTGTACA GTATGTTACT CTACTGAATA CTGTAGGCAA        60

TAGTAATACA GAAGCAAGTA TCTGTATATG TAAACATTAA AAAGGTACAG TGAAACTTCA       120

GTATTATAAT CTTAGGGACC ACCATTATAT ATGTGGTCCA TCATTGGCCA AAAAAAAAAA       180

AA                                                                      182

(2) INFORMATION FOR SEQ ID NO:290:

(i) SEQUENCE CHARACTERISTICS:
        (A) LENGTH: 1646 base pairs
        (B) TYPE: nucleic acid
        (C) STRANDEDNESS: single
        (D) TOPOLOGY: linear (xi) SEQUENCE DESCRIPTION: SEQ ID NO:290:

GGCACGAGGA GAAATGTAAT TCCATATTTT ATTTGAAACT TATTCCATAT TTTAATTGGA        60

TATTGAGTGA TTGGGTTATC AAACACCCAC AAACTTTAAT TTTGTTAAAT TTATATGGCT       120

TTGAAATAGA AGTATAAGTT GCTACCATTT TTTGATAACA TTGAAAGATA GTATTTTACC       180

ATCTTTAATC ATCTTGGAAA ATACAAGTCC TGTGAACAAC CACTCTTTCA CCTAGCAGCA       240

TGAGGCCAAA AGTAAAGGCT TTAAATTATA ACATATGGGA TTCTTAGTAG TATGTTTTTT       300

TCTTGAAACT CAGTGGCTCT ATCTAACCTT ACTATCTCCT CACTCTTTCT CTAAGACTAA       360

ACTCTAGGCT CTTAAAAATC TGCCCACACC AATCTTAGAA GCTCTGAAAA GAATTTGTCT       420

TTAAATATCT TTTAATAGTA ACATGTATTT TATGGACCAA ATTGACATTT TCGACTATTT       480

TTTCCAAAAA AGTCAGGTGA ATTTCAGCAC ACTGAGTTGG GAATTTCTTA TCCCAGAAGA       540

CCAACCAATT TCATATTTAT TTAAGATTGA TTCCATACTC CGTTTTCAAG GAGAATCCCT       600

GCAGTCTCCT TAAAGGTAGA ACAAATACTT TCTATTTTTT TTTCACCATT GTGGGATTGG       660

ACTTTAAGAG GTGACTCTAA AAAAACAGAG AACAAATATG TCTCAGTTGT ATTAAGCACG       720

GACCCATATT ATCATATTCA CTTAAAAAAA TGATTTCCTG TGCACCTTTT GGCAACTTCT       780

CTTTTCAATG TAGGGAAAAA CTTAGTCACC CTGAAAACCC ACAAAATAAA TAAAACTTGT       840

AGATGTGGGC AGAAGGTTTG GGGGTGGACA TTGTATGTGT TTAAATTAAA CCCTGTATCA       900

CTGAGAAGCT GTTGTATGGG TCAGAGAAAA TGAATGCTTA GAAGCTGTTC ACATCTTCAA       960

GAGCAGAAGC AAACCCACATG TCTCAGCTAT ATTATTATTT ATTTTTTATG CATAAAGTGA      1020

ATCATTTCTT CTGTATTAAT TTCCAAAGGG TTTTACCCTC TATTTAAATG CTTTGAAAAA      1080

```
CAGTGCATTG ACAATGGGTT GATATTTTTC TTTAAAAGAA AAATATAATT ATGAAAGCCA    1140

AGATAATCTG AAGCCTGTTT TATTTTAAAA CTTTTTATGT TCTGTGGTTG ATGTTGTTTG    1200

TTTGTTTGTT TCTATTTTGT TGGTTTTTTA CTTTGTTTTT TGTTTTGTTT TGTTTTGTTT    1260

KGCATACTAC ATGCAGTTCT TTAACCAATG TCTGTTTGGC TAATGTAATT AAAGTTGTTA    1320

ATTTATATGA GTGCATTTCA ACTATGTCAA TGGTTTCTTA ATATTTATTG TGTAGAAGTA    1380

CTGGTAATTT TTTTATTTAC AATATGTTTA AAGAGATAAC AGTTTGATAT GTTTTCATGT    1440

GTTTATAGCA GAAGTTATTT ATTTCTATGG CATTCCAGCG GATATTTTGG TGTTTGCGAG    1500

GCATGCAGTC AATATTTTGT ACAGTTAGTG GACAGTATTC AGCAACGCCT GATAGCTTCT    1560

TTGGCCTTAT GTTAAATAAA AAGACCTGTT TGGGATGTAT TTTTTATTTT TAAAAAAAAA    1620

AAAAAAAAAA AAAAAAAAA AAAAAA                                           1646

(2) INFORMATION FOR SEQ ID NO:291:

(i) SEQUENCE CHARACTERISTICS:
        (A) LENGTH: 1851 base pairs
        (B) TYPE: nucleic acid
        (C) STRANDEDNESS: single
        (D) TOPOLOGY: linear (xi) SEQUENCE DESCRIPTION: SEQ ID NO:291:

TCATCACCAT TGCCAGCAGC GGCACCGTTA GTCAGGTTTT CTGGGAATCC CACATGAGTA      60

CTTCCGTGTT CTTCATTCTT CTTCAATAGC CATAAATCTT CTAGCTCTGG CTGGCTGTTT     120

TCACTTCCTT TAAGCCTTTG TGACTCTTCC TCTGATGTCA GCTTTAAGTC TTGTTCTGGA     180

TTGCTGTTTT CAGAAGAGAT TTTTAACATC TGTTTTTCTT TGTAGTCAGA AAGTAACTGG     240

CAAATTACAT GATGATGACT AGAAACAGCA TACTCTCTGG CCGTCTTTCC AGATCTTGAG     300

AAGATACATC AACATTTTGC TCAAGTAGAG GGCTGACTAT ACTTGCTGAT CCACAACATA     360

CAGCAAGTAT GAGAGCAGTT CTTCCATATC TATCCAGCGC ATTTAAATTC GCTTTTTTCT     420

TGATTAAAAA TTTCACCACT TGCTGTTTTT GCTCATGTAT ACCAAGTAGC AGTGGTGTGA     480

GGCCATGCTT GTTTTTTGAT TCGATATCAG CACCGTATAA GAGCAGTGCT TTGGCCATTA     540

ATTTATCTTC ATTGTAGACA GCATAGTGTA GAGTGGTATT TCCATACTCA TCTGGAATAT     600

TTGGATCAGT GCCATGTTCC AGCAACATTA ACGCACATTC ATCTTCCTGG CATTGTACGG     660

CCTTTGTCAG AGCTGTCCTC TTTTTGTTGT CAAGGACATT AAGTTGACAT CGTCTGTCCA     720

GCACGAGTTT TACTACTTCT GAATTCCCAT TGGCAGAGGC CAGATGTAGA GCAGTCCTCT     780

TTTGCTTGTC CCTCTTGTTC ACATCCGTGT CCCTGAGCAT GACGATGAGA TCCTTTCTGG     840

GGACTTTACC CCACCAGGCA GCTCTGTGGA GCTTGTCCAG ATCTTCTCCA TGGACGTGGT     900

ACCTGGGATC CATGAAGGCG CTGTCATCGT AGTCTCCCCA AGCGACCACG TTGCTCTTGC     960

CGCTCCCCTG CAGCAGGGGA AGCAGTGGCA GCACCACTTG CACCTCTTGC TCCCAAGCGT    1020

CTTCACAGAG GAGTCGTTGT GGTCTCCAGA AGTGCCCACG TTGCTCTTGC CGCTCCCCCT    1080

GTCCATCCAG GGAGGAAGAA ATGCAGGAAA TGAAAGATGC ATGCACGATG GTATACTCCT    1140

CAGCCATCAA ACTTCTGGAC AGCAGGTCAC TTCCAGCAAG GTGGAGAAAG CTGTCCACCC    1200

ACAGAGGATG AGATCCAGAA ACCACAATAT CCATTCACAA ACAAACACTT TTCAGCCAGA    1260

CACAGGTACT GAAATCATGT CATCTGCGGC AACATGGTGG AACCTACCCA ATCACACATC    1320

AAGAGATGAA GACACTGCAG TATATCTGCA CAACGTAATA CTCTTCATCC ATAACAAAAT    1380

AATATAATTT TCCTCTGGAG CCATATGGAT GAACTATGAA GGAAGAACTC CCCGAAGAAG    1440
```

```
CCAGTCGCAG AGAAGCCACA CTGAAGCTCT GTCCTCAGCC ATCAGCGCCA CGGACAGGAR   1500

TGTGTTTCTT CCCCAGTGAT GCAGCCTCAA GTTATCCCGA AGCTGCCGCA GCACACGGTG   1560

GCTCCTGAGA ACACCCCAG CTCTTCCGGT CTAACACAGG CAAGTCAATA AATGTGATAA   1620

TCACATAAAC AGAATTAAAA GCAAAGTCAC ATAAGCATCT CAACAGACAC AGAAAAGGCA   1680

TTTGACAAAA TCCAGCATCC TTGTATTTAT TGTTGCAGTT CTCAGAGGAA ATGCTTCTAA   1740

CTTTTCCCCA TTTAGTATTA TGTTGGCTGT GGGCTTGTCA TAGGTGGTTT TTATTACTTT   1800

AAGGTATGTC CCTTCTATGC CTGTTTTGCT GAGGGTTTTA ATTCTCGTGC C            1851
```

(2) INFORMATION FOR SEQ ID NO:292:

(i) SEQUENCE CHARACTERISTICS:
       (A) LENGTH: 1851 base pairs
       (B) TYPE: nucleic acid
       (C) STRANDEDNESS: single
       (D) TOPOLOGY: linear (xi) SEQUENCE DESCRIPTION: SEQ ID NO:292:

```
TCATCACCAT TGCCAGCAGC GGCACCGTTA GTCAGGTTTT CTGGGAATCC CACATGAGTA    60

CTTCCGTGTT CTTCATTCTT CTTCAATAGC CATAAATCTT CTAGCTCTGG CTGGCTGTTT   120

TCACTTCCTT TAAGCCTTTG TGACTCTTCC TCTGATGTCA GCTTTAAGTC TTGTTCTGGA   180

TTGCTGTTTT CAGAAGAGAT TTTTAACATC TGTTTTTCTT TGTAGTCAGA AAGTAACTGG   240

CAAATTACAT GATGATGACT AGAAACAGCA TACTCTCTGG CCGTCTTTCC AGATCTTGAG   300

AAGATACATC AACATTTTGC TCAAGTAGAG GGCTGACTAT ACTTGCTGAT CCACAACATA   360

CAGCAAGTAT GAGAGCAGTT CTTCCATATC TATCCAGCGC ATTTAAATTC GCTTTTTCT    420

TGATTAAAAA TTTCACCACT TGCTGTTTTT GCTCATGTAT ACCAAGTAGC AGTGGTGTGA   480

GGCCATGCTT GTTTTTTGAT TCGATATCAG CACCGTATAA GAGCAGTGCT TTGGCCATTA   540

ATTTATCTTC ATTGTAGACA GCATAGTGTA GAGTGGTATT TCCATACTCA TCTGGAATAT   600

TTGGATCAGT GCCATGTTCC AGCAACATTA ACGCACATTC ATCTTCCTGG CATTGTACGG   660

CCTTTGTCAG AGCTGTCCTC TTTTTGTTGT CAAGGACATT AAGTTGACAT CGTCTGTCCA   720

GCACGAGTTT TACTACTTCT GAATTCCCAT TGGCAGAGGC CAGATGTAGA GCAGTCCTCT   780

TTTGCTTGTC CCTCTTGTTC ACATCCGTGT CCCTGAGCAT GACGATGAGA TCCTTTCTGG   840

GGACTTTACC CCACCAGGCA GCTCTGTGGA GCTTGTCCAG ATCTTCTCCA TGGACGTGGT   900

ACCTGGGATC CATGAAGGCG CTGTCATCGT AGTCTCCCCA AGCGACCACG TTGCTCTTGC   960

CGCTCCCCTG CAGCAGGGGA AGCAGTGGCA GCACCACTTG CACCTCTTGC TCCCAAGCGT  1020

CTTCACAGAG GAGTCGTTGT GGTCTCCAGA AGTGCCCACG TTGCTCTTGC CGCTCCCCCT  1080

GTCCATCCAG GGAGGAAGAA ATGCAGGAAA TGAAAGATGC ATGCACGATG GTATACTCCT  1140

CAGCCATCAA ACTTCTGGAC AGCAGGTCAC TTCCAGCAAG GTGGAGAAAG CTGTCCACCC  1200

ACAGAGGATG AGATCCAGAA ACCACAATAT CCATTCACAA ACAAACACTT TCAGCCAGA   1260

CACAGGTACT GAAATCATGT CATCTGCGGC AACATGGTGG AACCTACCCA ATCACACATC  1320

AAGAGATGAA GACACTGCAG TATATCTGCA CAACGTAATA CTCTTCATCC ATAACAAAAT  1380

AATATAATTT TCCTCTGGAG CCATATGGAT GAACTATGAA GGAAGAACTC CCCGAAGAAG  1440

CCAGTCGCAG AGAAGCCACA CTGAAGCTCT GTCCTCAGCC ATCAGCGCCA CGGACAGGAR  1500

TGTGTTTCTT CCCCAGTGAT GCAGCCTCAA GTTATCCCGA AGCTGCCGCA GCACACGGTG  1560

GCTCCTGAGA ACACCCCAG CTCTTCCGGT CTAACACAGG CAAGTCAATA AATGTGATAA   1620
```

| | |
|---|---|
| TCACATAAAC AGAATTAAAA GCAAAGTCAC ATAAGCATCT CAACAGACAC AGAAAAGGCA | 1680 |
| TTTGACAAAA TCCAGCATCC TTGTATTTAT TGTTGCAGTT CTCAGAGGAA ATGCTTCTAA | 1740 |
| CTTTTCCCCA TTTAGTATTA TGTTGGCTGT GGGCTTGTCA TAGGTGGTTT TTATTACTTT | 1800 |
| AAGGTATGTC CCTTCTATGC CTGTTTTGCT GAGGGTTTTA ATTCTCGTGC C | 1851 |

(2) INFORMATION FOR SEQ ID NO:293:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (xi) SEQUENCE DESCRIPTION: SEQ ID NO:293:

| | |
|---|---|
| CTTGAGCTTC CAAATAYGGA AGACTGGCCC TTACACASGT CAATGTTAAA ATGAATGCAT | 60 |
| TTCAGTATTT TGAAGATAAA ATTRGTAGAT CTATACCTTG TTTTTTGATT CGATATCAGC | 120 |
| ACCRTATAAG AGCAGTGCTT TGGCCATTAA TTTATCTTTC ATTRTAGACA GCRTAGTGYA | 180 |
| GAGTGGTATT TCCATACTCA TCTGGAATAT TTGGATCAGT GCCATGTTCC AGCAACATTA | 240 |
| ACGCACATTC ATCTTCCTGG CATTGTACGG CCTGTCAGTA TTAGACCCAA AAACAAATTA | 300 |
| CATATCTTAG GAATTCAAAA TAACATTCCA CAGCTTTCAC CAACTAGTTA TATTTAAAGG | 360 |
| AGAAAACTCA TTTTTATGCC ATGTATTGAA ATCAAACCCA CCTCATGCTG ATATAGTTGG | 420 |
| CTACTGCATA CCTTTATCAG AGCTGTCCTC TTTTTGTTGT CAAGGACATT AAGTTGACAT | 480 |
| CGTCTGTCCA GCAGGAGTTT TACTACTTCT GAATTCCCAT TGGCAGAGGC CAGATGTAGA | 540 |
| GCAGTCCTAT GAGAGTGAGA AGACTTTTTA GGAAATTGTA GTGCACTAGC TACAGCCATA | 600 |
| GCAATGATTC ATGTAACTGC AAACACTGAA TAGCCTGCTA TTACTCTGCC TTCAAAAAAA | 660 |
| AAAAAAAA | 668 |

(2) INFORMATION FOR SEQ ID NO:294:

(i) SEQUENCE CHARACTERISTICS:
        (A) LENGTH: 1512 base pairs
        (B) TYPE: nucleic acid
        (C) STRANDEDNESS: single
        (D) TOPOLOGY: linear (xi) SEQUENCE DESCRIPTION: SEQ ID NO:294:

| | |
|---|---|
| GGGTCGCCCA GGGGGSGCGT GGGCTTTCCT CGGGTGGGTG TGGGTTTTCC CTGGGTGGGG | 60 |
| TGGGCTGGGC TRGAATCCCC TGCTGGGGTT GGCAGGTTTT GGCTGGGATT GACTTTTYTC | 120 |
| TTCAAACAGA TTGGAAACCC GGAGTTACCT GCTAGTTGGT GAAACTGGTT GGTAGACGCG | 180 |
| ATCTGTTGGC TACTACTGGC TTCTCCTGGC TGTTAAAAGC AGATGGTGGT TGAGGTTGAT | 240 |
| TCCATGCCGG CTGCTTCTTC TGTGAAGAAG CCATTTGGTC TCAGGAGCAA GATGGGCAAG | 300 |
| TGGTGCTGCC GTTGCTTCCC CTGCTGCAGG GAGAGCGGCA AGAGCAACGT GGGCACTTCT | 360 |
| GGAGACCACG ACGACTCTGC TATGAAGACA CTCAGGAGCA AGATGGGCAA GTGGTGCCGC | 420 |
| CACTGCTTCC CCTGCTGCAG GGGGAGTGGC AAGAGCAACG TGGGCGCTTC TGGAGACCAC | 480 |
| GACGAYTCTG CTATGAAGAC ACTCAGGAAC AAGATGGGCA AGTGGTGCTG CCACTGCTTC | 540 |
| CCCTGCTGCA GGGGGAGCRG CAAGAGCAAG GTGGGCGCTT GGGGAGACTA CGATGACAGT | 600 |
| GCCTTCATGG AGCCCAGGTA CCACGTCCGT GGAGAAGATC TGGACAAGCT CCACAGAGCT | 660 |
| GCCTGGTGGG GTAAAGTCCC CAGAAAGGAT CTCATCGTCA TGCTCAGGGA CACTGACGTG | 720 |
| AACAAGAAGG ACAAGCAAAA GAGGACTGCT CTACATCTGG CCTCTGCCAA TGGGAATTCA | 780 |

```
GAAGTAGTAA AACTCSTGCT GGACAGACGA TGTCAACTTA ATGTCCTTGA CAACAAAAAG    840

AGGACAGCTC TGAYAAAGGC CGTACAATGC CAGGAAGATG AATGTGCGTT AATGTTGCTG    900

GAACATGGCA CTGATCCAAA TATTCCAGAT GAGTATGGAA ATACCACTCT RCACTAYGCT    960

RTCTAYAATG AAGATAAATT AATGGCCAAA GCACTGCTCT TATAYGGTGC TGATATCGAA   1020

TCAAAAAACA AGGTATAGAT CTACTAATTT TATCTTCAAA ATACTGAAAT GCATTCATTT   1080

TAACATTGAC GTGTGTAAGG GCCAGTCTTC CGTATTTGGA AGCTCAAGCA TAACTTGAAT   1140

GAAAATATTT TGAAATGACC TAATTATCTM AGACTTTATT TTAAATATTG TTATTTTCAA   1200

AGAAGCATTA GAGGGTACAG TTTTTTTTTT TTAAATGCAC TTCTGGTAAA TACTTTTGTT   1260

GAAAACACTG AATTTGTAAA AGGTAATACT TACTATTTTT CAATTTTTCC CTCCTAGGAT   1320

TTTTTTCCCC TAATGAATGT AAGATGGCAA AATTTGCCCT GAAATAGGTT TTACATGAAA   1380

ACTCCAAGAA AAGTTAAACA TGTTTCAGTG AATAGAGATC CTGCTCCTTT GGCAAGTTCC   1440

TAAAAAACAG TAATAGATAC GAGGTGATGC GCCTGTCAGT GGCAAGGTTT AAGATATTTC   1500

TGATCTCGTG CC                                                      1512

(2) INFORMATION FOR SEQ ID NO:295:

(i) SEQUENCE CHARACTERISTICS:
        (A) LENGTH: 1853 base pairs
        (B) TYPE: nucleic acid
        (C) STRANDEDNESS: single
        (D) TOPOLOGY: linear (xi) SEQUENCE DESCRIPTION: SEQ ID NO:295:

GGGTCGCCCA GGGGGSGCGT GGGCTTTCCT CGGGTGGGTG TGGGTTTTCC CTGGGTGGGG     60

TGGGCTGGGC TRGAATCCCC TGCTGGGGTT GGCAGGTTTT GGCTGGGATT GACTTTTYTC    120

TTCAAACAGA TTGGAAACCC GGAGTTACCT GCTAGTTGGT GAAACTGGTT GGTAGACGCG    180

ATCTGTTGGC TACTACTGGC TTCTCCTGGC TGTTAAAAGC AGATGGTGGT TGAGGTTGAT    240

TCCATGCCGG CTGCTTCTTC TGTGAAGAAG CCATTTGGTC TCAGGAGCAA GATGGGCAAG    300

TGGTGCTGCC GTTGCTTCCC CTGCTGCAGG GAGAGCGGCA AGAGCAACGT GGGCACTTCT    360

GGAGACCACG ACGACTCTGC TATGAAGACA CTCAGGAGCA AGATGGGCAA GTGGTGCCGC    420

CACTGCTTCC CCTGCTGCAG GGGGAGTGGC AAGAGCAACG TGGGCGCTTC TGGAGACCAC    480

GACGAYTCTG CTATGAAGAC ACTCAGGAAC AAGATGGGCA AGTGGTGCTG CCACTGCTTC    540

CCCTGCTGCA GGGGGAGCRG CAAGAGCAAG GTGGGCGCTT GGGGAGACTA CGATGACAGY    600

GCCTTCATGG AKCCCAGGTA CCACGTCCRT GGAGAAGATC TGGACAAGCT CCACAGAGCT    660

GCCTGGTGGG GTAAAGTCCC CAGAAAGGAT CTCATCGTCA TGCTCAGGGA CACKGAYGTG    720

AACAAGARGG ACAAGCAAAA GAGGACTGCT CTACATCTGG CCTCTGCCAA TGGGAATTCA    780

GAAGTAGTAA AACTCSTGCT GGACAGACGA TGTCAACTTA ATGTCCTTGA CAACAAAAAG    840

AGGACAGCTC TGAYAAAGGC CGTACAATGC CAGGAAGATG AATGTGCGTT AATGTTGCTG    900

GAACATGGCA CTGATCCAAA TATTCCAGAT GAGTATGGAA ATACCACTCT RCACTAYGCT    960

RTCTAYAATG AAGATAAATT AATGGCCAAA GCACTGCTCT TATAYGGTGC TGATATCGAA   1020

TCAAAAAACA AGCATGGCCT CACACCACTG YTACTTGGTR TACATGAGCA AAAACAGCAA   1080

GTSGTGAAAT TTTTAATYAA GAAAAAAGCG AATTTAAAAT GCRCTGGATA GATATGGAAG   1140

RACTGCTCTC ATACTTGCTG TATGTTGTGG ATCAGCAAGT ATAGTCAGCC YTCTACTTGA   1200

GCAAAATRTT GATGTATCTT CTCAAGATCT GGAAAGACGG CCAGAGAGTA TGCTGTTTCT   1260
```

```
AGTCATCATC ATGTAATTTG CCAGTTACTT TCTGACTACA AAGAAAAACA GATGTTAAAA    1320

ATCTCTTCTG AAAACAGCAA TCCAGAACAA GACTTAAAGC TGACATCAGA GGAAGAGTCA    1380

CAAAGGCTTA AAGGAAGTGA AAACAGCCAG CCAGAGGCAT GGAAACTTTT AAATTTAAAC    1440

TTTTGGTTTA ATGTTTTTTT TTTTTGCCTT AATAATATTA GATAGTCCCA AATGAAATWA    1500

CCTATGAGAC TAGGCTTTGA GAATCAATAG ATTCTTTTTT TAAGAATCTT TTGGCTAGGA    1560

GCGGTGTCTC ACGCCTGTAA TTCCAGCACC TTGAGAGGCT GAGGTGGGCA GATCACGAGA    1620

TCAGGAGATC GAGACCATCC TGGCTAACAC GGTGAAACCC CATCTCTACT AAAAATACAA    1680

AAACTTAGCT GGGTGTGGTG GCGGGTGCCT GTAGTCCCAG CTACTCAGGA RGCTGAGGCA    1740

GGAGAATGGC ATGAACCCGG GAGGTGGAGG TTGCAGTGAG CCGAGATCCG CCACTACACT    1800

CCAGCCTGGG TGACAGAGCA AGACTCTGTC TCAAAAAAAA AAAAAAAAA AAA           1853

(2) INFORMATION FOR SEQ ID NO:296:

(i) SEQUENCE CHARACTERISTICS:
        (A) LENGTH: 2184 base pairs
        (B) TYPE: nucleic acid
        (C) STRANDEDNESS: single
        (D) TOPOLOGY: linear (xi) SEQUENCE DESCRIPTION: SEQ ID NO:296:

GGCACGAGAA TTAAAACCCT CAGCAAAACA GGCATAGAAG GGACATACCT TAAAGTAATA      60

AAAACCACCT ATGACAAGCC CACAGCCAAC ATAATACTAA ATGGGGAAAA GTTAGAAGCA     120

TTTCCTCTGA GAACTGCAAC AATAAATACA AGGATGCTGG ATTTTGTCAA ATGCCTTTTC     180

TGTGTCTGTT GAGATGCTTA TGTGACTTTG CTTTTAATTC TGTTTATGTG ATTATCACAT     240

TTATTGACTT GCCTGTGTTA GACCGGAAGA GCTGGGGTGT TTCTCAGGAG CCACCGTGTG     300

CTGCGGCAGC TTCGGGATAA CTTGAGGCTG CATCACTGGG GAAGAAACAC AYTCCTGTCC     360

GTGGCGCTGA TGGCTGAGGA CAGAGCTTCA GTGTGGCTTC TCTGCGACTG GCTTCTTCGG     420

GGAGTTCTTC CTTCATAGTT CATCCATATG GCTCCAGAGG AAAATTATAT TATTTTGTTA     480

TGGATGAAGA GTATTACGTT GTGCAGATAT ACTGCAGTGT CTTCATCTCT TGATGTGTGA     540

TTGGGTAGGT TCCACCATGT TGCCGCAGAT GACATGATTT CAGTACCTGT GTCTGGCTGA     600

AAAGTGTTTG TTTGTGAATG GATATTGTGG TTTCTGGATC TCATCCTCTG TGGGTGGACA     660

GCTTTCTCCA CCTTGCTGGA AGTGACCTGC TGTCCAGAAG TTTGATGGCT GAGGAGTATA     720

CCATCGTGCA TGCATCTTTC ATTTCCTGCA TTTCTTCCTC CCTGGATGGA CAGGGGGAGC     780

GGCAAGAGCA ACGTGGGCAC TTCTGGAGAC CACAACGACT CCTCTGTGAA GACGCTTGGG     840

AGCAAGAGGT GCAAGTGGTG CTGCCACTGC TTCCCCTGCT GCAGGGGAGC GGCAAGAGCA     900

ACGTGGTCGC TTGGGGAGAC TACGATGACA GCGCCTTCAT GGATCCCAGG TACCACGTCC     960

ATGGAGAAGA TCTGGACAAG CTCCACAGAG CTGCCTGGTG GGGTAAAGTC CCCAGAAAGG    1020

ATCTCATCGT CATGCTCAGG GACACGGATG TGAACAAGAG GGACAAGCAA AAGAGGACTG    1080

CTCTACATCT GGCCTCTGCC AATGGGAATT CAGAAGTAGT AAAACTCGTG CTGGACAGAC    1140

GATGTCAACT TAATGTCCTT GACAACAAAA AGAGGACAGC TCTGACAAAG GCCGTACAAT    1200

GCCAGGAAGA TGAATGTGCG TTAATGTTGC TGGAACATGG CACTGATCCA AATATTCCAG    1260

ATGAGTATGG AAATACCACT CTACACTATG CTGTCTACAA TGAAGATAAA TTAATGGCCA    1320

AAGCACTGCT CTTATACGGT GCTGATATCG AATCAAAAAA CAAGCATGGC CTCACACCAC    1380

TGCTACTTGG TATACATGAG CAAAAACAGC AAGTGGTGAA ATTTTTAATC AAGAAAAAAG    1440
```

| | |
|---|---|
| CGAATTTAAA TGCGCTGGAT AGATATGGAA GAACTGCTCT CATACTTGCT GTATGTTGTG | 1500 |
| GATCAGCAAG TATAGTCAGC CCTCTACTTG AGCAAAATGT TGATGTATCT TCTCAAGATC | 1560 |
| TGGAAAGACG GCCAGAGAGT ATGCTGTTTC TAGTCATCAT CATGTAATTT GCCAGTTACT | 1620 |
| TTCTGACTAC AAAGAAAAAC AGATGTTAAA AATCTCTTCT GAAACAGCA ATCCAGAACA | 1680 |
| AGACTTAAAG CTGACATCAG AGGAAGAGTC ACAAAGGCTT AAAGGAAGTG AAAACAGCCA | 1740 |
| GCCAGAGGCA TGGAAACTTT TAAATTTAAA CTTTTGGTTT AATGTTTTTT TTTTTTGCCT | 1800 |
| TAATAATATT AGATAGTCCC AAATGAAATW ACCTATGAGA CTAGGCTTTG AGAATCAATA | 1860 |
| GATTCTTTTT TTAAGAATCT TTTGGCTAGG AGCGGTGTCT CACGCCTGTA ATTCCAGCAC | 1920 |
| CTTGAGAGGC TGAGGTGGGC AGATCACGAG ATCAGGAGAT CGAGACCATC CTGGCTAACA | 1980 |
| CGGTGAAACC CCATCTCTAC TAAAAATACA AAAACTTAGC TGGGTGTGGT GGCGGGTGCC | 2040 |
| TGTAGTCCCA GCTACTCAGG ARGCTGAGGC AGGAGAATGG CATGAACCCG GGAGGTGGAG | 2100 |
| GTTGCAGTGA GCCAGATCC GCCACTACAC TCCAGCCTGG GTGACAGAGC AAGACTCTGT | 2160 |
| CTCAAAAAAA AAAAAAAAAA AAAA | 2184 |

(2) INFORMATION FOR SEQ ID NO:297:

(i) SEQUENCE CHARACTERISTICS:
        (A) LENGTH: 1855 base pairs
        (B) TYPE: nucleic acid
        (C) STRANDEDNESS: single
        (D) TOPOLOGY: linear (xi) SEQUENCE DESCRIPTION: SEQ ID NO:297:

| | |
|---|---|
| TGCACGCATC GGCCAGTGTC TGTGCCACGT ACACTGACGC CCCCTGAGAT GTGCACGCCG | 60 |
| CACGCGCACG TTGCACGCGC GGCAGCGGCT TGGCTGGCTT GTAACGGCTT GCACGCGCAC | 120 |
| GCCGCCCCCG CATAACCGTC AGACTGGCCT GTAACGGCTT GCAGGCGCAC GCCGCACGCG | 180 |
| CGTAACGGCT TGGCTGCCCT GTAACGGCTT GCACGTGCAT GCTGCACGCG CGTTAACGGC | 240 |
| TTGGCTGGCA TGTAGCCGCT TGGCTTGGCT TTGCATTYTT TGCTKGGCTK GGCGTTGKTY | 300 |
| TCTTGGATTG ACGCTTCCTC CTTGGATKGA CGTTTCCTCC TTGGATKGAC GTTTCYTYTY | 360 |
| TCGCGTTCCT TTGCTGGACT TGACCTTTTY TCTGCTGGGT TTGGCATTCC TTTGGGGTGG | 420 |
| GCTGGGTGTT TTCTCCGGGG GGGKTKGCCC TTCCTGGGGT GGGCGTGGGK CGCCCCCAGG | 480 |
| GGGCGTGGGC TTTCCCCGGG TGGGTGTGGG TTTTCCTGGG GTGGGGTGGG CTGTGCTGGG | 540 |
| ATCCCCCTGC TGGGGTTGGC AGGGATTGAC TTTTTTCTTC AAACAGATTG GAAACCCGGA | 600 |
| GTAACNTGCT AGTTGGTGAA ACTGGTTGGT AGACGCGATC TGCTGGTACT ACTGTTTCTC | 660 |
| CTGGCTGTTA AAAGCAGATG GTGGCTGAGG TTGATTCAAT GCCGGCTGCT TCTTCTGTGA | 720 |
| AGAAGCCATT TGGTCTCAGG AGCAAGATGG GCAAGTGGTG CGCCACTGCT TCCCCTGCTG | 780 |
| CAGGGGAGC GGCAAGAGCA ACGTGGGCAC TTCTGGAGAC CACAACGACT CCTCTGTGAA | 840 |
| GACGCTTGGG AGCAAGAGGT GCAAGTGGTG CTGCCCACTG CTTCCCCTGC TGCAGGGGAG | 900 |
| CGGCAAGAGC AACGTGGKCG CTTGGGGAGA CTACGATGAC AGCGCCTTCA TGGAKCCCAG | 960 |
| GTACCACGTC CRTGGAGAAG ATCTGGACAA GCTCCACAGA GCTGCCTGGT GGGGTAAAGT | 1020 |
| CCCCAGAAAG GATCTCATCG TCATGCTCAG GGACACTGAY GTGAACAAGA RGGACAAGCA | 1080 |
| AAAGAGGACT GCTCTACATC TGGCCTCTGC CAATGGGAAT TCAGAAGTAG TAAAACTCGT | 1140 |
| GCTGGACAGA CGATGTCAAC TTAATGTCCT TGACAACAAA AAGAGGACAG CTCTGACAAA | 1200 |
| GGCCGTACAA TGCCAGGAAG ATGAATGTGC GTTAATGTTG CTGGAACATG GCACTGATCC | 1260 |

-continued

```
AAATATTCCA GATGAGTATG GAAATACCAC TCTACACTAT GCTGTCTACA ATGAAGATAA    1320

ATTAATGGCC AAAGCACTGC TCTTATACGG TGCTGATATC GAATCAAAAA ACAAGGTATA    1380

GATCTACTAA TTTTATCTTC AAAATACTGA AATGCATTCA TTTTAACATT GACGTGTGTA    1440

AGGGCCAGTC TTCCGTATTT GGAAGCTCAA GCATAACTTG AATGAAAATA TTTTGAAATG    1500

ACCTAATTAT CTAAGACTTT ATTTTAAATA TTGTTATTTT CAAAGAAGCA TTAGAGGGTA    1560

CAGTTTTTTT TTTTTAAATG CACTTCTGGT AAATACTTTT GTTGAAAACA CTGAATTTGT    1620

AAAAGGTAAT ACTTACTATT TTTCAATTTT TCCCTCCTAG GATTTTTTTC CCCTAATGAA    1680

TGTAAGATGG CAAAATTTGC CCTGAAATAG GTTTTACATG AAAACTCCAA GAAAAGTTAA    1740

ACATGTTTCA GTGAATAGAG ATCCTGCTCC TTTGGCAAGT TCCTAAAAAA CAGTAATAGA    1800

TACGAGGTGA TGCGCCTGTC AGTGGCAAGG TTTAAGATAT TTCTGATCTC GTGCC         1855
```